(12) United States Patent
Chao et al.

(10) Patent No.: US 11,718,619 B2
(45) Date of Patent: Aug. 8, 2023

(54) ISOXAZOLYL-CARBONYLOXY AZABICYCLO[3.2.1]OCTANYL COMPOUNDS AS FXR ACTIVATORS

(71) Applicant: ARDELYX, INC., Fremont, CA (US)

(72) Inventors: Jianhua Chao, Fremont, CA (US); Rakesh Jain, Fremont, CA (US); Lily Hu, Fremont, CA (US); Jason Gustaf Lewis, Fremont, CA (US); Helene Baribault, Fremont, CA (US); Jeremy Caldwell, Fremont, CA (US)

(73) Assignee: Ardelyx, Inc., Fremont, CA (US)

( * ) Notice: Subject to any disclaimer, the term of this patent is extended or adjusted under 35 U.S.C. 154(b) by 116 days.

(21) Appl. No.: 17/224,518

(22) Filed: Apr. 7, 2021

(65) Prior Publication Data

US 2021/0300927 A1 Sep. 30, 2021

Related U.S. Application Data

(62) Division of application No. 16/327,790, filed as application No. PCT/US2017/048277 on Aug. 23, 2017, now Pat. No. 11,091,482.

(60) Provisional application No. 62/419,452, filed on Nov. 8, 2016, provisional application No. 62/378,531, filed on Aug. 23, 2016.

(51) Int. Cl.
C07D 471/08 (2006.01)
A61P 1/16 (2006.01)

(52) U.S. Cl.
CPC .............. *C07D 471/08* (2013.01); *A61P 1/16* (2018.01)

(58) Field of Classification Search
CPC .................................. A61P 1/16; C07D 471/08
See application file for complete search history.

(56) References Cited

U.S. PATENT DOCUMENTS

| 4,988,691 | A | 1/1991 | Benelli et al. |
| 10,793,568 | B2 | 10/2020 | Chao et al. |
| 11,091,482 | B2 | 8/2021 | Chao et al. |
| 2013/0331349 | A1 | 12/2013 | Tully et al. |
| 2019/0308973 | A1 | 10/2019 | Chao et al. |
| 2021/0017177 | A1 | 1/2021 | Chao et al. |
| 2021/0024522 | A1 | 1/2021 | Fang et al. |
| 2021/0380585 | A1 | 12/2021 | Chao |

FOREIGN PATENT DOCUMENTS

| WO | 2009012125 A1 | 1/2009 |
| WO | 2011020615 A1 | 2/2011 |
| WO | 2012087519 A1 | 6/2012 |
| WO | 2012087520 A1 | 6/2012 |
| WO | 2012087521 A1 | 6/2012 |
| WO | 2016097933 A1 | 6/2016 |
| WO | 2016127924 A1 | 8/2016 |
| WO | 2018039386 A1 | 3/2018 |
| WO | 2019007418 A1 | 1/2019 |

OTHER PUBLICATIONS

Li, Frontiers in Pharmacology, Aug. 2020 | vol. 11 | Article 1247, 1-15.*
Gadaleta Biochimica et Biophysica Acta 1851 (2015) 30-39; Expert Opin. Drug Metab. Toxicol. (2015) 11(4):523-532.*
Ettmayer, P , et al., "Lessons Learned from Marketed and Investigational Prodrugs", Journal of Medicinal Chemistry 47(10), 2393-2404 (2004).
Han, H , "Targeted Prodrug Design to Optimize Drug Delivery", AAPS Pharmsci 2(1), Article 6, 11 pages (2000).
Moschetta, A , "Deciphering the nuclear bile acid receptor FXR paradigm", Nucl Recept Signal 8, e005, 28 pages (2010).
Testa, B , "Prodrug research: futile or fertile?", Biochemical Pharmacology 68, 2097-2106 (2004).
U.S. Appl. No. 16/327,791, U.S. Pat. 10,793,568.
U.S. Appl. No. 16/990,827, 2021-0017177.
U.S. Appl. No. 17/858,917.
U.S. Appl. No. 16/647,385, 2021-0380585.
Cannon, J , "Analog Design", Chapter Nineteen in Burger's Medicinal Chemistry and Drug Discovery, Fifth Ed. vol. I: Principles and Practice, 783-802 (1995).
Huang, W , et al., "FXR a metabolie regulator and cell protector", Cell Res 18, 1087-1095 (2008).
Matsubara, T , et al., "FXR signaling in the enterohepatic system", Mol Cell Endocrinol 368, 17-29 (2013).
Modica, S , et al., "Deciphering the nuclear bile acid receptor FXR paradigm", Nucl Recept Signal 8, e005, 28 pages (2010).
Patent Cooperation Treaty , International Searching Authority, Search Report and Written Opinion for PCT/US2017/048277, 8 pages, dated Oct. 30, 2017.

(Continued)

*Primary Examiner* — Nizal S Chandrakumar
(74) *Attorney, Agent, or Firm* — Viksnins Harris Padys Malen LLP

(57) ABSTRACT

The disclosure relates to activators of FXR useful in the treatment of autoimmune disorders, liver disease, intestinal disease, kidney disease, cancer, and other diseases in which FXR plays a role, having the Formula (I):

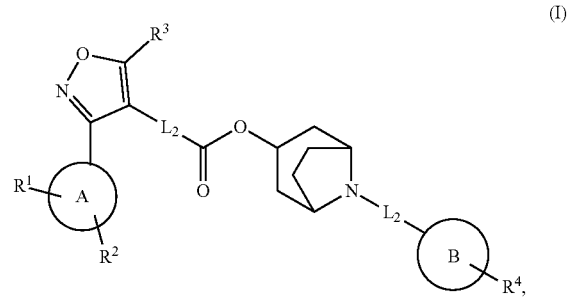

wherein $L_1$, $L_2$, A, B, $R_1$, $R_2$, $R_3$, and $R_4$ are described herein.

4 Claims, 21 Drawing Sheets

Specification includes a Sequence Listing.

(56) References Cited

OTHER PUBLICATIONS

Shaik, F , et al., "Role of farnesoid X receptor in inflammation and resolution", Inflamm Res 64, 9-20 (2015).
Tian, F , et al., "Factors affecting crystallization of hydrates", Journal of Pharmacy and Pharmacology 62, 1534-1546 (2010).
Vavassori, P , "The bile acid receptor FXR is a modulator of intestinal innate immunity", J Immunol 183, 6251-6261 (2009).
Venkatesh, S , et al., "Role of the Development Scientist in Compound Lead Selection and Optimization", Journal of Pharmaceutical Sciences 89 (2), 145-154 (2000).
Verbeke, L , "The FXR agonist obeticholic acid prevents gut barrier dysfunction and bacterial translocation in cholestatic rats", Am J Pathol 185, 409-419 (2015).
West, A , "Solid Solutions", Chapter 10, Solid State Chemistry and Its Applications, pp. 358 and 365 (1984).
Wolff , "Burger's Medicinal Chemistry and Drug Discovery", Fifth Edition, vol. 1: Principles and Practice, 975-977 (1995).

* cited by examiner $*p < 0.05$; $p < 0.01$; $*p < 0.001$ $\ p < 0.01;\ *\ p < 0.001;$ $*\ p < 0.05;\ \ p < 0.01;\ *\ p < 0.001.$

* $p < 0.05$;  $p < 0.01$; * $p < 0.001$.

* $p < 0.05$;  $p < 0.01$; * $p < 0.001$.

$*p < 0.05; p < 0.01; *p < 0.001.$

**p < 0.01

**** $p < 0.0001$ $*p < 0.05; p < 0.01; **p < 0.0001.$

ISOXAZOLYL-CARBONYLOXY AZABICYCLO[3.2.1]OCTANYL COMPOUNDS AS FXR ACTIVATORS

CROSS REFERENCE TO RELATED APPLICATIONS

This application is a divisional of U.S. application Ser. No. 16/327,790, filed on Feb. 22, 2019, which is a 35 U.S.C § 371 application of International Application No. PCT/US2017/048277, filed on Aug. 23, 2017, which claims priority to U.S. Provisional Application No. 62/378,531, filed Aug. 23, 2016 and U.S. Provisional Application No. 62/419,452, filed Nov. 8, 2016. The contents of each of these applications are incorporated by reference herein.

FIELD OF INVENTION

The present disclosure is directed to modulators of farnesoid X receptor (FXR) useful in the treatment of diseases or disorders associated with FXR proteins. Specifically, the disclosure is related to compounds and compositions, which activate FXR, methods of treating diseases or disorders associated with FXR, and methods of synthesis of these compounds.

DESCRIPTION OF THE TEXT FILE SUBMITTED ELECTRONICALLY

The instant application contains a Sequence Listing which has been submitted in ASCII format via EFS-Web and is hereby incorporated by reference in its entirety. Said ASCII copy, created on Aug. 23, 2017, is named 00888_022US2_SeqList.txt and is 4 kilobytes in size.

BACKGROUND OF THE INVENTION

FXR is a ligand-activated transcription factor. Upon binding of a ligand, FXR either binds to DNA at the FXR response elements (FXREs) as a monomer, or forms a heterodimer with retinoid X receptor (RXR) and then binds to FXREs, regulating the transcription of a variety of target genes. To date, more than 40 FXR target genes have been identified that are involved in a wide range of physiological functions including bile acid homeostasis (e.g., BACS, BAAT, BSEP, FGF15/19, etc.), cholesterol and lipoprotein metabolism (e.g., Apolipoprotein C-I, II, IV, Apolipoprotein E, MDR3, Human complement C3, ApoA-1, hepatic lipase, SREPB-1c), glucose metabolism (e.g., PEPCK, GSK3, AKR1B7, GLUT4, G6Pase), and xenobiotics metabolism (e.g., GSTα3, GSTα4, GSTµ1, GSTµ3, SULT1A1, SULT1A2). In addition to the regulation of metabolic related genes, recent results have identified FXR as a regulator of cellular inflammatory and immune responses. Activation of FXR can provide anti-inflammatory effects by negative regulation of nuclear factor κB (NFκB) pathway, reducing the expression of NFκB and the many pro-inflammatory cytokines associated with this pathway (Matsubara, T. et al., "FXR signaling in the enterohepatic system," *Mol. Cell Endocrinol.* 2013, 368, 17-29; Moschetta, A., "Deciphering the nuclear bile acid receptor FXR paradigm," *Nucl. Recept. Signal.*, 2010, 8, e005; Huang, W., et al., "FXR: a metabolic regulator and cell protector," *Cell Res.*, 2008, 1087-1095).

FXR plays a key role in the synthesis, transport and metabolism of bile acids (BAs) and the many physiological and pathophysiological conditions that involve BAs. In the liver, activation of FXR has been shown to lead to the increased expression of short heterodimer partner (SHP), which in turn inactivates liver receptor homolog-1 (LRH-1) and inhibits the cholesterol 7-alpha-hydroxylase (CYP7A1), the rate-limiting enzyme in the first step of biosynthesis of primary bile acids from cholesterol, thereby reduces the production of bile acids. Activation of FXR in the liver has also been shown to downregulate transporters like Na-taurocholate co-transporting polypeptide (NTCP) and organic anion-transporting peptides (OATPs) preventing the uptake of bile acids to liver. The accumulation of BAs in the liver plays a pivotal role in cholestasis-associated liver damage, pharmacological activation of FXR by synthetic ligands can provide therapeutic intervention.

FXR has also been shown to play an important role in the inflammation control of various liver and intestinal diseases (Shaik, F. B., et al., "Role of farnesoid X receptor in inflammation and resolution," *Inflamm. Res.* 2015, 64, 9-20). Activation of FXR has been shown to repress the NFκB pathway, a prototypical proinflammatory signaling pathway, and inhibit the expression of key cytokines such as TNFα, IL-1β, and IL-6. In the colon of FXR knockout mice, increased expression of both proinflammatory cytokines (e.g., TNFα, IL-1β, IFNγ) and profibrotic genes (e.g, Collagen α1, TIMP-1, and αSMA) has been observed, indicative of dysregulation in intestinal immunity and tissue remodeling. Activation of FXR with FXR activators in the TNBS induced murine inflammatory bowel disease model has been shown to inhibit the above cytokines and provide protection against inflammation and fibrosis, subsequently against the development of colitis (Vavassori, P., "The bile acid receptor FXR is a modulator of intestinal innate immunity," *J. Immunol.* 2009, 183, 6251-6261). Moreover, treatment with an FXR agonist in a rat model of cholestatic liver injury (bile-duct ligation) reduced NK cells and INFγ expression, leading to reduction in intestinal inflammation, reduction in bacterial translocation, and overall improvement in gut barrier function (Verbeke, L., "The FXR agonist obeticholic acid prevents gut barrier dysfunction and bacterial translocation in cholestatic rats," *Am. J. Pathol.* 2015, 185, 409-419).

Activation of FXR with small molecule activators has the potential to be a treatment for a range of diseases including bile acid related disorders, metabolic syndrome, type-2-diabetes, hyperlipidemia, hypertriglyceridemia, primary biliary cirrhosis (PBC), fatty liver disease, nonalcoholic steatohepatitis (NASH), inflammatory autoimmune diseases, Crohn's disease, multiple sclerosis, atherosclerosis, hepatic and colon cancers, and other disorders. However, known FXR activators have demonstrated toxicities, treatment limiting adverse effects, and other issues. For these reasons, there remains a need for novel and potent small molecule FXR activators.

SUMMARY OF THE DISCLOSURE

A first aspect of the disclosure relates to compounds of Formula (I):

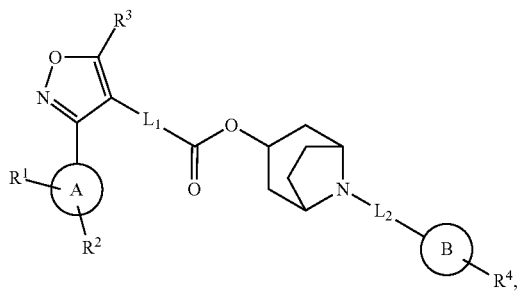

(I)

and pharmaceutically acceptable salts, hydrates, solvates, prodrugs, stereoisomers, and tautomers thereof,
wherein:
$L_1$ is a bond or —$(CH_2)_n$—;
$L_2$ is a bond or —$S(O)_2$—;
A is $(C_3-C_8)$ cycloalkyl, $(C_6-C_{10})$ aryl, heterocycloalkyl, or heteroaryl, and wherein each cycloalkyl, aryl, heterocycloalkyl, or heteroaryl is optionally substituted with one or more $R^7$;
B is $(C_6-C_{10})$ aryl or heteroaryl, wherein each aryl or heteroaryl is optionally substituted with one or more $R^5$;
$R^1$ and $R^2$ are each independently, at each occurrence, H, halogen, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_3-C_7)$ cycloalkyl, —OH, or —CN, wherein the cycloalkyl is optionally substituted with one or more $R^9$;
or when A is cycloalkyl or heterocycloalkyl, $R^1$ and $R^2$ together when attached to the same carbon atom form a $(C_3-C_8)$ spirocycloalkyl ring optionally substituted with one or more $R^8$; or when A is cycloalkyl or heterocycloalkyl, $R^1$ and $R^2$ together when attached to the same atom form a $(C_3-C_8)$ spiroheterocycloalkyl ring optionally substituted with one or more $R^8$; or $R^1$ and $R^2$ when on adjacent atoms together with the atoms to which they are attached form a $(C_3-C_8)$ cycloalkyl ring optionally substituted with one or more $R^8$; or $R^1$ and $R^2$ when on adjacent atoms together with the atoms to which they are attached form a heterocycloalkyl ring optionally substituted with one or more $R^8$; or $R^1$ and $R^2$ when on adjacent atoms together with the atoms to which they are attached form a $(C_6-C_{10})$ aryl ring optionally substituted with one or more $R^8$; or $R^1$ and $R^2$ when on adjacent atoms together with the atoms to which they are attached form a heteroaryl ring optionally substituted with one or more $R^8$; or when A is cycloalkyl or heterocycloalkyl, $R^1$ and $R^2$, when on non-adjacent atoms, together with the atoms to which they are attached form a $(C_4-C_8)$ cycloalkyl ring optionally substituted with one or more $R^8$; or when A is cycloalkyl or heterocycloalkyl, $R^1$ and $R^2$, when on non-adjacent atoms, together with the atoms to which they are attached form a heterocycloalkyl ring optionally substituted with one or more $R^8$;
$R^3$ is $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_1-C_6)$ hydroxyalkyl, or $(C_3-C_8)$ cycloalkyl, wherein the cycloalkyl is optionally substituted with one or more substituents each independently selected from halogen, $(C_1-C_6)$ alkyl, $(C_1-C_6)$ alkoxy, $(C_1-C_6)$ haloalkyl, $(C_1-C_6)$ haloalkoxy, and —OH;
$R^4$ is $COOR^{6a}$, —$(CH_2)_n$—$COOR^{6a}$, $CONR^{6b}OH$, $CONR^{6b}R^{6c}$, $CONH(CH_2)_nCOOR^{6a}$, $CONH(CH_2)_nR^{6a}$, —$(CH_2)_nCONH(CH_2)_nR^{6a}$, $CONR^{6b}SO_2R^{6d}$, $CONR^{6b}SO_2(CH_2)_nR^{6d}$, —$(CH_2)_n$—$CONR^{6b}SO_2R^{6d}$, $CONR^{6b}SO_2(CH_2)_nN(CO)R^{6d}$ $CONH(CH_2)_nSO_2R^{6e}$, $COR^{6f}$, $(CH_2)_nPO(OR^{6g})_2$, $COO(CH_2)_nPO(OR^{6g})_2$, $SO_2NR^{6b}(CH_2)_nCOOR^{6a}$, $SO_2R^{6e}$, $CN$, —$(CH_2)_n$—$NR^{6b}C(O)R^{6c}$, —$(CH_2)_n$—$N(OH)$—$C(O)R^{6c}$, OXO, alkyl, cycloalkyl, —$(CH_2)_n$-cycloalkyl, heterocycloalkyl, —$(CH_2)_n$-heterocycloalkyl, heteroaryl and —$(CH_2)_n$-heteroaryl; wherein said alkyl, cycloalkyl, —$(CH_2)_n$-cycloalkyl, heterocycloalkyl, —$(CH_2)_n$-heterocycloalkyl, heteroaryl and —$(CH_2)_n$-heteroaryl are optionally substituted with $COOR^{6a}$, —$(CH_2)_n$—$COOR^{6a}$, $CONR^{6b}OH$, $CONR^{6b}R^{6c}$, $CONH(CH_2)_nCOOR^{6a}$, $CONH(CH_2)_nR^{6a}$, —$(CH_2)_nCONH(CH_2)_nR^{6a}$, $CONR^{6b}SO_2R^{6d}$, $CONR^{6b}SO_2(CH_2)_nR^{6d}$, —$(CH_2)_n$—$CONR^{6b}SO_2R^{6d}$, $CONR^{6b}SO_2(CH_2)_nN(CO)R^{6d}$ $CONH(CH_2)_nSO_2R^{6e}$, $COR^{6f}$, $(CH_2)_nPO(OR^{6g})_2$, $COO(CH_2)_nPO(OR^{6g})_2$, $SO_2NR^{6b}(CH_2)_nCOOR^{6a}$, $SO_2R^{6e}$, $CN$, —$(CH_2)_n$—$NR^{6b}C(O)R^{6c}$, —$(CH_2)_n$—$N(OH)$—$C(O)R^{6c}$;
each $R^5$ is independently, at each occurrence, halogen, $(C_1-C_6)$ alkyl, $(C_1-C_6)$ haloalkyl, $(C_1-C_6)$ alkoxy, $(C_1-C_6)$ haloalkoxy, —OH, —CN, $(C_3-C_6)$ cycloalkyl, $(C_6-C_{10})$ aryl, heterocycloalkyl, or heteroaryl, and wherein each cycloalkyl, aryl, heterocycloalkyl or heteroaryl is optionally substituted with one or more substituents each independently selected from halogen, $(C_1-C_6)$ alkyl, $(C_1-C_6)$ haloalkyl, $(C_1-C_6)$ alkoxy, $(C_1-C_6)$ haloalkoxy, —OH, and oxo;
or $R^4$ and $R^5$ when on adjacent atoms together with the atoms to which they are attached form a $(C_4-C_8)$ cycloalkyl ring optionally substituted with one or more $R^{10}$; or $R^4$ and $R^5$ when on adjacent atoms together with the atoms to which they are attached form a heterocycloalkyl ring optionally substituted with one or more $R^{10}$;
$R^{6a}$ is H, $(C_1-C_6)$ alkyl, $(C_3-C_8)$ cycloalkyl, $(C_6-C_{10})$ aryl, heterocycloalkyl, or heteroaryl, and wherein each alkyl, cycloalkyl, aryl, heterocycloalkyl, or heteroaryl is optionally substituted with one or more substituents each independently selected from halogen, $(C_1-C_6)$ alkyl, $(C_1-C_6)$ haloalkyl, $(C_1-C_6)$ alkoxy, $N(R^{6d})(R^{6e})$, —$C(O)N(R^{6d})(R^{6e})$, and $(C_1-C_6)$ haloalkoxy;
$R^{6b}$ and $R^{6c}$ are each independently H, $(C_1-C_6)$ alkyl, $(C_3-C_8)$ cycloalkyl, $(C_6-C_{10})$ aryl, heterocycloalkyl, or heteroaryl, and wherein each alkyl, cycloalkyl, aryl, heterocycloalkyl, or heteroaryl is optionally substituted with one or more substituents each independently selected from halogen, $(C_1-C_6)$ alkyl, $(C_1-C_6)$ haloalkyl, $(C_1-C_6)$ alkoxy, and $(C_1-C_6)$ haloalkoxy;
$R^{6d}$ is $(C_1-C_6)$ alkyl, $(C_3-C_8)$ cycloalkyl, $(C_6-C_{10})$ aryl, heterocycloalkyl, or heteroaryl, and wherein each alkyl, cycloalkyl, aryl, heterocycloalkyl, or heteroaryl is optionally substituted with one or more substituents each independently selected from halogen, —OH, $(C_1-C_6)$ alkyl, $(C_1-C_6)$ haloalkyl, $(C_1-C_6)$ alkoxy, $(C_1-C_6)$ haloalkoxy, and $(C_3-C_8)$ cycloalkyl;
$R^{6e}$ is —OH, $(C_1-C_6)$ alkyl, $(C_3-C_8)$ cycloalkyl, $(C_6-C_{10})$ aryl, heterocycloalkyl, or heteroaryl, wherein each alkyl, cycloalkyl, aryl, heterocycloalkyl, or heteroaryl is optionally substituted with one or more substituents each independently selected from halogen, —OH, $(C_1-C_6)$ alkyl, $(C_1-C_6)$ haloalkyl, $(C_1-C_6)$ alkoxy, $(C_1-C_6)$ haloalkoxy, and $(C_3-C_8)$ cycloalkyl;
$R^{6f}$ is alkyl or haloalkyl;
$R^{6g}$ is H or alkyl optionally substituted with —O—CO-alkyl;
Each $R^7$ is independently, at each occurrence, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, halogen, or —CN;
each $R^8$ is independently, at each occurrence, $(C_1-C_6)$ alkyl, $(C_1-C_6)$ alkoxy, $(C_1-C_6)$ haloalkyl, $(C_1-C_6)$ haloalkoxy, halogen, or —OH;

each $R^9$ is independently, at each occurrence, $(C_1$-$C_6)$ alkyl, $(C_1$-$C_6)$ alkoxy, $(C_1$-$C_6)$ haloalkyl, $(C_1$-$C_6)$ haloalkoxy, halogen, or —OH;

each $R^{10}$ is independently, at each occurrence, $(C_1$-$C_6)$ alkyl, $(C_1$-$C_6)$ alkoxy, $(C_1$-$C_6)$ haloalkyl, $(C_1$-$C_6)$ haloalkoxy, halogen, oxo, or —OH;

n is 1 or 2; and m is 1, 2, 3, or 4.

Another aspect of the disclosure relates to a method of treating or preventing a disease or disorder in which FXR plays a role. The method comprises administering to a patient in need of a treatment for diseases or disorders in which FXR plays a role an effective amount of a compound of Formula (I), or a pharmaceutically acceptable salt, hydrate, solvate, prodrug, stereoisomer, or tautomer thereof.

Another aspect of the disclosure is directed to a method of modulating FXR. The method involves administering to a patient in need thereof an effective amount of a compound of Formula (I), or a pharmaceutically acceptable salt, hydrate, solvate, prodrug, stereoisomer, or tautomer thereof.

Another aspect of the disclosure is directed to a method of activating FXR. The method comprises administering to a patient in need thereof an effective amount of a compound of Formula (I), or a pharmaceutically acceptable salt, hydrate, solvate, prodrug, stereoisomer, or tautomer thereof.

Another aspect of the disclosure relates to a method of treating a liver disease. The method comprises administering to a patient in need of a treatment for a liver disease an effective amount of a compound of Formula (I), or a pharmaceutically acceptable salt, hydrate, solvate, prodrug, stereoisomer, or tautomer thereof.

Another aspect of the disclosure relates to a method of treating an intestinal disease. The method comprises administering to a patient in need of a treatment for an intestinal disease an effective amount of a compound of Formula (I), or a pharmaceutically acceptable salt, hydrate, solvate, prodrug, stereoisomer, or tautomer thereof.

Another aspect of the disclosure relates to a method of treating a kidney disease. The method comprises administering to a patient in need of a treatment for a kidney disease an effective amount of a compound of Formula (I), or a pharmaceutically acceptable salt, hydrate, solvate, prodrug, stereoisomer, or tautomer thereof.

Another aspect of the disclosure relates to a method of treating an autoimmune disorder. The method comprises administering to a patient in need of a treatment for an autoimmune disorder an effective amount of a compound of Formula (I), or a pharmaceutically acceptable salt, hydrate, solvate, prodrug, stereoisomer, or tautomer thereof.

Another aspect of the disclosure relates to a method of treating cancer. The method comprises administering to a patient in need of a treatment for cancer an effective amount of a compound of Formula (I), or a pharmaceutically acceptable salt, hydrate, solvate, prodrug, stereoisomer, or tautomer thereof.

Another aspect of the disclosure is directed to pharmaceutical compositions comprising a compound of Formula (I), or a pharmaceutically acceptable salt, hydrate, solvate, prodrug, stereoisomer, or tautomer thereof, and a pharmaceutically acceptable carrier. The pharmaceutical acceptable carrier may further include an excipient, diluent, or surfactant.

Another aspect of the present disclosure relates to a compound of Formula (I), or a pharmaceutically acceptable salt, hydrate, solvate, prodrug, stereoisomer, or tautomer thereof, for use in the manufacture of a medicament for treating a disease associated with activating FXR.

Another aspect of the present disclosure relates to a compound of Formula (I), or a pharmaceutically acceptable salt, hydrate, solvate, prodrug, stereoisomer, or tautomer thereof, for use in the manufacture of a medicament for treating a disease in which FXR plays a role.

Another aspect of the present disclosure relates to a compound of Formula (I), or a pharmaceutically acceptable salt, hydrate, solvate, prodrug, stereoisomer, or tautomer thereof, for use in the manufacture of a medicament for treating a liver disease.

Another aspect of the present disclosure relates to a compound of Formula (I), or a pharmaceutically acceptable salt, hydrate, solvate, prodrug, stereoisomer, or tautomer thereof, for use in the manufacture of a medicament for treating an intestinal disease.

Another aspect of the present disclosure relates to a compound of Formula (I), or a pharmaceutically acceptable salt, hydrate, solvate, prodrug, stereoisomer, or tautomer thereof, for use in the manufacture of a medicament for treating a kidney disease.

Another aspect of the present disclosure relates to a compound of Formula (I), or a pharmaceutically acceptable salt, hydrate, solvate, prodrug, stereoisomer, or tautomer thereof, for use in the manufacture of a medicament for treating an autoimmune disorder.

Another aspect of the present disclosure relates to a compound of Formula (I), or a pharmaceutically acceptable salt, hydrate, solvate, prodrug, stereoisomer, or tautomer thereof, for use in the manufacture of a medicament for treating cancer.

Another aspect of the present disclosure relates to a compound of Formula (I), or a pharmaceutically acceptable salt, hydrate, solvate, prodrug, stereoisomer, or tautomer thereof, for use in the treatment of a disease associated with activating FXR.

Another aspect of the present disclosure relates to a compound of Formula (I), or a pharmaceutically acceptable salt, hydrate, solvate, prodrug, stereoisomer, or tautomer thereof, for use in the treatment of a disease in which FXR plays a role.

Another aspect of the present disclosure relates to a compound of Formula (I), or a pharmaceutically acceptable salt, hydrate, solvate, prodrug, stereoisomer, or tautomer thereof, for use in the treatment of a liver disease.

Another aspect of the present disclosure relates to a compound of Formula (I), or a pharmaceutically acceptable salt, hydrate, solvate, prodrug, stereoisomer, or tautomer thereof, for use in the treatment of an intestinal disease.

Another aspect of the present disclosure relates to a compound of Formula (I), or a pharmaceutically acceptable salt, hydrate, solvate, prodrug, stereoisomer, or tautomer thereof, for use in the treatment of a kidney disease.

Another aspect of the present disclosure relates to a compound of Formula (I), or a pharmaceutically acceptable salt, hydrate, solvate, prodrug, stereoisomer, or tautomer thereof, for use in the treatment of an autoimmune disorder.

Another aspect of the present disclosure relates to a compound of Formula (I), or a pharmaceutically acceptable salt, hydrate, solvate, prodrug, stereoisomer, or tautomer thereof, for use in the treatment of cancer.

The present disclosure further provides methods of treating a disease or disorder associated with modulation of FXR including, but not limited to, liver diseases, intestinal diseases, kidney disease, autoimmune disorders, or cancer, comprising administering to a patient suffering from at least one of said diseases or disorder a compound of Formula (I), or a pharmaceutically acceptable salt, hydrate, solvate, prodrug, stereoisomer, or tautomer thereof.

The present disclosure provides activators of FXR that are therapeutic agents in the treatment of diseases, such as liver diseases, intestinal diseases, kidney disease, autoimmune disorders, and cancer. Ultimately the present disclosure provides the medical community with a novel pharmacological strategy for the treatment of diseases and disorders associated with the modulation of FXR.

BRIEF DESCRIPTION OF THE DRAWINGS

FIG. 2 shows the intestinal-selective effects of a compound of the disclosure on the expression of selected farnesoid X receptor (FXR) target genes in C57BL/6 mice fed a standard diet.

FIG. 3 shows the effects of treating C57BL/6 mice on a western diet with an FXR agonist.

FIG. 5 shows the effects of a compound of the disclosure on the expression of FXR target gene expression in C57BL/6 mice fed a western diet.

FIG. 6 shows the intestinal-selective effects of a compound of the disclosure on the expression of FXR target gene expression in C57BL/6 mice fed a western diet.

DETAILED DESCRIPTION OF THE DISCLOSURE

Figure 1A:
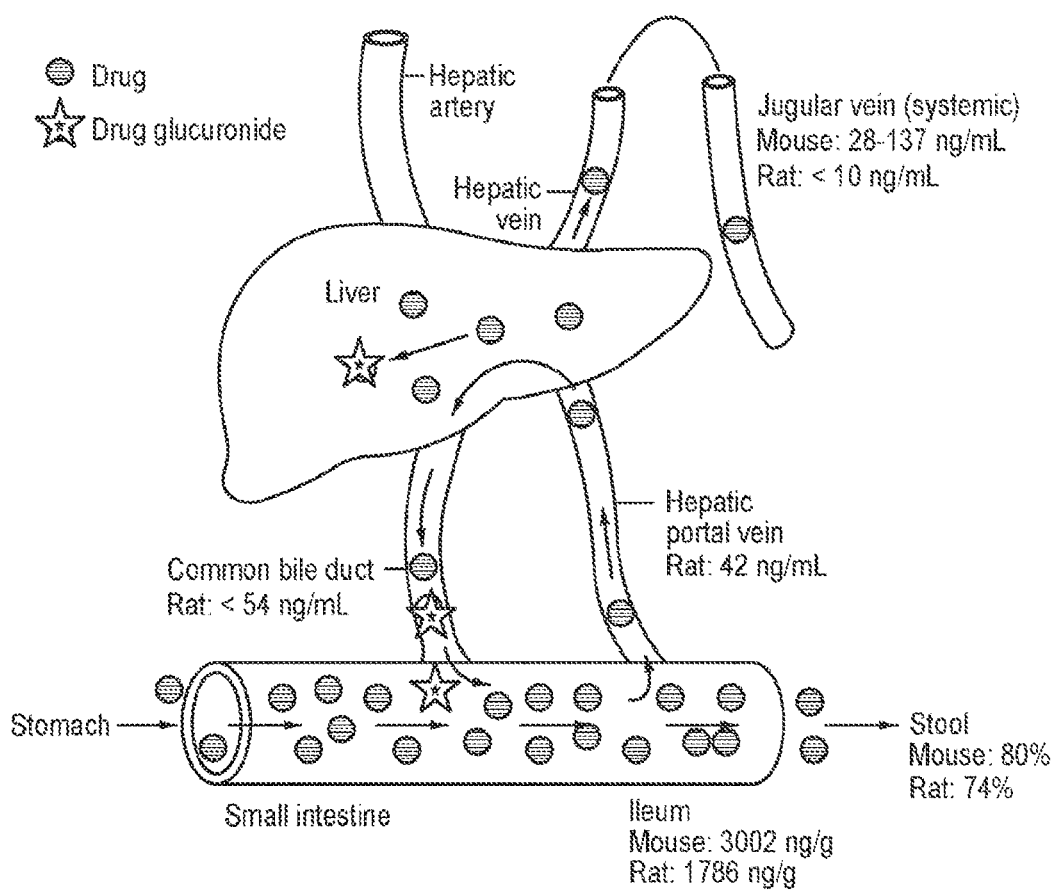
FIG. 1A shows PK measurements (illustrated with $C_{max}$ for bile duct, portal vein and jugular vein, C6h for ileum obtained from respective studies; stool recovery of parent after 48 h was expressed in percentage) in Sprague-Dawley rats and C57BL/6 mice when dosed with Compound I-2.

The present disclosure relates to compounds and compositions that are capable of modulating the activity of FXR. The disclosure features methods of treating, preventing or ameliorating a disease or disorder in which FXR plays a role by administering to a patient in need thereof a therapeutically effective amount of a compound of Formula (I), or a pharmaceutically acceptable salt, hydrate, solvate, prodrug, stereoisomer, or tautomer thereof. The methods of the present disclosure can be used in the treatment of a variety of FXR dependent diseases and disorders by increasing the activity of nuclear receptor FXR. Activation or modulation of FXR provides a novel approach to the treatment, prevention, or amelioration of diseases including, but not limited to, liver diseases, intestinal diseases, kidney diseases, autoimmune disorders, and cancer.

In a first aspect of the disclosure, the compounds of Formula (I) are described:

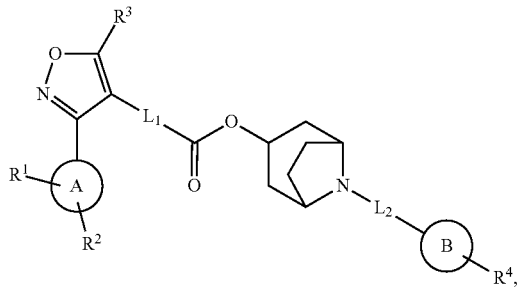

and pharmaceutically acceptable salts, hydrates, solvates, prodrugs, stereoisomers, and tautomers thereof, wherein L1, L2, A, B, R1, R2, R3, and R4 are as described herein.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definitions

The articles "a" and "an" are used in this disclosure to refer to one or more than one (e.g., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g, heteroatoms). For instance, an alkyl group that is optionally substituted can be a fully saturated alkyl chain (e.g, a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—(C$_1$-C$_6$) alkyl, (C$_1$-C$_6$) alkyl, (C$_1$-C$_6$) alkenyl, (C$_1$-C$_6$) alkynyl, (C$_1$-C$_6$) hydroxyalkyl, (C$_1$-C$_6$) alkoxy, (C$_1$-C$_6$) haloalkyl, (C$_1$-C$_6$) haloalkoxy, (C$_3$-C$_7$) cycloalkyl, (C$_6$-C$_{10}$) aryl, heterocycloalkyl, heteroaryl, —O—(C$_2$-C$_6$) alkenyl, —O—(C$_2$-C$_6$) alkynyl, (C$_2$-C$_6$) alkenyl, (C$_2$-C$_6$) alkynyl, —OP(O)(OH)$_2$, —OC(O)(C$_1$-C$_6$) alkyl, —C(O)(C$_1$-C$_6$) alkyl, —OC(O)O(C$_1$-C$_6$) alkyl, —NH$_2$, —NH((C$_1$-C$_6$) alkyl), —N((C$_1$-C$_6$) alkyl)$_2$, —NHC(O)(C$_1$-C$_6$) alkyl, —C(O)NH(C$_1$-C$_6$) alkyl, —S(O)$_2$(C$_1$-C$_6$) alkyl, —S(O)$_2$NH(C$_1$-C$_6$) alkyl, and S(O)$_2$N((C$_1$-C$_6$) alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g, naphthyl). The aryl group may be optionally substituted by one or more substituents, e.g., 1 to 5 substituents, at any point of attachment. Exemplary substituents include, but are not limited to, —H, -halogen, —O—(C$_1$-C$_6$) alkyl, (C$_1$-C$_6$) alkyl, —O—(C$_2$-C$_6$) alkenyl, —O—(C$_2$-C$_6$) alkynyl, (C$_2$-C$_6$) alkenyl, (C$_2$-C$_6$) alkynyl, —OH, —OP(O)(OH)$_2$, —OC(O)(C$_1$-C$_6$) alkyl, —C(O)(C$_1$-C$_6$) alkyl, —OC(O)O(C$_1$-C$_6$) alkyl, —NH$_2$, NH((C$_1$-C$_6$) alkyl), N((C$_1$-C$_6$) alkyl)$_2$, —S(O)$_2$—(C$_1$-C$_6$) alkyl, —S(O)$_2$NH(C$_1$-C$_6$) alkyl, and —S(O)$_2$N((C$_1$-C$_6$) alkyl)$_2$. The substituents can themselves be optionally substituted. Furthermore when containing two fused rings an aryl group herein defined may be fused to an unsaturated or partially saturated ring, or fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from the group consisting of N, O, and S, the remaining ring atoms being C. Heteroaryl as herein defined also means a bicyclic heteroaromatic group wherein the heteroatom is selected from the group consisting of N, O, and S. The aromatic radical is optionally substituted independently with one or more substituents described herein. In some embodiments, a heteroaryl comprises one or two 5- or 6-membered rings. In some embodiments, a heteroaryl group comprises 1-4 heteroatoms selected from the group consisting of N, O and S. In some embodiments, a heteroaryl group comprises one or two 5- or 6-membered rings and 1-4 heteroatoms selected from the group consisting of N, O and S. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d] thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may be fused to an unsaturated or partially saturated ring containing a heteroatom selected from the group consisting of N, O and S; or fused with a fully saturated ring containing a heteroatom selected from the group consisting of N, O and S. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" refers to fluorine, chlorine, bromine, or iodine.

"Alkyl" refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, e.g., —O(alkyl). Examples of alkoxy groups include without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propanyl, n-butynyl, iso-butynyl, pentynyl, or hexynyl. An alkynyl group can be unsubstituted or substituted.

"Cycloalkyl" or "carbocyclyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl and derivatives thereof. A $C_3$-$C_8$ cycloalkyl is a cycloalkyl group containing between 3 and 8 carbon atoms. A cycloalkyl group can be fused (e.g., decalin) or bridged (e.g., norbornane).

"Heterocyclyl" or "heterocycloalkyl" monocyclic or polycyclic rings containing carbon and heteroatoms taken from oxygen, nitrogen, or sulfur and wherein there is not delocalized n electrons (aromaticity) shared among the ring carbon or heteroatoms. In some embodiments, a heterocycloalkyl comprises one or two 5- to 7-membered rings. In some embodiments, a heterocycloalkyl comprises 1-4 heteroatoms selected from the group consisting of N, O and S. In some embodiments, the heterocycloalkyl comprises one or two 5- to 7-membered rings and 1-4 heteroatoms selected from the group consisting of N, O and S. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl.

The term "hydroxyalkyl" means an alkyl group as defined above, where the alkyl group is substituted with one or more —OH groups. Examples of hydroxyalkyl groups include HO—$CH_2$—, HO—$CH_2$—$CH_2$— and $CH_3$—CH(OH)—.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, e.g., C≡N.

The term "carbonyl" refers to a functional group composing a carbon atom double-bonded to an oxygen atom. It can be abbreviated herein as C(O), or as C=O.

The term "oxo" refers to an oxygen atom that is double-bonded to another atom. An "oxo" group can be connected to a carbon atom (e.g., to form a carbonyl, as defined above) or can be connected to a heteroatom such as sulfur (e.g., to form a sulfoxide or a sulfone) or phosphorous (e.g., to form a phosphorous ylide).

"Spirocycloalkyl" or "spirocyclyl" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring.

The term "spiroheterocycloalkyl" or "spiroheterocyclyl" is understood to mean a spirocycle wherein at least one of the rings is a heterocycle (e.g., at least one of the rings is furanyl, morpholinyl, or piperadinyl).

As defined herein, "GW4064" is a known FXR agonist having the following structure:

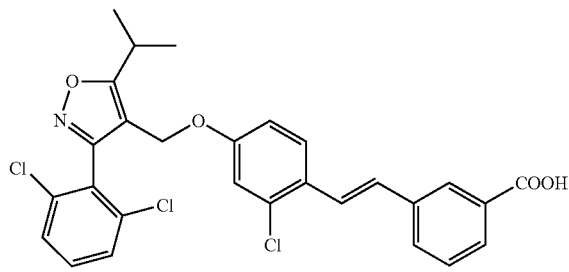

GW4064

The term "solvate" refers to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The term "autoimmune disease" includes, but is not limited to, the following autoimmune diseases: irritable bowel syndrome, Amyotrophic Lateral Sclerosis (ALS), Autoimmune Atherosclerosis, Autoimmune Diabetes Insipidus, Autoimmune Gastritis, Autoimmune Hepatitis, Autoimmune Interstitial Cystitis, Autoimmune Uveitis, Autoimmune Vasculitis, Behcet's Disease, Celiac Disease, Chronic Fatigue Syndrome, Crohn's Disease, Cutaneous Lupus, chronic active hepatitis, Diabetes Mellitus, Multiple Sclerosis, PBC, Primary Biliary Cirrhosis, Primary Glomerulonephritis, Primary Sclerosing Cholangitis, Psoriasis, Psoriatic Arthritis, Scleroderma, Sjogren's Syndrome, Systemic Lupus Erythematosus, Ulcerative Colitis, and Vasculitis.

The term "kidney disease" includes, but is not limited to the following kidney diseases: fibrotic renal disease and diabetic nephropathy.

The term "liver disease" includes, but is not limited to, the following liver diseases: primary biliary cirrhosis (PBC), primary sclerosing cholangitis (PSC), non-alcoholic fatty liver disease (NAFLD), non-alcoholic steatohepatitis (NASH), alcoholic liver disease, intra- and extra-cholestasis, portal vein hypertension (PAH), obesity and Type 2 Diabetes.

The term "intestinal disease" includes, but is not limited to the following intestinal diseases: inflammatory bowel disease, Crohn's disease, ulcerative colitis, proctitis, pouchitis, Celiac's disease and bile acid diarrhea.

The term "cancer" includes, but is not limited to, the following cancers: hepatocellular carcinoma, hepatocellular adenoma, cholangiocarcinoma, colorectal cancer, colorectal adenoma, ileal adenoma, renal cancer, oesophageal cancer, gastric cancer, gastric carcinoma, colon carcinoma, gastrointestinal stromal carcinoma, bile duct carcinoma, renal carcinoma, breast cancer, and Barett's esophagus, and combinations thereof.

Compounds of the Disclosure

The present disclosure relates to compounds or pharmaceutically acceptable salts, hydrates, solvates, prodrugs, stereoisomers, or tautomers thereof, capable of activating FXR, which are useful for the treatment of diseases and disorders associated with modulation of a FXR protein or receptor. The disclosure further relates to compounds, or pharmaceutically acceptable salts, hydrates, solvates, prodrugs, stereoisomers, or tautomers thereof, which are useful for activating FXR.

The present invention relates to compounds or pharmaceutically acceptable salts, hydrates, solvates, prodrugs, stereoisomers, or tautomers thereof, capable of activating FXR, which are useful for the treatment of diseases and disorders associated with modulation of a FXR protein. The invention further relates to compounds, or pharmaceutically acceptable salts, hydrates, solvates, prodrugs, stereoisomers, or tautomers thereof, which are useful for activating FXR.

In an embodiment, compounds of the invention have the structure of Formula (I):

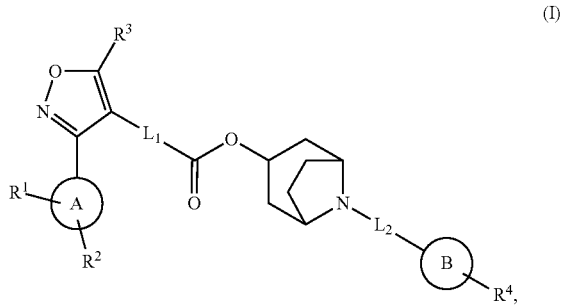

and pharmaceutically acceptable salts, hydrates, solvates, prodrugs, stereoisomers, and tautomers thereof, wherein:

$L_1$ is a bond or —$(CH_2)_n$—;

$L_2$ is a bond or —$S(O)_2$—;

A is $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the cycloalkyl, aryl, heterocycloalkyl, or heteroaryl are optionally substituted with one or more $R^7$;

B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$;

$R^1$ and $R^2$ are each independently H, halogen, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_3-C_7)$ cycloalkyl, —OH, or —CN, wherein the cycloalkyl is optionally substituted with one or more $R^9$;

or $R^1$ and $R^2$ together when attached to the same carbon atom form a $(C_3-C_8)$ spirocycloalkyl ring optionally substituted with one or more $R^8$; or $R^1$ and $R^2$ together when attached to the same atom form a $(C_3-C_8)$ spiroheterocycloalkyl ring optionally substituted with one or more $R^8$; or $R^1$ and $R^2$ on adjacent atoms together with the atoms to which they are attached form a $(C_3-C_8)$ cycloalkyl ring optionally substituted with one or more $R^8$; or $R^1$ and $R^2$ on adjacent atoms together with the atoms to which they are attached form a heterocycloalkyl ring optionally substituted with one or more $R^8$; or $R^1$ and $R^2$ on adjacent atoms together with the atoms to which they are attached form a $(C_6-C_{10})$ aryl ring optionally substituted with one or more $R^8$; or $R^1$ and $R^2$ on adjacent atoms together with the atoms to which they are attached form a heteroaryl ring optionally substituted with one or more $R^8$; or when A is cycloalkyl or heterocycloalkyl, $R^1$ and $R^2$ together with the atoms to which they are attached form a $(C_4-C_8)$ cycloalkyl ring optionally substituted with one or more $R^8$; or when cycloalkyl or heterocycloalkyl, $R^1$ and $R^2$ together with the atoms to which they are attached form a heterocycloalkyl ring optionally substituted with one or more $R^8$;

$R^3$ is $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_1-C_6)$ hydroxyalkyl, or $(C_3-C_7)$ cycloalkyl optionally substituted with one or more substituents each independently selected from the group consisting of halogen, $(C_1-C_6)$ alkyl, $(C_1-C_6)$ alkoxy, $(C_1-C_6)$ haloalkyl, $(C_1-C_6)$ haloalkoxy, and —OH;

$R^4$ is $COOR^{6a}$, $CONR^{6b}R^{6c}$, $CONH(CH_2)_mCOOR^{6a}$, $CONHSO_2R^{6d}$, $CONH(CH_2)_mSO_2R^{6e}$, —CN, or heteroaryl;

each $R^5$ is independently at each occurrence halogen, $(C_1-C_6)$ alkyl, $(C_1-C_6)$ haloalkyl, $(C_1-C_6)$ alkoxy, $(C_1-C_6)$ haloalkoxy, —OH, —CN, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the cycloalkyl, aryl, heterocycloalkyl or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, —OH, and oxo;

or $R^4$ and $R^5$ when on adjacent atoms together with the atoms to which they are attached form a $(C_4-C_8)$ cycloalkyl ring optionally substituted with one or more $R^{10}$; or $R^4$ and $R^5$ when on adjacent atoms together with the atoms to which they are attached form a heterocycloalkyl ring optionally substituted with one or more $R^{10}$;

$R^{6a}$ is H, $(C_1-C_6)$ alkyl, $(C_1-C_6)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy;

$R^{6b}$ and $R^{6c}$ are each independently H, $(C_1-C_6)$ alkyl, $(C_1-C_6)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy;

$R^{6d}$ is $(C_1-C_6)$ alkyl, $(C_1-C_6)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl are optionally substituted with one or more substituents each independently selected from the group consisting of halogen, —OH, $(C_1-C_6)$ alkyl, $(C_1-C_6)$ haloalkyl, $(C_1-C_6)$ alkoxy, $(C_1-C_6)$ haloalkoxy, and $(C_3-C_8)$ cycloalkyl;

$R^{6e}$ is —OH, $(C_1-C_6)$ alkyl, $(C_1-C_6)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl are optionally substituted with one or more substituents each independently selected from the group consisting of halogen, —OH, $(C_1-C_6)$ alkyl, $(C_1-C_6)$ haloalkyl, $(C_1-C_6)$ alkoxy, $(C_1-C_6)$ haloalkoxy, and $(C_3-C_8)$ cycloalkyl;

each $R^7$ is independently at each occurrence $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, halogen, or —CN;

each $R^8$ is independently at each occurrence $(C_1-C_6)$ alkyl, $(C_1-C_6)$ alkoxy, $(C_1-C_6)$ haloalkyl, $(C_1-C_6)$ haloalkoxy, halogen, or —OH;

each $R^9$ is independently at each occurrence $(C_1-C_6)$ alkyl, $(C_1-C_6)$ alkoxy, $(C_1-C_6)$ haloalkyl, $(C_1-C_6)$ haloalkoxy, halogen, or —OH;

each $R^{10}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, oxo, or —OH;

n is 1 or 2; and m is 1, 2, 3, or 4.

In one embodiment, the compounds of Formula (I) have the structure of Formula (Ia):

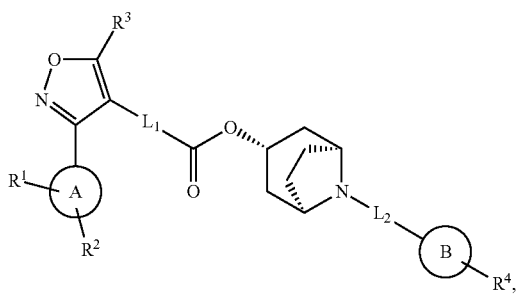

(Ia)

and pharmaceutically acceptable salts, hydrates, solvates, prodrugs, stereoisomers, and tautomers thereof.

In another embodiment, the compounds of Formula (I) have the structure of Formula (Ib):

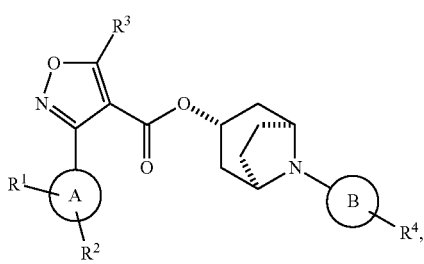

(Ib)

and pharmaceutically acceptable salts, hydrates, solvates, prodrugs, stereoisomers, and tautomers thereof.

In another embodiment, the compounds of Formula (I) have the structure of Formula (Ic):

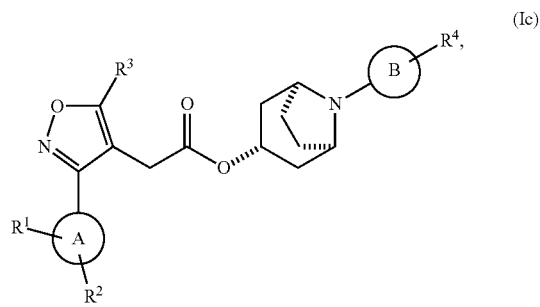

(Ic)

and pharmaceutically acceptable salts, hydrates, solvates, prodrugs, stereoisomers, and tautomers thereof.

In another embodiment, the compounds of Formula (I) have the structure of Formula (Id):

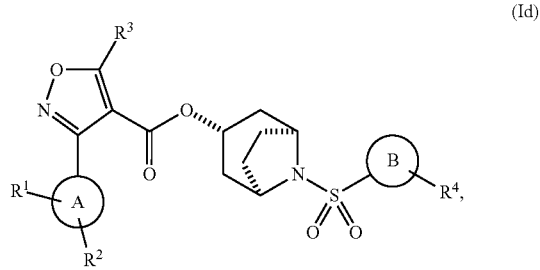

(Id)

and pharmaceutically acceptable salts, hydrates, solvates, prodrugs, stereoisomers, and thereof.

In another embodiment, the compounds of Formula (I) have the structure of Formula (Ie):

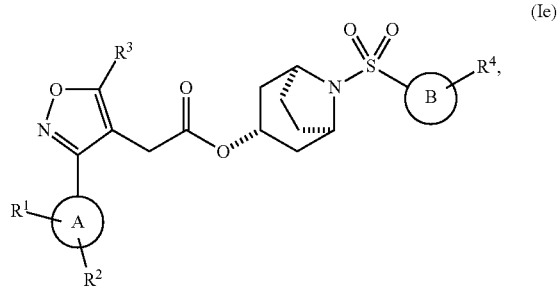

(Ie)

and pharmaceutically acceptable salts, hydrates, solvates, prodrugs, stereoisomers, and tautomers thereof.

In another embodiment, the compounds of Formula (I) have the structure of Formula (If):

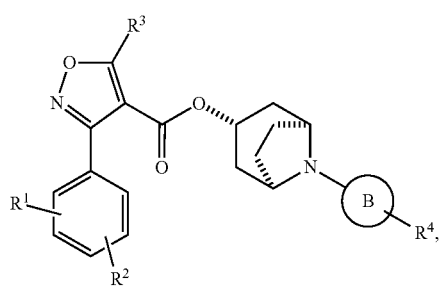

(If)

and pharmaceutically acceptable salts, hydrates, solvates, prodrugs, stereoisomers, and tautomers thereof.

In another embodiment, the compounds of Formula (I) have the structure of Formula (Ig):

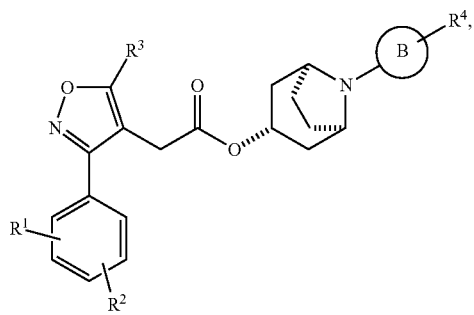

(Ig)

and pharmaceutically acceptable salts, hydrates, solvates, prodrugs, stereoisomers, and tautomers thereof.

In another embodiment, the compounds of Formula (I) have the structure of Formula (Ih):

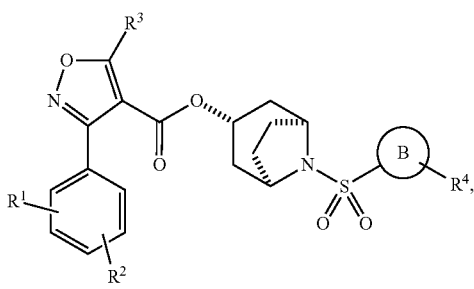

(Ih)

and pharmaceutically acceptable salts, hydrates, solvates, prodrugs, stereoisomers, and tautomers thereof.

In another embodiment, the compounds of Formula (I) have the structure of Formula (Ii):

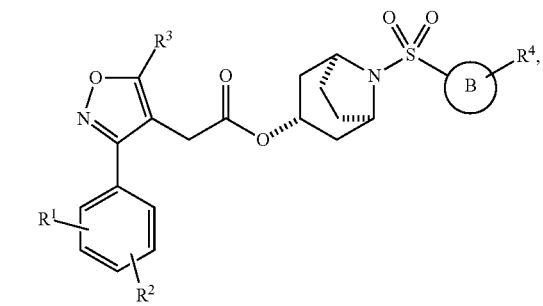

(Ii)

and pharmaceutically acceptable salts, hydrates, solvates, prodrugs, stereoisomers, and tautomers thereof.

In another embodiment, the compounds of Formula (I) have the structure of Formula (Ij):

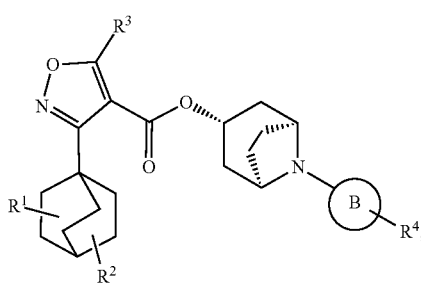

(Ij)

and pharmaceutically acceptable salts, hydrates, solvates, prodrugs, stereoisomers, and tautomers thereof.

In another embodiment, the compounds of Formula (I) have the structure of Formula (Ik):

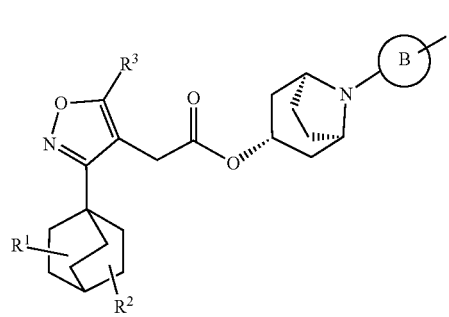

(Ik)

and pharmaceutically acceptable salts, hydrates, solvates, prodrugs, stereoisomers, and tautomers thereof.

In another embodiment, the compounds of Formula (I) have the structure of Formula (II):

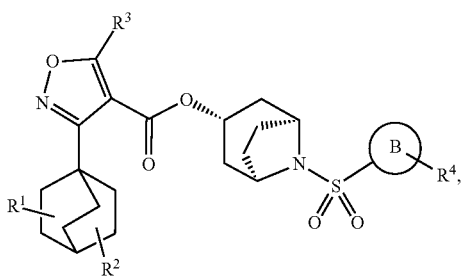

(II)

and pharmaceutically acceptable salts, hydrates, solvates, prodrugs, stereoisomers, and tautomers thereof.

In another embodiment, the compounds of Formula (I) have the structure of Formula m):

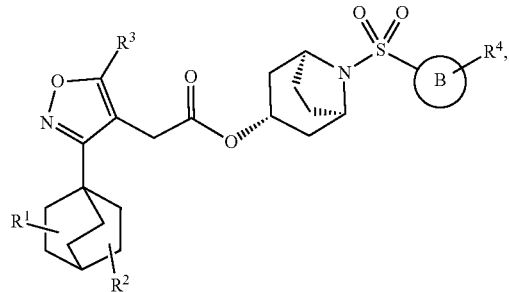

(Im)

and pharmaceutically acceptable salts, hydrates, solvates, prodrugs, stereoisomers, and tautomers thereof.

In another embodiment, the compounds of Formula (I) have the structure of Formula (In):

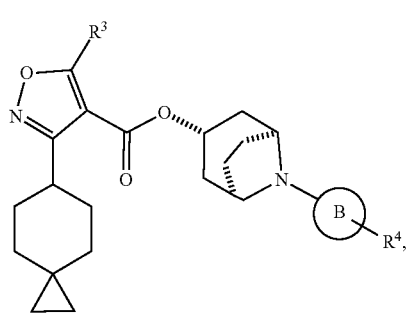

(In)

and pharmaceutically acceptable salts, hydrates, solvates, prodrugs, stereoisomers, and tautomers thereof.

In another embodiment, the compounds of Formula (I) have the structure of Formula (Io):

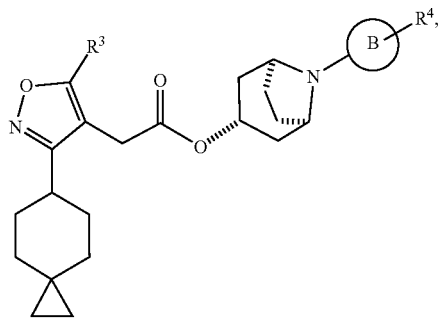

(Io)

and pharmaceutically acceptable salts, hydrates, solvates, prodrugs, stereoisomers, and tautomers thereof.

In another embodiment, the compounds of Formula (I) have the structure of Formula (Ip):

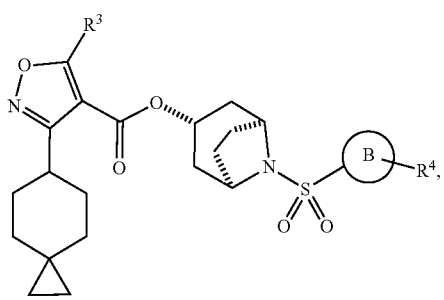

(Ip)

and pharmaceutically acceptable salts, hydrates, solvates, prodrugs, stereoisomers, and tautomers thereof.

In another embodiment, the compounds of Formula (I) have the structure of Formula (Iq):

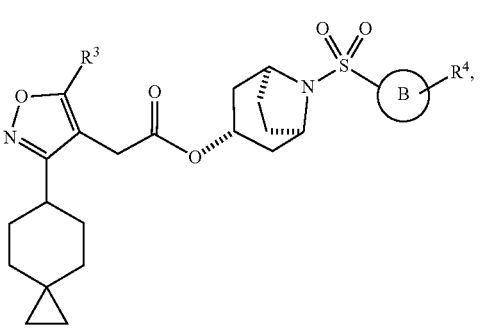

(Iq)

and pharmaceutically acceptable salts, hydrates, solvates, prodrugs, stereoisomers, and tautomers thereof.

In some embodiments of the Formulae above, $L_1$ is a bond. In another embodiment $L_1$ is —$(CH_2)_n$—.

In some embodiments of the Formulae above, $L_2$ is a bond. In another embodiment $L_2$ is —$S(O)_2$—;

In some embodiments of the Formulae above, A is ($C_3$-$C_8$) cycloalkyl, or heterocycloalkyl wherein the heterocycloalkyl comprises one or two 5- to 7-membered rings and 1-4 heteroatoms selected from the group consisting of N, O and S, and wherein the cycloalkyl or heterocycloalkyl are optionally substituted with one or more $R^7$. In another embodiment, A is $(C_6-C_{10})$ aryl or heteroaryl comprising one or two 5- or 6-member rings and 1-4 heteroatoms selected from the group consisting of N, O and S, wherein the aryl or heteroaryl is optionally substituted with one or more $R^7$. In yet another embodiment, A is $(C_3-C_8)$ cycloalkyl or $(C_6-C_{10})$ aryl, wherein the cycloalkyl or aryl are optionally substituted with one or more $R^7$. In another embodiment, A is heterocycloalkyl comprising one or two 5- to 7-membered rings and 1-4 heteroatoms selected from the group consisting of N, O and S, or heteroaryl comprising one or two 5- or 6-member rings and 1-4 heteroatoms selected from the group consisting of N, O and S, wherein the heterocycloalkyl or heteroaryl are optionally substituted with one or more $R^7$. In one embodiment, A is $(C_6-C_{10})$ aryl. In another embodiment, A is $(C_6-C_{10})$ aryl substituted with one or more $R^7$. In another embodiment, A is $(C_3-C_8)$ cycloalkyl. In another embodiment, A is $(C_3-C_8)$ cycloalkyl substituted with one or more $R^7$. In yet another embodiment, A is heterocycloalkyl comprising one or two 5- to 7-membered rings and 1-4 heteroatoms selected from the group consisting of N, O and S. In yet another embodiment, A is heterocycloalkyl comprising one or two 5- to 7-membered rings and 1-4 heteroatoms selected from the group consisting of N, O and S, substituted with one or more $R^7$. In another embodiment, A is heteroaryl comprising one or two 5- or 6-member rings and 1-4 heteroatoms selected from the group consisting of N, O and S. In another embodiment, A is heteroaryl comprising one or two 5- or 6-member rings and 1-4 heteroatoms selected from the group consisting of N, O and S substituted with one or more $R^7$.

In some embodiments of the Formulae above, A is $(C_6-C_{10})$ aryl or $(C_3-C_8)$ cycloalkyl. In another embodiment, A is phenyl. In yet another embodiment, A is bicyclo[2.2.2.]octanyl, or spiro[2.5]octanyl. In some embodiments, A is $(C_6-C_{10})$ aryl.

In some embodiments of the Formulae above, B is unsubstituted heteroaryl comprising one or two 5- or 6-member rings and 1-4 heteroatoms selected from the group consisting of N, O and S.

In some embodiments of the Formulae above, B is heteroaryl comprising one or two 5- or 6-member rings and 1-4 heteroatoms selected from the group consisting of N, O and S, substituted with one or more halogen, $(C_1-C_6)$ alkyl, $(C_1-C_6)$ alkoxy, or $(C_1-C_6)$ haloalkoxy.

In some embodiments of the Formulae above, B is unsubstituted $(C_6-C_{10})$ aryl. In some embodiments, A is $(C_3-C_8)$ cycloalkyl.

In some embodiments of the Formulae above, B is $(C_6-C_{10})$ aryl substituted with one or more halogen, $(C_1-C_6)$ alkyl, $(C_1-C_6)$ alkoxy, or $(C_1-C_6)$ haloalkyl.

In some embodiments of the Formulae above, B is pyrimidinyl, furanyl, benzo[d]thiazolyl, 1-methyl-1H-benzo[d]imidazolyl, 1-methyl-1H-indolyl, benzo[d]isoxazolyl, 2,2-difluoro-1-methylindolin-3-onyl, or 7-fluoro-1-methyl-1H-benzo[d]imidazolyl, wherein each B is optionally substituted with one or more halogen, $(C_1-C_6)$ alkyl, $(C_1-C_6)$ alkoxy, or $(C_1-C_6)$ haloalkyl.

In some embodiments of the Formulae above, B is $(C_6-C_{10})$ aryl optionally substituted with one or more $R^5$. In another embodiment, B is heteroaryl comprising one or two 5- or 6-member rings and 1-4 heteroatoms selected from the group consisting of N, O and S, optionally substituted with one or more $R^5$. In another embodiment, B is $(C_6-C_{10})$ aryl optionally substituted with one to four $R^5$. In another embodiment, B is heteroaryl comprising one or two 5- or 6-member rings and 1-4 heteroatoms selected from the group consisting of N, O and S, optionally substituted with one to four $R^5$. In another embodiment, B is $(C_6-C_{10})$ aryl. In another embodiment, B is heteroaryl comprising one or two 5- or 6-member rings and 1-4 heteroatoms selected from the group consisting of N, O and S. In another embodiment, B is $(C_6-C_{10})$ aryl substituted with one or more $R^5$. In another embodiment, B is heteroaryl comprising one or two 5- or 6-member rings and 1-4 heteroatoms selected from the group consisting of N, O and S, substituted with one or more $R^5$. In another embodiment, B is $(C_6-C_{10})$ aryl substituted with one to four $R^5$. In another embodiment, B is heteroaryl comprising one or two 5- or 6-member rings and 1-4 heteroatoms selected from the group consisting of N, O and S, substituted with one to four $R^5$. In another embodiment, B is $(C_6-C_{10})$ aryl or heteroaryl, wherein the heteroaryl comprises one or two 5- or 6-member rings and 1-4 heteroatoms selected from the group consisting of N, O and S. In another embodiment, B is $(C_6-C_{10})$ aryl or heteroaryl herein the heteroaryl comprises one or two 5- or 6-member rings and 1-4 heteroatoms selected from the group consisting of N, O and S, and wherein the aryl or heteroaryl are substituted with one or more $R^5$. In another embodiment, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one to four $R^5$. In another embodiment, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl are substituted with one to four $R^5$.

In some embodiments of the Formulae above, $R^1$ is halogen, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_3-C_7)$ cycloalkyl, —OH, or —CN, wherein the cycloalkyl is optionally substituted with one or more $R^9$. In another embodiment, $R^1$ is halogen, $(C_1-C_4)$ alkyl, $(C_2-C_4)$ alkenyl, $(C_2-C_4)$ alkynyl, $(C_1-C_4)$ alkoxy, $(C_1-C_4)$ haloalkyl, $(C_1-C_4)$ haloalkoxy, $(C_3-C_7)$ cycloalkyl, —OH, or —CN, wherein the cycloalkyl is optionally substituted with one or more $R^9$. In yet another embodiment, $R^1$ is halogen, $(C_1-C_3)$ alkyl, $(C_2-C_3)$ alkenyl, $(C_2-C_3)$ alkynyl, $(C_1-C_3)$ alkoxy, $(C_1-C_3)$ haloalkyl, $(C_1-C_3)$ haloalkoxy, $(C_3-C_7)$ cycloalkyl, —OH, or —CN, wherein the cycloalkyl is optionally substituted with one or more $R^9$. In another embodiment, $R^1$ is halogen, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, or $(C_3-C_7)$ cycloalkyl, wherein the cycloalkyl is optionally substituted with one or more $R^9$. In yet another embodiment, $R^1$ is halogen, $(C_1-C_4)$ alkyl, $(C_2-C_4)$ alkenyl, $(C_2-C_4)$ alkynyl, $(C_1-C_4)$ alkoxy, $(C_1-C_4)$ haloalkyl, $(C_1-C_4)$ haloalkoxy, or $(C_3-C_7)$ cycloalkyl, wherein the cycloalkyl is optionally substituted with one or more $R^9$. In another embodiment, $R^1$ is halogen, $(C_1-C_3)$ alkyl, $(C_2-C_3)$ alkenyl, $(C_2-C_3)$ alkynyl, $(C_1-C_3)$ alkoxy, $(C_1-C_3)$ haloalkyl, $(C_1-C_3)$ haloalkoxy, or $(C_3-C_7)$ cycloalkyl, wherein the cycloalkyl is optionally substituted with one or more $R^9$.

In another embodiment, $R^1$ is halogen, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, —OH or —CN. In yet another embodiment, $R^1$ is halogen, $(C_1-C_4)$ alkyl, $(C_2-C_4)$ alkenyl, $(C_2-C_4)$ alkynyl, $(C_1-C_4)$ alkoxy, $(C_1-C_4)$ haloalkyl, $(C_1-C_4)$ haloalkoxy, —OH or —CN. In another embodiment, $R^1$ is halogen, $(C_1-C_3)$ alkyl, $(C_2-C_3)$ alkenyl, $(C_2-C_3)$ alkynyl, $(C_1-C_3)$ alkoxy, $(C_1-C_3)$ haloalkyl, $(C_1-C_4)$ haloalkoxy, —OH or —CN. In another embodiment, $R^1$ is H, halogen, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, —OH or —CN. In yet another embodiment, $R^1$ is H, halogen, $(C_1-C_4)$ alkyl, $(C_2-C_4)$ alkenyl, $(C_2-C_4)$ alkynyl, $(C_1-C_4)$ alkoxy, $(C_1-C_4)$ haloalkyl, $(C_1-C_4)$ haloalkoxy, —OH or —CN. In another embodiment, $R^1$ is H, halogen, $(C_1-C_3)$ alkyl, $(C_2-C_3)$ alkenyl, $(C_2-C_3)$ alkynyl, $(C_1-C_3)$ alkoxy, $(C_1-C_3)$ haloalkyl, $(C_1-C_3)$ haloalkoxy, —OH or —CN. In another embodiment, $R^1$ is H, halogen, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, or $(C_3-C_7)$ cycloalkyl, wherein the cycloalkyl is optionally substituted with one or more $R^9$. In yet another embodiment, $R^1$ is H, halogen, $(C_1-C_4)$ alkyl, $(C_2-C_4)$ alkenyl, $(C_2-C_4)$ alkynyl, $(C_1-C_4)$ alkoxy, $(C_1-C_4)$ haloalkyl, $(C_1-C_4)$ haloalkoxy, or $(C_3-C_7)$ cycloalkyl, wherein the cycloalkyl is optionally substituted with one or more $R^9$. In another embodiment, $R^1$ is H, halogen, $(C_1-C_3)$ alkyl, $(C_2-C_3)$ alkenyl, $(C_2-C_3)$ alkynyl, $(C_1-C_3)$ alkoxy, $(C_1-C_3)$ haloalkyl, $(C_1-C_3)$ haloalkoxy, or $(C_3-C_7)$ cycloalkyl, wherein the cycloalkyl is optionally substituted with one or more $R^9$.

In another embodiment, $R^1$ is H, halogen, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, or $(C_1-C_6)$ haloalkoxy. In yet another embodiment, $R^1$ is H, halogen, $(C_1-C_4)$ alkyl, $(C_2-C_4)$ alkenyl, $(C_2-C_4)$ alkynyl, $(C_1-C_4)$ alkoxy, $(C_1-C_4)$ haloalkyl, or $(C_1-C_4)$ haloalkoxy. In another embodiment $R^1$ is H, halogen, $(C_1-C_3)$ alkyl, $(C_2-C_3)$ alkenyl, $(C_2-C_3)$ alkynyl, $(C_1-C_3)$ alkoxy, or $(C_1-C_3)$ haloalkyl. In another embodiment, $R^1$ is H, halogen, $(C_1-C_3)$ alkyl, $(C_2-C_3)$ alkenyl, $(C_2-C_3)$ alkynyl, $(C_1-C_3)$ alkoxy, or $(C_1-C_3)$ haloalkyl. In another embodiment, $R^1$ is H, halogen, $(C_1-C_6)$ alkyl, $(C_1-C_6)$ alkoxy, $(C_1-C_6)$ haloalkyl, or $(C_1-C_6)$ haloalkoxy. In another embodiment, $R^1$ is H, halogen, $(C_1-C_6)$ alkyl, $(C_1-C_6)$ alkoxy, or $(C_1-C_6)$ haloalkoxy. In another embodiment, $R^1$ is halogen, $(C_1-C_6)$ alkyl, $(C_1-C_6)$ alkoxy, $(C_1-C_6)$ haloalkyl, or $(C_1-C_6)$ haloalkoxy. In another embodiment, $R^1$ is halogen, $(C_1-C_6)$ alkyl, $(C_1-C_6)$ alkoxy, or $(C_1-C_6)$ haloalkoxy.

In some embodiments of the Formulae above, $R^2$ is halogen, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_3-C_7)$ cycloalkyl, —OH, or —CN, wherein the cycloalkyl is optionally substituted with one or more $R^9$. In another embodiment $R^2$ is halogen, $(C_1-C_4)$ alkyl, $(C_2-C_4)$ alkenyl, $(C_2-C_4)$ alkynyl, $(C_1-C_4)$ alkoxy, $(C_1-C_4)$ haloalkyl, $(C_1-C_4)$ haloalkoxy, $(C_3-C_7)$ cycloalkyl, —OH, or —CN, wherein the cycloalkyl is optionally substituted with one or more $R^9$. In yet another embodiment $R^2$ is halogen, $(C_1-C_3)$ alkyl, $(C_2-C_3)$ alkenyl, $(C_2-C_3)$ alkynyl, $(C_1-C_3)$ alkoxy, $(C_1-C_3)$ haloalkyl, $(C_1-C_3)$ haloalkoxy, $(C_3-C_7)$ cycloalkyl, —OH, or —CN, wherein the cycloalkyl is optionally substituted with one or more $R^9$. In another embodiment $R^2$ is halogen, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, or $(C_3-C_7)$ cycloalkyl, wherein the cycloalkyl is optionally substituted with one or more $R^9$. In yet another embodiment $R^2$ is halogen, $(C_1-C_4)$ alkyl, $(C_2-C_4)$ alkenyl, $(C_2-C_4)$ alkynyl, $(C_1-C_4)$ alkoxy, $(C_1-C_4)$ haloalkyl, $(C_1-C_4)$ haloalkoxy, or $(C_3-C_7)$ cycloalkyl, wherein the cycloalkyl is optionally substituted with one or more $R^9$. In another embodiment $R^2$ is halogen, $(C_1-C_3)$ alkyl, $(C_2-C_3)$ alkenyl, $(C_2-C_3)$ alkynyl, $(C_1-C_3)$ alkoxy, $(C_1-C_3)$ haloalkyl, $(C_1-C_3)$ haloalkoxy, or $(C_3-C_7)$ cycloalkyl, wherein the cycloalkyl is optionally substituted with one or more $R^9$.

In another embodiment, $R^2$ is halogen, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, —OH or —CN. In yet another embodiment $R^2$ is halogen, $(C_1-C_4)$ alkyl, $(C_2-C_4)$ alkenyl, $(C_2-C_4)$ alkynyl, $(C_1-C_4)$ alkoxy, $(C_1-C_4)$ haloalkyl, $(C_1-C_4)$ haloalkoxy, —OH or —CN. In another embodiment, $R^2$ is halogen, $(C_1-C_3)$ alkyl, $(C_2-C_3)$ alkenyl, $(C_2-C_3)$ alkynyl, $(C_1-C_3)$ alkoxy, $(C_1-C_3)$ haloalkyl, $(C_1-C_3)$ haloalkoxy, —OH or —CN. In another embodiment, $R^2$ is H, halogen, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, —OH or —CN. In yet another embodiment, $R^2$ is H, halogen, $(C_1-C_4)$ alkyl, $(C_2-C_4)$ alkenyl, $(C_2-C_4)$ alkynyl, $(C_1-C_4)$ alkoxy, $(C_1-C_4)$ haloalkyl, $(C_1-C_4)$ haloalkoxy, —OH or —CN. In another embodiment, $R^2$ is H, halogen, $(C_1-C_3)$ alkyl, $(C_2-C_3)$ alkenyl, $(C_2-C_3)$ alkynyl, $(C_1-C_3)$ alkoxy, $(C_1-C_3)$ haloalkyl, $(C_1-C_3)$ haloalkoxy, —OH or —CN. In another embodiment, $R^2$ is H, halogen, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, or $(C_3-C_7)$ cycloalkyl, wherein the cycloalkyl is optionally substituted with one or more $R^9$.

In yet another embodiment, $R^2$ is H, halogen, $(C_1-C_4)$ alkyl, $(C_2-C_4)$ alkenyl, $(C_2-C_4)$ alkynyl, $(C_1-C_4)$ alkoxy, $(C_1-C_4)$ haloalkyl, $(C_1-C_4)$ haloalkoxy, or $(C_3-C_7)$ cycloalkyl, wherein the cycloalkyl is optionally substituted with one or more $R^9$. In another embodiment, $R^2$ is H, halogen, $(C_1-C_3)$ alkyl, $(C_2-C_3)$ alkenyl, $(C_2-C_3)$ alkynyl, $(C_1-C_3)$ alkoxy, $(C_1-C_3)$ haloalkyl, $(C_1-C_6)$ haloalkoxy, or $(C_3-C_7)$ cycloalkyl, wherein the cycloalkyl is optionally substituted with one or more $R^9$. In another embodiment, $R^2$ is H, halogen, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, or $(C_1-C_6)$ haloalkoxy. In yet another embodiment, $R^2$ is H, halogen, $(C_1-C_4)$ alkyl, $(C_2-C_4)$ alkenyl, $(C_2-C_4)$ alkynyl, $(C_1-C_4)$ alkoxy, $(C_1-C_4)$ haloalkyl, or $(C_1-C_4)$ haloalkoxy. In another embodiment, $R^2$ is H, halogen, $(C_1-C_3)$ alkyl, $(C_2-C_3)$ alkenyl, $(C_2-C_3)$ alkynyl, $(C_1-C_3)$ alkoxy, or $(C_1-C_3)$ haloalkyl. In another embodiment, $R^2$ is H, halogen, $(C_1-C_6)$ alkyl, $(C_1-C_6)$ alkoxy, $(C_1-C_6)$ haloalkyl, or $(C_1-C_6)$ haloalkoxy. In another embodiment, $R^2$ is H, halogen, $(C_1-C_6)$ alkyl, $(C_1-C_6)$ alkoxy, or $(C_1-C_6)$ haloalkoxy. In another embodiment, $R^2$ is halogen, $(C_1-C_6)$ alkyl, $(C_1-C_6)$ alkoxy, $(C_1-C_6)$ haloalkyl, or $(C_1-C_6)$ haloalkoxy. In another embodiment, $R^2$ is halogen, $(C_1-C_6)$ alkyl, $(C_1-C_6)$ alkoxy, or $(C_1-C_6)$ haloalkoxy.

In some embodiments of the Formulae above, $R^1$ and $R^2$ are each independently H, halogen, $(C_1-C_6)$ alkoxy, $(C_1-C_6)$ haloalkoxy, $(C_1-C_6)$ alkyl, or $(C_1-C_6)$ haloalkyl.

In some embodiments of the Formulae above, $R^1$ and $R^2$ together when attached to the same carbon atom form a $(C_3-C_8)$ spirocycloalkyl ring optionally substituted with one or more $R^8$. In another embodiment, $R^1$ and $R^2$ together when attached to the same carbon atom form a $(C_3-C_8)$ spirocycloalkyl ring optionally substituted with one to three $R^8$.

In some embodiments of the Formulae above, $R^1$ and $R^2$ together when attached to the same atom form a $(C_3-C_8)$ spiroheterocycloalkyl ring optionally substituted with one or more $R^8$. In another embodiment, $R^1$ and $R^2$ together when attached to the same atom form a $(C_3-C_8)$ spiroheterocycloalkyl ring optionally substituted with one to three $R^8$.

In some embodiments of the Formulae above, $R^1$ and $R^2$ on adjacent atoms together with the atoms to which they are attached form a $(C_3-C_8)$ cycloalkyl ring optionally substituted with one or more $R^8$. In another embodiment, $R^1$ and $R^2$ on adjacent atoms together with the atoms to which they are attached form a $(C_3-C_8)$ cycloalkyl ring optionally substituted with one to three $R^8$.

In some embodiments of the Formulae above, $R^1$ and $R^2$ on adjacent atoms together with the atoms to which they are attached form a heterocycloalkyl ring optionally substituted with one or more $R^8$. In another embodiment, $R^1$ and $R^2$ on adjacent atoms together with the atoms to which they are attached form a heterocycloalkyl ring optionally substituted with one to three $R^8$.

In some embodiments of the Formulae above, $R^1$ and $R^2$ on adjacent atoms together with the atoms to which they are attached form a $(C_6-C_{10})$ aryl ring optionally substituted with one or more $R^8$. In another embodiment, $R^1$ and $R^2$ on adjacent atoms together with the atoms to which they are attached form a $(C_6-C_{10})$ aryl ring optionally substituted with one to three $R^8$.

In some embodiments of the Formulae above, $R^1$ and $R^2$ on adjacent atoms together with the atoms to which they are attached form a heteroaryl ring optionally substituted with one or more $R^8$. In another embodiment, $R^1$ and $R^2$ on adjacent atoms together with the atoms to which they are attached form a heteroaryl ring optionally substituted with one to three $R^8$.

In some embodiments of the Formulae above, when A is cycloalkyl or heterocycloalkyl, $R^1$ and $R^2$ together with the atoms to which they are attached form a $(C_4-C_8)$ cycloalkyl ring optionally substituted with one or more $R^8$. In another embodiment, when A is cycloalkyl or heterocycloalkyl, $R^1$ and $R^2$ together with the atoms to which they are attached form a $(C_4-C_8)$ cycloalkyl ring optionally substituted with one to three $R^8$.

In some embodiments of the Formulae above, when A is cycloalkyl or heterocycloalkyl, $R^1$ and $R^2$ together with the atoms to which they are attached form a heterocycloalkyl ring optionally substituted with one or more $R^8$. In another embodiment, when A is cycloalkyl or heterocycloalkyl, $R^1$ and $R^2$ together with the atoms to which they are attached form a heterocycloalkyl ring optionally substituted with one to three $R^8$.

In some embodiments of the Formulae above, $R^3$ is $(C_1-C_4)$ alkyl, $(C_2-C_4)$ alkenyl, $(C_2-C_4)$ alkynyl, $(C_1-C_4)$ alkoxy, $(C_1-C_4)$ haloalkyl, $(C_1-C_4)$ haloalkoxy, $(C_1-C_4)$ hydroxyalkyl, or $(C_3-C_7)$ cycloalkyl optionally substituted with one or more substituents each independently selected from the group consisting of halogen, $(C_1-C_6)$ alkyl, $(C_1-C_6)$ alkoxy, $(C_1-C_6)$ haloalkyl, $(C_1-C_6)$ haloalkoxy, and —OH. In another embodiment, $R^3$ is $(C_1-C_3)$ alkyl, $(C_2-C_3)$ alkenyl, $(C_2-C_3)$ alkynyl, $(C_1-C_3)$ alkoxy, $(C_1-C_3)$ haloalkyl, $(C_1-C_3)$ haloalkoxy, $(C_1-C_3)$ hydroxyalkyl, or $(C_3-C_7)$ cycloalkyl optionally substituted with one or more substituents each independently selected from the group consisting of halogen, $(C_1-C_6)$ alkyl, $(C_1-C_6)$ alkoxy, $(C_1-C_6)$ haloalkyl, $(C_1-C_6)$ haloalkoxy, and —OH. In another embodiment, $R^3$ is $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_1-C_6)$ hydroxyalkyl, or $(C_3-C_7)$ cycloalkyl optionally substituted with one or more substituents each independently selected from the group consisting of halogen, $(C_1-C_6)$ alkyl, $(C_1-C_6)$ alkoxy, $(C_1-C_6)$ haloalkyl, $(C_1-C_6)$ haloalkoxy, and —OH.

In some embodiments of the Formulae above, $R^3$ is $(C_3-C_8)$ cycloalkyl optionally substituted with halogen or $(C_1-C_6)$ alkyl. In another embodiment $R^3$ is unsubstituted $(C_3-C_8)$ cycloalkyl.

In another embodiment, $R^3$ is $(C_1-C_4)$ alkyl, $(C_2-C_4)$ alkenyl, $(C_2-C_4)$ alkynyl, $(C_1-C_4)$ alkoxy, or $(C_3-C_7)$ cycloalkyl optionally substituted with one or more substituents each independently selected from the group consisting of halogen, $(C_1-C_6)$ alkyl, $(C_1-C_6)$ alkoxy, $(C_1-C_6)$ haloalkyl, $(C_1-C_6)$ haloalkoxy, and —OH. In yet another embodiment, $R^3$ is $(C_1-C_3)$ alkyl, $(C_2-C_3)$ alkenyl, $(C_2-C_3)$ alkynyl, $(C_1-C_3)$ alkoxy, or $(C_3-C_7)$ cycloalkyl optionally substituted with one or more substituents each independently selected from the group consisting of halogen, $(C_1-C_6)$ alkyl, $(C_1-C_6)$ alkoxy, $(C_1-C_6)$ haloalkyl, $(C_1-C_6)$ haloalkoxy, and —OH. In another embodiment, $R^3$ is $(C_1-C_6)$ alkyl, $(C_2-C_6)$ alkenyl, $(C_2-C_6)$ alkynyl, $(C_1-C_6)$ alkoxy, or $(C_3-C_7)$ cycloalkyl optionally substituted with one or more substituents each independently selected from the group consisting of halogen, $(C_1-C_6)$ alkyl, $(C_1-C_6)$ alkoxy, $(C_1-C_6)$ haloalkyl, $(C_1-C_6)$ haloalkoxy, and —OH.

In another embodiment, $R^3$ is $(C_3-C_7)$ cycloalkyl optionally substituted with one or more substituents each independently selected from the group consisting of halogen, $(C_1-C_4)$ alkyl, $(C_1-C_4)$ alkoxy, $(C_1-C_4)$ haloalkyl, and $(C_1-C_4)$ haloalkoxy. In another embodiment, $R^3$ is $(C_3-C_7)$ cycloalkyl optionally substituted with one or more substituents each independently selected from the group consisting of halogen, $(C_1-C_3)$ alkyl, $(C_1-C_3)$ alkoxy, $(C_1-C_3)$ haloalkyl, $(C_1-C_3)$ haloalkoxy, and —OH. In another embodiment, $R^3$ is $(C_1-C_6)$ alkyl or $(C_3-C_7)$ cycloalkyl optionally substituted with one or more substituents each independently selected from the group consisting of halogen and $(C_1-C_6)$ alkyl. In another embodiment, $R^3$ is $(C_1-C_6)$ alkyl or $(C_3-C_7)$ cycloalkyl substituted with one or more substituents independently selected from the group consisting of halogen and $(C_1-C_6)$ alkyl. In another embodiment, $R^3$ is $(C_1-C_6)$ alkyl or $(C_3-C_7)$ cycloalkyl.

In some embodiments of the Formulae above, $R^4$ is $COOR^{6a}$, $CONH(CH_2)_mCOOR^{6a}$, $CONH(CH_2)_mSO_2R^{6e}$, $CONR^{6b}R^{6c}$, or —CN.

In some embodiments of the Formulae above, $R^4$ is $COOR^{6a}$, $CONR^{6b}R^{6c}$, $CONH(CH_2)_mCOOR^{6a}$, $CONHSO_2R^{6d}$, $CONH(CH_2)_mSO_2R^{6e}$, or —CN. In another embodiment, $R^4$ is $COOR^{6a}$, $CONR^{6b}R^{6c}$, $CONH(CH_2)_mCOOR^{6a}$, $CONHSO_2R^{6d}$, $CONH(CH_2)_mSO_2R^{6e}$, or heteroaryl. In yet another embodiment, $R^4$ is $COOR^{6a}$, $CONR^{6b}R^{6c}$, $CONH(CH_2)_mCOOR^{6a}$, $CONHSO_2R^{6d}$, or $CONH(CH_2)_mSO_2R^{6e}$. In another embodiment, $R^4$ is $COOR^{6a}$, $CONHSO_2R^{6d}$, $CONH(CH_2)_mSO_2R^{6e}$, —CN, or heteroaryl. In yet another embodiment, $R^4$ is $COOR^{6a}$, $CONR^{6b}R^{6c}$, $CONH(CH_2)_mCOOR^{6a}$, —CN, or heteroaryl. In another embodiment, $R^4$ is $CONR^{6b}R^{6c}$, $CONH(CH_2)_mCOOR^{6a}$, $CONHSO_2R^{6d}$, $CONH(CH_2)_mSO_2R^{6e}$, —CN, or heteroaryl. In yet another embodiment, $R^4$ is $COOR^{6a}$, $CONHSO_2R^{6d}$, or $CONH(CH_2)_mSO_2R^{6e}$. In another embodiment, $R^4$ is $COOR^{6a}$, $CONR^{6b}R^{6c}$, or $CONH(CH_2)_mCOOR^{6a}$. In yet another embodiment, $R^4$ is $CONR^{6b}R^{6c}$, $CONH(CH_2)_mCOOR^{6a}$, $CONHSO_2R^{6d}$, or $CONH(CH_2)_mSO_2R^{6e}$. In another embodiment, $R^4$ is $COOR^{6a}$. In yet another embodiment, $R^4$ is $CONR^{6b}R^{6c}$. In another embodiment, $R^4$ is $CONH(CH_2)_mCOOR^{6a}$. In yet another embodiment, $R^4$ is $CONHSO_2R^{6d}$. In another embodiment, $R^4$ is $CONH(CH_2)_mSO_2R^{6e}$.

In some embodiments of the Formulae above, $R^5$ is independently at each occurrence halogen, $(C_1-C_4)$ alkyl, $(C_1-C_4)$ haloalkyl, $(C_1-C_4)$ alkoxy, $(C_1-C_4)$ haloalkoxy, —OH, —CN. In another embodiment, $R^5$ is independently at each occurrence halogen, $(C_1-C_3)$ alkyl, $(C_1-C_3)$ haloalkyl, $(C_1-C_3)$ alkoxy, $(C_1-C_3)$ haloalkoxy, —OH, —CN, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the cycloalkyl, aryl, heterocycloalkyl or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, —OH, and oxo. In another embodiment, $R^5$ is independently at each occurrence halogen, $(C_1-C_6)$ alkyl, $(C_1-C_6)$ haloalkyl, $(C_1-C_6)$ alkoxy, $(C_1-C_6)$ haloalkoxy, —OH, —CN, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the cycloalkyl, aryl, heterocycloalkyl or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, —OH, and oxo. In another embodiment, $R^5$ is independently at each occurrence halogen, $(C_1-C_6)$ alkyl, $(C_1-C_6)$ haloalkyl, $(C_1-C_6)$ alkoxy, $(C_1-C_6)$ haloalkoxy, —OH or —CN. In another embodiment, $R^5$ is independently at each occurrence halogen, $(C_1-C_4)$ alkyl, $(C_1-C_4)$ haloalkyl, $(C_1-C_4)$ alkoxy, $(C_1-C_4)$ haloalkoxy, —OH, —CN, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the cycloalkyl, aryl, heterocycloalkyl or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, —OH, and oxo. In another embodiment each $R^5$ is independently at each occurrence halogen, $(C_1-C_3)$ alkyl, $(C_1-C_3)$ haloalkyl, $(C_1-C_3)$ alkoxy, $(C_1-C_3)$ haloalkoxy, —OH, or —CN.

In another embodiment, $R^5$ is independently at each occurrence halogen, $(C_1-C_6)$ alkyl, $(C_1-C_6)$ haloalkyl, $(C_1-C_6)$ alkoxy, $(C_1-C_6)$ haloalkoxy, —OH, —CN, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the cycloalkyl, aryl, heterocycloalkyl or heteroaryl are optionally substituted with one or more substituents each independently selected from the group consisting of $(C_1-C_3)$ alkyl, $(C_1-C_3)$ alkoxy, and oxo. In another embodiment, $R^5$ is independently at each occurrence halogen, $(C_1-C_4)$ alkyl, $(C_1-C_4)$ haloalkyl, $(C_1-C_4)$ alkoxy, $(C_1-C_4)$ haloalkoxy, —OH, —CN, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the cycloalkyl, aryl, heterocycloalkyl or heteroaryl are optionally substituted with one or more substituents each independently selected from the group consisting of $(C_1-C_3)$ alkyl, $(C_1-C_3)$ alkoxy, and oxo. In another embodiment, $R^5$ is independently at each occurrence halogen, $(C_1-C_3)$ alkyl, $(C_1-C_3)$ haloalkyl, $(C_1-C_3)$ alkoxy, $(C_1-C_3)$ haloalkoxy, —OH, —CN, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the cycloalkyl, aryl, heterocycloalkyl or heteroaryl are optionally substituted with one or more substituents each independently selected from the group consisting of $(C_1-C_3)$ alkyl, $(C_1-C_3)$ alkoxy, and oxo. In another embodiment, $R^5$ is independently at each occurrence $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the cycloalkyl, aryl, heterocycloalkyl or heteroaryl are optionally substituted with one or more substituents each independently selected from the group consisting of halogen, $(C_1-C_3)$ alkyl, $(C_1-C_3)$ haloalkyl, $(C_1-C_3)$ alkoxy, $(C_1-C_3)$ haloalkoxy, —OH, and oxo. In another embodiment $R^5$ is independently at each occurrence $(C_1-C_6)$ alkyl, $(C_1-C_6)$ haloalkyl, $(C_1-C_6)$ alkoxy, $(C_1-C_6)$ haloalkoxy, —OH, or $(C_3-C_8)$ cycloalkyl optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, —OH, and oxo. In yet another embodiment $R^5$ is independently at each occurrence $(C_1-C_6)$ alkyl, $(C_1-C_6)$ haloalkyl, $(C_1-C_6)$ alkoxy, $(C_1-C_6)$ haloalkoxy, —OH, or $(C_3-C_8)$ cycloalkyl.

In some embodiments of the Formulae above, $R^4$ and $R^5$ on adjacent atoms together with the atoms to which they are attached form a $(C_3-C_8)$ cycloalkyl ring optionally substituted with one or more $R^{10}$. In another embodiment, $R^4$ and $R^5$ on adjacent atoms together with the atoms to which they are attached form a heterocycloalkyl ring optionally substituted with one or more $R^{10}$. In some embodiments of the Formulae above, $R^4$ and $R^5$ on adjacent atoms together with the atoms to which they are attached form a $(C_3-C_8)$ cycloalkyl ring optionally substituted with one to four $R^{10}$. In another embodiment, $R^4$ and $R^5$ on adjacent atoms together with the atoms to which they are attached form a heterocycloalkyl ring optionally substituted with one to four $R^{10}$.

In some embodiments of the Formulae above, $R^4$ and $R^5$ on adjacent atoms together with the atoms to which they are attached form a heterocycloalkyl ring optionally substituted with one or more $R^{10}$. In another embodiment, $R^4$ and $R^5$ on adjacent atoms together with the atoms to which they are attached form a heterocycloalkyl ring optionally substituted with one or more $R^{10}$ and $R^{10}$ is oxo.

In some embodiments of the Formulae above, $R^4$ and $R^5$ when on adjacent atoms together with the atoms to which they are attached form a heterocycloalkyl ring optionally substituted with one or more $R^{10}$.

In some embodiments of the Formulae above, $R^{6a}$ is H, $(C_1-C_6)$ alkyl, $(C_1-C_6)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy. In another embodiment, $R^{6a}$ is $(C_1-C_6)$ alkyl, $(C_1-C_6)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy. In another embodiment, $R^{6a}$ is $(C_1-C_4)$ alkyl, $(C_1-C_4)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl are optionally substituted with one or more substituents each independently selected from the group consisting of halogen, $(C_1-C_4)$ alkyl, $(C_1-C_4)$ haloalkyl, $(C_1-C_4)$ alkoxy, and $(C_1-C_4)$ haloalkoxy. In another embodiment, $R^{6a}$ is $(C_1-C_3)$ alkyl, $(C_1-C_3)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl are optionally substituted with one or more substituents each independently selected from the group consisting of halogen, $(C_1-C_3)$ alkyl, $(C_1-C_3)$ haloalkyl, $(C_1-C_3)$ alkoxy, and $(C_1-C_3)$ haloalkoxy. In another embodiment, $R^{6a}$ is H, $(C_1-C_6)$ alkyl, or $(C_1-C_6)$ haloalkyl, wherein the alkyl is optionally substituted with one or more substituents each independently selected from the group consisting of $(C_1-C_6)$ alkoxy, and $(C_1-C_6)$ haloalkoxy. In another embodiment $R^{6a}$ is H, $(C_1-C_4)$ alkyl, or $(C_1-C_4)$ haloalkyl, wherein the alkyl is optionally substituted with one or more substituents each independently selected from the group consisting of $(C_1-C_6)$ alkoxy, and $(C_1-C_6)$ haloalkoxy. In yet another embodiment $R^{6a}$ is H, $(C_1-C_3)$ alkyl, or $(C_1-C_3)$ haloalkyl, wherein the alkyl is optionally substituted with one or more substituents each independently selected from the group consisting of $(C_1-C_6)$ alkoxy, and $(C_1-C_6)$ haloalkoxy. In another embodiment, $R^{6a}$ is H, $(C_1-C_6)$ alkyl, or $(C_1-C_6)$ haloalkyl, wherein the alkyl is optionally substituted with one or more substituents each independently selected from the group consisting of $(C_1-C_3)$ alkoxy and $(C_1-C_3)$ haloalkoxy. In another embodiment $R^{6a}$ is H, $(C_1-C_4)$ alkyl, or $(C_1-C_4)$ haloalkyl, wherein the alkyl is optionally substituted with one or more substituents each independently selected from the group consisting of $(C_1-C_3)$ alkoxy and $(C_1-C_3)$ haloalkoxy.

In yet another embodiment $R^{6a}$ is H, $(C_1-C_3)$ alkyl, or $(C_1-C_3)$ haloalkyl, wherein the alkyl is optionally substituted with one or more substituents each independently selected from the group consisting of $(C_1-C_3)$ alkoxy and $(C_1-C_3)$ haloalkoxy. In another embodiment $R^{6a}$ is $(C_3-C_8)$ cycloalkyl or heterocycloalkyl wherein the heterocycloalkyl comprises one or two 5- to 7-membered rings and 1-4 heteroatoms selected from the group consisting of N, O and S, and wherein cycloalkyl or heterocycloalkyl are optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy. In another embodiment $R^{6a}$ is $(C_6-C_{10})$ aryl or heteroaryl wherein the heteroaryl comprises one or two 5- or 6-membered rings and 1-4 heteroatoms selected from the group consisting of N, O and S, and wherein aryl or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy. In another embodiment $R^{6a}$ is H. In yet another embodiment $R^{6a}$ is $(C_1-C_6)$ alkyl. In another embodiment $R^{6a}$ is H or $(C_1-C_6)$ alkyl. In yet another embodiment $R^{6a}$ is H or $(C_1-C_6)$ alkyl optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy.

In some embodiments of the Formulae above, $R^{6b}$ is H, $(C_1-C_6)$ alkyl, $(C_1-C_6)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy. In another embodiment, $R^{6b}$ is $(C_1-C_6)$ alkyl, $(C_1-C_6)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy. In another embodiment, $R^{6b}$ is $(C_1-C_4)$ alkyl, $(C_1-C_4)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl are optionally substituted with one or more substituents each independently selected from the group consisting of halogen, $(C_1-C_4)$ alkyl, $(C_1-C_4)$ haloalkyl, $(C_1-C_4)$ alkoxy, and $(C_1-C_4)$ haloalkoxy. In another embodiment, $R^{6b}$ is $(C_1-C_3)$ alkyl, $(C_1-C_3)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl are optionally substituted with one or more substituents each independently selected from the group consisting of halogen, $(C_1-C_3)$ alkyl, $(C_1-C_3)$ haloalkyl, $(C_1-C_3)$ alkoxy, and $(C_1-C_3)$ haloalkoxy. In another embodiment, $R^{6b}$ is H, $(C_1-C_6)$ alkyl, or $(C_1-C_6)$ haloalkyl, wherein the alkyl is optionally substituted with one or more substituents each independently selected from the group consisting of $(C_1-C_6)$ alkoxy, and $(C_1-C_6)$ haloalkoxy. In another embodiment $R^{6b}$ is H, $(C_1-C_4)$ alkyl, or $(C_1-C_4)$ haloalkyl, wherein the alkyl is optionally substituted with one or more substituents each independently selected from the group consisting of $(C_1-C_6)$ alkoxy, and $(C_1-C_6)$ haloalkoxy. In yet another embodiment $R^{6b}$ is H, $(C_1-C_3)$ alkyl, or $(C_1-C_3)$ haloalkyl, wherein the alkyl is optionally substituted with one or more substituents each independently selected from the group consisting of $(C_1-C_6)$ alkoxy, and $(C_1-C_6)$ haloalkoxy. In another embodiment, $R^{6b}$ is H, $(C_1-C_6)$ alkyl, or $(C_1-C_6)$ haloalkyl, wherein the alkyl is optionally substituted with one or more substituents each independently selected from the group consisting of $(C_1-C_3)$ alkoxy and $(C_1-C_3)$ haloalkoxy.

In another embodiment $R^{6b}$ is H, $(C_1-C_4)$ alkyl, or $(C_1-C_4)$ haloalkyl, wherein the alkyl is optionally substituted with one or more substituents each independently selected from the group consisting of $(C_1-C_3)$ alkoxy and $(C_1-C_3)$ haloalkoxy. In yet another embodiment $R^{6b}$ is H, $(C_1-C_3)$ alkyl, or $(C_1-C_3)$ haloalkyl, wherein the alkyl is optionally substituted with one or more substituents each independently selected from the group consisting of $(C_1-C_3)$ alkoxy and $(C_1-C_3)$ haloalkoxy. In another embodiment $R^{6b}$ is $(C_3-C_8)$ cycloalkyl or heterocycloalkyl wherein the heterocycloalkyl comprises one or two 5- to 7-membered rings and 1-4 heteroatoms selected from the group consisting of N, O and S, and wherein cycloalkyl or heterocycloalkyl are optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy. In another embodiment $R^{6b}$ is $(C_6-C_{10})$ aryl or heteroaryl wherein the heteroaryl comprises one or two 5- or 6-membered rings and 1-4 heteroatoms selected from the group consisting of N, O and S, and wherein aryl or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy. In another embodiment $R^{6b}$ is H. In yet another embodiment $R^{6b}$ is $(C_1-C_6)$ alkyl. In another embodiment $R^{6b}$ is H or $(C_1-C_6)$ alkyl. In yet another embodiment $R^{6b}$ is H or $(C_1-C_6)$ alkyl optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy.

In some embodiments of the Formulae above, $R^{6a}$ and $R^{6b}$ are each independently H, $(C_1-C_6)$ alkyl or $(C_3-C_8)$ cycloalkyl.

In some embodiments of the Formulae above, $R^{6c}$ is H, $(C_1-C_6)$ alkyl, $(C_1-C_6)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy. In another embodiment, $R^{6c}$ is $(C_1-C_6)$ alkyl, $(C_1-C_6)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy. In another embodiment, $R^{6c}$ is $(C_1-C_4)$ alkyl, $(C_1-C_4)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl are optionally substituted with one or more substituents each independently selected from the group consisting of halogen, $(C_1-C_4)$ alkyl, $(C_1-C_4)$ haloalkyl, $(C_1-C_4)$ alkoxy, and $(C_1-C_4)$ haloalkoxy. In another embodiment, $R^{6c}$ is $(C_1-C_3)$ alkyl, $(C_1-C_3)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl are optionally substituted with one or more substituents each independently selected from the group consisting of halogen, $(C_1-C_3)$ alkyl, $(C_1-C_3)$ haloalkyl, $(C_1-C_3)$ alkoxy, and $(C_1-C_3)$ haloalkoxy. In another embodiment, $R^{6c}$ is H, $(C_1-C_6)$ alkyl, or $(C_1-C_6)$ haloalkyl, wherein the alkyl is optionally substituted with one or more substituents each independently selected from the group consisting of $(C_1-C_6)$ alkoxy, and $(C_1-C_6)$ haloalkoxy.

In another embodiment $R^{6c}$ is H, $(C_1-C_4)$ alkyl, or $(C_1-C_4)$ haloalkyl, wherein the alkyl is optionally substituted with one or more substituents each independently selected from the group consisting of $(C_1-C_6)$ alkoxy, and $(C_1-C_6)$ haloalkoxy. In yet another embodiment $R^{6c}$ is H, $(C_1-C_3)$ alkyl, or $(C_1-C_3)$ haloalkyl, wherein the alkyl is optionally substituted with one or more substituents each independently selected from the group consisting of $(C_1-C_6)$ alkoxy, and $(C_1-C_6)$ haloalkoxy. In another embodiment, $R^{6c}$ is H, $(C_1-C_6)$ alkyl, or $(C_1-C_6)$ haloalkyl, wherein the alkyl is optionally substituted with one or more substituents each independently selected from the group consisting of $(C_1-C_3)$ alkoxy and $(C_1-C_3)$ haloalkoxy. In another embodiment $R^{6c}$ is H, $(C_1-C_4)$ alkyl, or $(C_1-C_4)$ haloalkyl, wherein the alkyl is optionally substituted with one or more substituents each independently selected from the group consisting of $(C_1-C_3)$ alkoxy and $(C_1-C_3)$ haloalkoxy. In yet another embodiment $R^{6c}$ is H, $(C_1-C_3)$ alkyl, or $(C_1-C_3)$ haloalkyl, wherein the alkyl is optionally substituted with one or more substituents each independently selected from the group consisting of $(C_1-C_3)$ alkoxy and $(C_1-C_3)$ haloalkoxy. In another embodiment $R^{6c}$ is $(C_3-C_8)$ cycloalkyl or heterocycloalkyl wherein the heterocycloalkyl comprises one or two 5- to 7-membered rings and 1-4 heteroatoms selected from the group consisting of N, O and S, and wherein cycloalkyl or heterocycloalkyl are optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy. In another embodiment $R^{6c}$ is $(C_6-C_{10})$ aryl or heteroaryl wherein the heteroaryl comprises one or two 5- or 6-membered rings and 1-4 heteroatoms selected from the group consisting of N, O and S, and wherein aryl or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy. In another embodiment $R^{6c}$ is H. In yet another embodiment $R^{6c}$ is $(C_1-C_6)$ alkyl. In another embodiment $R^{6c}$ is H or (C₁-C₆) alkyl. In yet another embodiment R$^{6c}$ is H or (C₁-C₆) alkyl optionally substituted with one or more substituents each independently selected from the group consisting of halogen, (C₁-C₆) alkyl, (C₁-C₆) haloalkyl, (C₁-C₆) alkoxy, and (C₁-C₆) haloalkoxy.

In some embodiments of the Formulae above, R$^{6d}$ is (C₁-C₆) alkyl or (C₁-C₆) haloalkyl, wherein the alkyl is optionally substituted with one or more substituents each independently selected from the group consisting of —OH, (C₁-C₆) alkoxy, and (C₁-C₆) haloalkoxy. In another embodiment, R$^{6d}$ is (C₁-C₄) alkyl or (C₁-C₄) haloalkyl, wherein the alkyl is optionally substituted with one or more substituents each independently selected from the group consisting of —OH, (C₁-C₆) alkoxy, and (C₁-C₆) haloalkoxy. In yet another embodiment, R$^{6d}$ is (C₁-C₃) alkyl or (C₁-C₃) haloalkyl, wherein the alkyl is optionally substituted with one or more substituents each independently selected from the group consisting of —OH, (C₁-C₆) alkoxy, and (C₁-C₆) haloalkoxy. In another embodiment, R$^{6d}$ is (C₁-C₆) alkyl or (C₁-C₆) haloalkyl, wherein the alkyl is optionally substituted with one or more substituents each independently selected from the group consisting of —OH, (C₁-C₃) alkoxy and (C₁-C₃) haloalkoxy. In another embodiment, R$^{6d}$ is (C₁-C₄) alkyl or (C₁-C₄) haloalkyl, wherein the alkyl is optionally substituted with one or more substituents each independently selected from the group consisting of —OH, (C₁-C₃) alkoxy, and (C₁-C₃) haloalkoxy. In yet another embodiment, R$^{6d}$ is (C₁-C₃) alkyl or (C₁-C₃) haloalkyl, wherein the alkyl is optionally substituted with one or more substituents each independently selected from the group consisting of —OH, (C₁-C₃) alkoxy and (C₁-C₃) haloalkoxy. In another embodiment, R$^{6d}$ is (C₃-C₈) cycloalkyl or heterocycloalkyl, wherein cycloalkyl or heterocycloalkyl are optionally substituted with one or more substituents each independently selected from the group consisting of halogen, —OH, (C₁-C₆) alkyl, (C₁-C₆) haloalkyl, (C₁-C₆) alkoxy, and (C₁-C₆) haloalkoxy. In another embodiment, R$^{6d}$ is (C₆-C₁₀) aryl or heteroaryl, wherein aryl or heteroaryl are optionally substituted with one or more substituents each independently selected from the group consisting of halogen, —OH, (C₁-C₆) alkyl, (C₁-C₆) haloalkyl, (C₁-C₆) alkoxy, and (C₁-C₆) haloalkoxy. In yet another embodiment R$^{6d}$ is (C₁-C₆) alkyl. In yet another embodiment, R$^{6d}$ is (C₁-C₆) alkyl optionally substituted with one or more substituents each independently selected from the group consisting of halogen, —OH, (C₁-C₆) alkyl, (C₁-C₆) haloalkyl, (C₁-C₆) alkoxy, (C₁-C₆) haloalkoxy, and (C₃-C₈) cycloalkyl. In another embodiment, R$^{6d}$ is (C₃-C₈) cycloalkyl. In yet another embodiment, R$^{6d}$ is (C₁-C₆) alkyl or (C₃-C₈) cycloalkyl. In yet another embodiment, R$^{6d}$ is (C₃-C₈) cycloalkyl or (C₁-C₆) alkyl optionally substituted with one or more substituents each independently selected from the group consisting of halogen, —OH, (C₁-C₆) alkyl, (C₁-C₆) haloalkyl, (C₁-C₆) alkoxy, (C₁-C₆) haloalkoxy, and (C₃-C₈) cycloalkyl. In another embodiment, R$^{6d}$ is (C₃-C₈) cycloalkyl or (C₁-C₆) alkyl optionally substituted with one or more substituents each independently selected from the group consisting of —OH and (C₃-C₈) cycloalkyl.

In some embodiments of the Formulae above, R$^{6e}$ is —OH, (C₃-C₈) cycloalkyl, or (C₁-C₆) alkyl optionally substituted with (C₃-C₈) cycloalkyl.

In some embodiments of the Formulae above, R$^{6e}$ is —OH, (C₁-C₆) alkyl, or (C₁-C₆) haloalkyl, wherein the alkyl is optionally substituted with one or more substituents each independently selected from the group consisting of —OH, (C₁-C₆) alkoxy, and (C₁-C₆) haloalkoxy. In another embodiment R$^{6e}$ is —OH, (C₁-C₄) alkyl, or (C₁-C₄) haloalkyl, wherein the alkyl is optionally substituted with one or more substituents each independently selected from the group consisting of —OH, (C₁-C₆) alkoxy, and (C₁-C₆) haloalkoxy. In yet another embodiment R$^{6e}$ is —OH, (C₁-C₃) alkyl, or (C₁-C₃) haloalkyl, wherein the alkyl is optionally substituted with one or more substituents each independently selected from the group consisting of —OH, (C₁-C₆) alkoxy, and (C₁-C₆) haloalkoxy. In another embodiment, R$^{6e}$ is —OH, (C₁-C₆) alkyl, or (C₁-C₆) haloalkyl, wherein the alkyl is optionally substituted with one or more substituents each independently selected from the group consisting of —OH, (C₁-C₃) alkoxy and (C₁-C₃) haloalkoxy. In another embodiment R$^{6e}$ is —OH, (C₁-C₄) alkyl, or (C₁-C₄) haloalkyl, wherein the alkyl is optionally substituted with one or more substituents each independently selected from the group consisting of —OH, (C₁-C₃) alkoxy and (C₁-C₃) haloalkoxy. In yet another embodiment R$^{6e}$ is —OH, (C₁-C₃) alkyl, or (C₁-C₃) haloalkyl, wherein the alkyl is optionally substituted with one or more substituents each independently selected from the group consisting of —OH, (C₁-C₃) alkoxy and (C₁-C₃) haloalkoxy. In another embodiment R$^{6e}$ is (C₃-C₈) cycloalkyl or heterocycloalkyl, wherein cycloalkyl or heterocycloalkyl are optionally substituted with one or more substituents each independently selected from the group consisting of halogen, —OH, (C₁-C₆) alkyl, (C₁-C₆) haloalkyl, (C₁-C₆) alkoxy, and (C₁-C₆) haloalkoxy. In another embodiment R$^{6e}$ is (C₆-C₁₀) aryl or heteroaryl, wherein aryl or heteroaryl are optionally substituted with one or more substituents each independently selected from the group consisting of halogen, —OH, (C₁-C₆) alkyl, (C₁-C₆) haloalkyl, (C₁-C₆) alkoxy, and (C₁-C₆) haloalkoxy. In yet another embodiment R$^{6e}$ is (C₁-C₆) alkyl. In yet another embodiment R$^{6e}$ is (C₁-C₆) alkyl optionally substituted with one or more substituents each independently selected from the group consisting of halogen, —OH, (C₁-C₆) alkyl, (C₁-C₆) haloalkyl, (C₁-C₆) alkoxy, (C₁-C₆) haloalkoxy, and (C₃-C₈) cycloalkyl. In another embodiment R$^{6e}$ is (C₃-C₈) cycloalkyl. In yet another embodiment R$^{6e}$ is (C₁-C₆) alkyl or (C₃-C₈) cycloalkyl. In yet another embodiment R$^{6e}$ is (C₃-C₈) cycloalkyl or (C₁-C₆) alkyl optionally substituted with one or more substituents each independently selected from the group consisting of halogen, —OH, (C₁-C₆) alkyl, (C₁-C₆) haloalkyl, (C₁-C₆) alkoxy, (C₁-C₆) haloalkoxy, and (C₃-C₈) cycloalkyl. In yet another embodiment R$^{6e}$ is (C₃-C₈) cycloalkyl or (C₁-C₆) alkyl optionally substituted with one or more substituents each independently selected from the group consisting of —OH and (C₃-C₈) cycloalkyl. In some embodiments, R$^{6e}$ is —OH, (C₃-C₈) cycloalkyl, or (C₁-C₆) alkyl optionally substituted with (C₃-C₈) cycloalkyl.

In some embodiments of the Formulae above, R$^{7}$ is independently at each occurrence (C₁-C₆) alkyl, (C₂-C₆) alkenyl, (C₂-C₆) alkynyl, (C₁-C₆) alkoxy, or —CN. In another embodiment, each R$^{7}$ is independently at each occurrence (C₁-C₆) haloalkyl, (C₁-C₆) haloalkoxy, halogen, or —CN. In yet another embodiment, R$^{7}$ is independently at each occurrence (C₁-C₆) haloalkyl, halogen, or (C₁-C₆) haloalkoxy. In another embodiment, R$^{7}$ is independently at each occurrence (C₁-C₄) alkyl, (C₂-C₄) alkenyl, (C₂-C₄) alkynyl, (C₁-C₄) alkoxy, or —CN. In yet another embodiment, R$^{7}$ is independently at each occurrence (C₁-C₄) haloalkyl, (C₁-C₄) haloalkoxy, halogen, or —CN. In another embodiment, R$^{7}$ is independently at each occurrence (C₁-C₄) haloalkyl, (C₁-C₄) haloalkoxy or halogen. In yet another embodiment, R$^{7}$ is independently at each occurrence (C₁-C₃) alkyl, (C₂-C₃) alkenyl, (C₂-C₃) alkynyl, (C₁-C₃) alkoxy, or —CN. In another embodiment, each $R^7$ is independently at each occurrence $(C_1-C_3)$ haloalkyl, $(C_1-C_3)$ haloalkoxy, halogen, or —CN. In another embodiment, $R^7$ is independently at each occurrence $(C_1-C_3)$ haloalkyl, $(C_1-C_3)$ haloalkoxy or halogen. In another embodiment, $R^7$ is independently at each occurrence $(C_1-C_6)$ alkyl, $(C_2-C_6)$ alkenyl, $(C_2-C_6)$ alkynyl, or $(C_1-C_6)$ alkoxy. In another embodiment, each $R^7$ is independently at each occurrence $(C_1-C_6)$ haloalkyl, $(C_1-C_6)$ haloalkoxy, halogen, or —CN. In another embodiment, $R^7$ is independently at each occurrence $(C_1-C_6)$ alkyl, $(C_2-C_6)$ alkenyl, or $(C_2-C_6)$ alkynyl.

In some embodiments of the Formulae above, $R^8$ is independently at each occurrence $(C_1-C_6)$ alkyl, $(C_1-C_6)$ alkoxy, or —OH. In another embodiment, $R^8$ is independently at each occurrence $(C_1-C_6)$ haloalkyl, $(C_1-C_6)$ haloalkoxy, halogen, or —OH. In yet another embodiment, $R^8$ is independently at each occurrence $(C_1-C_6)$ haloalkyl, or $(C_1-C_6)$ haloalkoxy. In another embodiment, $R^8$ is independently at each occurrence $(C_1-C_4)$ alkyl, $(C_1-C_4)$ alkoxy, halogen, or —OH. In yet another embodiment, $R^8$ is independently at each occurrence $(C_1-C_4)$ haloalkyl, $(C_1-C_4)$ haloalkoxy, halogen, or —OH. In another embodiment, $R^8$ is independently at each occurrence $(C_1-C_4)$ haloalkyl, $(C_1-C_4)$ haloalkoxy, or halogen. In yet another embodiment, $R^8$ is independently at each occurrence $(C_1-C_3)$ alkyl, $(C_1-C_3)$ alkoxy, or —OH. In another embodiment, $R^8$ is independently at each occurrence $(C_1-C_3)$ haloalkyl, $(C_1-C_3)$ haloalkoxy, halogen, or —OH. In another embodiment, $R^8$ is independently at each occurrence $(C_1-C_3)$ haloalkyl, $(C_1-C_3)$ haloalkoxy, or halogen. In another embodiment, $R^8$ is independently at each occurrence $(C_1-C_6)$ alkyl, $(C_2-C_6)$ alkenyl, $(C_2-C_6)$ alkynyl, or $(C_1-C_6)$ alkoxy. In another embodiment, each $R^8$ is independently at each occurrence $(C_1-C_6)$ haloalkyl, $(C_1-C_6)$ haloalkoxy, halogen, or —OH. In another embodiment, $R^8$ is independently at each occurrence $(C_1-C_6)$ alkyl, $(C_2-C_6)$ alkenyl, or $(C_2-C_6)$ alkynyl.

In some embodiments of the Formulae above, $R^9$ is independently at each occurrence $(C_1-C_6)$ alkyl, $(C_1-C_6)$ alkoxy, halogen, or —OH. In another embodiment, $R^9$ is independently at each occurrence $(C_1-C_6)$ haloalkyl, $(C_1-C_6)$ haloalkoxy, halogen, or —OH. In yet another embodiment, $R^9$ is independently at each occurrence $(C_1-C_6)$ haloalkyl or $(C_1-C_6)$ haloalkoxy. In another embodiment, $R^9$ is independently at each occurrence $(C_1-C_4)$ alkyl, $(C_1-C_4)$ alkoxy, halogen, or —OH. In yet another embodiment, $R^9$ is independently at each occurrence $(C_1-C_4)$ haloalkyl, $(C_1-C_4)$ haloalkoxy, halogen, or —OH. In another embodiment, $R^9$ is independently at each occurrence $(C_1-C_4)$ haloalkyl, or $(C_1-C_4)$ haloalkoxy. In yet another embodiment, $R^9$ is independently at each occurrence $(C_1-C_3)$ alkyl, $(C_1-C_3)$ alkoxy, halogen, or —OH. In another embodiment, $R^9$ is independently at each occurrence $(C_1-C_3)$ haloalkyl, $(C_1-C_3)$ haloalkoxy, halogen, or —OH. In another embodiment, $R^9$ is independently at each occurrence $(C_1-C_3)$ haloalkyl, or $(C_1-C_3)$ haloalkoxy. In another embodiment, $R^9$ is independently at each occurrence $(C_1-C_6)$ alkyl, $(C_1-C_6)$ alkoxy, $(C_1-C_6)$ haloalkyl, or $(C_1-C_6)$ haloalkoxy. In another embodiment, $R^9$ is independently at each occurrence halogen or —OH.

In some embodiments of the Formulae above, $R^{10}$ is oxo.

In some embodiments of the Formulae above, each $R^{10}$ is independently at each occurrence $(C_1-C_6)$ alkyl, $(C_1-C_6)$ alkoxy, oxo, halogen, or —OH. In another embodiment, each $R^{10}$ is independently at each occurrence $(C_1-C_6)$ haloalkyl, $(C_1-C_6)$ haloalkoxy, halogen, oxo, or —OH. In yet another embodiment, each $R^{10}$ is independently at each occurrence $(C_1-C_6)$ haloalkyl, $(C_1-C_6)$ haloalkoxy, or oxo. In another embodiment each $R^{10}$ is independently at each occurrence $(C_1-C_4)$ alkyl, $(C_1-C_4)$ alkoxy, oxo, halogen, or —OH. In yet another embodiment, each $R^{10}$ is independently at each occurrence $(C_1-C_4)$ haloalkyl, $(C_1-C_4)$ haloalkoxy, halogen, oxo, or —OH. In another embodiment, each $R^{10}$ is independently at each occurrence $(C_1-C_4)$ haloalkyl, $(C_1-C_4)$ haloalkoxy, or oxo. In yet another embodiment each $R^{10}$ is independently at each occurrence $(C_1-C_3)$ alkyl, $(C_1-C_3)$ alkoxy, oxo, halogen, or —OH. In another embodiment, each $R^{10}$ is independently at each occurrence $(C_1-C_3)$ haloalkyl, $(C_1-C_3)$ haloalkoxy, halogen, oxo, or —OH. In another embodiment, each $R^{10}$ is independently at each occurrence $(C_1-C_3)$ haloalkyl, $(C_1-C_3)$ haloalkoxy, or oxo.

In some embodiments of the Formulae above, n is 1. In some embodiments of the Formulae above, n is 2.

In some embodiments of the Formulae above, m is 1, 2, or 3. In yet another embodiment, m is 1 or 2. In another embodiment, m is 2, 3, or 4. In another embodiment, m is 2 or 3. In yet another embodiment, m is 3 or 4. In another embodiment, m is 1. In another embodiment, m is 2. In another embodiment, m is 3. In another embodiment, m is 4.

In some embodiments of the Formulae above, $L_1$ is a bond, $L_2$ is a bond, and $R^4$ is $COOR^{6a}$, $CONHCOOR^{6a}$, $CONH(CH_2)_mSO_2R^{6e}$, $CONR^{6b}R^{6c}$ or —CN.

In some embodiments of the Formulae above, $L_1$ is a bond, $L_2$ is a bond, $R^4$ is $COOR^{6a}$, $CONHCOOR^{6a}$, $CONH(CH_2)_mSO_2R^{6e}$, $CONR^{6b}R^{6c}$, or —CN, $R^{6a}$ is H or $(C_1-C_3)$ alkyl, and $R^{6d}$ is H.

In some embodiments of the Formulae above, $L_1$ is —$CH_2$—, $L_2$ is a bond, and $R^4$ is $COOR^{6a}$, $CONHCOOR^{6a}$, $CONH(CH_2)_mSO_2R^{6e}$, $CONR^{6b}R^{6c}$, or —CN.

In some embodiments of the Formulae above, $L_1$ is —$CH_2$—, $L_2$ is a bond, $R^4$ is $COOR^{6a}$, $CONHCOOR^{6a}$, $CONH(CH_2)_mSO_2R^{6e}$, $CONR^{6b}R^{6c}$, or —CN, $R^{6a}$ is H or $(C_1-C_3)$ alkyl, and $R^{6d}$ is H.

In some embodiments of the Formulae above, $L_1$ is a bond, $L_2$ is —$S(O)_2$—, and $R^4$ is $COOR^{6a}$, $CONHCOOR^{6a}$, $CONH(CH_2)_mSO_2R^{6e}$, $CONR^{6b}R^{6c}$, or —CN.

In some embodiments of the Formulae above, $L_1$ is a bond, $L_2$ is —$S(O)_2$—, $R^4$ is $COOR^{6a}$, $CONHCOOR^{6a}$, $CONH(CH_2)_mSO_2R^{6e}$, $CONR^{6b}R^{6c}$, or —CN, $R^{6a}$ is H or $(C_1-C_3)$ alkyl, and $R^{6d}$ is H.

In some embodiments of the Formulae above, $L_1$ is —$CH_2$—, $L_2$ is —$S(O)_2$—, and $R^4$ is $COOR^{6a}$, $CONHCOOR^{6a}$, $CONH(CH_2)_mSO_2R^{6e}$, $CONR^{6b}R^{6c}$, or —CN.

In some embodiments of the Formulae above, $L_1$ is —$CH_2$—, $L_2$ is —$S(O)_2$—, $R^4$ is $COOR^{6a}$, $CONHCOOR^{6a}$, $CONH(CH_2)_mSO_2R^{6e}$, $CONR^{6b}R^{6c}$, or —CN, $R^{6a}$ is H or $(C_1-C_3)$ alkyl, and $R^{6d}$ is H.

In some embodiments of the Formulae above, $L_1$ is a bond, $L_2$ is a bond, $R^4$ is $COOR^{6a}$, $CONHCOOR^{6a}$, $CONH(CH_2)_mSO_2R^{6e}$, $CONR^{6b}R^{6c}$, or —CN, and A is aryl. In another embodiment, $L_1$ is a bond, $L_2$ is a bond, $R^4$ is $COOR^{6a}$, $CONHCOOR^{6a}$, $CONH(CH_2)_mSO_2R^{6e}$, $CONR^{6b}R^{6c}$, or —CN, and A is phenyl.

In some embodiments of the Formulae above, $L_1$ is —$CH_2$—, $L_2$ is a bond, $R^4$ is $COOR^{6a}$, $CONHCOOR^{6a}$, $CONH(CH_2)_mSO_2R^{6e}$, $CONR^{6b}R^{6c}$, or —CN, and A is aryl. In another embodiment, $L_1$ is —$CH_2$—, $L_2$ is a bond, $R^4$ is $COOR^{6a}$, $CONHCOOR^{6a}$, $CONH(CH_2)_mSO_2R^{6e}$, $CONR^{6b}R^{6c}$, or —CN, and A is phenyl.

In some embodiments of the Formulae above, $L_1$ is a bond, $L_2$ is —$S(O)_2$—, $R^4$ is $COOR^{6a}$, $CONHCOOR^{6a}$, $CONH(CH_2)_mSO_2R^{6e}$, $CONR^{6b}R^{6c}$, or —CN, and A is aryl. In another embodiment $L_1$ is a bond, $L_2$ is —$S(O)_2$—, $R^4$ is COOR$^{6a}$, CONHCOOR$^{6a}$, CONH(CH$_2$)$_m$SO$_2$R$^{6e}$, CONR$^{6b}$R$^{6c}$, or —CN, and A is phenyl.

In some embodiments of the Formulae above, L$_1$ is —CH$_2$—, L$_2$-S(O)$_2$—, R$^4$ is COOR$^{6a}$, CONHCOOR$^{6a}$, CONH(CH$_2$)$_m$SO$_2$R$^{6e}$, CONR$^{6b}$R$^{6c}$, or —CN, and A is aryl. In another embodiment, L$_1$ is —CH$_2$—, L$_2$-S(O)$_2$—, R$^4$ is COOR$^{6a}$, CONHCOOR$^{6a}$, CONH(CH$_2$)$_m$SO$_2$R$^{6e}$, CONR$^{6b}$R$^{6c}$, or —CN, and A is phenyl.

In some embodiments of the Formulae above, L$_1$ is a bond, L$_2$ is a bond, R$^4$ is COOR$^{6a}$, CONHCOOR$^{6a}$, CONH(CH$_2$)$_m$SO$_2$R$^{6e}$, CONR$^{6b}$R$^{6c}$, or —CN, and A is (C$_3$-C$_8$) cycloalkyl. In another embodiment, L$_1$ is a bond, L$_2$ is a bond, R$^4$ is COOR$^{6a}$, CONHCOOR$^{6a}$, CONH(CH$_2$)$_m$SO$_2$R$^{6e}$, CONR$^{6b}$R$^{6c}$, or —CN, and A is bicyclo[2.2.2.]octanyl or spiro[2.5]octanyl.

In some embodiments of the Formulae above, L$_1$ is —CH$_2$—, L$_2$ is a bond, R$^4$ is COOR$^{6a}$, CONHCOOR$^{6a}$, CONH(CH$_2$)$_m$SO$_2$R$^{6e}$, CONR$^{6b}$R$^{6c}$, or —CN, and A is (C$_3$-C$_8$) cycloalkyl. In another embodiment, L$_1$ is —CH$_2$—, L$_2$ is a bond, R$^4$ is COOR$^{6a}$, CONHCOOR$^{6a}$, CONH(CH$_2$)$_m$SO$_2$R$^{6e}$, CONR$^{6b}$R$^{6c}$, or —CN, and A is bicyclo[2.2.2.]octanyl or spiro[2.5]octanyl.

In some embodiments of the Formulae above, L$_1$ is a bond, L$_2$ is —S(O)$_2$—, R$^4$ is COOR$^{6a}$, CONHCOOR$^{6a}$, CONH(CH$_2$)$_m$SO$_2$R$^{6e}$, CONR$^{6b}$R$^{6c}$, or —CN, and A is (C$_3$-C$_8$) cycloalkyl. In another embodiment, L$_1$ is a bond, L$_2$ is —S(O)$_2$—, R$^4$ is COOR$^{6a}$, CONHCOOR$^{6a}$, CONH(CH$_2$)$_m$SO$_2$R$^{6e}$, CONR$^{6b}$R$^{6c}$, or —CN, and A is bicyclo[2.2.2.]octanyl or spiro[2.5]octanyl.

In some embodiments of the Formulae above, L$_1$ is —CH$_2$—, L$_2$-S(O)$_2$—, R$^4$ is COOR$^{6a}$, CONHCOOR$^{6a}$, CONH(CH$_2$)$_m$SO$_2$R$^{6e}$, CONR$^{6b}$R$^{6c}$, or —CN, and A is (C$_3$-C$_8$) cycloalkyl. In another embodiment, L1 is —CH$_2$—, L$_2$ is —S(O)$_2$—, R$^4$ is COOR$^{6a}$, CONHCOOR$^{6a}$, CONH(CH$_2$)$_m$SO$_2$R$^{6e}$, CONR$^{6b}$R$^{6c}$, or —CN, and A is bicyclo[2.2.2.]octanyl or spiro[2.5]octanyl.

In some embodiments of the Formulae above, A is (C$_6$-C$_{10}$) aryl or (C$_3$-C$_8$) cycloalkyl optionally substituted with halogen, (C$_1$-C$_6$) haloalkoxy or (C$_1$-C$_6$) alkoxy and R$^3$ is (C$_3$-C$_6$) cycloalkyl optionally substituted with halogen or (C$_1$-C$_6$) alkyl.

In some embodiments of the Formulae above, L$_2$ is a bond and B is substituted heteroaryl comprising one or two 5- or 6-member rings and 1-4 heteroatoms selected from the group consisting of N, O and S, R$^5$ is halogen, (C$_1$-C$_6$) alkyl, (C$_1$-C$_6$) haloalkyl, (C$_1$-C$_6$) alkoxy, (C$_1$-C$_6$) haloalkoxy, or (C$_3$-C$_8$) cycloalkyl, R$^4$ is COOR$^{6a}$, CONR$^{6b}$R$^{6c}$, CONHSO$_2$R$^{6d}$ or, CONH(CH$_2$)$_m$SO$_2$R$^{6e}$, R$^{6a}$ is H, or (C$_1$-C$_6$) alkyl, R$^{6a}$ and R$^{6b}$ are each H, R$^{6d}$ is (C$_1$-C$_6$) alkyl optionally substituted with —OH or (C$_3$-C$_8$) cycloalkyl, R$^{6e}$ is —OH, or (C$_1$-C$_6$) alkyl, and m is 1 or 2.

In some embodiments of the Formulae above, L$_2$ is a bond and B is substituted heteroaryl comprising one or two 5- or 6-member rings and 1-4 heteroatoms selected from the group consisting of N, O and S, R$^5$ is halogen, (C$_1$-C$_6$) alkyl, (C$_1$-C$_6$) haloalkyl, (C$_1$-C$_6$) alkoxy, (C$_1$-C$_6$) haloalkoxy, or (C$_3$-C$_8$) cycloalkyl, R$^4$ is COOR$^{6a}$, CONR$^{6b}$R$^{6c}$, CONHSO$_2$R$^{6d}$ or, CONH(CH$_2$)$_m$SO$_2$R$^{6e}$, R$^{6a}$ is H, or (C$_1$-C$_6$) alkyl, R$^{6a}$ and R$^{6b}$ are each H, R$^{6d}$ is (C$_3$-C$_8$) cycloalkyl or (C$_1$-C$_6$) alkyl, and m is 1 or 2.

In some embodiments of the Formulae above, L$_2$ is a bond and B is unsubstituted (C$_6$-C$_{10}$) aryl.

In some embodiments of the Formulae above, L$_2$ is a bond and B is (C$_6$-C$_{10}$) aryl substituted with halogen, (C$_1$-C$_6$) alkyl, (C$_1$-C$_6$) haloalkyl, (C$_1$-C$_6$) alkoxy, (C$_1$-C$_6$) haloalkoxy, or —OH, R$^4$ is COOR$^{6a}$, and R$^{6a}$ is H.

In some embodiments of the Formulae above, L$_2$ is a bond and B is unsubstituted (C$_6$-C$_{10}$) aryl, R$^4$ is —CN, CONHSO$_2$R$^{6d}$, COOR$^{6a}$, and R$^{6d}$ is (C$_1$-C$_6$) alkyl optionally substituted with —OH or (C$_3$-C$_8$) cycloalkyl.

In some embodiments of the Formulae above, L$_2$ is-S(O)$_2$—, B is unsubstituted (C$_6$-C$_{10}$) aryl and R$^4$ is COOH. In some embodiments of the Formulae above, L$_2$ is-S(O)$_2$— and B is (C$_6$-C$_{10}$) aryl substituted with halogen and R$^4$ is COOH.

In some embodiments of the Formulae above, L$_1$ is a bond and L$_2$ is a bond. In another embodiment, L$_1$ is a bond, L$_2$ is a bond and A is (C$_3$-C$_8$) cycloalkyl or (C$_6$-C$_{10}$) aryl wherein the cycloalkyl or aryl are optionally substituted with one or more R$^7$. In another embodiment, L$_1$ is a bond, L$_2$ is a bond, A is (C$_3$-C$_8$) cycloalkyl or (C$_6$-C$_{10}$) aryl wherein the cycloalkyl or aryl are optionally substituted with one or more R$^7$, and B is (C$_6$-C$_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more R$^5$. In another embodiment, L$_1$ is a bond, L$_2$ is a bond, A is (C$_3$-C$_8$) cycloalkyl or (C$_6$-C$_{10}$) aryl wherein the cycloalkyl or aryl are optionally substituted with one or more R$^7$, B is (C$_6$-C$_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more R$^5$, and R$^1$ is H, halogen, (C$_1$-C$_4$) alkoxy, (C$_1$-C$_4$) haloalkyl, or (C$_1$-C$_4$) haloalkoxy.

In another embodiment, L$_1$ is a bond, L$_2$ is a bond, A is (C$_3$-C$_8$) cycloalkyl or (C$_6$-C$_{10}$) aryl wherein the cycloalkyl or aryl are optionally substituted with one or more R$^7$, B is (C$_6$-C$_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more R$^5$, R$^1$ is H, halogen, (C$_1$-C$_4$) alkoxy, (C$_1$-C$_4$) haloalkyl, or (C$_1$-C$_4$) haloalkoxy, and R$^2$ is H, halogen, (C$_1$-C$_4$) alkoxy, (C$_1$-C$_4$) haloalkyl, or (C$_1$-C$_4$) haloalkoxy. In another embodiment, L$_1$ is a bond, L$_2$ is a bond, A is (C$_3$-C$_8$) cycloalkyl or (C$_6$-C$_{10}$) aryl wherein the cycloalkyl or aryl are optionally substituted with one or more R$^7$, B is (C$_6$-C$_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more R$^5$, R$^1$ is H, halogen, (C$_1$-C$_4$) alkoxy, (C$_1$-C$_4$) haloalkyl, or (C$_1$-C$_4$) haloalkoxy, R$^2$ is H, halogen, (C$_1$-C$_4$) alkoxy, (C$_1$-C$_4$) haloalkyl, or (C$_1$-C$_4$) haloalkoxy, and R$^3$ is (C$_1$-C$_4$) alkyl or (C$_3$-C$_7$) cycloalkyl optionally substituted with one or more substituents each independently selected from the group consisting of halogen or (C$_1$-C$_4$) alkyl.

In another embodiment, L$_1$ is a bond, L$_2$ is a bond, A is (C$_3$-C$_8$) cycloalkyl or (C$_6$-C$_{10}$) aryl wherein the cycloalkyl or aryl are optionally substituted with one or more R$^7$, B is (C$_6$-C$_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more R$^5$, R$^1$ is H, halogen, (C$_1$-C$_4$) alkoxy, (C$_1$-C$_4$) haloalkyl, or (C$_1$-C$_4$) haloalkoxy, and R$^2$ is halogen, (C$_1$-C$_4$) alkoxy, (C$_1$-C$_4$) haloalkyl, or (C$_1$-C$_4$) haloalkoxy. In another embodiment, L$_1$ is a bond, L$_2$ is a bond, A is (C$_3$-C$_8$) cycloalkyl or (C$_6$-C$_{10}$) aryl wherein the cycloalkyl or aryl are optionally substituted with one or more R$^7$, B is (C$_6$-C$_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In some embodiments of the Formulae above, $L_1$ is a bond, $L_2$ is a bond and A is $(C_3-C_8)$ cycloalkyl optionally substituted with one or more $R^7$. In another embodiment, $L_1$ is a bond, $L_2$ is a bond, A is $(C_3-C_8)$ cycloalkyl optionally substituted with one or more $R^7$, and B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is a bond, $L_2$ is a bond, A is $(C_3-C_8)$ cycloalkyl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, $(C_1-C_4)$ alkoxy, $(C_1-C_4)$ haloalkyl, or $(C_1-C_4)$ haloalkoxy.

In another embodiment, $L_1$ is a bond, $L_2$ is a bond, A is $(C_3-C_8)$ cycloalkyl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is H, halogen, $(C_1-C_4)$ alkoxy, $(C_1-C_4)$ haloalkyl, or $(C_1-C_4)$ haloalkoxy. In another embodiment, $L_1$ is a bond, $L_2$ is a bond, A is $(C_3-C_8)$ cycloalkyl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is H, halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In another embodiment, $L_1$ is a bond, $L_2$ is a bond, A is $(C_3-C_8)$ cycloalkyl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is halogen, $(C_1-C_4)$ alkoxy, $(C_1-C_4)$ haloalkyl, or $(C_1-C_4)$ haloalkoxy. In another embodiment, $L_1$ is a bond, $L_2$ is a bond, A is $(C_3-C_8)$ cycloalkyl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In some embodiments of the Formulae above, $L_1$ is a bond, $L_2$ is a bond and A is $(C_6-C_{10})$ aryl optionally substituted with one or more $R^7$. In another embodiment, $L_1$ is a bond, $L_2$ is a bond, A is $(C_6-C_{10})$ aryl optionally substituted with one or more $R^7$, and B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is a bond, $L_2$ is a bond, A is $(C_6-C_{10})$ aryl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, $(C_1-C_4)$ alkoxy, $(C_1-C_4)$ haloalkyl, or $(C_1-C_4)$ haloalkoxy.

In another embodiment, $L_1$ is a bond, $L_2$ is a bond, A is $(C_6-C_{10})$ aryl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is H, halogen, $(C_1-C_4)$ alkoxy, $(C_1-C_4)$ haloalkyl, or $(C_1-C_4)$ haloalkoxy. In another embodiment, $L_1$ is a bond, $L_2$ is a bond, A is $(C_6-C_{10})$ aryl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is H, halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In another embodiment, $L_1$ is a bond, $L_2$ is a bond, A is $(C_6-C_{10})$ aryl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is halogen, $(C_1-C_4)$ alkoxy, $(C_1-C_4)$ haloalkyl, or $(C_1-C_4)$ haloalkoxy. In another embodiment, $L_1$ is a bond, $L_2$ is a bond, A is $(C_6-C_{10})$ aryl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In some embodiments of the Formulae above, $L_1$ is a bond and $L_2$ is $-S(O)_2-$. In another embodiment, $L_1$ is a bond, $L_2$ is $-S(O)_2-$ and A is $(C_3-C_8)$ cycloalkyl or $(C_6-C_{10})$ aryl wherein the cycloalkyl or aryl are optionally substituted with one or more $R^7$. In another embodiment, $L_1$ is a bond, $L_2$ is $-S(O)_2-$, A is $(C_3-C_8)$ cycloalkyl or $(C_6-C_{10})$ aryl wherein the cycloalkyl or aryl are optionally substituted with one or more $R^7$, and B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is a bond, $L_2$ is —S(O)$_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, ($C_1$-$C_4$) alkoxy, ($C_1$-$C_4$) haloalkyl, or ($C_1$-$C_4$) haloalkoxy.

In another embodiment, $L_1$ is a bond, $L_2$ is —S(O)$_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is H, halogen, ($C_1$-$C_4$) alkoxy, ($C_1$-$C_4$) haloalkyl, or ($C_1$-$C_4$) haloalkoxy. In another embodiment, $L_1$ is a bond, $L_2$ is —S(O)$_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is H, halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In another embodiment, $L_1$ is a bond, $L_2$ is —S(O)$_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is halogen, ($C_1$-$C_4$) alkoxy, ($C_1$-$C_4$) haloalkyl, or ($C_1$-$C_4$) haloalkoxy. In another embodiment, $L_1$ is a bond, $L_2$ is —S(O)$_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In some embodiments of the Formulae above, $L_1$ is a bond, $L_2$ is —S(O)$_2$— and A is ($C_3$-$C_8$) cycloalkyl optionally substituted with one or more $R^7$. In another embodiment, $L_1$ is a bond, $L_2$ is —S(O)$_2$—, A is ($C_3$-$C_8$) cycloalkyl optionally substituted with one or more $R^7$, and B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is a bond, $L_2$ is —S(O)$_2$—, A is ($C_3$-$C_8$) cycloalkyl optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, ($C_1$-$C_4$) alkoxy, ($C_1$-$C_4$) haloalkyl, or ($C_1$-$C_4$) haloalkoxy.

In another embodiment, $L_1$ is a bond, $L_2$ is —S(O)$_2$—, A is ($C_3$-$C_8$) cycloalkyl optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is H, halogen, ($C_1$-$C_4$) alkoxy, ($C_1$-$C_4$) haloalkyl, or ($C_1$-$C_4$) haloalkoxy. In another embodiment, $L_1$ is a bond, $L_2$ is —S(O)$_2$—, A is ($C_3$-$C_8$) cycloalkyl optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is H, halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In another embodiment, $L_1$ is a bond, $L_2$ is —S(O)$_2$—, A is ($C_3$-$C_8$) cycloalkyl optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is halogen, ($C_1$-$C_4$) alkoxy, ($C_1$-$C_4$) haloalkyl, or ($C_1$-$C_4$) haloalkoxy. In another embodiment, $L_1$ is a bond, $L_2$ is —S(O)$_2$—, A is ($C_3$-$C_8$) cycloalkyl optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In some embodiments of the Formulae above, $L_1$ is a bond, $L_2$ is —S(O)$_2$—, and A is ($C_6$-$C_{10}$) aryl optionally substituted with one or more $R^7$. In another embodiment, $L_1$ is a bond, $L_2$ is —S(O)$_2$—, A is ($C_6$-$C_{10}$) aryl optionally substituted with one or more $R^7$, and B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is a bond, $L_2$ is —S(O)$_2$—, A is ($C_6$-$C_{10}$) aryl optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, ($C_1$-$C_4$) alkoxy, ($C_1$-$C_4$) haloalkyl, or ($C_1$-$C_4$) haloalkoxy.

In another embodiment, $L_1$ is a bond, $L_2$ is —S(O)$_2$—, A is ($C_6$-$C_{10}$) aryl optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is H, halogen, ($C_1$-$C_4$) alkoxy, ($C_1$-$C_4$) haloalkyl, or ($C_1$-$C_4$) haloalkoxy. In another embodiment, $L_1$ is a bond, $L_2$ is —S(O)$_2$—, A is ($C_6$-$C_{10}$) aryl optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is H, halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In another embodiment, $L_1$ is a bond, $L_2$ is —S(O)$_2$—, A is ($C_6$-$C_{10}$) aryl optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is halogen, ($C_1$-$C_4$) alkoxy, ($C_1$-$C_4$) haloalkyl, or ($C_1$-$C_4$) haloalkoxy. In another embodiment, $L_1$ is a bond, $L_2$ is —S(O)$_2$—, A is ($C_6$-$C_{10}$) aryl optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —(CH$_2$)$_n$— and $L_2$ is a bond. In another embodiment, $L_1$ is —(CH$_2$)$_n$—, $L_2$ is a bond and A is ($C_3$-$C_8$) cycloalkyl or ($C_6$-$C_{10}$) aryl wherein the cycloalkyl or aryl are optionally substituted with one or more $R^7$. In another embodiment, $L_1$ is —(CH$_2$)$_n$—, $L_2$ is a bond, A is ($C_3$-$C_8$) cycloalkyl or ($C_6$-$C_{10}$) aryl wherein the cycloalkyl or aryl are optionally substituted with one or more $R^7$, and B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —(CH$_2$)$_n$—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, ($C_1$-$C_4$) alkoxy, ($C_1$-$C_4$) haloalkyl, or ($C_1$-$C_4$) haloalkoxy.

In another embodiment, $L_1$ is —(CH$_2$)$_n$—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is H, halogen, ($C_1$-$C_4$) alkoxy, ($C_1$-$C_4$) haloalkyl, or ($C_1$-$C_4$) haloalkoxy. In another embodiment, $L_1$ is —(CH$_2$)$_n$—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is H, halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In another embodiment, $L_1$ is —(CH$_2$)$_n$—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is halogen, ($C_1$-$C_4$) alkoxy, ($C_1$-$C_4$) haloalkyl, or ($C_1$-$C_4$) haloalkoxy. In another embodiment, $L_1$ is —(CH$_2$)$_n$—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —(CH$_2$)$_n$—, $L_2$ is a bond and A is ($C_3$-$C_8$) cycloalkyl optionally substituted with one or more $R^7$. In another embodiment, $L_1$ is —(CH$_2$)$_n$—, $L_2$ is a bond, A is ($C_3$-$C_8$) cycloalkyl optionally substituted with one or more $R^7$, and B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —(CH$_2$)$_n$—, $L_2$ is a bond, A is ($C_3$-$C_8$) cycloalkyl optionally substituted with one or more $R^7$, B is ($C_6$-$C_{10}$) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, $(C_1-C_4)$ alkoxy, $(C_1-C_4)$ haloalkyl, or $(C_1-C_4)$ haloalkoxy.

In another embodiment, $L_1$ is $-(CH_2)_n-$, $L_2$ is a bond, A is $(C_3-C_8)$ cycloalkyl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is H, halogen, $(C_1-C_4)$ alkoxy, $(C_1-C_4)$ haloalkyl, or $(C_1-C_4)$ haloalkoxy. In another embodiment, $L_1$ is $-(CH_2)_n-$, $L_2$ is a bond, A is $(C_3-C_8)$ cycloalkyl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is H, halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In another embodiment, $L_1$ is $-(CH_2)_n-$, $L_2$ is a bond, A is $(C_3-C_8)$ cycloalkyl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is halogen, $(C_1-C_4)$ alkoxy, $(C_1-C_4)$ haloalkyl, or $(C_1-C_4)$ haloalkoxy. In another embodiment, $L_1$ is $-(CH_2)_n-$, $L_2$ is a bond, A is $(C_3-C_8)$ cycloalkyl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In some embodiments of the Formulae above, $L_1$ is $-(CH_2)_n-$, $L_2$ is a bond and A is $(C_6-C_{10})$ aryl optionally substituted with one or more $R^7$. In another embodiment, $L_1$ is $-(CH_2)_n-$, $L_2$ is a bond, A is $(C_6-C_{10})$ aryl optionally substituted with one or more $R^7$, and B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is $-(CH_2)_n-$, $L_2$ is a bond, A is $(C_6-C_{10})$ aryl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, $(C_1-C_4)$ alkoxy, $(C_1-C_4)$ haloalkyl, or $(C_1-C_4)$ haloalkoxy.

In another embodiment, $L_1$ is $-(CH_2)_n-$, $L_2$ is a bond, A is $(C_6-C_{10})$ aryl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is H, halogen, $(C_1-C_4)$ alkoxy, $(C_1-C_4)$ haloalkyl, or $(C_1-C_4)$ haloalkoxy. In another embodiment, $L_1$ is $-(CH_2)_n-$, $L_2$ is a bond, A is $(C_6-C_{10})$ aryl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is H, halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In another embodiment, $L_1$ is $-(CH_2)_n-$, $L_2$ is a bond, A is $(C_6-C_{10})$ aryl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In some embodiments of the Formulae above, $L_1$ is $-(CH_2)_n-$ and $L_2$ is $-S(O)_2-$. In another embodiment, $L_1$ is $-(CH_2)_n-$, $L_2$ is $-S(O)_2-$ and A is $(C_3-C_8)$ cycloalkyl or $(C_6-C_{10})$ aryl wherein the cycloalkyl or aryl are optionally substituted with one or more $R^7$. In another embodiment, $L_1$ is $-(CH_2)_n-$, $L_2$ is $-S(O)_2-$, A is $(C_3-C_8)$ cycloalkyl or $(C_6-C_{10})$ aryl wherein the cycloalkyl or aryl are optionally substituted with one or more $R^7$, and B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is $-(CH_2)_n-$, $L_2$ is $-S(O)_2-$, A is $(C_3-C_8)$ cycloalkyl or $(C_6-C_{10})$ aryl wherein the cycloalkyl or aryl are optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, $(C_1-C_4)$ alkoxy, $(C_1-C_4)$ haloalkyl, or $(C_1-C_4)$ haloalkoxy.

In another embodiment, $L_1$ is $-(CH_2)_n-$, $L_2$ is $-S(O)_2-$, A is $(C_3-C_8)$ cycloalkyl or $(C_6-C_{10})$ aryl wherein the cycloalkyl or aryl are optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is H, halogen, $(C_1-C_4)$ alkoxy, $(C_1-C_4)$ haloalkyl, or $(C_1-C_4)$ haloalkoxy. In another embodiment, $L_1$ is $—(CH_2)_n—$, $L_2$ is $—S(O)_2—$, A is $(C_3-C_8)$ cycloalkyl or $(C_6-C_{10})$ aryl wherein the cycloalkyl or aryl are optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is H, halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In another embodiment, $L_1$ is $—(CH_2)_n—$, $L_2$ is $—S(O)_2—$, A is $(C_3-C_8)$ cycloalkyl or $(C_6-C_{10})$ aryl wherein the cycloalkyl or aryl are optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is halogen, $(C_1-C_4)$ alkoxy, $(C_1-C_4)$ haloalkyl, or $(C_1-C_4)$ haloalkoxy. In another embodiment, $L_1$ is $—(CH_2)_n—$, $L_2$ is $—S(O)_2—$, A is $(C_3-C_8)$ cycloalkyl or $(C_6-C_{10})$ aryl wherein the cycloalkyl or aryl are optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In some embodiments of the Formulae above, $L_1$ is $—(CH_2)_n—$, $L_2$ is $—S(O)_2—$, and A is $(C_3-C_8)$ cycloalkyl optionally substituted with one or more $R^7$. In another embodiment, $L_1$ is $—(CH_2)_n—$, $L_2$ is $—S(O)_2—$, A is $(C_3-C_8)$ cycloalkyl optionally substituted with one or more $R^7$, and B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is $—(CH_2)_n—$, $L_2$ is $—S(O)_2—$, A is $(C_3-C_8)$ cycloalkyl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, $(C_1-C_4)$ alkoxy, $(C_1-C_4)$ haloalkyl, or $(C_1-C_4)$ haloalkoxy.

In another embodiment, $L_1$ is $—(CH_2)_n—$, $L_2$ is $—S(O)_2—$, A is $(C_3-C_8)$ cycloalkyl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is H, halogen, $(C_1-C_4)$ alkoxy, $(C_1-C_4)$ haloalkyl, or $(C_1-C_4)$ haloalkoxy. In another embodiment, $L_1$ is $—(CH_2)_n—$, $L_2$ is $—S(O)_2—$, A is $(C_3-C_8)$ cycloalkyl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is H, halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In another embodiment, $L_1$ is $—(CH_2)_n—$, $L_2$ is $—S(O)_2—$, A is $(C_3-C_8)$ cycloalkyl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In some embodiments of the Formulae above, $L_1$ is $—(CH_2)_n—$, $L_2$ is $—S(O)_2—$, and A is $(C_6-C_{10})$ aryl optionally substituted with one or more $R^7$. In another embodiment, $L_1$ is $—(CH_2)_n—$, $L_2$ is $—S(O)_2—$, A is $(C_6-C_{10})$ aryl optionally substituted with one or more $R^7$, and B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is $—(CH_2)_n—$, $L_2$ is $—S(O)_2—$, A is $(C_6-C_{10})$ aryl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, $(C_1-C_4)$ alkoxy, $(C_1-C_4)$ haloalkyl, or $(C_1-C_4)$ haloalkoxy.

In another embodiment, $L_1$ is $—(CH_2)_n—$, $L_2$ is $—S(O)_2—$, A is $(C_6-C_{10})$ aryl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is H, halogen, $(C_1-C_4)$ alkoxy, $(C_1-C_4)$ haloalkyl, or $(C_1-C_4)$ haloalkoxy. In another embodiment, $L_1$ is $—(CH_2)_n—$, $L_2$ is $—S(O)_2—$, A is $(C_6-C_{10})$ aryl optionally substituted with one or more R⁷, B is (C₆-C₁₀) aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is H, halogen, $(C_1-C_4)$ alkyl, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In another embodiment, $L_1$ is —$(CH_2)_n$—, $L_2$ is —$S(O)_2$—, A is $(C_6-C_{10})$ aryl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is halogen, $(C_1-C_4)$ alkyl, $(C_1-C_4)$ haloalkyl, or $(C_1-C_4)$ haloalkoxy. In another embodiment, $L_1$ is —$(CH_2)_n$—, $L_2$ is —$S(O)_2$—, A is $(C_6-C_{10})$ aryl optionally substituted with one or more $R^7$, B is $(C_6-C_{10})$ aryl or heteroaryl, wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is halogen, $(C_1-C_4)$ alkyl, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

Non-limiting illustrative compounds of the disclosure include:

Methyl 2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1,3-benzothiazole-6-carboxylate (I-1);

2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1,3-benzothiazole-6-carboxylic acid (I-2);

(1R,3R,5S)-8-(6-carbamoyl-4-fluoro-1,3-benzothiazol-2-yl)-8-azabicyclo[3.2.1]octan-3-yl 5-cyclopropyl-3-(2,6-dichlorophenyl)-1,2-oxazole-4-carboxylate (I-3);

2-({2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1,3-benzothiazol-6-yl}formamido)acetic acid (I-4);

2-({2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1,3-benzothiazol-6-yl}formamido)ethane-1-sulfonic acid (I-5);

(1R,3R,5S)-8-[4-fluoro-6-(methanesulfonylcarbamoyl)-1,3-benzothiazol-2-yl]-8-azabicyclo[3.2.1]octan-3-yl 5-cyclopropyl-3-(2,6-dichlorophenyl)-1,2-oxazole-4-carboxylate (I-6);

2-[(1R,3R,5S)-3-[5-cyclopropyl-3-(2,6-dichlorophenyl)-1,2-oxazole-4-carbonyloxy]-8-azabicyclo[3.2.1]octan-8-yl]-5-methoxy-1,3-benzothiazole-6-carboxylic acid (I-7);

2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-methoxy-1,3-benzothiazole-6-carboxylic acid (I-8);

2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-(trifluoromethoxy)-1,3-benzothiazole-6-carboxylic acid (I-9);

2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-(trifluoromethyl)-1,3-benzothiazole-6-carboxylic acid (I-10);

2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-methyl-1,3-benzothiazole-6-carboxylic acid (I-11);

4-cyclopropyl-2-[(1R,3R,5S)-3-[5-cyclopropyl-3-(2,6-dichlorophenyl)-1,2-oxazole-4-carbonyloxy]-8-azabicyclo[3.2.1]octan-8-yl]-1,3-benzothiazole-6-carboxylic acid (I-12);

2-[(1R,3R,5S)-3-(5-cyclopropyl-3-phenyl-1,2-oxazole-4-carbonyloxy)-8-azabicyclo[3.2.1]octan-8-yl]-4-fluoro-1,3-benzothiazole-6-carboxylic acid (I-13);

2-[(1R,3R,5S)-3-{5-cyclopropyl-3-[2-(trifluoromethoxy)phenyl]-1,2-oxazole-4-carbonyloxy}-8-azabicyclo[3.2.1]octan-8-yl]-4-fluoro-1,3-benzothiazole-6-carboxylic acid (I-14);

2-[(1R,3R,5S)-3-{3-[2-chloro-6-(difluoromethoxy)phenyl]-5-cyclopropyl-1,2-oxazole-4-carbonyloxy}-8-azabicyclo[3.2.1]octan-8-yl]-4-fluoro-1,3-benzothiazole-6-carboxylic acid (I-15);

2-[(1R,3R,5S)-3-[5-cyclopropyl-3-(2,6-difluorophenyl)-1,2-oxazole-4-carbonyloxy]-8-azabicyclo[3.2.1]octan-8-yl]-4-fluoro-1,3-benzothiazole-6-carboxylic acid (I-16);

2-[(1R,3R,5S)-3-[5-cyclopropyl-3-(2,6-difluorophenyl)-1,2-oxazole-4-carbonyloxy]-8-azabicyclo[3.2.1]octan-8-yl]-4-methoxy-1,3-benzothiazole-6-carboxylic acid (I-17);

2-[(1R,3R,5S)-3-[5-cyclopropyl-3-(2,6-difluorophenyl)-1,2-oxazole-4-carbonyloxy]-8-azabicyclo[3.2.1]octan-8-yl]-5-methoxy-1,3-benzothiazole-6-carboxylic acid (I-18);

2-[(1R,3R,5S)-3-(5-cyclopropyl-3-{spiro[2.5]octan-6-yl}-1,2-oxazole-4-carbonyloxy)-8-azabicyclo[3.2.1]octan-8-yl]-4-fluoro-1,3-benzothiazole-6-carboxylic acid (I-19);

2-[(1R,3R,5S)-3-(3-{bicyclo[2.2.2]octan-1-yl}-5-cyclopropyl-1,2-oxazole-4-carbonyloxy)-8-azabicyclo[3.2.1]octan-8-yl]-4-fluoro-1,3-benzothiazole-6-carboxylic acid (I-20);

2-[(1R,3R,5S)-3-(3-{bicyclo[2.2.2]octan-1-yl}-5-cyclopropyl-1,2-oxazole-4-carbonyloxy)-8-azabicyclo[3.2.1]octan-8-yl]-4-methoxy-1,3-benzothiazole-6-carboxylic acid (I-21);

2-[(1R,3R,5S)-3-(3-{bicyclo[2.2.2]octan-1-yl}-5-cyclopropyl-1,2-oxazole-4-carbonyloxy)-8-azabicyclo[3.2.1]octan-8-yl]-5-methoxy-1,3-benzothiazole-6-carboxylic acid (I-22);

2-[(1R,3S,5S)-3-[3-(2,6-dichlorophenyl)-5-methyl-1,2-oxazole-4-carbonyloxy]-8-azabicyclo[3.2.1]octan-8-yl]-4-fluoro-1,3-benzothiazole-6-carboxylic acid (I-23);

2-[(1R,3R,5S)-3-[5-cyclobutyl-3-(2,6-dichlorophenyl)-1,2-oxazole-4-carbonyloxy]-8-azabicyclo[3.2.1]octan-8-yl]-4-fluoro-1,3-benzothiazole-6-carboxylic acid (I-24);

2-[(1R,3S,5S)-3-[5-tert-butyl-3-(2,6-dichlorophenyl)-1,2-oxazole-4-carbonyloxy]-8-azabicyclo[3.2.1]octan-8-yl]-4-fluoro-1,3-benzothiazole-6-carboxylic acid (I-25);

2-[(1R,3S,5S)-3-[3-(2,6-dichlorophenyl)-5-(1-methylcyclopropyl)-1,2-oxazole-4-carbonyloxy]-8-azabicyclo[3.2.1]octan-8-yl]-4-fluoro-1,3-benzothiazole-6-carboxylic acid (I-26);

2-[(1R,3R,5S)-3-[3-(2,6-dichlorophenyl)-5-(1-fluorocyclopropyl)-1,2-oxazole-4-carbonyloxy]-8-azabicyclo[3.2.1]octan-8-yl]-4-fluoro-1,3-benzothiazole-6-carboxylic acid (I-27);

6-[(1R,3R,5S)-3-[5-cyclopropyl-3-(2,6-dichlorophenyl)-1,2-oxazole-4-carbonyloxy]-8-azabicyclo[3.2.1]octan-8-yl]-1-methyl-1H-indole-3-carboxylic acid (I-28);

6-[(1R,3R,5S)-3-[5-cyclopropyl-3-(2,6-dichlorophenyl)-1,2-oxazole-4-carbonyloxy]-8-azabicyclo[3.2.1]octan-8-yl]-1,2-benzoxazole-3-carboxylic acid (I-29);

(1R,3R,5S)-8-(2,2-difluoro-1-methyl-3-oxo-2,3-dihydro-1H-indol-6-yl)-8-azabicyclo[3.2.1]octan-3-yl 5-cyclopropyl-3-(2,6-dichlorophenyl)-1,2-oxazole-4-carboxylate (I-30);

2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1-methyl-1H-1,3-benzodiazole-6-carboxylic acid (I-31);

2-[(1R,3R,5S)-3-({2-[5-cyclopropyl-3-(2,6-dichlorophenyl)-1,2-oxazol-4-yl]acetyl}oxy)-8-azabicyclo[3.2.1]octan-8-yl]-4-fluoro-1,3-benzothiazole-6-carboxylic acid (I-32);

2-[(1R,3R,5S)-3-({2-[5-cyclopropyl-3-(2,6-dichlorophenyl)-1,2-oxazol-4-yl]acetyl}oxy)-8-azabicyclo[3.2.1]octan-8-yl]-4-fluoro-1-methyl-1H-1,3-benzodiazole-6-carboxylic acid (I-33);

4-[(1R,3R,5S)-3-[5-cyclopropyl-3-(2,6-dichlorophenyl)-1,2-oxazole-4-carbonyloxy]-8-azabicyclo[3.2.1]octan-8-yl]benzoic acid (I-34);

4-[(1R,3R,5S)-3-[5-cyclopropyl-3-(2,6-dichlorophenyl)-1,2-oxazole-4-carbonyloxy]-8-azabicyclo[3.2.1]octan-8-yl]-3-fluorobenzoic acid (I-35);

3-chloro-4-[(1R,3R,5S)-3-[5-cyclopropyl-3-(2,6-dichlorophenyl)-1,2-oxazole-4-carbonyloxy]-8-azabicyclo[3.2.1]octan-8-yl]benzoic acid (I-36);

4-[(1R,3R,5S)-3-[5-cyclopropyl-3-(2,6-dichlorophenyl)-1,2-oxazole-4-carbonyloxy]-8-azabicyclo[3.2.1]octan-8-yl]-2-(trifluoromethyl)benzoic acid (I-37);

4-[(1R,3R,5S)-3-[5-cyclopropyl-3-(2,6-dichlorophenyl)-1,2-oxazole-4-carbonyloxy]-8-azabicyclo[3.2.1]octan-8-yl]-3-(trifluoromethyl)benzoic acid (I-38);

4-[(1R,3R,5S)-3-[5-cyclopropyl-3-(2,6-dichlorophenyl)-1,2-oxazole-4-carbonyloxy]-8-azabicyclo[3.2.1]octan-8-yl]-2-methoxybenzoic acid (I-39);

4-[(1R,3R,5S)-3-[5-cyclopropyl-3-(2,6-dichlorophenyl)-1,2-oxazole-4-carbonyloxy]-8-azabicyclo[3.2.1]octan-8-yl]-3-methoxybenzoic acid (I-40);

4-[(1R,3R,5S)-3-[5-cyclopropyl-3-(2,6-dichlorophenyl)-1,2-oxazole-4-carbonyloxy]-8-azabicyclo[3.2.1]octan-8-yl]-2-fluorobenzoic acid (I-41);

3-[(1R,3R,5S)-3-[5-cyclopropyl-3-(2,6-dichlorophenyl)-1,2-oxazole-4-carbonyloxy]-8-azabicyclo[3.2.1]octan-8-yl]-5-fluorobenzoic acid (I-42);

4-[(1R,3R,5S)-3-{3-[2-chloro-6-(difluoromethoxy)phenyl]-5-cyclopropyl-1,2-oxazole-4-carbonyloxy}-8-azabicyclo[3.2.1]octan-8-yl]-3-fluorobenzoic acid (I-43);

(1R,3R,5S)-8-[4-(methanesulfonylcarbamoyl)phenyl]-8-azabicyclo[3.2.1]octan-3-yl 5-cyclopropyl-3-(2,6-dichlorophenyl)-1,2-oxazole-4-carboxylate (I-44);

(1R,3R,5S)-8-{4-[(propane-1-sulfonyl)carbamoyl]phenyl}-8-azabicyclo[3.2.1]octan-3-yl 5-cyclopropyl-3-(2,6-dichlorophenyl)-1,2-oxazole-4-carboxylate (I-45);

(1R,3R,5S)-8-{4-[(pentane-1-sulfonyl)carbamoyl]phenyl}-8-azabicyclo[3.2.1]octan-3-yl 5-cyclopropyl-3-(2,6-dichlorophenyl)-1,2-oxazole-4-carboxylate (I-46);

(1R,3R,5S)-8-{4-[(propane-2-sulfonyl)carbamoyl]phenyl}-8-azabicyclo[3.2.1]octan-3-yl 5-cyclopropyl-3-(2,6-dichlorophenyl)-1,2-oxazole-4-carboxylate (I-47);

(1R,3S,5S)-8-{4-[(cyclopropanesulfonyl)carbamoyl]phenyl}-8-azabicyclo[3.2.1]octan-3-yl 5-cyclopropyl-3-(2,6-dichlorophenyl)-1,2-oxazole-4-carboxylate (I-48);

(1R,3S,5S)-8-[4-(cyclopropylmethanesulfonylcarbamoyl)phenyl]-8-azabicyclo[3.2.1]octan-3-yl 5-cyclopropyl-3-(2,6-dichlorophenyl)-1,2-oxazole-4-carboxylate (I-49);

(1R,3R,5S)-8-{4-[(3-hydroxypropanesulfonyl)carbamoyl]phenyl}-8-azabicyclo[3.2.1]octan-3-yl 5-cyclopropyl-3-(2,6-dichlorophenyl)-1,2-oxazole-4-carboxylate (I-50);

(1R,3R,5S)-8-[2-fluoro-4-(methanesulfonylcarbamoyl)phenyl]-8-azabicyclo[3.2.1]octan-3-yl 5-cyclopropyl-3-(2,6-dichlorophenyl)-1,2-oxazole-4-carboxylate (I-51);

(1R,3R,5S)-8-[2-chloro-4-(methanesulfonylcarbamoyl)phenyl]-8-azabicyclo[3.2.1]octan-3-yl 5-cyclopropyl-3-(2,6-dichlorophenyl)-1,2-oxazole-4-carboxylate (I-52);

(1R,3R,5S)-8-(4-cyano-3-hydroxyphenyl)-8-azabicyclo[3.2.1]octan-3-yl 5-cyclopropyl-3-(2,6-dichlorophenyl)-1,2-oxazole-4-carboxylate (I-53);

5-[(1R,3R,5S)-3-[5-cyclopropyl-3-(2,6-dichlorophenyl)-1,2-oxazole-4-carbonyloxy]-8-azabicyclo[3.2.1]octan-8-yl]pyrimidine-2-carboxylic acid (I-54);

3-{[(1R,3R,5S)-3-[5-cyclopropyl-3-(2,6-dichlorophenyl)-1,2-oxazole-4-carbonyloxy]-8-azabicyclo[3.2.1]octan-8-yl]sulfonyl}benzoic acid (I-55);

3-{[(1R,3R,5S)-3-[5-cyclopropyl-3-(2,6-dichlorophenyl)-1,2-oxazole-4-carbonyloxy]-8-azabicyclo[3.2.1]octan-8-yl]sulfonyl}-5-fluorobenzoic acid (I-56);

2-[(1R,3R,5S)-3-(3-{bicyclo[2.2.2]octan-1-yl}-5-cyclopropyl-1,2-oxazole-4-carbonyloxy)-8-azabicyclo[3.2.1]octan-8-yl]-4-(trifluoromethoxy)-1,3-benzothiazole-6-carboxylic acid (I-57);

2-[(1R,3S,5S)-3-(5-cyclopropyl-3-{4-methoxybicyclo[2.2.2]octan-1-yl}-1,2-oxazole-4-carbonyloxy)-8-azabicyclo[3.2.1]octan-8-yl]-4-(trifluoromethoxy)-1,3-benzothiazole-6-carboxylic acid (I-58); and 2-[(1R,3R,5S)-3-[3-(2,6-dichlorophenyl)-5-(1-fluorocyclopropyl)-1,2-oxazole-4-carbonyloxy]-8-azabicyclo[3.2.1]octan-8-yl]-4-methyl-1,3-benzothiazole-6-carboxylic acid (I-59).

In another embodiment of the disclosure, the compounds of Formula (I) are enantiomers. In some embodiments the compounds are the (S)-enantiomer. In other embodiments the compounds are the (A)-enantiomer. In yet other embodiments, the compounds of Formula (I) may be (+) or (−) enantiomers.

It should be understood that all isomeric forms are included within the present disclosure, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the disclosure, and pharmaceutically acceptable salts, hydrates, solvates, stereoisomers and prodrugs thereof may exist in their tautomeric form (for example, as an amide or imino ether). All such tautomeric forms are contemplated herein as part of the present disclosure.

The compounds of the disclosure may contain asymmetric or chiral centers, and, therefore, exist in different stereoisomeric forms. It is intended that all stereoisomeric forms of the compounds of the disclosure as well as mixtures thereof, including racemic mixtures, form part of the present disclosure. In addition, the present disclosure embraces all geometric and positional isomers. For example, if a compound of the disclosure incorporates a double bond or a fused ring, both the cis- and trans-forms, as well as mixtures, are embraced within the scope of the disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the disclosure may be atropisomers (e.g, substituted biaryls) and are considered as part of this disclosure. Enantiomers can also be separated by use of a chiral HPLC column.

It is also possible that the compounds of the disclosure may exist in different tautomeric forms, and all such forms are embraced within the scope of the disclosure. Also, for example, all keto-enol and imine-enamine forms of the compounds are included in the disclosure.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the disclosure. Also, for example, all keto-enol and imine-enamine forms of the compounds are included in the disclosure.) Individual stereoisomers of the compounds of the disclosure may, for example, be substantially free of other isomers, or may be admixed, for example, as racemates or with all other, or other selected, stereoisomers. The chiral centers of the present disclosure can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this disclosure. Reference to a compound of the Formula herein is understood to include reference to salts thereof, unless otherwise indicated.

The present disclosure relates to compounds which are modulators of FXR. In one embodiment, the compounds of the present disclosure are activators of FXR.

The disclosure is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present disclosure may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereof as appreciated by those skilled in the art. These methods include, but are not limited to, those described below. Compounds of the present invention can be synthesized by following the steps outlined in General Schemes 1, 2 and 3 which comprise different sequences of assembling intermediates 2a-2k, 3a-3i, 4a and 4b. Starting materials are either commercially available or made by known procedures in the reported literature or as illustrated.

General Scheme 1

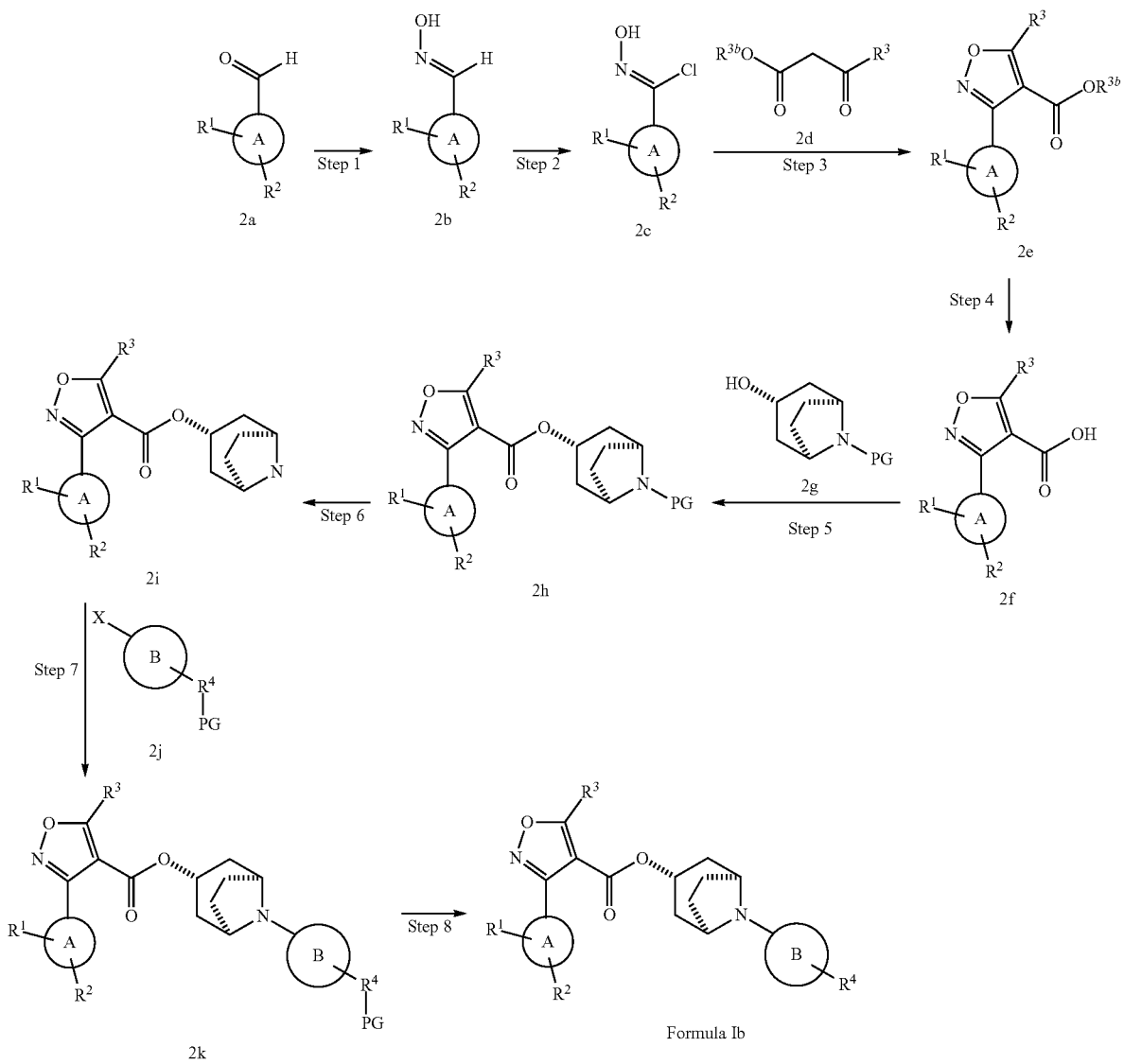

wherein A, B, and R¹-R⁴, are defined as in Formula (I), $R^{3b}$ is an alkyl group, X is halogen (e.g., Cl, F, etc.) or another suitable leaving group (e.g., mesylate), $L_1$ and $L_2$ are both a bond, and PG is a protecting group (e.g., tert-butyl carbonate (BOC)).

The general manner of preparing target compounds of Formula (I) by using intermediates 2a trough 2k, is outlined above in General Scheme 1. Condensation of aldehyde 2a, with hydroxylamine hydrochloride in the presence of a base (e.g. sodium hydroxide (NaOH)) and in a solvent (e.g, water (FLO) and/or ethanol (EtOH)) optionally at elevated temperature provides intermediate 2b. Intermediate 2c is then prepared by treatment of 2b with a chlorinating agent, i.e. N-chlorosuccinimide in a solvent (e.g, N,N-dimethylformamide (DMF)). Cyclization of 2c with beta-keto ester 2d in the presence of a base (e.g, $NEt_3$, NaOMe, and or tBuOK) and in a solvent (e.g., dichloromethane) yields intermediate 2e. Hydrolysis of 2e in the presence of a base (e.g, lithium hydroxide monohydrate) and in a solvent (e.g., EtOH/$H_2O$) optionally at elevated temperature generates the acid 2f. Acid 2f is treated with activating agent (e.g., 1,1'-Carbonyldiimidazole (CDI)) and then reacted with protected tropine intermediate 2g in a solvent (e.g., DMF) optionally at elevated temperature to form isoxazolyl-tropine ester 2h. Alternatively, acid 2f can be converted to an acid chloride using a chlorinating agent (e.g., thienyl chloride) in a solvent (e.g., DMF) and then reacted with protected tropine intermediate 2g in the presence of DMAP and a base (e.g, triethylamine ($Et_3N$)) and in a solvent (e.g, DMF) to form isoxazolyl-tropine ester 2h. Deprotection of intermediate 2h (e.g., when PG is an acid labile group, e.g, BOC) in the presence of a strong acid (e.g., trifluoroacetic acid (TFA)) and in a solvent (e.g., dichloromethane (DCM)) affords the intermediate 2i. Coupling of 2i with 2j, wherein R⁴ in reagent 2j is optionally protected, using a catalytic amount of a palladium catalyst and ligand (e.g., palladium (II) acetate (Pd(OAc)$_2$) and 1,1'-Ferrocenediyl-bis(diphenylphosphine) (dppf)) and acetic anhydride in a solvent, e.g., DMF, at elevated temperature affords the desired product of Formula (I) when $R^4$ is unprotected, or advanced intermediate 2k when $R^4$ is protected. Alternatively, 2i and 2j, wherein $R^4$ in reagent 2j is optionally protected, are treated with a base in a solvent and optionally at elevated temperature to afford the desired product of Formula (I) when $R^4$ is unprotected, or advanced intermediate 2k when $R^4$ is protected. Deprotection intermediate 2k provides the desired product of Formula (I).

chloride in a solvent (e.g, DCM) provides chloride 3b. Cyanation of 3b in the presence of, for instance, potassium cyanide or sodium cyanide in a solvent (e.g, water) optionally at elevated temperature affords intermediate 3c. Hydrolysis of nitrile 3c using a base (e.g., sodium hydroxide (NaOH)) in a solvent (e.g., $H_2O$ and/or EtOH) and optionally at elevated temperature provides 3d. Alternatively, Alcohol 3a can be oxidized to the aldehyde 3e, which is further converted to the two carbon elongated α,β-unsaturated ester

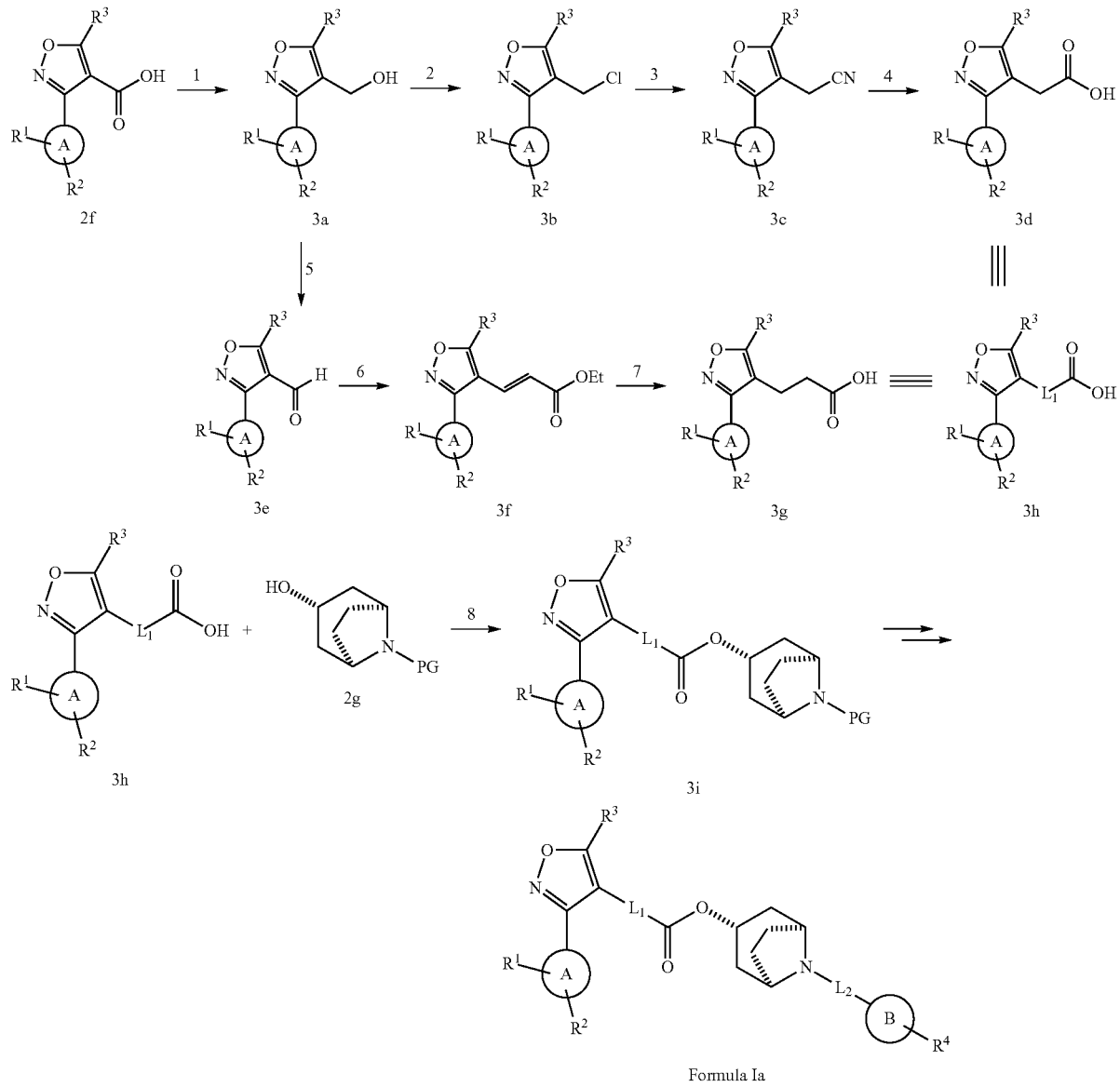

General Scheme 2 wherein A, B, $R^1$-$R^4$, PG, and $L_2$ are defined as in Formula (I).

The general manner of preparing target compounds of Formula (I) wherein $L_1$ is —$(CH_2)_n$—, by using intermediates 2f and 3a through 3i, is outlined above in General Scheme 2. Reduction of intermediate 2f using a reducing agent (e.g., lithium aluminum hydride (LAH)) in a solvent (e.g, tetrahydrofuran (THF)) provides alcohol 3a. Treatment of alcohol 3a with a halogenating agent such as thienyl 3f via a standard Wittig reaction conditions (e.g, (Carboxymethyl)triphenylphosphonium bromide ethyl ester, abase (e.g, potassium tert-butoxide) and a solvent (e.g, THF)). Hydrogenation of 3f in the presence of a metal catalyst (e.g, palladium on carbon), hydrogen gas and in a solvent (e.g, DCM) and subsequent hydrolysis of the resulting ester in the presence of a base (e.g., lithium hydroxide monohydrate) and in a solvent (e.g., EtOH/$H_2O$) optionally at elevated temperature provides acid 3g. 3d or 3h and tropine intermediate 2g are coupled using standard acylation conditions (e.g, treatment of 3h and 2g with DMAP and 1-ethyl-3-(3-dimethylaminopropyl)carbodiimide in a solvent (e.g, DCM)) to form the ester 3i. Intermediate 3i can be converted to the desired product of Formula (I), for instance as described above in steps 6 to 8 of General Scheme 1 or below in General Scheme 3.

General Scheme 3

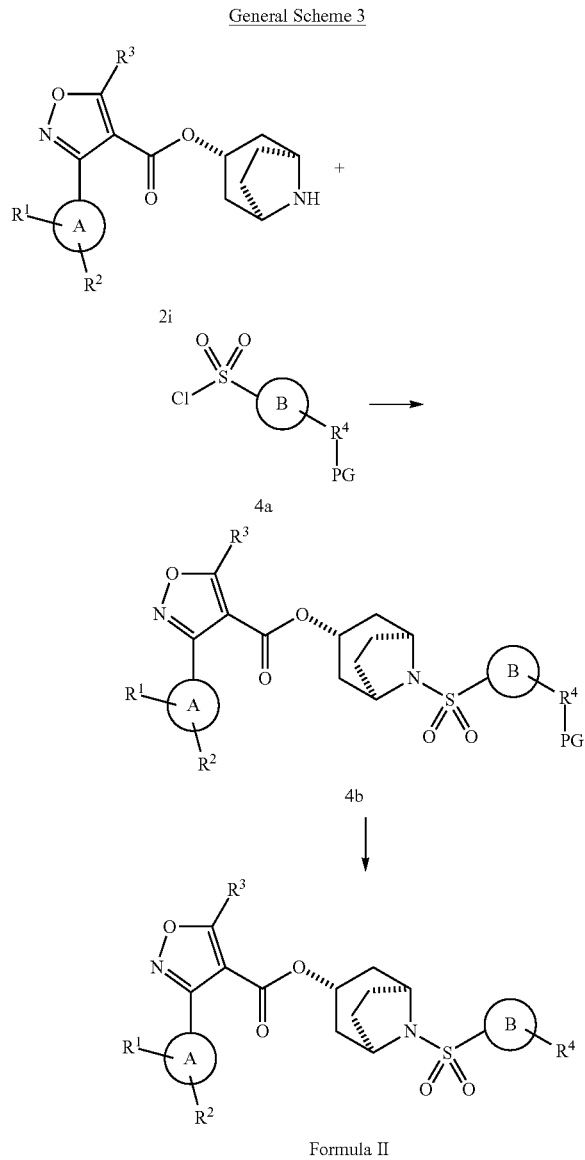

Formula II wherein A, B, PG, and $R^1$-$R^4$ are defined as in Formula (I)

Alternatively compounds of Formula (I) wherein $L_1$ is a bond and $L_2$ is —S(O)$_2$— can be prepared using intermediates 2i, 4a and 4b, as outlined above in General Scheme 3. Sulfonation of the ester-substituted tropine intermediate 2i with a substituted sulfonyl chloride 4a in the presence of a base (e.g, N, A-diisopropylethylamine (DIEA)) and in a solvent (e.g, DCM) affords the sulfonamide compound intermediate 4b. Deprotection of intermediate 4b provides the desired product of Formula (I).

It should be understood that in the description and formula shown above, the various groups $L_1$, $L_2$, A, B, $R^1$, $R^2$, $R^3$, $R^4$, $R^5$, $R^{6a}$, $R^{6b}$, $R^{6c}$, $R^{6d}$, $R^{6e}$, $R^7$, $R^8$, $R^9$, $R^{10}$, m, and n, and other variables are as defined above, except where otherwise indicated. Furthermore, for synthetic purposes, the compounds of General Schemes 1, 2 and 3 are mere representative with elected radicals to illustrate the general synthetic methodology of the compounds of Formula (I) as defined herein.

Methods of Using the Disclosed Compounds

Another aspect of the disclosure is directed to a method of modulating FXR. The method comprises administering to a patient in need thereof an effective amount of a compound of Formula (I), or a pharmaceutically acceptable salt, hydrate, solvate, prodrug, stereoisomer, or tautomer thereof.

Another aspect of the disclosure is directed to a method of modulating FXR. The method comprises administering to a patient in need thereof an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

In another aspect, the disclosure is directed to a method of activating FXR. The method involves administering to a patient in need thereof an effective amount of a compound of Formula (I), or a pharmaceutically acceptable salt, hydrate, solvate, prodrug, stereoisomer, or tautomer thereof.

In another aspect, the disclosure is directed to a method of activating FXR. The method involves administering to a patient in need thereof an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

Another aspect of the disclosure relates to a method of treating, preventing, inhibiting, or eliminating a disease or disorder in which FXR plays a role. The method comprises administering to a patient in need of a treatment for diseases or disorders in which FXR plays a role an effective amount of a compound of Formula (I), or a pharmaceutically acceptable salt, hydrate, solvate, prodrug, stereoisomer, or tautomer thereof. In one embodiment, the disease or disorder is a liver disease, an intestinal disease, a kidney disease, an autoimmune disorder, or cancer.

Another aspect of the disclosure relates to a method of treating, preventing, inhibiting, or eliminating a disease or disorder in which FXR plays a role. The method comprises administering to a patient in need of a treatment for diseases or disorders in which FXR plays a role an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier. In one embodiment, the disease or disorder is a liver disease, an intestinal disease, a kidney disease, an autoimmune disorder, or cancer.

Another aspect of the disclosure relates to a method of modulating FXR. The method comprises administering to a patient in need thereof an effective amount of a compound of Formula (I), or a pharmaceutically acceptable salt, hydrate, solvate, prodrug, stereoisomer, or tautomer thereof.

Another aspect of the disclosure relates to a method of modulating FXR. The method comprises administering to a patient in need thereof an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

Another aspect of the present disclosure relates to a method of treating, preventing, inhibiting, or eliminating a disease or disorder in a patient associated with the activation of FXR, the method comprising administering to a patient in need thereof an effective amount of a compound of Formula (I), or a pharmaceutically acceptable salt, hydrate, solvate, prodrug, stereoisomer, or tautomer thereof. In one embodiment, the disease or disorder is a liver disease, an intestinal disease, a kidney disease, an autoimmune disorder, or cancer.

Another aspect of the present disclosure relates to a method of treating, preventing, inhibiting, or eliminating a disease or disorder in a patient associated with the activation of FXR, the method comprising administering to a patient in need thereof an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier. In one embodiment, the disease or disorder is a liver disease, an intestinal disease, a kidney disease, an autoimmune disorder, or cancer.

In another aspect, the present invention relates to a method of treating, preventing, inhibiting, or eliminating a liver disease. The method comprises administering to a patient in need of a treatment for a liver disease an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating a liver disease. The method comprises administering to a patient in need of a treatment for a liver disease an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

In another aspect, the present invention relates to a method of treating, preventing, inhibiting, or eliminating an intestinal disease. The method comprises administering to a patient in need of a treatment for an intestinal disease an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating an intestinal disease. The method comprises administering to a patient in need of a treatment for an intestinal disease an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

In another aspect, the present invention relates to a method of treating, preventing, inhibiting, or eliminating a kidney disease. The method comprises administering to a patient in need of a treatment for a kidney disease an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating a kidney disease. The method comprises administering to a patient in need of a treatment for a kidney disease an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

In another aspect, the present invention relates to a method of treating, preventing, inhibiting, or eliminating an autoimmune disease. The method comprises administering to a patient in need of a treatment for an autoimmune disease an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating an autoimmune disease. The method comprises administering to a patient in need of a treatment for an autoimmune disease an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

In another aspect, the present invention relates to a method of treating, preventing, inhibiting, or eliminating cancer. The method comprises administering to a patient in need of a treatment for cancer an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating cancer. The method comprises administering to a patient in need of a treatment for cancer an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

Another aspect of the present invention relates to a compound of Formula (I), or a pharmaceutically acceptable salt, hydrate, solvate, prodrug, stereoisomer, or tautomer thereof, for use in the treatment, prevention, inhibition, or elimination of a disease or disorder in which FXR plays a role. In one embodiment, the disease or disorder is a liver disease, an intestinal disease, a kidney disease, an autoimmune disorder, or cancer.

Another aspect of the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of a disease or disorder in which FXR plays a role. In one embodiment, the disease or disorder is a liver disease, an intestinal disease, a kidney disease, an autoimmune disorder, or cancer.

Another aspect of the present disclosure relates to a compound of Formula (I), or a pharmaceutically acceptable salt, hydrate, solvate, prodrug, stereoisomer, or tautomer thereof, for use in the treatment, prevention, inhibition, or elimination of a disease associated with activating FXR.

In another aspect, the present invention relates to a compound of Formula (I), or a pharmaceutically acceptable salt, hydrate, solvate, prodrug, stereoisomer, or tautomer thereof, for use in the treatment, prevention, inhibition, or elimination of a liver disease.

In another aspect, the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of a liver disease.

In another aspect, the present invention relates to a compound of Formula (I), or a pharmaceutically acceptable salt, hydrate, solvate, prodrug, stereoisomer, or tautomer thereof, for use in the treatment, prevention, inhibition, or elimination of an intestinal disease.

In another aspect, the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of an intestinal disease.

In another aspect, the present invention relates to a compound of Formula (I), or a pharmaceutically acceptable salt, hydrate, solvate, prodrug, stereoisomer, or tautomer thereof, for use in the treatment, prevention, inhibition, or elimination of a kidney disease.

In another aspect, the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of a kidney disease.

In another aspect, the present invention relates to a compound of Formula (I) or (Ia), or a pharmaceutically acceptable salt, hydrate, solvate, prodrug, stereoisomer, or tautomer thereof, for use in the treatment, prevention, inhibition, or elimination of an autoimmune disorder.

In another aspect, the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of an autoimmune disorder.

In another aspect, the present invention relates to a compound of Formula (I) or (Ia), or a pharmaceutically acceptable salt, hydrate, solvate, prodrug, stereoisomer, or tautomer thereof, for use in the treatment, prevention, inhibition, or elimination of cancer.

In another aspect, the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of cancer.

Another aspect of the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a disease or disorder in which FXR plays a role. In one embodiment, the disease or disorder is a liver disease, an intestinal disease, a kidney disease, an autoimmune disorder or cancer.

Another aspect of the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating a disease or disorder in which FXR plays a role. In one embodiment, the disease or disorder is a liver disease, an intestinal disease, a kidney disease, an autoimmune disorder or cancer.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a liver disease.

In another aspect, the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating a liver disease.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating an intestinal disease.

In another aspect, the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating an intestinal disease.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a kidney disease.

In another aspect, the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating a kidney disease.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating an autoimmune disease.

In another aspect, the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating an autoimmune disease.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a cancer.

In another aspect, the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating a cancer.

Another aspect of the present disclosure relates to a compound of Formula (I), or a pharmaceutically acceptable salt, hydrate, solvate, prodrug, stereoisomer, or tautomer thereof, for use in the manufacture of a medicament for treating a disease associated with activating FXR.

Another aspect of the present disclosure relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating a disease associated with activating FXR.

Another aspect of the present disclosure relates to a compound of Formula (I), or a pharmaceutically acceptable salt, hydrate, solvate, prodrug, stereoisomer, or tautomer thereof, for use in the manufacture of a medicament for treating a disease in which FXR plays a role.

Another aspect of the present disclosure relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating a disease in which FXR plays a role.

Another aspect of the present disclosure relates to a compound of Formula (I), or a pharmaceutically acceptable salt, hydrate, solvate, prodrug, stereoisomer, or tautomer thereof, for use in the manufacture of a medicament for treating a liver disease.

Another aspect of the present disclosure relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating a liver disease.

Another aspect of the present disclosure relates to a compound of Formula (I), or a pharmaceutically acceptable salt, hydrate, solvate, prodrug, stereoisomer, or tautomer thereof, for use in the manufacture of a medicament for treating an intestinal disease.

Another aspect of the present disclosure relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating an intestinal disease.

Another aspect of the present disclosure relates to a compound of Formula (I), or a pharmaceutically acceptable salt, hydrate, solvate, prodrug, stereoisomer, or tautomer thereof, for use in the manufacture of a medicament for treating a kidney disease.

Another aspect of the present disclosure relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating a kidney disease.

Another aspect of the present disclosure relates to a compound of Formula (I), or a pharmaceutically acceptable salt, hydrate, solvate, prodrug, stereoisomer, or tautomer thereof, for use in the manufacture of a medicament for treating an autoimmune disorder.

Another aspect of the present disclosure relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating an autoimmune disorder.

Another aspect of the present disclosure relates to a compound of Formula (I), or a pharmaceutically acceptable salt, hydrate, solvate, prodrug, stereoisomer, or tautomer thereof, for use in the manufacture of a medicament for treating cancer.

Another aspect of the present disclosure relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating cancer.

In other embodiments, the present invention relates to the use of an activator of FXR for the preparation of a medicament used in the treatment, prevention, inhibition or elimination of a liver disease.

In other embodiments, the present invention relates to the use of an activator of FXR for the preparation of a medicament used in the treatment, prevention, inhibition or elimination of an intestinal disease.

In other embodiments, the present invention relates to the use of an activator of FXR for the preparation of a medicament used in the treatment, prevention, inhibition or elimination of a kidney disease.

In other embodiments, the present invention relates to the use of an activator of FXR for the preparation of a medicament used in the treatment, prevention, inhibition or elimination of an autoimmune disorder.

In other embodiments, the present invention relates to the use of an activator of FXR for the preparation of a medicament used in the treatment, prevention, inhibition or elimination of a cancer.

The present disclosure also relates to the use of an activator of FXR for the preparation of a medicament used in the treatment, prevention, inhibition, or elimination of a disease or condition in which FXR plays a role, wherein the medicament comprises a compound of Formula (I).

In another aspect, the present disclosure relates to a method for the manufacture of a medicament for treating, preventing, inhibiting, or eliminating a disease or condition mediated by FXR, wherein the medicament comprises a compound of Formula (I), or a pharmaceutically acceptable salt, hydrate, solvate, prodrug, stereoisomer, or tautomer thereof.

In some embodiments of the methods described herein, the disease or condition is selected from the group consisting of liver disease, intestinal disease, kidney disease, an autoimmune disorder, or cancer. In other embodiments, the disease can be any disease including, but not limited to, Alagille syndrome (ALGS), atherosclerosis, biliary atresia, Byler disease, gallstone disease, hyperlipidemia, hepatocellular carcinoma, hepatocellular adenoma, cholangiocarcinoma, colorectal cancer, colorectal adenoma, ileal adenoma, renal cancer, oesophageal cancer, obesity, type-2 diabetes mellitus, or gastric cancer.

In any of the embodiments of the disclosure, the liver disease can be any liver disease, including, but not limited to, primary biliary cirrhosis (PBC), primary sclerosing cholangitis (PSC), non-alcoholic fatty liver disease (NAFLD), non-alcoholic steatohepatitis (NASH), alcoholic liver disease, intra- and extra-cholestasis, and portal vein hypertension (PAH).

In any of the embodiments of the disclosure, the intestinal disease can be any intestinal disease, including, but not limited to, inflammatory bowel disease, Crohn's disease, ulcerative colitis, proctitis, pouchitis, Celiac's disease or bile acid diarrhea.

In any of the embodiments of the disclosure, the kidney disease can be any kidney disease, including, but not limited to, fibrotic renal disease or diabetic nephrophathy.

In any of the embodiments of the disclosure, the autoimmune disorder can be any autoimmune disorder, including, but not limited to, fibrotic renal disease or diabetic nephrophathy.

In any of the embodiments of the disclosure, the autoimmune disorder can be inflammatory bowel disease, autoimmune liver disease (e.g., primary biliary cirrhosis (PBC), or primary sclerosing cholangitis (PSC)), autoimmune hepatitis, or multiple sclerosis.

In any of the embodiments of the disclosure, the cancer can be any cancer including, but not limited to, a cancer is selected from the group consisting of hepatocellular carcinoma, hepatocellular adenoma, cholangiocarcinoma, colorectal cancer, colorectal adenoma, ileal adenoma, renal cancer, oesophageal cancer, or gastric cancer.

In another embodiment, the present disclosure relates to a compound of Formula (I), or a pharmaceutically acceptable salt, hydrate, solvate, prodrug, stereoisomer, or tautomer thereof, or a pharmaceutical composition comprising a compound, or a pharmaceutically acceptable salt, hydrate, solvate, prodrug, stereoisomer, or tautomer thereof, of the present disclosure and a pharmaceutically acceptable carrier used for the treatment of diseases including, but not limited to liver diseases, intestinal diseases, kidney diseases, autoimmune disorders or cancer.

Another aspect of the disclosure is directed to pharmaceutical compositions comprising a compound of Formula (I), or a pharmaceutically acceptable salt, hydrate, solvate, prodrug, stereoisomer, or tautomer thereof, and a pharmaceutically acceptable carrier. The pharmaceutical acceptable carrier may further include an excipient, diluent, or surfactant.

In one embodiment, are provided methods of treating a disease or disorder in which FXR plays a role including a liver disease, an intestinal disease, a kidney disease or an autoimmune disorder comprising administering to a patient suffering from at least one of said diseases or disorder a compound of Formula (I).

One therapeutic use of the compounds or compositions of the present disclosure which activate FXR is to provide treatment to patients or subjects suffering from a liver disease, an intestinal disease, a kidney disease, an autoimmune disorder, or cancer.

The disclosed compounds of the disclosure can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, poly epsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a poly carboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the disclosure is directed to pharmaceutical compositions comprising a compound of Formula (I) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims. Analytical Methods, Materials, and Instrumentation Unless otherwise noted, reagents and solvents were used as received from commercial suppliers. Proton nuclear magnetic resonance (NMR) spectra were obtained with either a Varian spectrometer at 400 MHz or Brucker spectrometer at 300 MHz and 500 MHz. Spectra are given in ppm (δ) and coupling constants, J, are reported in Hertz. Tetramethylsilane (TMS) or the solvent peak was used as an internal standard. If not otherwise specified, purity and low resolution mass spectral data were measured using a Thermo Finnigan Surveyor HPLC system with Surveyor photo diode array (PDA) detection and a Thermo LCQ Fleet™ ion trap mass spectrometer. Column: Synergi 4 micron, hydro-RP80A, 30×2.0 mm, Flow rate: 0.500 mL/min; Solvent A (water+0.1% formic acid), Solvent B (acetonitrile+0.1% formic acid); Gradient: 2% B at t=0 to 95% B at 3 min to 95% B at 3.3 min.

Abbreviations used in the following examples and elsewhere herein are:
AcOH acetic acid
ACN acetonitrile
aq. Aqueous
BINAP 2,2'-Bis(diphenylphosphino)-1,1'-binaphthyl
Boc tert-butyl carbonate
tert-BuONO tert-butyl nitrite
CDI carbonyldiimidazole
CS$_2$CO$_3$ cesium carbonate
CuBr$_2$ copper(II)bromide
DCM dichloromethane
DIEA N, A-diisopropylethylamine
DMA dimethylacetamide
DMAP 4-dimethylaminopyridine
DMF N,N-dimethylformamide
DMSO dimethylsulfoxide
dppf bis(diphenylphosphino)ferrocene
EDCI 1-ethyl-3-(3-dimethylaminopropyl)carbodiimide
equiv. equivalents
ESI electrospray ionization
Et$_2$O diethyl ether
EtOAc ethyl acetate
EtOH ethanol
h hours
HATU 1-[bis(dimethylamino)methylene]-1H-1,2,3-triazolo[4,5-b]pyridinium 3-oxid hexafluorophosphate
HCl hydrogen chloride
HPLC high performance liquid chromatography
LCMS liquid chromatography-mass spectrometry
LAH lithium aluminium hydride
LiOH lithium hydroxide
MeOH methanol
min minutes
MeCN acetonitrile
MeI methyl iodide
MS mass spectrometry
NaOMe sodium methoxide
NaOH sodium hydroxide
NaSCN sodium thiocyanate
NEt$_3$ triethylamine
NH$_2$OH.HCl hydroxylamine hydrochloride
NCS N-chlorosuccinimide
NIS A-Iodosuccinimide
Pd(OAc)$_2$ palladium (II) acetate
Pd$_2$(dba)$_3$ tris(dibenzylideneacetone)dipalladium
PE petroleum ether
RT room temperature
TEA triethylamine
TMSCH$_2$N$_2$ trimethylsilyldiazomethane
THF tetrahydrofuran
TFA trifluoroacetic acid Example 1: Intermediate A-1. Methyl 2-bromo-4-fluorobenzo[d]thiazole-6-carboxylate

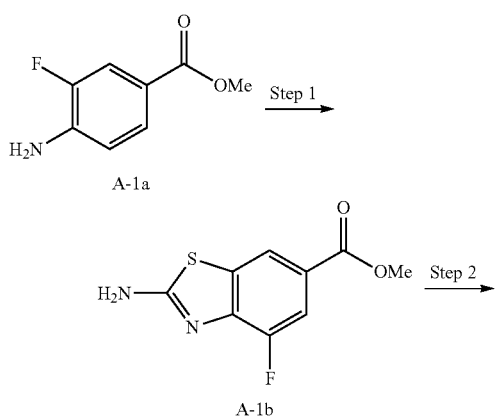

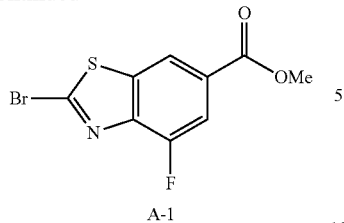

A-1

Step 1. Methyl 2-amino-4-fluoro-1,3-benzothiazole-6-carboxylate (A-1b)

To a 1 L round-bottom flask was added methyl 4-amino-3-fluorobenzoate A-1a (20 g, 118.24 mmol, 1.0 equiv.), AcOH (400 mL), and NaSCN (38.34 g, 473.33 mmol, 4.0 equiv.) followed by the dropwise addition of bromine (18.7 g, 117.01 mmol, 1.0 equiv.) at 0° C. The reaction mixture was stirred at 0° C. for 2 hours, then at 30° C. for 3 days. The resulting mixture was quenched with water (400 mL) and the pH value of the solution was adjusted to 9 using sodium hydroxide. Solids were collected by filtration and dried in an oven under reduced pressure, to give of methyl 2-amino-4-fluoro-1,3-benzothiazole-6-carboxylate A-1b (28 g) as a yellow solid. The product was carried on to the next step without further purification.

Step 2. Methyl 2-bromo-4-fluoro-1,3-benzothiazole-6-carboxylate (A1)

To a 250 mL round-bottom flask containing CuBr$_2$ (2.96 g, 1.5 equiv.) and MeCN (100 mL) at 0° C. was added tert-BuONO (2.4 mL) dropwise followed by the batchwise addition of methyl 2-amino-4-fluoro-1,3-benzothiazole-6-carboxylate A-1b (2 g, 8.84 mmol, 1.0 equiv.). The resulting mixture was stirred overnight at 30° C. and then concentrated in vacuo. The crude product was purified by Flash-Prep-HPLC, using the following conditions: Column, silica gel; mobile phase, PE:EtOAc=100:0 increasing to PE:EtOAc=90:10 within 10 min; Detector, ETV 254 nm, to afford methyl 2-bromo-4-fluoro-1,3-benzothiazole-6-carboxylate A1 (507.9 mg, 20%) as a light yellow solid. $^1$HNMR (300 MHz, DMSO-d$_6$) δ: 8.67 (d, J=1.4 Hz, 1H), 7.84 (dt, J=11.1, 1.2 Hz, 1H), 3.92 (s, 3H); MS (ES, m/z): [M+1]=290.

Example 2: Intermediate A-2. Methyl 2-bromo-5-methoxy-1,3-benzothiazole-6-carboxylate

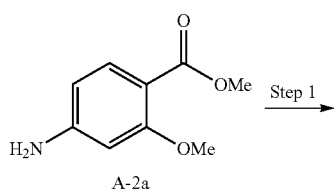

A-2a

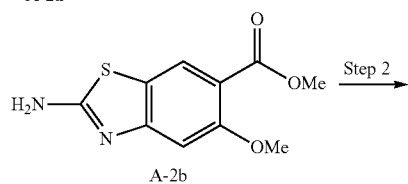

A-2b

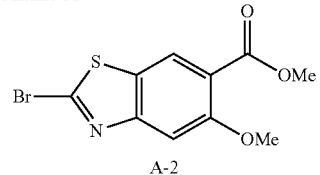

A-2

Step 1. Methyl 2-amino-5-methoxy-1,3-benzothiazole-6-carboxylate (A2b)

To a 250 mL 3-necked round-bottom flask was added methyl 4-amino-2-methoxybenzoate A-2a (9.0 g, 49.67 mmol, 1.0 equiv.), AcOH (50 mL), and NaSCN (32.4 g, 399.65 mmol, 8.0 equiv.), followed by the dropwise addition of Br$_2$ (15.9 g, 99.49 mmol, 2.0 equiv.) in AcOH (50 mL) over the course of 1 h at 0° C. The resulting mixture was then stirred at 30° C. for 24 h and quenched with water (200 mL). The pH value of the aqueous mixture was adjusted to 9 using sodium hydroxide. The solids were collected by filtration and dried in an oven under reduced pressure to give methyl 2-amino-5-methoxy-1,3-benzothiazole-6-carboxylate A-2b (10 g, 84%) as a brown solid.

Step 2. Methyl 2-bromo-5-methoxy-1,3-benzothiazole-6-carboxylate (A-2)

To a 250-mL round-bottom flask was added methyl 2-amino-5-methoxy-1,3-benzothiazole-6-carboxylate A-2b (4.8 g, 20.15 mmol, 1.0 equiv.), MeCN (80 mL), and CuBr$_2$ (6.7 g, 30.0 mmol, 1.5 equiv.), followed by the dropwise addition of tert-BuONO (6.2 g, 60.12 mmol, 3.0 equiv.) at 0° C. The resulting mixture was stirred overnight at 30° C., and then concentrated in vacuo. The crude product was purified by silica gel column chromatography eluting with EtOAc: PE (1:10) to afford methyl 2-bromo-5-methoxy-1,3-benzothiazole-6-carboxylate A2 as a light yellow solid (1.5 g, 25%, purity 98% by LCMS).
$^1$HNMR (300 MHz, CDCl$_3$) δ: 8.424 (s, 1H), 7.547 (s, 1H), 3.974 (s, 3H), 3.931 (s, 3H); MS (ES, m/z): [M+1]=301.85.

Example 3: Intermediate A-3. 2-Bromo-4-methoxy-1,3-benzothiazole-6-carboxylate

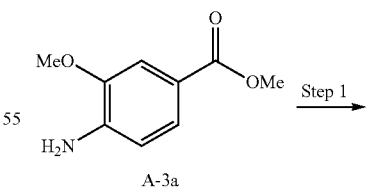

A-3a

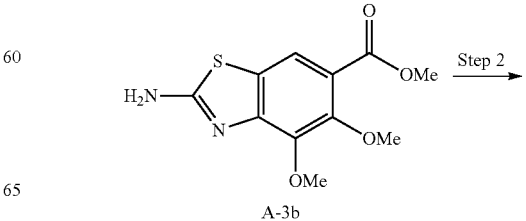

A-3b

-continued

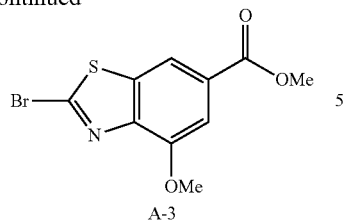
A-3

Step 1. Methyl 2-amino-4-methoxy-1,3-benzothiazole-6-carboxylate (A-3b)

To a 500 mL 3-necked round-bottom flask containing methyl 4-amino-3-methoxybenzoate A-3a (10 g, 55.19 mmol, 1.0 equiv.), AcOH (150 mL), and NaSCN (17.9 g). was added a solution of bromine (8.8 g, 55.07 mmol, 1.0 equiv.) in AcOH (50 mL) dropwise at 0-5° C. The resulting mixture was stirred at 30° C. overnight and H$_2$O (1000 mL) was then added. The pH value of the resulting solution was adjusted to 9 using potassium carbonate and the resulting solids were collected by filtration to give methyl 2-amino-4-methoxy-1,3-benzothiazole-6-carboxylate A-3b (12.5 g, 95%) as a yellow solid. The product was carried on to the next step without further purification.

Step 2. 2-Bromo-4-methoxy-1,3-benzothiazole-6-carboxylate (A-3)

To a 1 L round-bottom flask was added methyl 2-amino-4-methoxy-1,3-benzothiazole-6-carboxylate A-3b (9.2 g, 38.61 mmol, 1.0 equiv.), CH$_3$CN (200 mL), CuBr$_2$ (12.9 g), and tert-butyl nitrite (9 g, 87.28 mmol, 2.26 equiv.). The resulting mixture was stirred overnight at 30° C. and concentrated in vacuo. The crude product was purified via silica gel column chromatography eluting with ethyl acetate/petroleum ether (1:3) to give 2-bromo-4-methoxy-1,3-benzothiazole-6-carboxylate A-3 (4.7 g, 40%) as a light yellow solid

Example 4: Intermediate A-4. Methyl 2-bromo-4-(trifluoromethoxy)-1,3-benzothiazole-6-carboxylate

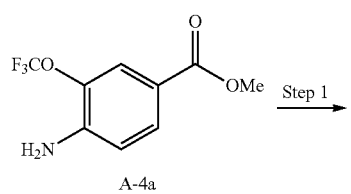
A-4a

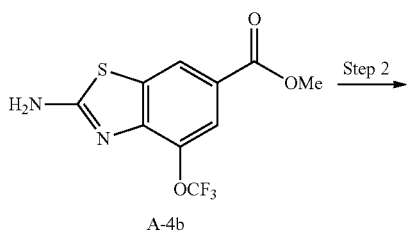
A-4b

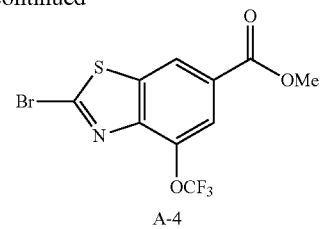
A-4

Step 1. Methyl 2-amino-4-(trifluoromethoxy)-1,3-benzothiazole-6-carboxylate (A-4b)

To a 500 mL round-bottom flask was added methyl 4-amino-3-(trifluoromethoxy)benzoate (7.1 g, 30.19 mmol, 1.0 equiv.), AcOH (100 mL), and NaSCN (12.1 g, 149.25 mmol, 5.0 equiv.) followed by the dropwise addition of bromine (9.6 g, 60.07 mmol, 2.0 equiv.) in AcOH (50 mL) at 0° C. over a 1 h. The mixture was stirred at 0° C. for 2 h, and then at 40° C. overnight. The reaction mixture was again cooled to 0° C., and NaSCN (12.2 g, 150.49 mmol, 5.0 equiv.) was added, followed by the dropwise addition of bromine (9.6 g, 60.07 mmol, 2.0 equiv.) in AcOH (50 mL) over a 1 hr period. The reaction mixture was stirred at 0° C. for 2 h, then at 40° C. for 3 days. The resulting mixture was diluted with water (200 mL) and the pH value of the solution was adjusted to 9 using sodium hydroxide. The resulting solids were collected by filtration, washed with water (20 ml×2), and dried in an oven at 60° C. for 6 h to provide methyl 2-amino-4-(trifluoromethoxy)-1,3-benzothiazole-6-carboxylate A4b (5.4 g, 61%) as a brown solid.

Step 2. Methyl 2-bromo-4-(trifluoromethoxy)-1,3-benzothiazole-6-carboxylate (A-4)

To a 250 mL round-bottom flask was added methyl 2-amino-4-(trifluoromethoxy)-1,3-benzothiazole-6-carboxylate A-4b (2.9 g, 9.92 mmol, 1.0 equiv.), MeCN (100 mL), and CuBr$_2$ (3.4 g, 15.22 mmol, 1.5 equiv.), followed by the dropwise addition of t-BuONO (3.1 g, 30.06 mmol, 3.0 equiv.). The resulting mixture was stirred at 30° C. overnight, and then concentrated in vacuo. The crude product was purified by silica gel column chromatography, eluting with EtOAc:PE (1:10) affording methyl 2-bromo-4-(trifluoromethoxy)-1,3-benzothiazole-6-carboxylate A-4 (1.8 g, 51%) as a white solid. $^1$HNMR (300 MHz, CD$_3$OD) δ: 8.681 (s, 1H), 8.020 (s, 1H), 3.955 (s, 3H). MS (ES, m/z): [M+1]=356, [M+3]=358.

Example 5: Intermediate A-5. Methyl 2-bromo-4-(trifluoromethyl)-1,3-benzothiazole-6-carboxylate

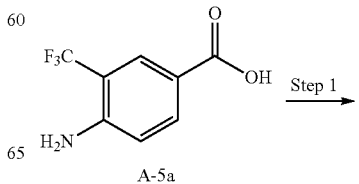
A-5a

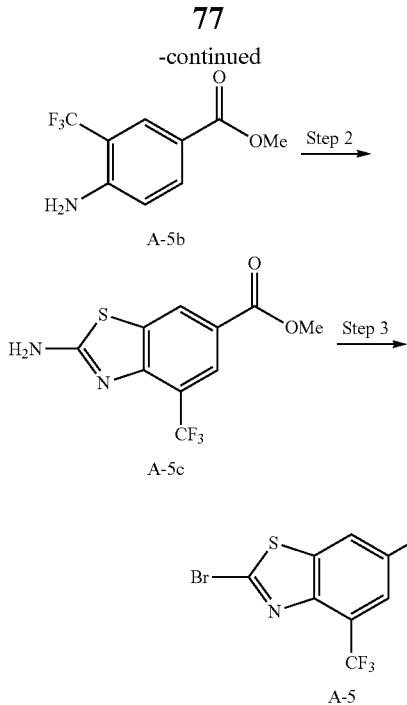

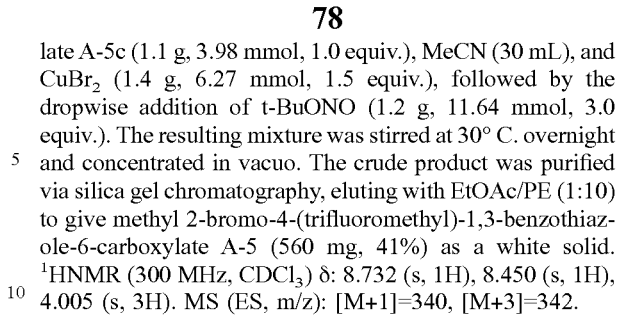

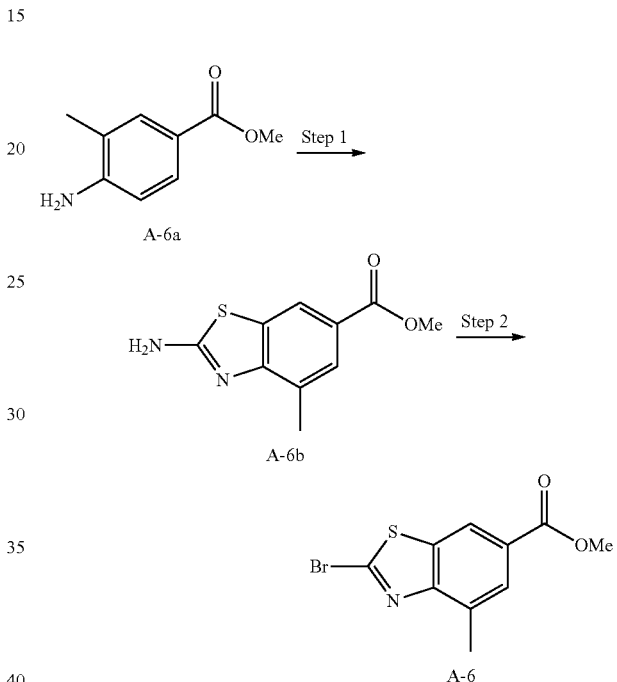

Step 1. Methyl 4-amino-3-(trifluoromethyl)benzoate (A-5b)

To a 250 mL round bottom flask was added 4-amino-3-(trifluoromethyl)benzoic acid A-5a (8 g, 39.0 mmol, 1.0 equiv.), THF (40 mL), MeOH (40 mL), and TMSCHN$_2$ (40 mL, 2.0 equiv.). The resulting mixture was stirred at room temperature overnight and then concentrated in vacuo. The crude product was purified via silica gel column chromatography, eluting with EtOAc:PE (1:5) to give methyl 4-amino-3-(trifluoromethyl)benzoate A-5b (7 g, 82%) as a colorless solid.

Step 2. Methyl 2-amino-4-(trifluoromethyl)-1,3-benzothiazole-6-carboxylate (A-5c)

To a 250 mL round-bottom flask was added methyl 4-amino-3-(trifluoromethyl)benzoate A-5b (2.2 g, 10.04 mmol, 1.0 equiv.), NaSCN (4.0 g, 49.34 mmol, 5.0 equiv.), and AcOH (50 mL), followed by the dropwise addition of bromine (3.2 g, 20.03 mmol, 2.0 equiv.) in AcOH (20 mL) at 0° C. over 1 h. The reaction mixture was stirred for 1 h at 0° C., then overnight at 40° C. NaSCN (4.1 g, 50.57 mmol, 5.0 equiv.) was added at 0° C., followed by the addition of bromine (3.2 g, 20.03 mmol, 2.0 equiv.) in AcOH (20 mL) over 1 h period. The reaction was stirred at 0° C. for 1 h, then at 40° C. for 5 days. The resulting mixture was diluted with of water (100 mL) and the pH of the resulting solution was adjusted to 9 using sodium hydroxide. The solids were collected by filtration, washed with water (20 ml×2), and dried in an oven at 60° C. for 6 h to provide 1.3 g (47%) of methyl 2-amino-4-(trifluoromethyl)-1,3-benzothiazole-6-carboxylate A-5c (1.3 g, 47%) as a brown solid. The product was carried on to the next step without further purification.

Step 3. Methyl 2-bromo-4-(trifluoromethyl)-1,3-benzothiazole-6-carboxylate (A-5)

To a 100 mL round bottom flask was added methyl 2-amino-4-(trifluoromethyl)-1,3-benzothiazole-6-carboxylate A-5c (1.1 g, 3.98 mmol, 1.0 equiv.), MeCN (30 mL), and CuBr$_2$ (1.4 g, 6.27 mmol, 1.5 equiv.), followed by the dropwise addition of t-BuONO (1.2 g, 11.64 mmol, 3.0 equiv.). The resulting mixture was stirred at 30° C. overnight and concentrated in vacuo. The crude product was purified via silica gel chromatography, eluting with EtOAc/PE (1:10) to give methyl 2-bromo-4-(trifluoromethyl)-1,3-benzothiazole-6-carboxylate A-5 (560 mg, 41%) as a white solid. $^1$HNMR (300 MHz, CDCl$_3$) δ: 8.732 (s, 1H), 8.450 (s, 1H), 4.005 (s, 3H). MS (ES, m/z): [M+1]=340, [M+3]=342.

Example 6: Intermediate A-6. Methyl 2-bromo-4-methyl-1,3-benzothiazole-6-carboxylate

Step 1. Methyl 2-amino-4-methyl-1,3-benzothiazole-6-carboxylate (A-6b)

To a 500 mL round-bottom flask was added methyl 4-amino-3-methylbenzoate A-6a (10.0 g, 60.54 mmol, 1.0 equiv.), AcOH (200 mL), and NaSCN (19.6 g, 4.0 equiv.), followed by the dropwise addition of bromine (9.7 g, 60.70 mmol, 1.0 equiv.) in AcOH (100 mL) at 0° C. The resulting mixture was stirred at 30° C. for 16 h and then quenched with ice water (500 mL). The pH value of the solution was adjusted to 9 using sodium hydroxide. The aqueous mixture was extracted with ethyl acetate (500 mL×3), and the combined organic layers were washed with brine (500 mL×3), dried over anhydrous sodium sulfate, filtered, and concentrated in vacuo to afford methyl 2-amino-4-methyl-1,3-benzothiazole-6-carboxylate A-6b (15 g) as a yellow solid. The product was carried on to the next step without further purification.

Step 2. Methyl 2-bromo-4-methyl-1,3-benzothiazole-6-carboxylate

To a 500 mL round-bottom flask was added methyl 2-amino-4-methyl-1,3-benzothiazole-6-carboxylate A-6b (15 g, 67.49 mmol, 1.0 equiv.), CH₃CN (200 mL), t-BuONO (20 g, 2.26 equiv.), and CuBr₂ (22.4 g, 1.5 equiv.). The resulting mixture was stirred for 16 h at 50° C. The reaction mixture was concentrated in vacuo and the resulting residue was purified by silica gel column chromatography eluting with ethyl acetate/petroleum ether (1:3) to yield methyl 2-bromo-4-methyl-1,3-benzothiazole-6-carboxylate A-6 (15.2 g, 79%) as a yellow solid.

Example 7: Intermediate A-7. Methyl 2-bromo-4-cyclopropyl-1,3-benzothiazole-6-carboxylate

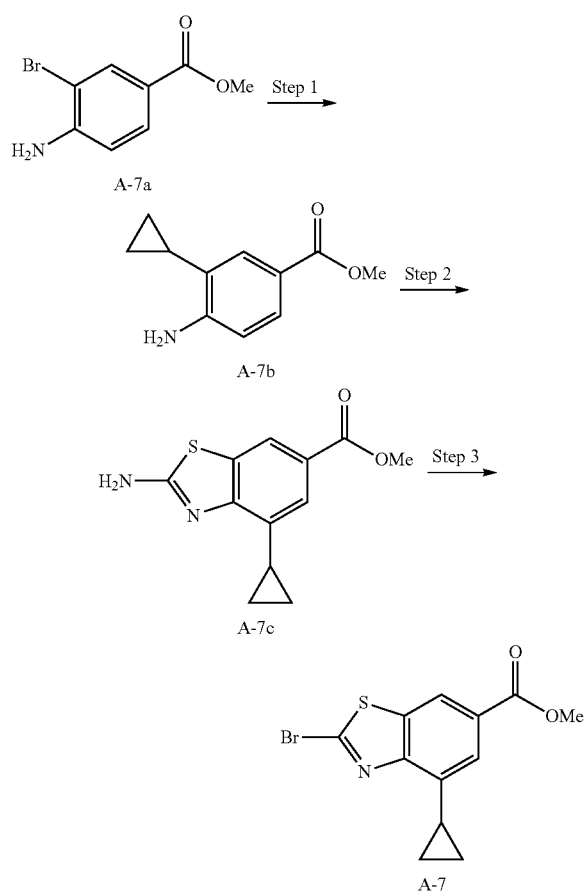

Step 1. Methyl 4-amino-3-cyclopropylbenzoate (A-7b)

To a 1 L round-bottom flask, purged and maintained under an inert atmosphere of nitrogen, was added methyl 4-amino-3-bromobenzoate A-7a (25 g, 108.67 mmol, 1.0 equiv.), K₃PO₄ (65 g, 306.21 mmol, 2.82 equiv.), toluene (50 mL), water (100 mL), P(Cy)₃ (2.8 g, 0.05 equiv.), Pd(OAc)₂ (2.25 g, 10.02 mmol, 0.09 equiv.), and cyclopropyl boronic acid (26 g, 302.69 mmol, 2.79 equiv.). The resulting mixture was heated at 100° C. overnight. The resulting solids were removed by filtration. The filtrate was diluted with H₂O (200 mL) and extracted with ethyl acetate (200 mL×3). The combined organic layers were concentrated in vacuo and the resulting residue was purified via silica gel column chromatography eluting with EtOAc/PE (1:20 to 1:10 and to 1:5) to provide methyl 4-amino-3-cyclopropylbenzoate A-7b (19.9 g, 96%) as a light brown solid.

Step 2. Methyl 2-amino-4-cyclopropyl-1,3-benzothiazole-6-carboxylate (A-7c)

To a 500 mL round-bottom flask was added methyl 4-amino-3-cyclopropylbenzoate A-7b (16 g, 83.67 mmol, 1.0 equiv.), AcOH (200 mL) and NaSCN (27.13 g, 334.64 mmol, 4.0 equiv.). and the resulting mixture was stirred for 0.5 h at 5-10° C. A solution of bromine (13.3 g, 83.22 mmol, 0.99 equiv.) in AcOH (100 mL) was then added dropwise at 0-5° C. and the resulting mixture was stirred at 0-5° C. for 10 min, then at 30° C. overnight. H₂O was added (1500 mL) and the pH of the solution was adjusted to 8-9 using potassium carbonate. The resulting solids were collected by filtration and dried in an oven under reduced pressure to afford methyl 2-amino-4-cyclopropyl-1,3-benzothiazole-6-carboxylate A-7c (24 g) as an orange solid. The product was carried on to the next step without further purification.

Step 3. Methyl 2-bromo-4-cyclopropyl-1,3-benzothiazole-6-carboxylate (A-7)

To a 500 mL round-bottom flask was added methyl 2-amino-4-cyclopropyl-1,3-benzothiazole-6-carboxylate A-7c (12 g, 48.33 mmol, 1.0 equiv.), CH₃CN (200 mL), and CuBr₂ (16.19 g), followed by the dropwise addition of tert-BuONO (11.26 g). The resulting mixture was stirred at 30° C. for 12 hours and concentrated in vacuo. The crude product was purified via silica gel column chromatography, eluting with EtOAc:PE (1:20 to 1:10, and then 1:5) to provide methyl 2-bromo-4-cyclopropyl-1,3-benzothiazole-6-carboxylate A-7 (11.2 g, 74%) as a light yellow solid. ¹HNMR (300 MHz, CDCl₃) δ: 8.33 (d, J=1.6 Hz, 1H), 7.60 (d, J=1.6 Hz, 1H), 3.97 (s, 3H), 2.82 (tt, J=8.5, 5.2 Hz, 1H), 1.32-1.12 (m, 2H), 1.05-0.93 (m, 2H). MS (ES, m/z): [M+1]=312.

Example 8: Intermediate A-8. tert-Butyl 6-bromo-1-methyl-1H-indole-3-carboxylate

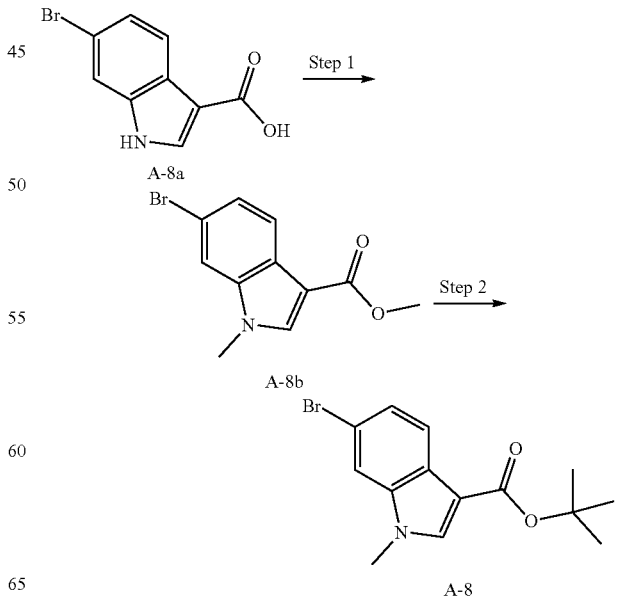

Step 1. Methyl 6-bromo-1-methyl-1H-indole-3-carboxylate (A-8b)

To a 250 mL round bottom flask was added 6-bromo-1H-indole-3-carboxylic acid A-8a (5 g, 20.83 mmol, 1.0 equiv.), N,N-dimethylformamide (150 mL), MeI (5.9 g), and sodium hydride (3.5 g, 60% in mineral oil, 145.83 mmol, 7.0 equiv.). The resulting mixture was stirred at 10-25° C. for 1 h and then diluted with $H_2O$ (1500 mL). The aqueous mixture was extracted with ethyl acetate (200 mL×3) and the combined organic layers were dried over anhydrous magnesium sulfate, filtered and concentrated in vacuo. The crude product was purified by re-crystallization from PE. The solids were collected by filtration to yield methyl 6-bromo-1-methyl-1H-indole-3-carboxylate A-8b (3.5 g, 63%) as a light yellow solid.

Step 2. tert-Butyl 6-bromo-1-methyl-1H-indole-3-carboxylate (A-8)

To a 250 mL round-bottom flask was added methyl 6-bromo-1-methyl-1H-indole-3-carboxylate (2 g, 7.46 mmol, 1.0 equiv.), toluene (100 mL), and sodium-tert-butyloxide (3.6 g, 37.46 mmol, 5.02 equiv.) and the resulting mixture was stirred at 110° C. overnight. The resulting mixture was cooled to RT and diluted with $H_2O$ (200 mL). The aqueous mixture was extracted with ethyl acetate (200 mL×3) and the combined organic layers were dried over anhydrous sodium sulfate, filtered, and concentrated in vacuo to provide tert-butyl 6-bromo-1-methyl-1H-indole-3-carboxylate A-8 (2.1 g, 91%) as a light yellow solid.

Example 9: Intermediate A-9. tert-Butyl 4-bromo-3-fluorobenzoate

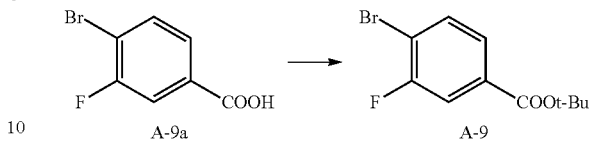

To a 250 mL round-bottom flask was added 4-bromo-3-fluorobenzoic acid A-9a (10 g, 45.66 mmol, 1.0 equiv.), 4-dimethylaminopyridine (560 mg, 4.58 mmol, 0.1 equiv.), di-tert-butyl dicarbonate (14.9 g, 68.27 mmol, 1.5 equiv.), and tert-butanol (100 mL). The resulting mixture was stirred at 50° C. overnight and $H_2O$ (200 mL) was then added. The aqueous mixture was extracted with ethyl acetate (200 mL×2). The combined organic layers were washed with brine (200 mL×2), dried over anhydrous sodium sulfate, filtered, and concentrated in vacuo. The crude product was purified by Flash-Prep-HPLC using the following conditions: Column, silica gel; mobile phase, eluting with PE:EtOAc, 100:0 to 92:8 within 5 min; Detector, UV 254 nm, providing of tert-butyl 4-bromo-3-fluorobenzoate A-9 (6.5 g, 52%) as colorless oil. $^1$HNMR (300 MHz, DMSO-$d_6$) δ: 7.94-7.81 (m, 1H), 7.82-7.61 (m, 2H), 1.56 (s, 9H).

The Intermediates in Table 1 below were synthesized according to the procedures outlined above for Example 9, Intermediate A-9, using the appropriate synthetic precursors.

TABLE 1

| | Preparation of intermediates A-10 to A-15 | |
|---|---|---|
| Intermediate No.: | Structure | $^1$HNMR |
| A-10 | Br-, Cl-, COOtBu substituted benzene | $^1$HNMR (400 MHz, Methanol-$d_4$) δ: 8.01 (q, J = 2.2 Hz, 1H), 7.76 (dddd, J = 10.7, 8.4, 4.4, 2.5 Hz, 2H), 1.59 (s, 9H) |
| A-11 | Br-, CF$_3$, COOtBu substituted benzene | $^1$HNMR (400 MHz, DMSO-$d_6$) δ: 7.85-7.76 (m, 2H), 7.60 (ddd, J = 9.0, 2.4, 1.3 Hz, 1H), 1.52 (s, 9H). |
| A-12 | Br-, F$_3$C-, COOt-Bu substituted benzene | $^1$HNMR (300 MHz, DMSO-$d_6$) δ: 8.13 (d, J = 2.0 Hz, 1H), 8.02 (dt, J = 2.6, 1.2 Hz, 2H), 1.55 (d, J = 1.1 Hz, 9H). |
| A-13 | Br-, OCH$_3$, COOt-Bu substituted benzene | $^1$HNMR (300 MHz, DMSO-$d_6$) δ: 7.51 (d, J = 8.2 Hz, 1H), 7.33 (d, J = 1.8 Hz, 1H), 7.20 (dd, J = 8.2, 1.8 Hz, 1H), 3.85 (s, 3H), 1.51 (s, 9H). |
| A-14 | Br-, H$_3$CO-, COOt-Bu substituted benzene | $^1$HNMR (300 MHz, DMSO-$d_6$) δ: 7.72 (d, J = 8.2 Hz, 1H), 7.57-7.33 (m, 2H), 3.92 (s, 3H), 1.55 (s, 9H). |

TABLE 1-continued

Preparation of intermediates A-10 to A-15

| Intermediate No.: | Structure | ¹HNMR |
|---|---|---|
| A-15 | 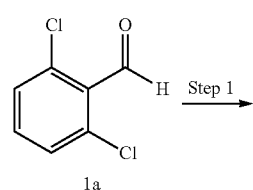 | |

Example 10: Methyl 2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1,3-benzothiazole-6-carboxylate (I-1)

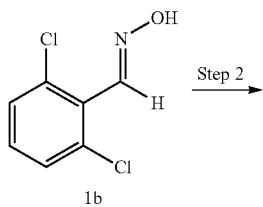

1a

Step 1

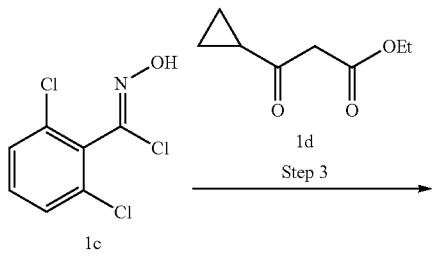

1b

Step 2

1c

Step 3

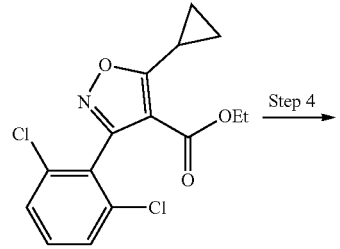

1e

Step 4

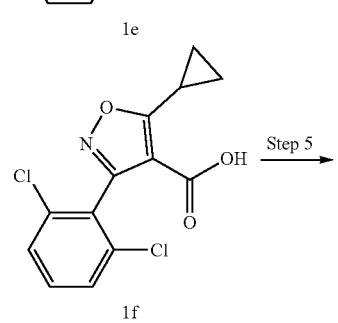

1f

Step 5

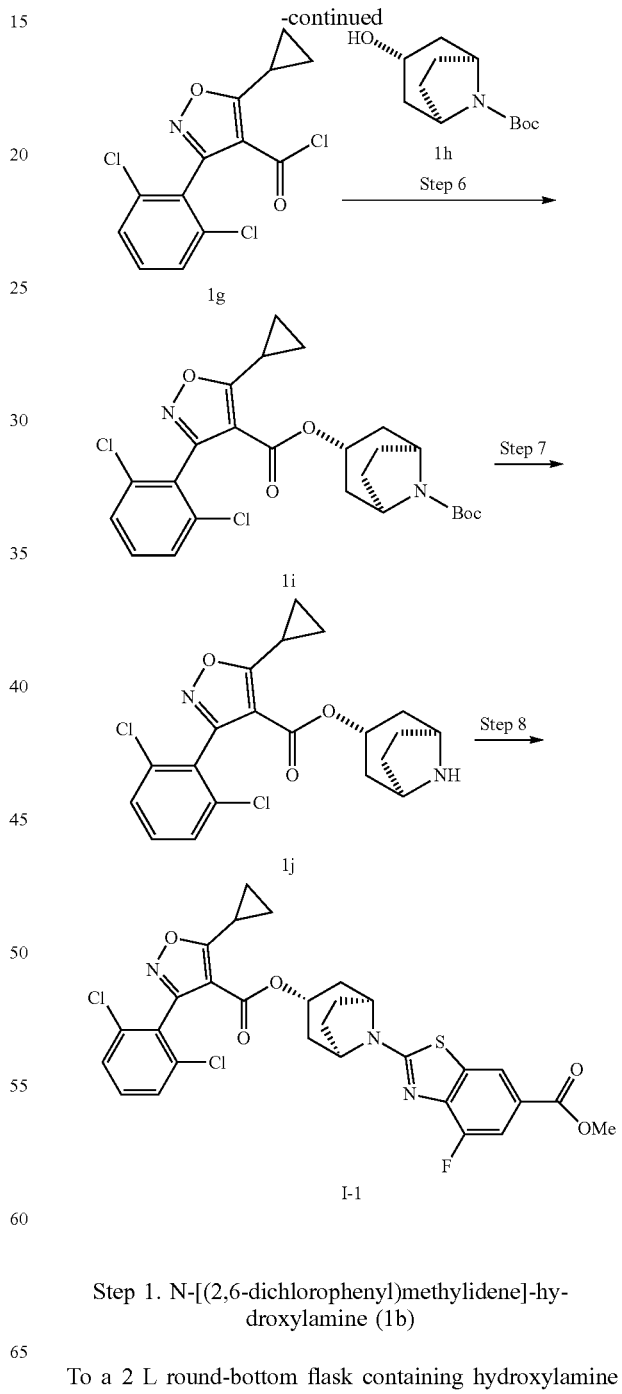

Step 1. N-[(2,6-dichlorophenyl)methylidene]-hydroxylamine (1b)

To a 2 L round-bottom flask containing hydroxylamine hydrochloride (108 g, 1.55 mol, 1.3 equiv.), sodium hydroxide (60 g, 1.50 mol, 1.3 equiv.), and water (200 mL) was added 2,6-dichlorobenzaldehyde 1a (200 g, 1.14 mol, 1.0 equiv.), followed by ethanol (500 mL) at 0° C. The resulting mixture was stirred at 90° C. overnight and then concentrated in vacuo. The resulting solids were collected by filtration and dried in an oven under reduced pressure, providing N-[(2,6-dichlorophenyl)methylidene]-hydroxylamine 1b (210 g, 97%) as an off-white solid. The product was carried onto the next step without further purification.

Step 2.
2,6-dichloro-N-hydroxylbenzene-1-carbonimidoyl chloride (1c)

To a 1 L round-bottom flask was added N-[(2,6-dichlorophenyl) methylidene]hydroxylamine 1b (60 g, 315.74 mmol, 1.0 equiv.), N,N-dimethylformamide (250 mL), and N-chlorosuccinimide (42.5 g, 318.28 mmol, 1.0 equiv.). The resulting mixture was stirred for 2 h at RT and then quenched by with ice/brine (500 mL). The aqueous mixture was extracted with EtOAc (1 L×3). The combined organic layers were washed with brine (1 L×3), and concentrated in vacuo to give 2,6-dichloro-N-hydroxylbenzene-1-carbonimidoyl chloride 1c (68 g, 96%) as a white solid. The product was carried onto the next step without further purification.

Step 3. Ethyl 5-cyclopropyl-3-(2,6-dichlorophenyl)-1,2-oxazole-4-carboxylate (1e)

To a 1 L round bottom flask was added 2,6-dichloro-A-hydroxybenzene-1-carbonimidoyl chloride 1c (68 g, 302.93 mmol, 1.0 equiv.), triethylamine (500 mL), and ethyl 3-cyclopropyl-3-oxopropanoate 1d (71.3 g, 456.53 mmol, 1.5 equiv.). The resulting mixture was stirred for 16 h at RT and then quenched with ice/brine (1 L). The aqueous mixture was extracted with ethyl acetate (1 L×3) and the combined organic layers were washed with brine (1 L×3), dried over anhydrous sodium sulfate, filtered, and concentrated in vacuo to afford ethyl 5-cyclopropyl-3-(2,6-dichlorophenyl)-1,2-oxazole-4-carboxylate 1e (118 g) as a yellow oil. The product was carried on to the next step without further purification. MS (ES, m/z) [M+1]=325.90.

Step 4. 5-Cyclopropyl-3-(2,6-dichlorophenyl)-1,2-oxazole-4-carboxylic acid (1f)

To a 1 L round-bottom flask was added ethyl 5-cyclopropyl-3-(2,6-dichlorophenyl)-1,2-oxazole-4-carboxylate 1e (52 g, 159.42 mmol, 1.0 equiv.), ethanol (300 mL), water (150 mL), and LiOH (67 g, 2.80 mol, 10.0 equiv.). The resulting mixture was heated at 50° C. for 16 h, and then concentrated in vacuo. The resulting residue was dissolved in H$_2$O (500 mL) and the pH of the solution was adjusted to 9 using HCl (3 M). The aqueous mixture was extracted with of ethyl acetate (500 mL×5) and the combined organic layers were dried over anhydrous sodium sulfate, filtered, and concentrated in vacuo. The resulting residue was purified via silica gel column chromatography eluting with EtOAc:PE (1:1, v/v) to afford 5-cyclopropyl-3-(2,6-dichlorophenyl)-1,2-oxazole-4-carboxylic acid 1f (26 g, 55%) as a yellow solid. $^1$HNMR (300 MHz, CDCl$_3$) δ: 13.09 (s, 1H), 7.69-7.47 (m, 3H), 2.91 (tt, J=8.2, 5.1 Hz, 1H), 1.41-1.14 (m, 4H). MS (ES, m/z): [M+1]=297.90.

Step 5. 5-Cyclopropyl-3-(2,6-dichlorophenyl)-1,2-oxazole-4-carbonyl chloride (1g)

To a 250 mL round-bottom flask was added 5-cyclopropyl-3-(2,6-dichlorophenyl)-1,2-oxazole-4-carboxylic acid 1f (3 g, 10.06 mmol), thionyl chloride (20 mL), and N,N-dimethylformamide (0.06 mL). The resulting mixture was stirred overnight at 60° C. in an oil bath and then was concentrated in vacuo to yield 5-cyclopropyl-3-(2,6-dichlorophenyl)-1,2-oxazole-4-carbonyl chloride 1g (3.1 g, 97%) as a light yellow oil. The product was carried onto the next step without further purification.

Step 6. tert-Butyl (1R,3S,5S)-3-[[5-cyclopropyl-3-(2,6-dichlorophenyl)-1,2-oxazol-4-yl]carbonyloxy]-8-azabicyclo[3.2.1]octane-8-carboxylate (1i)

To a stirred solution of tert-butyl (1R,3R,5S)-3-hydroxy-8-azabicyclo[3.2.1]octane-8-carboxylate 1 h (2.57 g, 11.31 mmol, 3.0 equiv.) in dichloromethane (10 mL) was added 4-dimethylaminopyridine (160 mg, 1.31 mmol, 0.4 equiv.) and triethylamine (950 mg, 9.39 mmol, 3.0 equiv.). A solution of 5-cyclopropyl-3-(2,6-dichlorophenyl)-1,2-oxazole-4-carbonyl chloride 1g (3.1 g, 9.79 mmol, 1.0 equiv.) in dichloromethane (3 mL) was added at 0° C. The reaction mixture was stirred overnight at 30° C. and then quenched with sodium bicarbonate (aq., 5 mL). The aqueous mixture was extracted with dichloromethane (100 mL), and the combined organic layers were washed with brine (20 mL×2), dried over anhydrous sodium sulfate, filtered, and concentrated in vacuo. This crude product was purified via silica gel column chromatography eluting with EtOAc:PE (1:5, v/v) to provide tert-butyl (1R,3S,5S)-3-[[5-cyclopropyl-3-(2,6-dichlorophenyl)-1,2-oxazol-4-yl]carbonyloxy]-8-azabicyclo[3.2.1]octane-8-carboxylate 1i (3.2 g, 64%) as a yellow oil. The product was carried onto the next step without further purification.

Step 7. (1R,3R,5S)-8-azabicyclo[3.2.1]octan-3-yl 5-cyclopropyl-3-(2,6-dichlorophenyl)-1,2-oxazole-4-carboxylate (1j)

To a solution of tert-butyl (1R,3R,5S)-3-[[5-cyclopropyl-3-(2,6-dichlorophenyl)-1,2-oxazol-4-yl]carbonyloxy]-8-azabicyclo[3.2.1]octane-8-carboxylate 1i (3.2 g, 6.31 mmol, 1.0 equiv.) in dichloromethane (30 mL) was added 5 mL of trifluoroacetic acid. The resulting mixture was stirred at RT for 1 h. Aqueous sodium bicarbonate solution was then added and the resulting mixture was extracted with dichloromethane (2×150 mL). The combined organic layers were washed with brine (2×100 mL), dried over anhydrous sodium sulfate, filtered, and concentrated in vacuo to afford (1R,3R,5S)-8-azabicyclo[3.2.1]octan-3-yl 5-cyclopropyl-3-(2,6-dichlorophenyl)-1,2-oxazole-4-carboxylate 1j (2.4 g, 93%) as a light yellow oil. The product was carried onto the next step without further purification.

Step 8. Methyl 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-fluoro-1,3-benzothiazole-6-carboxylate (I-1)

To a 100 mL round-bottom flask, purged and maintained under an inert atmosphere of nitrogen, was added (1R,3R,5S)-8-azabicyclo[3.2.1]octan-3-yl 5-cyclopropyl-3-(2,6-dichlorophenyl)-1,2-oxazole-4-carboxylate 1j (1.6 g, 3.93 mmol, 1.0 equiv.), methyl 2-bromo-4-fluoro-1,3-benzothiazole-6-carboxylate A-1 (1.4 g, 4.83 mmol, 1.2 equiv.), Cs$_2$CO$_3$ (2.6 g, 7.98 mmol, 2.0 equiv.), and dimethylacetamide (40 mL). The reaction mixture was stirred overnight at 60° C. and the pH value of the resulting solution was adjusted to 6 using HCl (1M). The resulting aqueous mixture was extracted with ethyl acetate (200 mL×2) and the combined organic layers were washed with brine (20 mL×3), dried over anhydrous sodium sulfate, filtered, and concentrated in vacuo. The residue was purified via silica gel column chromatography eluting with ethyl acetate/petroleum ether (1:1, v/v) to give methyl 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-fluoro-1,3-benzothiazole-6-carboxylate I-1 as a light yellow oil. This product was further purified by Prep-HPLC using the following conditions: XBridge C18 OBD Prep Column (19 mm×250 mm); mobile phase: water (0.05% TFA) and ACN (80.0% ACN up to 90.0% in 8 min); detector, UV 254 nm. The title compound I-1 (2.1 g, 87%) was obtained as a colorless solid. $^1$H-NMR (300 MHz, CD$_3$OD) δ: 8.116 (1H, m), 7.650 (1H, m), 7.479 (3H, m), 5.110 (1H, m), 4.278 (2H, m), 3.869 (3H, m), 3.008 (1H, m), 2.293 (2H, m), 1.860 (4H, m), 1.417 (2H, m), 1.335 (4H, m). MS (ES, m/z): [M+1]=616.0.

Example 11: 2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1,3-benzothiazole-6-carboxylic acid (I-2)

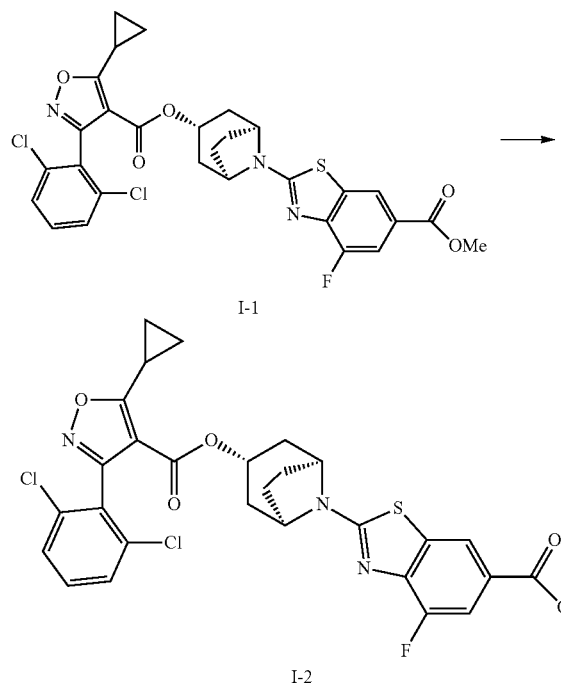

To a 250 mL round bottom flask was added methyl 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-fluoro-1,3-benzothiazole-6-carboxylate I-1 (6.2 g, 10 mmol, 1.0 equiv.), lithium iodide (13.4 g, 10.0 equiv.). and pyridine (60 mL) and the resulting mixture was heated at 125° C. for 40 h with stirring. After cooling to RT, the mixture was quenched with water/ice (100 mL) and the pH of the aqueous mixture was adjusted to 3-4 using HCl. The acidic mixture was extracted with ethyl acetate (2×100 mL) and the combined organic layers were washed with brine (2×100 mL), dried over anhydrous sodium sulfate, filtered, and concentrated in vacuo. The crude product was purified by Prep-HPLC using the following conditions: XSelect CSH Prep C18 OBD Column (5 µm, 19×150 mm); mobile phase: water (0.05% TFA) and ACN (70.0% to 90.0% CAN in 8 min); detector, UV 254 nm to provide 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-fluoro-1,3-benzothiazole-6-carboxylic acid I-2 (2.2 g, 36%) as an off-white solid. $^1$HNMR (300 MHz, DMSO-d$_6$) δ: 12.98 (s, 1H), 8.23 (d, J=1.5 Hz, 1H), 7.75-7.54 (m, 4H), 5.09 (t, J=5.4 Hz, 1H), 3.33 (s, 1H), 2.95 (tt, J=8.0, 5.3 Hz, 1H), 2.29 (dt, J=15.6, 4.5 Hz, 2H), 1.83 (dt, J=6.5, 2.8 Hz, 2H), 1.77-1.64 (m, 2H), 1.44-1.26 (m, 6H). MS (ES, m/z): [M+1]=602.0.

Example 12: (1R,3R,5S)-8-(6-carbamoyl-4-fluoro-1,3-benzothiazol-2-yl)-8-azabicyclo[3.2.1]octan-3-yl 5-cyclopropyl-3-(2,6-dichlorophenyl)-1,2-oxazole-4-carboxylate (I-3)

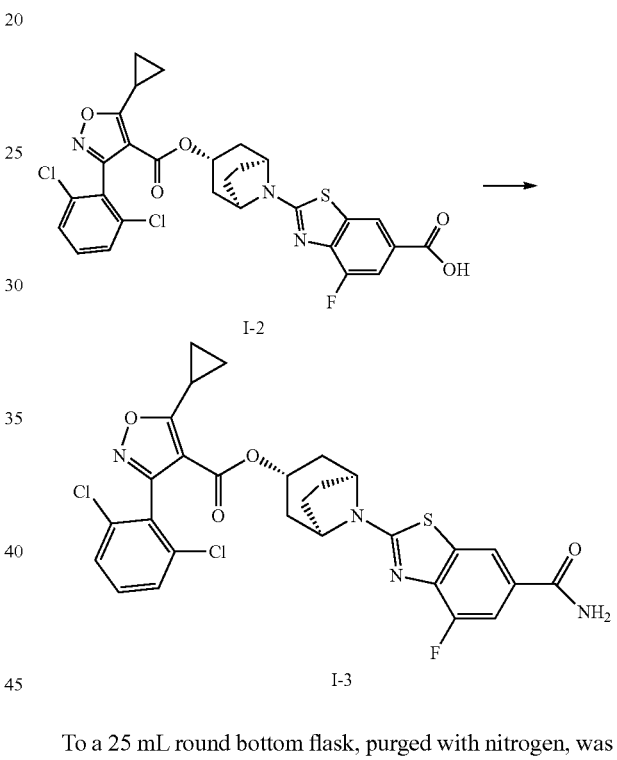

To a 25 mL round bottom flask, purged with nitrogen, was added 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-fluoro-1,3-benzothiazole-6-carboxylic acid I-2 (60 mg, 0.10 mmol, 1.0 equiv.), NH$_4$Cl (10.5 mg, 0.20 mmol, 2.0 equiv.), N,N-dimethylformamide (2 mL), BOP (53 mg, 1.3 equiv.), and DIEA (39 mg, 0.30 mmol, 3.0 equiv.). The resulting mixture was stirred at room temperature for 2 h and then extracted with ethyl acetate (30 mL×3). The combined organic layers were washed with brine (20 mL), dried over anhydrous sodium sulfate, filtered, and concentrated in vacuo. The crude product was purified by Prep-HPLC using the following conditions: XBridge C18 OBD Prep Column (19 mm×250 mm); mobile phases: water (0.05% TFA) and ACN (65.0% to 78.0% CAN over 8 min); detector, UV 220 nm provide I-3 (57.4 mg, 96%) as an off-white solid. $^1$HNMR (300 MHz, CD$_3$OD) δ: 7.99 (d, J=1.6 Hz, 1H), 7.62-7.45 (m, 4H), 5.11 (t, J=5.4 Hz, 1H), 4.27 (s, 2H), 2.42-2.28 (m, 2H), 2.00 (s, 1H), 1.90-1.71 (m, 4H), 1.47-1.23 (m, 6H). MS (ES, m/z): [M+1]=601.15.

Example 13: 2-({2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1,3-benzothiazol-6-yl}formamido) acetic acid

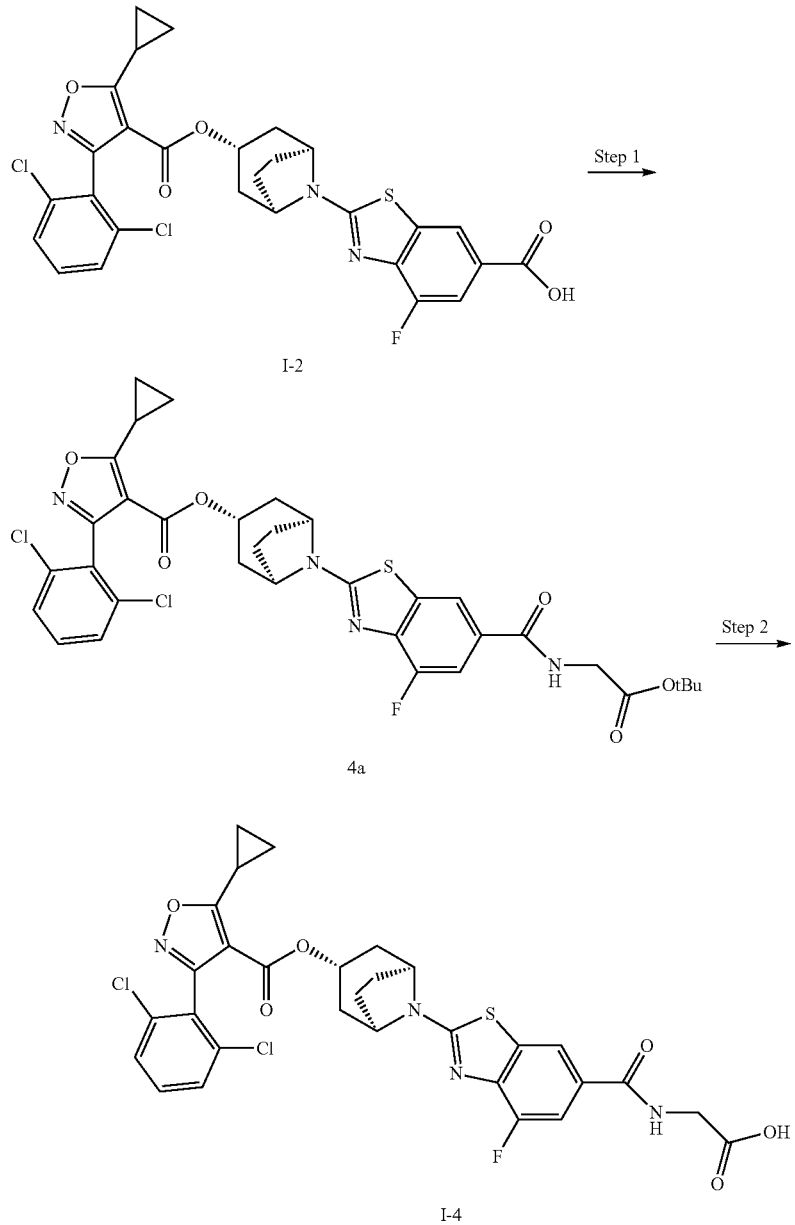

Step 1. (1R,3R,5S)-8-(6-[[2-(tert-Butoxy)-2-oxoethyl]carbamoyl]-4-fluoro-1,3-benzothiazol-2-yl)-8-azabicyclo[3.2.1]octan-3-yl 5-cyclopropyl-3-(2,6-dichlorophenyl)-1,2-oxazole-4-carboxylate (4a)

To a 8 mL sealed tube was added 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-fluoro-1,3-benzothiazole-6-carboxylic acid (I-2, 80 mg, 0.13 mmol, 1.0 equiv.), HATU (91.2 mg, 0.24 mmol, 1.8 equiv.), DIEA (69 mg, 0.53 mmol, 4.0 equiv.), tert-butyl 2-aminoacetate hydrochloride (44 mg, 0.26 mmol, 2.0 equiv.), and N,N-dimethylformamide (2 mL). The resulting mixture was stirred overnight at 30° C. H₂O (30 mL) was then added and the aqueous mixture was extracted with ethyl acetate (100 mL×2). The combined organic layers were washed with brine (100 mL×2), dried over anhydrous sodium sulfate, filtered, and concentrated in vacuo. The residue was purified via silica gel column chromatography eluting with EtOAc:PE ether (1:4) to give (1R,3R,5S)-8-(6-[[2-(7c/7-butoxy)-2-oxoethyl]carbamoyl]-4-fluoro-1,3-benzothiazol-2-yl)-8-azabicyclo[3.2.1]octan-3-yl 5-cyclopropyl-3-(2,6-dichlorophenyl)-1,2-oxazole-4-carboxylate 4a (0.09 g, 95%) as a yellow solid.

Step 2. 2-({2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1,3-benzothiazol-6-yl} formamido)acetic acid (I-4)

To a 25 mL round-bottom flask was added (1R,3R,5S)-8-(6-[[2-(tert-butoxy)-2-oxoethyl]carbamoyl]-4-fluoro-1,3-benzothiazol-2-yl)-8-azabicyclo[3.2.1]octan-3-yl 5-cyclopropyl-3-(2,6-dichlorophenyl)-1,2-oxazole-4-carboxylate 4a (90 mg, 0.13 mmol, 1.0 equiv.), trifluoroacetic acid (4 mL) and dichloromethane (8 mL). The resulting mixture was stirred for 30 min at RT, and quenched with brine (20 mL). The aqueous mixture was extracted with dichloromethane (50 mL×2) and the combined organic layers were dried over anhydrous sodium sulfate, filtered, and concentrated in vacuo. The crude product was purified by Prep-HPLC using the following conditions: XBridge Shield RP18 OBD Column (5 μm, 19×150 mm); mobile phase: water (0.05% NH$_3$) and ACN (35.0% to 60.0% over 8 min); detector, UV 254 nm to provide 2-({2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1,3-benzothiazol-6-yl}formamido)acetic acid I-4 (24.7 mg, 30%) as a colorless solid. $^1$HNMR (300 MHz, MeOH-A) δ: 8.03 (d, J=1.6 Hz, 1H), 7.67-7.50 (m, 5H), 5.17 (s, 1H), 4.32 (s, 3H), 4.05 (s, 2H), 2.42 (s, 2H), 1.93-1.76 (m, 5H), 1.50-1.33 (m, 7H). MS (ES, m/z): [M+1]=659.

Example 14: 2-({2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1,3-benzothiazol-6-yl}formamido)ethane-1-sulfonic acid (I-5)

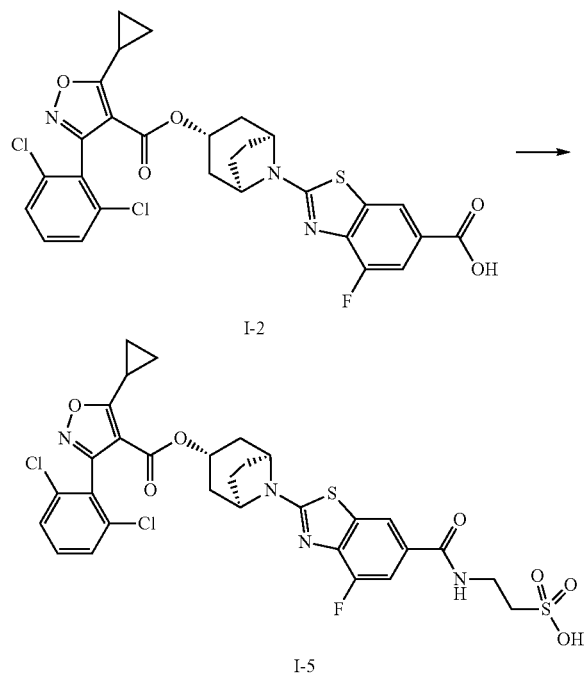

I-2

I-5

To a 25 mL round-bottom flask, purged and maintained under an inert atmosphere of nitrogen, was added 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-fluoro-1,3-benzothiazole-6-carboxylic acid I-2 (100 mg, 0.17 mmol, 1.0 equiv.), PyBOP (125 mg, 0.24 mmol, 1.3 equiv.), N,N-dimethylformamide (2 mL), DIEA (110 mg, 0.85 mmol, 4.0 equiv.), and 2-aminoethane-1-sulfonic acid (35 mg, 0.28 mmol, 1.5 equiv.). The resulting mixture was stirred for 2.5 h at 80° C. then cooled to RT, and quenched with water. The aqueous mixture was extracted with ethyl acetate (30 mL×3) and the combined organic layers were washed with brine (30 mL), dried over anhydrous sodium sulfate, filtered, and concentrated in vacuo. The crude product was purified by Prep-HPLC using the following conditions: XBridge Prep C18 OBD Column (19×150 mm 5 μm); mobile phases: Water (0.05% TFA) and ACN (48.0% to 62.0% over 8 min); detector, UV 254 nm to provide 2-([2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-fluoro-1,3-benzothiazol-6-yl]formamido) ethane-1-sulfonic acid I-5 (57.8 mg, 49%) as an off-white solid. $^1$HNMR (300 MHz, CD$_3$OD) δ: 7.59 (dt, J=11.0, 5.7 Hz, 4H), 5.17 (s, 1H), 4.33 (s, 2H), 3.83 (s, 2H), 3.15-2.99 (m, 4H), 2.47-2.33 (m, 2H), 1.94-1.76 (m, 4H), 1.42 (dd, J=22.3, 7.3 Hz, 6H). MS (ES, m/z): [M+1]=709.15.

Example 15: (1R,3R,5S)-8-[4-fluoro-6-(methanesulfonylcarbamoyl)-1,3-benzothiazol-2-yl]-8-azabicyclo[3.2.1]octan-3-yl 5-cyclopropyl-3-(2,6-dichlorophenyl)-1,2-oxazole-4-carboxylate (I-6)

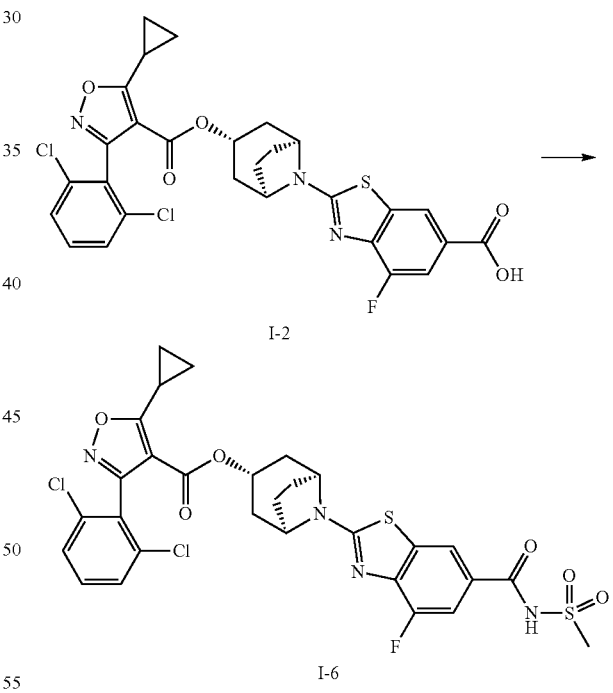

I-2

I-6

To a 8 mL sealed tube was added 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-fluoro-1,3-benzothiazole-6-carboxylic acid (I-2, 100 mg, 0.17 mmol, 1.0 equiv.), 4-dimethylaminopyridine (30.4 mg, 0.25 mmol, 1.5 equiv.), EDCI (48 mg, 0.25 mmol, 1.5 equiv.), methanesulfonamide (19 mg, 0.20 mmol, 1.2 equiv.), and N,N-dimethylformamide (2 mL). The resulting mixture was stirred overnight at RT and then quenched with brine. The aqueous mixture was extracted with ethyl acetate (20 mL×3), and the combined organic layers were dried over anhydrous sodium sulfate, filtered and concentrated in vacuo. The crude product which was purified by Prep-HPLC using the following conditions: Column, XBridge C18 OBD Prep Column, 19 mm×250 mm; mobile phase, water (0.05% TFA) and ACN (62.0% to 95.0% over 8 min); detector, UV 254 nm to provide (1R,3R,5S)-8-[4-fluoro-6-(methanesulfonylcarbamoyl)-1,3-benzothiazol-2-yl]-8-azabicyclo[3.2.1]octan-3-yl 5-cyclopropyl-3-(2,6-dichlorophenyl)-1,2-oxazole-4-carboxylate, I-6 (31.2 mg, 28%) as a colorless solid. ¹HNMR (300 MHz, Methanol-d₄) δ: 8.10 (d, J=1.7 Hz, 1H), 7.71-7.50 (m, 5H), 5.17 (s, 1H), 4.35 (s, 3H), 3.39 (s, 4H), 3.06 (t, J=6.7 Hz, 1H), 2.40 (d, J=15.3 Hz, 3H), 1.95-1.78 (m, 5H), 1.47 (d, J=7.8 Hz, 2H), 1.38 (d, J=6.8 Hz, 5H). MS (ES, m/z): [M+1]=679.

Example 16: 2-[(1R,3R,5S)-3-[5-cyclopropyl-3-(2,6-dichlorophenyl)-1,2-oxazole-4-carbonyloxy]-8-azabicyclo[3.2.1]octan-8-yl]-5-methoxy-1,3-benzothiazole-6-carboxylic acid (I-7)

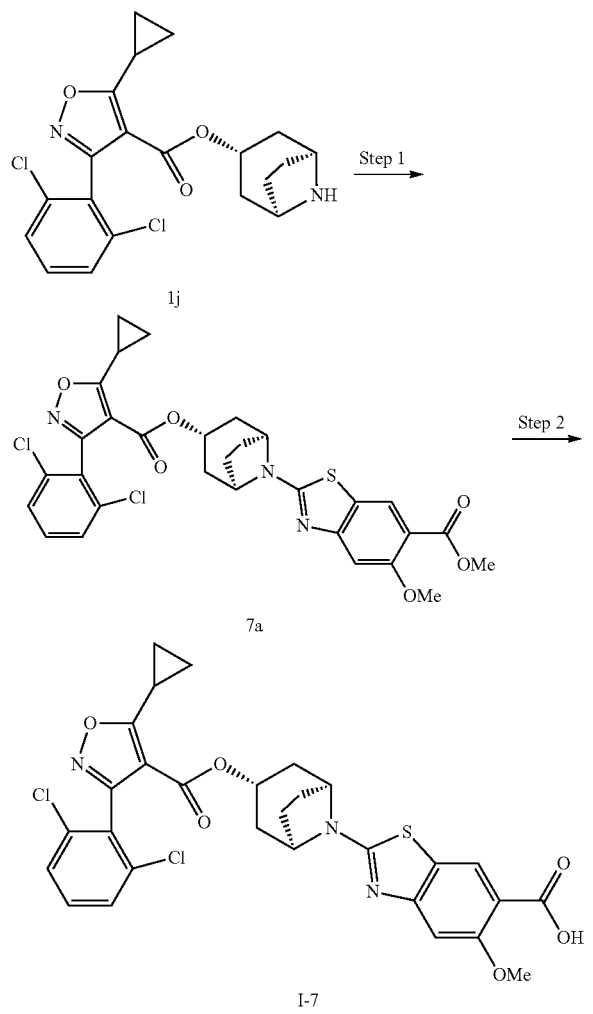

Step 1. Methyl 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-5-methoxy-1,3-benzothiazole-6-carboxylate (7a)

Methyl 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-5-methoxy-1,3-benzothiazole-6-carboxylate 7a (0.25 g, 81%) was obtained as yellow oil following the procedure outlined in Example 10, step 8, using intermediates (1R,3R,5S)-8-azabicyclo[3.2.1]octan-3-yl 5-cyclopropyl-3-(2,6-dichlorophenyl)-1,2-oxazole-4-carboxylate (200 mg, 0.49 mmol, 1.0 equiv.) 1j and methyl 2-bromo-5-methoxy-1,3-benzothiazole-6-carboxylate (178 mg, 0.59 mmol, 1.2 equiv.) A-2.

Step 2. 2-[(1R,3R,5S)-3-[[5-Cyclopropyl-3-(2,6-dichlorophenyl)-1,2-oxazol-4-yl]carbonyloxy]-8-azabicyclo[3.2.1]octan-8-yl]-5-methoxy-1,3-benzothiazole-6-carboxylic acid (I-7)

2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-5-methoxy-1,3-benzothiazole-6-carboxylic acid I-7 (19.5 mg, 13%) was obtained as a yellow solid following the procedure outlined in example Example 11, starting from methyl 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-5-methoxy-1,3-benzothiazole-6-carboxylate (7a, 150 mg, 0.24 mmol, 1.0 equiv.). ¹HNMR (400 MHz, Methanol-d₄) δ: 8.18 (s, 1H), 7.63-7.49 (m, 3H), 7.14 (s, 1H), 5.14 (t, J=5.3 Hz, 1H), 4.27 (s, 2H), 3.95 (s, 3H), 3.09-2.98 (m, 1H), 2.36 (dt, J=15.7, 4.8 Hz, 2H), 1.92-1.77 (m, 4H), 1.45 (t, J=7.1 Hz, 2H), 1.39-1.26 (m, 5H). MS (ES, m/z): [M+1]=614.

Example 17: 2-[(1R,3R,5S)-3-[5-Cyclopropyl-3-(2,6-dichlorophenyl)-1,2-oxazole-4-carbonyloxy]-8-azabicyclo[3.2.1]octan-8-yl]-4-methoxy-1,3-benzothiazole-6-carboxylic acid (I-8)

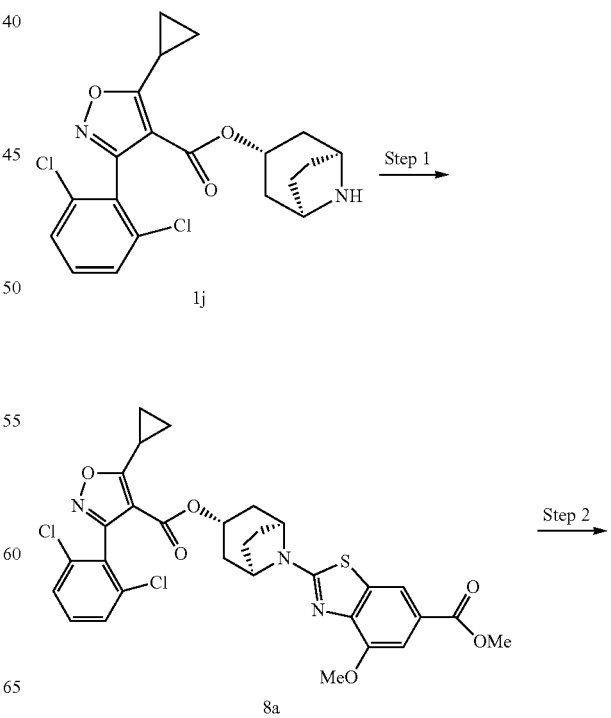

-continued

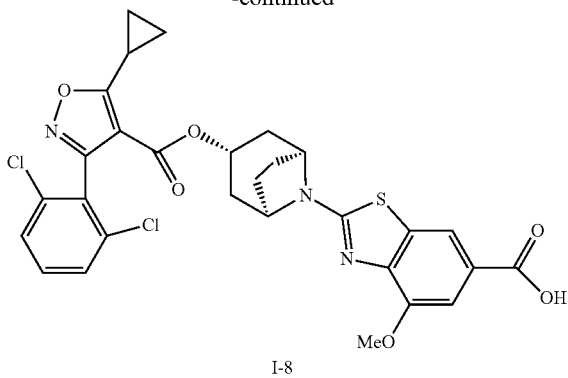

I-8

Step 1. Methyl 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-methoxy-1,3-benzothiazole-6-carboxylate (8a)

Methyl 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-methoxy-1,3-benzothiazole-6-carboxylate, 8a (190 mg, 49%) was obtained in as a light yellow solid following the procedure outlined in Example 10, step 8, from intermediates (1R,3R,5S)-8-azabicyclo[3.2.1]octan-3-yl 5-cyclopropyl-3-(2,6-dichlorophenyl)-1,2-oxazole-4-carboxylate 1j (250 mg, 0.61 mmol, 1.0 equiv.) and methyl 2-bromo-4-methoxy-1,3-benzothiazole-6-carboxylate A-3 (222.5 mg, 0.74 mmol, 1.2 equiv.).

Step 2. 2-[(1R,3R,5S)-3-[[5-Cyclopropyl-3-(2,6-dichlorophenyl)-1,2-oxazol-4-yl]carbonyloxy]-8-azabicyclo[3.2.1]octan-8-yl]-4-methoxy-1,3-benzothiazole-6-carboxylic acid (I-8)

2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-methoxy-1,3-benzothiazole-6-carboxylic acid I-8 (65 mg, 35%) was obtained as a colorless solid following the procedure outlined in Example 11, from intermediate 8a (190 mg, 0.30 mmol, 1.0 equiv.). $^1$HNMR (400 MHz, DMSO-$d_6$) δ: 7.97 (d, J=1.5 Hz, 1H), 7.74-7.56 (m, 4H), 7.36 (d, J=1.5 Hz, 1H), 5.05 (t, J=5.3 Hz, 1H), 4.18 (s, 2H), 3.87 (s, 3H), 2.93 (ddd, J=12.0, 8.4, 5.3 Hz, 1H), 2.25 (dt, J=15.3, 4.5 Hz, 2H), 1.82-1.74 (m, 2H), 1.65 (d, J=15.3 Hz, 2H), 1.40-1.25 (m, 6H), 1.25-1.11 (m, 1H). MS (ES, m/z): [M+1]=614.5.

Example 18: 2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-(trifluoromethoxy)-1,3-benzothiazole-6-carboxylic acid (I-9)

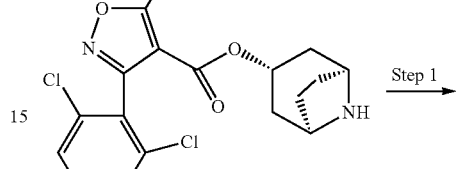

1j

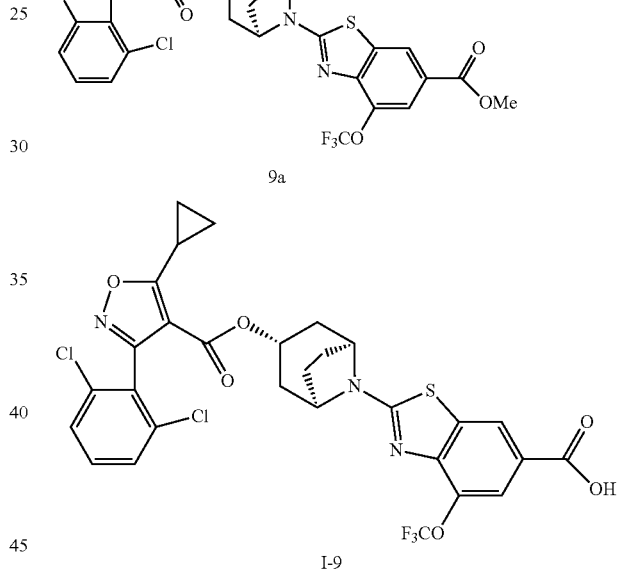

Step 1. Methyl 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-(trifluoromethoxy)-1,3-benzothiazole-6-carboxylate (9a)

Methyl 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-(trifluoromethoxy)-1,3-benzothiazole-6-carboxylate 9a (200 mg, 95%), was obtained as a colorless solid following the procedure outlined in Example 10, step 8, from intermediates (1R,3R,5S)-8-azabicyclo[3.2.1]octan-3-yl 5-cyclopropyl-3-(2,6-dichlorophenyl)-1,2-oxazole-4-carboxylate (138 mg, 0.34 mmol, 1.1 equiv.) 1j and methyl 2-bromo-4-(trifluoromethoxy)-1,3-benzothiazole-6-carboxylate (110 mg, 0.31 mmol, 1.0 equiv.) A-4.

Step 2. 2-[(1R,3S,5S)-3-[[5-Cyclopropyl-3-(2,6-dichlorophenyl)-1,2-oxazol-4-yl]carbonyloxy]-8-azabicyclo[3.2.1]octan-8-yl]-4-(trifluoromethoxy)-1,3-benzothiazole-6-carboxylic acid (I-9)

2-[(1R,3S,5S)-3-[[5-cyclopropyl-3-(2,6-dichlorophenyl)-1,2-oxazol-4-yl]carbonyloxy]-8-azabicyclo[3.2.1]octan-8-yl]-4-(trifluoromethoxy)-1,3-benzothiazole-6-carboxylic acid, I-9 (114.7 mg, 59%) as a white solid following the procedure outlined in Example 11, from intermediate 9a (200 mg, 0.29 mmol, 1.0 equiv.). $^1$HNMR (400 MHz, DMSO-$d_6$) δ: 13.09 (s, 1H), 8.41 (d, J=1.5 Hz, 1H), 7.77-7.58 (m, 4H), 5.08 (t, J=5.3 Hz, 1H), 4.26 (s, 2H), 2.95 (tt, J=8.2, 5.2 Hz, 1H), 2.28 (dt, J=15.7, 4.6 Hz, 2H), 2.08 (s, 2H), 1.83 (dd, J=8.2, 4.0 Hz, 2H), 1.71 (d, J=15.4 Hz, 2H), 1.42-1.27 (m, 6H); MS (ES, m/z): [M+1]=668.10.

Example 19: 2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-(trifluoromethyl)-1,3-benzothiazole-6-carboxylic acid (I-10)

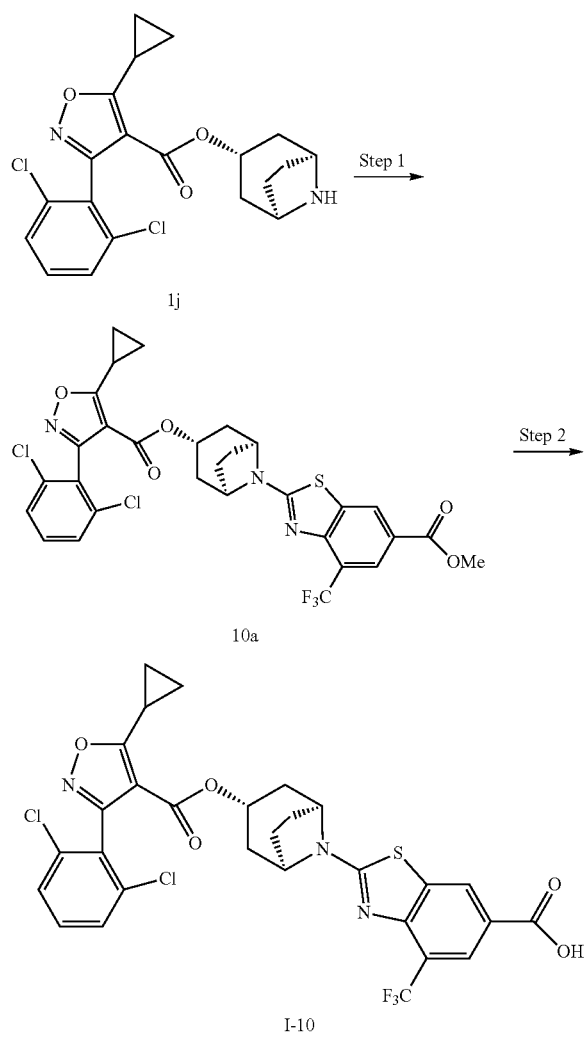

Step 1. Methyl 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-(trifluoromethyl)-1,3-benzothiazole-6-carboxylate (10a)

Methyl 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-(trifluoromethyl)-1,3-benzothiazole-6-carboxylate 10a (100 mg, 34%) was obtained as a light yellow solid following the procedure outlined in Example 10, step 8, from intermediates (1R,3R,5S)-8-azabicyclo[3.2.1]octan-3-yl 5-cyclopropyl-3-(2,6-dichlorophenyl)-1,2-oxazole-4-carboxylate (215 mg, 0.53 mmol, 1.2 equiv.) 1j and methyl 2-bromo-4-(trifluoromethyl)-1,3-benzothiazole-6-carboxylate (150 mg, 0.44 mmol, 1.0 equiv.) A-5.

Step 2. 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-(trifluoromethyl)-1,3-benzothiazole-6-carboxylic acid (I-10)

2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-(trifluoromethyl)-1,3-benzothiazole-6-carboxylic acid I-10 (27.1 mg, 28%), as a colorless solid following the procedure outlined in Example 11, from intermediate 10a (100 mg, 0.15 mmol, 1.0 equiv.). $^1$HNMR (300 MHz, DMSO-$d_6$) δ: 13.10 (s, 1H), 8.62 (d, J=1.6 Hz, 1H), 8.05 (d, J=1.7 Hz, 1H), 7.73-7.54 (m, 3H), 5.06 (t, J=5.3 Hz, 1H), 4.26 (s, 2H), 2.99-2.85 (m, 1H), 2.26 (dt, J=15.3, 4.7 Hz, 2H), 1.82 (d, J=7.0 Hz, 2H), 1.76-1.64 (m, 2H), 1.42-1.18 (m, 7H); MS (ES, m/z): [M+1]=652.15.

Example 20: 2-[(1R,3R,5S)-3-[5-Cyclopropyl-3-(2,6-dichlorophenyl)-1,2-oxazole-4-carbonyloxy]-8-azabicyclo[3.2.1]octan-8-yl]-4-methyl-1,3-benzothiazole-6-carboxylic acid (I-11)

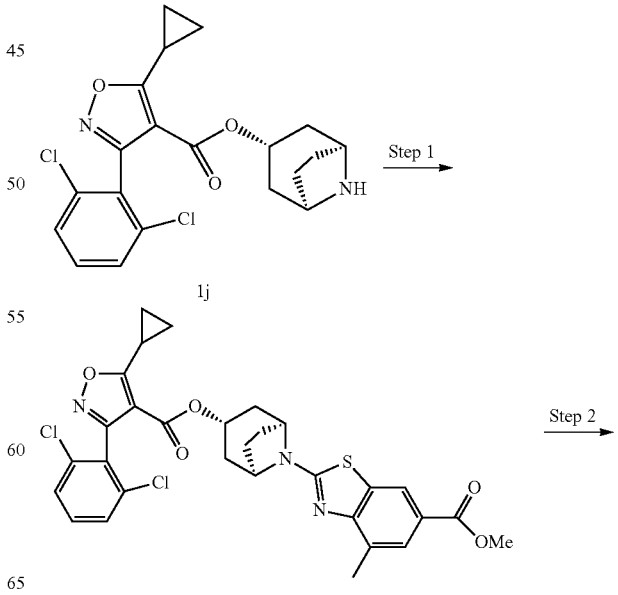

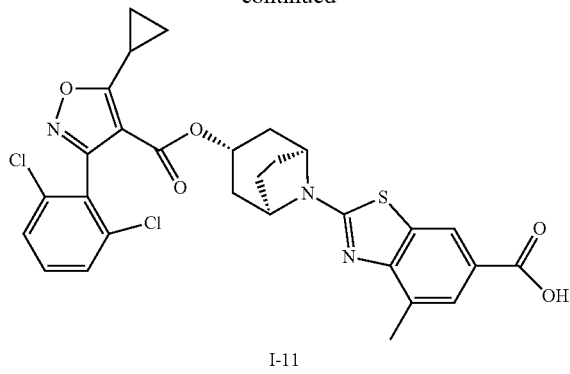

I-11

Step 1. Methyl 2-[(1R,3S,5S)-3-[[5-Cyclopropyl-3-(2,6-dichlorophenyl)-1,2-oxazol-4-yl]carbonyloxy]-8-azabicyclo[3.2.1]octan-8-yl]-4-methyl-1,3-benzothiazole-6-carboxylate (11a)

Methyl 2-[(1R,3S,5S)-3-[[5-cyclopropyl-3-(2,6-dichlorophenyl)-1,2-oxazol-4-yl]carbonyloxy]-8-azabicyclo[3.2.1]octan-8-yl]-4-methyl-1,3-benzothiazole-6-carboxylate 11a (225 mg, 100%), was obtained as a colorless solid following the procedure outlined in Example 10, step 8, and from intermediates (1R,3R,5S)-8-azabicyclo[3.2.1]octan-3-yl 5-cyclopropyl-3-(2,6-dichlorophenyl)-1,2-oxazole-4-carboxylate (150 mg, 0.37 mmol, 1.0 equiv.) 1j and methyl 2-bromo-4-methyl-1,3-benzothiazole-6-carboxylate (126 mg, 0.44 mmol, 1.2 equiv.) A-6.

Step 2. 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-methyl-1,3-benzothiazole-6-carboxylic acid (I-11)

2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-methyl-1,3-benzothiazole-6-carboxylic acid I-11 (84.8 mg, 58%) was obtained as a white solid following the procedure outlined in Example 11, from intermediate 11a (150 mg, 0.24 mmol, 1.0 equiv.). ¹HNMR (300 MHz, DMSO-$d_6$) δ: 12.61 (s, 1H), 8.18 (d, J=1.7 Hz, 1H), 7.75-7.56 (m, 4H), 5.08 (t, J=5.2 Hz, 1H), 3.33 (s, 2H), 2.96 (tt, J=8.1, 5.3 Hz, 1H), 2.47 (s, 3H), 2.37-2.22 (m, 2H), 1.86-1.76 (m, 2H), 1.69 (d, J=15.3 Hz, 2H), 1.44-1.21 (m, 6H). MS (ES, m/z): [M+1]=598.10.

Example 21: 2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-(cyclopropyl)-1,3-benzothiazole-6-carboxylic acid (I-12)

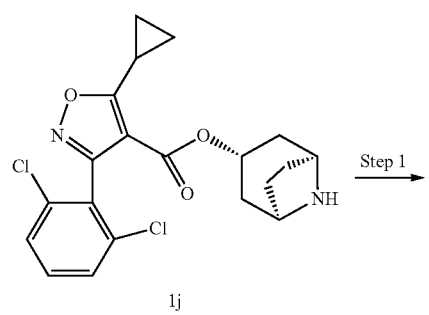

1j

Step 1 →

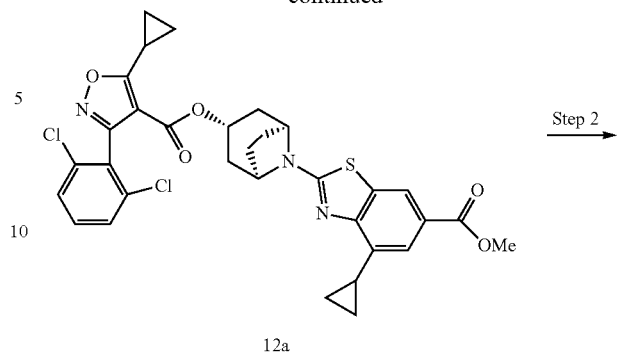

12a

Step 2 →

I-12

Step 1. Methyl 2-[(1R,3R,5S)-3-[[5-Cyclopropyl-3-(2,6-dichlorophenyl)-1,2-oxazol-4-yl]carbonyloxy]-8-azabicyclo[3.2.1]octan-8-yl]-4-(cyclopropyl)-1,3-benzothiazole-6-carboxylate (12a)

Methyl 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-(cyclopropyl)-1,3-benzothiazole-6-carboxylate 12a was obtained following the procedure outlined in Example 10, step 8, from intermediates (1R,3R,5S)-8-azabicyclo[3.2.1]octan-3-yl 5-cyclopropyl-3-(2,6-dichlorophenyl)-1,2-oxazole-4-carboxylate (1.1 equiv.) 1j and methyl 2-bromo-4-(cyclopropyl)-1,3-benzothiazole-6-carboxylate (1.0 equiv.) A7.

Step 2. 2-[(1R,3S,5S)-3-[[5-Cyclopropyl-3-(2,6-dichlorophenyl)-1,2-oxazol-4-yl] carbonyloxy]-8-azabicyclo[3.2.1]octan-8-yl]-4-(cyclopropyl)-1,3-benzothiazole-6-carboxylic acid (I-12)

2-[(1R,3S,5S)-3-[[5-cyclopropyl-3-(2,6-dichlorophenyl)-1,2-oxazol-4-yl]carbonyloxy]-8-azabicyclo[3.2.1]octan-8-yl]-4-(cyclopropyl)-1,3-benzothiazole-6-carboxylic acid I-12 was obtained following the procedure outlined in Example 11, from hydrolysis of intermediate 12a.

Example 22: 2-[(1R,3R,5S)-3-(5-Cyclopropyl-3-phenyl-1,2-oxazole-4-carbonyloxy)-8-azabicyclo[3.2.1]octan-8-yl]-4-fluoro-1,3-benzothiazole-6-carboxylic acid (I-13)

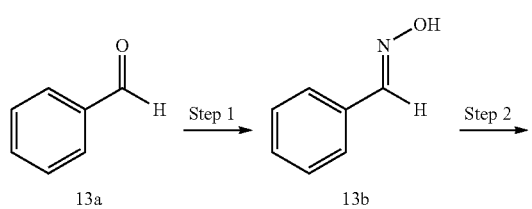

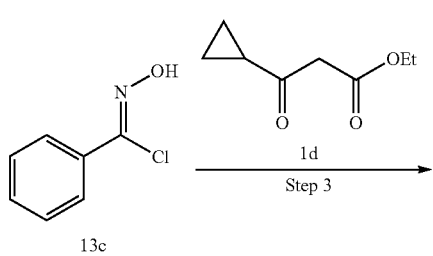

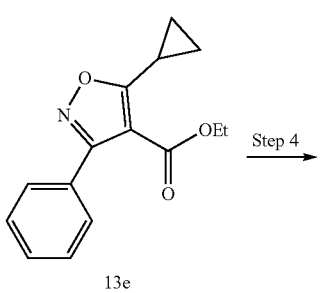

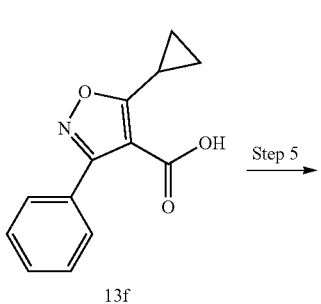

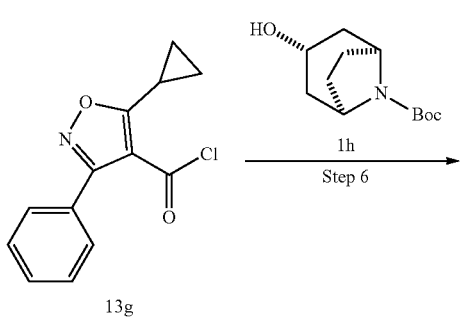

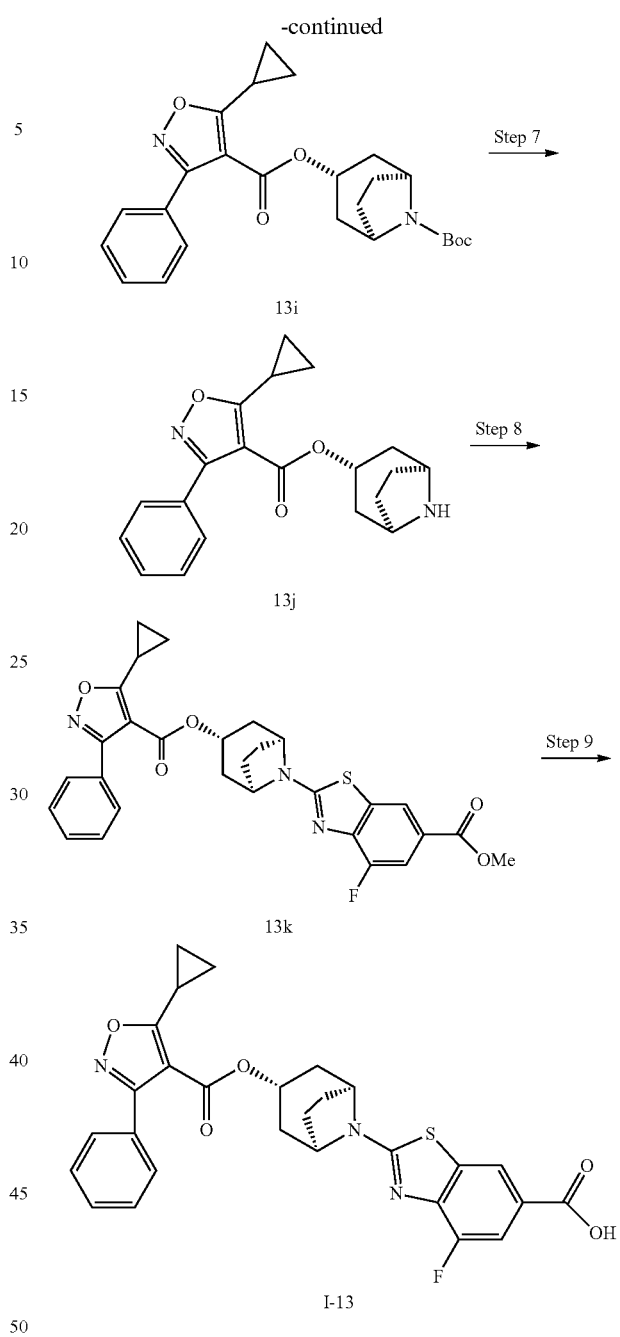

Step 1. N-(Phenylmethylidene)hydroxylamine (13b)

To a 500 mL round-bottom flask was added a solution of benzaldehyde 13a (5.31 g, 50.04 mmol, 1.0 equiv.) in ethanol:$H_2O$ (2:1, 90 mL), followed by the batchwise addition of $NH_2OH \cdot HCl$ (5.21 g, 75.51 mmol, 1.5 equiv.) and sodium carbonate (3.97 g, 37.46 mmol, 0.75 equiv.) at 0° C. Ethanol:$H_2O$ (1:1, v/v, 60 mL) was added and the resulting mixture was stirred for at RT for 2 h, then diluted with EtOAc (500 mL). The organic layer was washed with aqueous sodium bicarbonate (50 mL×3) and brine (100 mL×3), dried over anhydrous sodium sulfate, filtered, and concentrated in vacuo to give of A-(phenylmethylidene)hydroxylamine 13b (6.06 g, 100%) as a colorless oil.

Step 2. A-Hydroxybenzene-1-carbonimidoyl chloride (13c)

To a 500 mL round-bottom flask was added a N-(phenylmethylidene)-hydroxylamine 13b (6.06 g, 50.03 mmol, 1.0 equiv.) in N,N-dimethylformamide (100 mL), followed by the batchwise addition of NCS (6.71 g, 50.25 mmol, 1.0 equiv.), at 0° C. The resulting mixture was stirred at RT overnight. Ethyl acetate was added (500 mL) and the organic mixture was washed with brine (100 mL×3), dried over anhydrous sodium sulfate, filtered, and concentrated in vacuo to give N-hydroxybenzene-1-carbonimidoyl chloride 13c (5.82 g, 75%) as a light yellow oil.

Step 3. Ethyl 5-cyclopropyl-3-phenyl-1,2-oxazole-4-carboxylate (13e)

To a 500 mL round-bottom flask was added N-hydroxybenzene-1-carbonimidoyl chloride 13c (5.82 g, 37.41 mmol, 1.0 equiv.) in dichloromethane (100 mL) followed by ethyl 3-cyclopropyl-3-oxopropanoate 1d (9.69 g, 62.04 mmol, 1.5 equiv.) and TEA (100 mL). The resulting mixture was stirred overnight at RT, and then concentrated in vacuo. The resulting residue was diluted with ethyl acetate (100 mL) and the organic layer was washed with HCl (3M, 50 mL×3) and brine (100 mL×3), dried over anhydrous sodium sulfate, filtered, and concentrated in vacuo. The residue was purified via silica gel column chromatography eluting with PE:EtOAc (5:1) to afford ethyl 5-cyclopropyl-3-phenyl-1,2-oxazole-4-carboxylate 13e (5 g, 52%) as a light yellow oil.

Step 4. 5-Cyclopropyl-3-phenyl-1,2-oxazole-4-carboxylic acid (13f)

To a 500 mL round-bottom flask was added a solution of ethyl 5-cyclopropyl-3-phenyl-1,2-oxazole-4-carboxylate 13e (5 g, 19.43 mmol, 1.0 equiv.) in ethanol-$H_2O$ (330 mL, 10:1) followed by the addition of lithium hydroxide monohydrate (8.14 g, 193.99 mmol, 10.0 equiv.). The resulting mixture was stirred at 50° C. overnight and then concentrated in vacuo. $H_2O$ (500 mL) was added and the aqueous mixture was extracted with ethyl acetate (300 mL×3). The combined organic layers were dried over anhydrous sodium sulfate, filtered, and concentrated in vacuo to give 5-cyclopropyl-3-phenyl-1,2-oxazole-4-carboxylic acid 13f (3.8 g, 85%) as a pink solid.

Step 5. 5-Cyclopropyl-3-phenyl-1,2-oxazole-4-carbonyl chloride (13g)

To a 50 mL round-bottom flask was added 5-cyclopropyl-3-phenyl-1,2-oxazole-4-carboxylic acid 13f (500 mg, 2.18 mmol, 1.0 equiv.) and thionyl chloride (10 mL), followed by a catalytic amount of N,N-dimethylformamide. The resulting mixture was stirred at 60° C. overnight, then concentrated in vacuo to give 5-cyclopropyl-3-phenyl-1,2-oxazole-4-carbonyl chloride 13g (500 mg, 93%) as a colorless oil.

Step 6. tert-butyl (1R,3R,5S)-3-[(5-cyclopropyl-3-phenyl-1,2-oxazol-4-yl)carbonyloxy]-8-azabicyclo[3.2.1]octane-8-carboxylate (13i)

To a 50 mL round-bottom flask was added tert-butyl (1R,3R,5S)-3-hydroxy-8-azabicyclo[3.2.1]octane-8-carboxylate 1 h (552 mg, 2.43 mmol, 1.5 equiv.) in dichloromethane (10 mL), 4-Dimethylaminopyridine (79 mg, 0.65 mmol, 0.4 equiv.) and TEA (489 mg, 4.83 mmol, 3.0 equiv.), followed by the dropwise addition of 5-cyclopropyl-3-phenyl-1,2-oxazole-4-carbonyl chloride 13g (400 mg, 1.62 mmol, 1.0 equiv.) in dichloromethane (5 mL) at 0° C. The resulting mixture was stirred overnight at 30° C., then quenched with $H_2O$ (50 mL). The aqueous mixture was extracted with dichloromethane (30 mL×3), and the combined organic layers were dried over sodium sulfate, filtered, and concentrated in vacuo. The resulting residue was purified via silica gel chromatography eluting with PE:EtOAc (1:1) to give tert-butyl (1R,3R,5S)-3-[(5-cyclopropyl-3-phenyl-1,2-oxazol-4-yl)carbonyloxy]-8-azabicyclo[3.2.1] octane-8-carboxylate 13i (600 mg, 85%) as an off-white solid. The product was carried on to the next step without further purification.

Step 7. (1R,3S,5S)-8-Azabicyclo[3.2.1]octan-3-yl 5-cyclopropyl-3-phenyl-1,2-oxazole-4-carboxylate (13j)

To a 50 mL round-bottom flask was added tert-butyl (1R,3S,5S)-3-[(5-cyclopropyl-3-phenyl-1,2-oxazol-4-yl)carbonyloxy]-8-azabicyclo[3.2.1]octane-8-carboxylate 13i (600 mg, 1.37 mmol, 1.0 equiv.) in dichloromethane (10 mL) and trifluoroacetic acid (2 mL). The resulting mixture was stirred for 2 h at RT, and then quenched with $H_2O$ (50 mL). The pH of the solution was adjusted to 9-10 using sodium bicarbonate (aq., sat.). The resulting aqueous mixture was extracted with dichloromethane (30 mL×3) and the combined organic layers were dried over sodium sulfate, filtered, and concentrated in vacuo to provide (1R,3S,5S)-8-azabicyclo[3.2.1]octan-3-yl 5-cyclopropyl-3-phenyl-1,2-oxazole-4-carboxylate 13j (500 mg) as an off-white solid. The product was carried on to the next step without further purification.

Step 8. Methyl 2-[(1R,3R,5S)-3-[(5-cyclopropyl-3-phenyl-1,2-oxazol-4-yl)carbonyloxy]-8-azabicyclo[3.2.1]octan-8-yl]-4-fluoro-1,3-benzothiazole-6-carboxylate (13k)

To a 100 mL round-bottom flask purged with nitrogen was added (1R,3R,5S)-8-azabicyclo[3.2.1]octan-3-yl 5-cyclopropyl-3-phenyl-1,2-oxazole-4-carboxylate 13j (500 mg, 1.48 mmol, 1.0 equiv.) in DMA (20 mL), methyl 2-bromo-4-fluoro-1,3-benzothiazole-6-carboxylate A1 (475 mg, 1.64 mmol, 1.1 equiv.), and $Cs_2CO_3$ (965 mg, 2.96 mmol, 2.0 equiv.). The resulting mixture was stirred overnight at 60° C. and ethyl acetate (100 mL) was then added. The mixture was washed with brine (30 mL×3), dried over anhydrous sodium sulfate, filtered, and concentrated in vacuo. The residue was purified via silica gel column chromatography eluting with ethyl acetate/petroleum ether (1:3) to give of methyl 2-[(1R, 3R,5S)-3-[(5-cyclopropyl-3-phenyl-1,2-oxazol-4-yl)carbonyloxy]-8-azabicyclo[3.2.1] octan-8-yl]-4-fluoro-1,3-benzothiazole-6-carboxylate 13k (500 mg, 62%) as an off-white solid.

Step 9. 2-[(1R,3S,5S)-3-[(5-cyclopropyl-3-phenyl-1,2-oxazol-4-yl)carbonyloxy]-8-azabicyclo[3.2.1]octan-8-yl]-4-fluoro-1,3-benzothiazole-6-carboxylic acid (I-13)

To a 100 mL round-bottom flask purged with nitrogen was added a solution of methyl 2-[(1R,3S,5S)-3-[(5-cyclopropyl-3-phenyl-1,2-oxazol-4-yl)carbonyloxy]-8-azabicyclo[3.2.1]octan-8-yl]-4-fluoro-1,3-benzothiazole-6-carboxylate 13k (300 mg, 0.55 mmol, 1.0 equiv.) in pyridine (10 mL) and LiI (735 mg, 5.49 mmol, 10.0 equiv.). The resulting mixture was stirred overnight at 125° C., and ethyl acetate (100 mL) was then added. The mixture was washed with HCl (1 M, 30 mL×3) and brine (30 mL×3), dried over anhydrous sodium sulfate, filtered, and concentrated in vacuo. The crude product was purified by Prep-HPLC using the following conditions: Column, XBridge C18 OBD Prep Column, 10 μm, 19 mm×250 mm; mobile phases: water (0.05% TFA) and ACN (62% ACN up to 82% in 6 min); Detector, UV 254 nm, to provide 2-[(1R,3R,5S)-3-[(5-cyclopropyl-3-phenyl-1,2-oxazol-4-yl)carbonyloxy]-8-azabicyclo[3.2.1]octan-8-yl]-4-fluoro-1,3-benzothiazole-6-carboxylic acid I-13 (134.01 mg, 46%) as an off-white solid. $^1$HNMR (300 MHz, CD$_3$OD) δ: 8.15 (d, J=1.5 Hz, 1H), 7.73-7.47 (m, 6H), 5.22 (t, J=5.1 Hz, 1H), 4.30 (s, 2H), 2.99 (p, J=6.8 Hz, 1H), 2.35 (dt, J=15.5, 4.5 Hz, 2H), 1.98-1.85 (m, 2H), 1.79 (dd, J=8.4, 4.5 Hz, 2H), 1.34 (dd, J=9.6, 7.2 Hz, 6H). MS (ES, m/z): [M+1]=534.

Example 23: 2-[(1R,3R,5S)-3-{5-cyclopropyl-3-[2-(trifluoromethoxy)phenyl]-1,2-oxazole-4-carbonyloxy}-8-azabicyclo[3.2.1]octan-8-yl]-4-fluoro-1,3-benzothiazole-6-carboxylic acid (I-14)

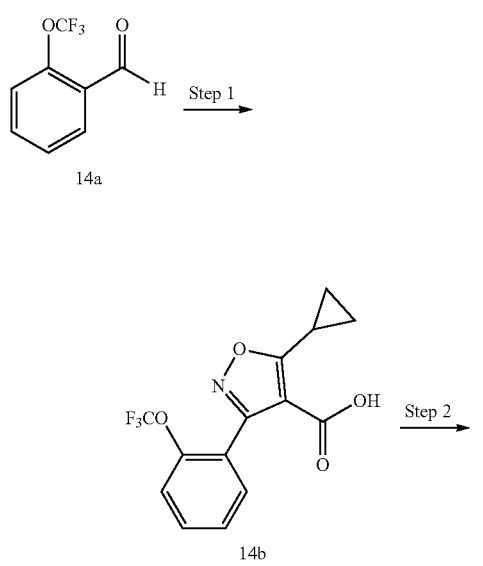

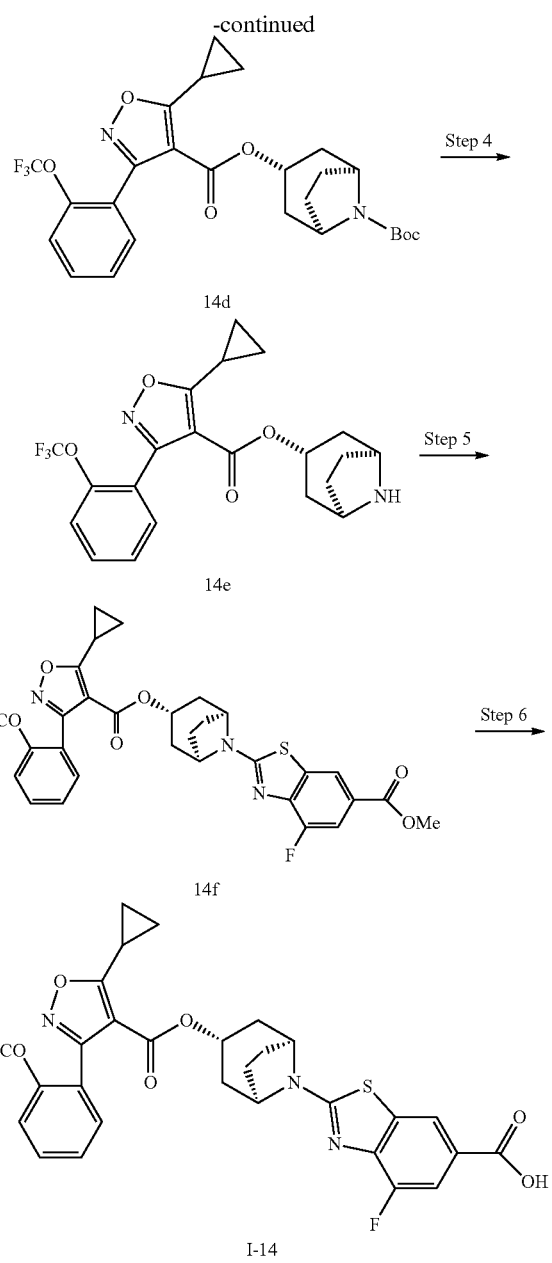

Step 1. 5-Cyclopropyl-3-[2-(trifluoromethoxy)phenyl]-1,2-oxazole-4-carboxylic acid (14b)

5-cyclopropyl-3-[2-(trifluoromethoxy)phenyl]-1,2-oxazole-4-carboxylic acid 14b was obtained following the procedure outlined in Example 22 steps 1 to 4, from 2-trifluoromethoxyphenyl aldehyde 14a.

Step 2. 5-Cyclopropyl-3-[2-(trifluoromethoxy)phenyl]-1,2-oxazole-4-carbonyl chloride (14c)

To a 100 mL round-bottom flask purged with nitrogen was added 5-cyclopropyl-3-[2-(trifluoromethoxy)phenyl]-1,2-oxazole-4-carboxylic acid (500 mg, 1.6 mmol, 1.0 equiv.), thionyl chloride (10 mL) and DMF (0.05 mL). The resulting mixture was stirred overnight at 40° C., and concentrated in vacuo to give 5-cyclopropyl-3-[2-(trifluoromethoxy)phenyl]-1,2-oxazole-4-carbonyl chloride 14c (0.5 g, 94%) as a yellow oil. The product was carried on to the next step without further purification.

Step 3. tert-Butyl (1R,3S,5S)-3-([5-cyclopropyl-3-[2-(trifluoromethoxy)phenyl]-1,2-oxazol-4-yl]carbonyloxy)-8-azabicyclo[3.2.1]octane-8-carboxylate (14d)

To a 100-mL round-bottom flask was added tert-butyl (1R,3S,5S)-3-hydroxy-8-azabicyclo[3.2.1]octane-8-carboxylate 1 h (362 mg, 1.59 mmol, 1.0 equiv.), dichloromethane (10 mL), 4-dimethylaminopyridine (78 mg, 0.64 mmol, 0.4 equiv.), and triethylamine (485 mg, 4.79 mmol, 3.0 equiv.), followed by the addition of 5-cyclopropyl-3-[2-(trifluoromethoxy) phenyl]-1,2-oxazole-4-carbonyl chloride 14c (500 mg, 1.51 mmol, 1.0 equiv.) in dichloromethane (2 mL) at 0° C. The resulting mixture was stirred overnight at 30° C. and quenched with H$_2$O. The aqueous mixture was extracted with dichloromethane (200 mL×2) and the combined organic layers were washed with brine (50 mL×2), dried over anhydrous sodium sulfate, filtered, and concentrated in vacuo. The resulting residue was purified via silica gel chromatography eluting with ethyl acetate/petroleum ether (1:5) to provide tert-butyl (1R,3S,5S)-3-([5-cyclopropyl-3-[2-(trifluoromethoxy)phenyl]-1,2-oxazol-4-yl]carbonyloxy)-8-azabicyclo[3.2.1]octane-8-carboxylate 14d (450 mg, 57%) as a light yellow solid.

Step 4. (1R,3S,5S)-8-Azabicyclo[3.2.1]octan-3-yl 5-cyclopropyl-3-[2-(trifluoromethoxy) phenyl]-1,2-oxazole-4-carboxylate (14e)

To a 100 mL round-bottom flask was added tert-butyl (1R,3S,5S)-3-([5-cyclopropyl-3-[2-(trifluoromethoxy)phenyl]-1,2-oxazol-4-yl]carbonyloxy)-8-azabicyclo[3.2.1]octane-8-carboxylate 14d (450 mg, 0.86 mmol, 1.0 equiv.), 2,2,2-trifluoroacetaldehyde (2 mL), and dichloromethane (10 mL). The resulting solution was stirred for 1 h at RT, and then quenched with water (20 mL). The pH of the solution was adjusted to 10 using sodium bicarbonate (aq.). The aqueous mixture was extracted with ethyl acetate (30 mL×3) and the combined organic layers were washed with brine (20 mL×3), dried over anhydrous sodium sulfate, filtered, and concentrated in vacuo to provide (1R,3S,5S)-8-azabicyclo[3.2.1]octan-3-yl 5-cyclopropyl-3-[2-(trifluoromethoxy)phenyl]-1,2-oxazole-4-carboxylate 14e (360 mg, 99%) as a light yellow oil. The product was carried on to the next step without further purification.

Step 5. Methyl 2-[(1R,3R,5S)-3-([5-cyclopropyl-3-[2-(trifluoromethoxy)phenyl]-1,2-oxazol-4-yl]carbonyloxy)-8-azabicyclo[3.2.1]octan-8-yl]-4-fluoro-1,3-benzothiazole-6-carboxylate (14f)

To a 100 mL round-bottom flask purged with nitrogen was added (1R,3R,5S)-8-azabicyclo[3.2.1]octan-3-yl 5-cyclopropyl-3-[2-(trifluoromethoxy)phenyl]-1,2-oxazole-4-carboxylate 14e (360 mg, 0.85 mmol, 1.0 equiv.), DMSO (10 mL), methyl 2-bromo-4-fluoro-1,3-benzothiazole-6-carboxylate A1 (294 mg, 1.01 mmol, 1.2 equiv.), and CsF (389 mg, 3.0 equiv.). The resulting mixture was stirred overnight at 115° C. and then ethyl acetate was added (100 mL). The resulting mixture was washed with brine (20 mL×2), dried over anhydrous sodium sulfate, filtered, and concentrated in vacuo. The resulting residue was purified via silica gel chromatography eluting with ethyl acetate/petroleum ether (1:2) to afford methyl 2-[(1R,3R,5S)-3-([5-cyclopropyl-3-[2-(trifluoromethoxy)phenyl]-1,2-oxazol-4-yl]carbonyloxy)-8-azabicyclo[3.2.1]octan-8-yl]-4-fluoro-1,3-benzothiazole-6-carboxylate 14f (440 mg, 82%) as a light yellow solid.

Step 6. 2-[(1R,3R,5S)-3-([5-Cyclopropyl-3-[2-(trifluoromethoxy)phenyl]-1,2-oxazol-4-yl]carbonyloxy)-8-azabicyclo[3.2.1]octan-8-yl]-4-fluoro-1,3-benzothiazole-6-carboxylic acid (I-14)

To a 100-mL round-bottom flask purged with nitrogen was added methyl 2-[(1R,3R,5S)-3-([5-cyclopropyl-3-[2-(trifluoromethoxy)phenyl]-1,2-oxazol-4-yl]carbonyloxy)-8-azabicyclo[3.2.1]octan-8-yl]-4-fluoro-1,3-benzothiazole-6-carboxylate 14f (440 mg, 0.70 mmol, 1.0 equiv.), pyridine (10 mL), and LiI (938 mg, 10.0 equiv.). The resulting solution was stirred overnight at 125° C., and then concentrated in vacuo. The resulting residue was dissolved in 100 mL of EtOAc, washed with HCl (1 M, 20 mL×2), and concentrated in vacuo. The crude product was purified by Prep-HPLC using the following conditions: Column, XBridge C18 OBD Prep Column, 10 μm, 19 mm×250 mm; mobile phases: Water (0.05% TFA) and ACN (58.0% ACN to 78.0% over 8 min); Detector, UV 254 nm to provide 2-[(1R,3R,5S)-3-([5-cyclopropyl-3-[2-(trifluoromethoxy) phenyl]-1,2-oxazol-4-yl]carbonyloxy)-8-azabicyclo[3.2.1] octan-8-yl]-4-fluoro-1,3-benzothiazole-6-carboxylic acid I-14 (246.4 mg, 57%) was obtained as an off-white solid. $^1$HNMR (300 MHz, CD$_3$OD) δ: 8.15 (d, J=1.5 Hz, 1H), 7.77-7.48 (m, 5H), 5.18 (t, J=5.1 Hz, 1H), 4.31 (s, 2H), 2.96 (p, J=6.7 Hz, 1H), 2.37 (dt, J=15.7, 4.4 Hz, 2H), 1.92-1.80 (m, 4H), 1.38 (dd, J=19.2, 7.2 Hz, 6H). MS (ES, m/z): [M+1]=618.20.

Example 24: 2-[(1R,3R,5S)-3-{3-[2-chloro-6-(difluoromethoxy)phenyl]-5-cyclopropyl-1,2-oxazole-4-carbonyloxy}-8-azabicyclo[3.2.1]octan-8-yl]-4-fluoro-1,3-benzothiazole-6-carboxylic acid (I-15)

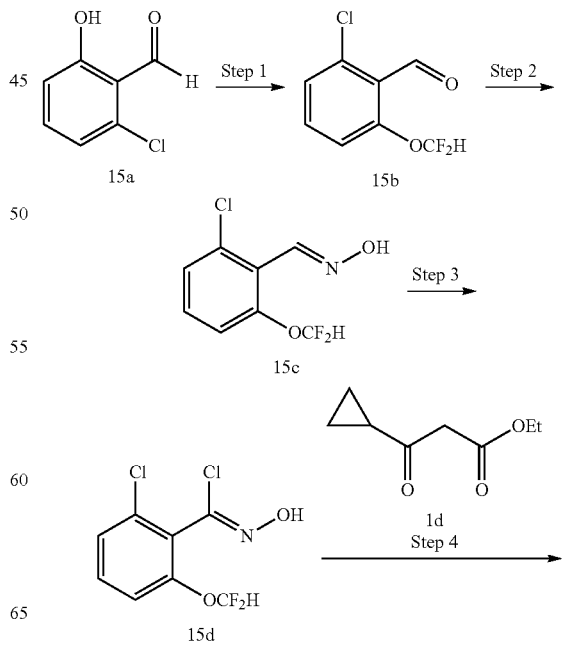

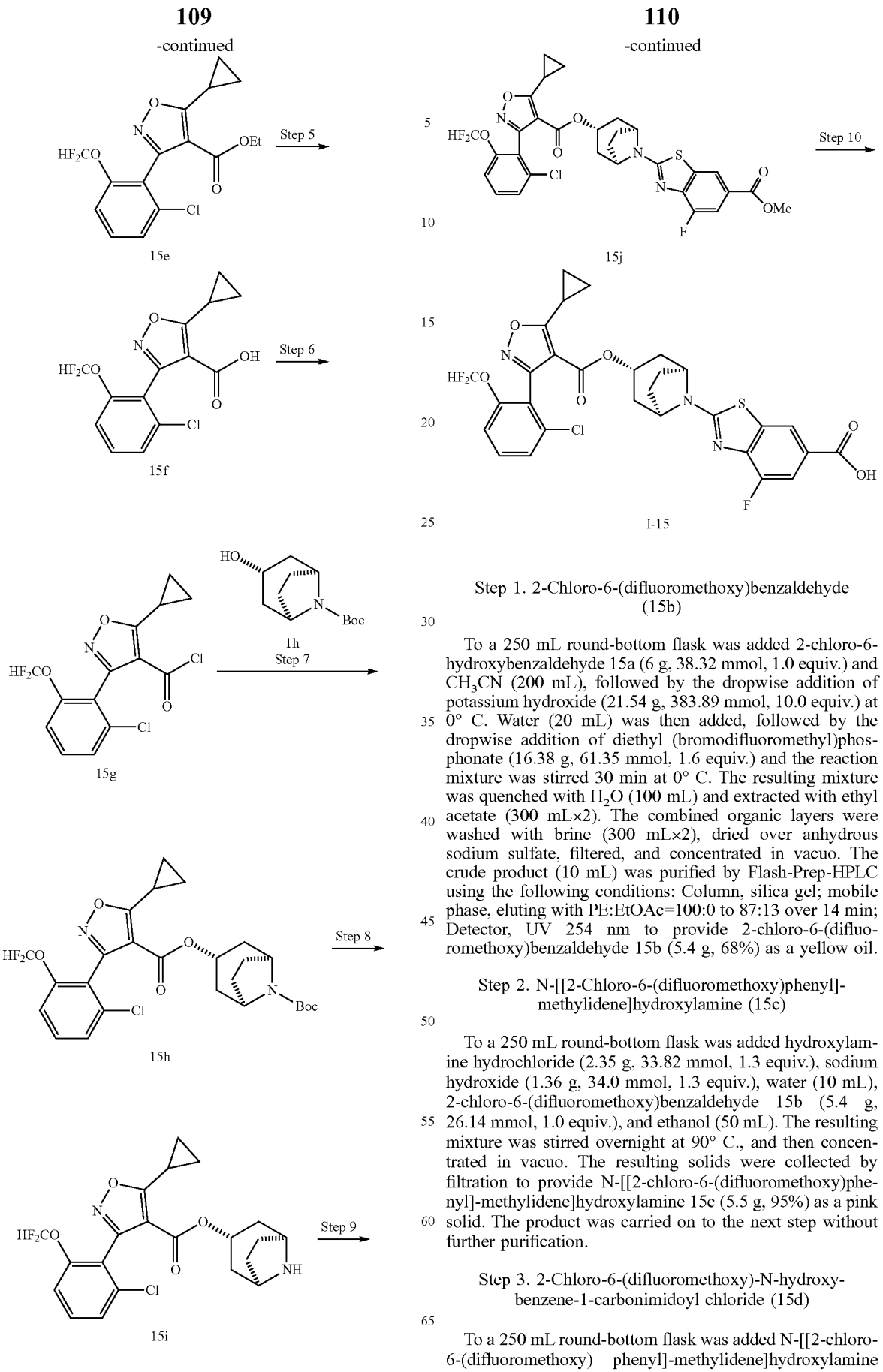

Step 1. 2-Chloro-6-(difluoromethoxy)benzaldehyde (15b)

To a 250 mL round-bottom flask was added 2-chloro-6-hydroxybenzaldehyde 15a (6 g, 38.32 mmol, 1.0 equiv.) and $CH_3CN$ (200 mL), followed by the dropwise addition of potassium hydroxide (21.54 g, 383.89 mmol, 10.0 equiv.) at 0° C. Water (20 mL) was then added, followed by the dropwise addition of diethyl (bromodifluoromethyl)phosphonate (16.38 g, 61.35 mmol, 1.6 equiv.) and the reaction mixture was stirred 30 min at 0° C. The resulting mixture was quenched with $H_2O$ (100 mL) and extracted with ethyl acetate (300 mL×2). The combined organic layers were washed with brine (300 mL×2), dried over anhydrous sodium sulfate, filtered, and concentrated in vacuo. The crude product (10 mL) was purified by Flash-Prep-HPLC using the following conditions: Column, silica gel; mobile phase, eluting with PE:EtOAc=100:0 to 87:13 over 14 min; Detector, UV 254 nm to provide 2-chloro-6-(difluoromethoxy)benzaldehyde 15b (5.4 g, 68%) as a yellow oil.

Step 2. N-[[2-Chloro-6-(difluoromethoxy)phenyl]-methylidene]hydroxylamine (15c)

To a 250 mL round-bottom flask was added hydroxylamine hydrochloride (2.35 g, 33.82 mmol, 1.3 equiv.), sodium hydroxide (1.36 g, 34.0 mmol, 1.3 equiv.), water (10 mL), 2-chloro-6-(difluoromethoxy)benzaldehyde 15b (5.4 g, 26.14 mmol, 1.0 equiv.), and ethanol (50 mL). The resulting mixture was stirred overnight at 90° C., and then concentrated in vacuo. The resulting solids were collected by filtration to provide N-[[2-chloro-6-(difluoromethoxy)phenyl]-methylidene]hydroxylamine 15c (5.5 g, 95%) as a pink solid. The product was carried on to the next step without further purification.

Step 3. 2-Chloro-6-(difluoromethoxy)-N-hydroxybenzene-1-carbonimidoyl chloride (15d)

To a 250 mL round-bottom flask was added N-[[2-chloro-6-(difluoromethoxy) phenyl]-methylidene]hydroxylamine 15c (3 g, 13.54 mmol, 1.0 equiv.) and N,N-dimethylformamide (50 mL) followed by the batchwise addition of NCS (1.82 g, 13.63 mmol, 1.0 equiv.) at 0° C. The resulting mixture was stirred at RT for 2 h, and then quenched with $H_2O$ (200 mL). The aqueous mixture was extracted with ethyl acetate (200 mL×2), and the combined organic layers were washed with brine (200 mL×2), dried over anhydrous sodium sulfate, filtered, and concentrated in vacuo, to provide 2-chloro-6-(difluoromethoxy)-N-hydroxybenzene-1-carbonimidoyl chloride 15d (3.07 g, 89%) as a colorless oil.

Step 4. Ethyl 3-[2-chloro-6-(difluoromethoxy)phenyl]-5-cyclopropyl-1,2-oxazole-4-carboxylate (15e)

To a 250 mL round-bottom flask was added 2-chloro-6-(difluoromethoxy)-N-hydroxybenzene-1-carbonimidoyl chloride 15d (3.07 g, 11.99 mmol, 1.0 equiv.) and TEA (100 mL), followed by the dropwise addition of ethyl 3-cyclopropyl-3-oxopropanoate 1d (3.37 g, 21.58 mmol, 1.5 equiv.) at 0° C. The resulting mixture was stirred overnight at RT and then concentrated in vacuo. $H_2O$ (100 mL) was added. The aqueous mixture was extracted with ethyl acetate (200 mL×2); and the combined organic layers were washed with brine (200 mL×2), and dried, filtered, and concentrated in vacuo to give ethyl 3-[2-chloro-6-(difluoromethoxy)phenyl]-5-cyclopropyl-1,2-oxazole-4-carboxylate 15e (5.4 g) as a yellow oil. The product was carried on to the next step without further purification.

Step 5. 3-[2-Chloro-6-(difluoromethoxy)phenyl]-5-cyclopropyl-1,2-oxazole-4-carboxylic acid (15f)

To a 250 mL round-bottom flask was added ethyl 3-[2-chloro-6-(difluoromethoxy) phenyl]-5-cyclopropyl-1,2-oxazole-4-carboxylate 15e (3.1 g, 8.67 mmol, 1.0 equiv.), ethanol (50 mL), water (5 mL), and LiOH (3.64 g, 151.98 mmol, 10.0 equiv.). The resulting mixture was stirred overnight at 60° C. $H_2O$ (50 mL) was added and the pH of the solution was adjusted to 3-4 using HCl. The aqueous mixture was extracted with ethyl acetate (100 mL×2) and the combined organic layers were washed with brine (100 mL×2), dried over anhydrous sodium sulfate, filtered, and concentrated in vacuo to give a crude product (10 mL) which was purified by Flash-Prep-HPLC using the following conditions (IntelFlash-1): Column, silica gel; mobile phase, eluting with PE:EtOAc, 100:0 to 90:10 within 15 min; Detector, UV 254 nm. Removal of solvents afforded 3-[2-chloro-6-(difluoromethoxy)phenyl]-5-cyclopropyl-1,2-oxazole-4-carboxylic acid 15f (1.5 g, 53%) as a yellow oil.

Step 6. 3-[2-Chloro-6-(difluoromethoxy)phenyl]-5-cyclopropyl-1,2-oxazole-4-carbonyl chloride (15g)

To a 50 mL round-bottom flask was placed 3-[2-chloro-6-(difluoromethoxy)phenyl]-5-cyclopropyl-1,2-oxazole-4-carboxylic acid 15f (700 mg, 2.12 mmol, 1.0 equiv.), thionyl chloride (10 mL), and N,N-dimethylformamide (0.04 mL). The resulting mixture was stirred overnight at 60° C., and then concentrated in vacuo to give 3-[2-chloro-6-(difluoromethoxy)phenyl]-5-cyclopropyl-1,2-oxazole-4-carbonyl chloride 15g (700 mg, 95%) as a yellow oil. The product was carried on to the next step without further purification.

Step 7. tert-Butyl (1R,3R,5S)-3-([3-[2-chloro-6-(difluoromethoxy)phenyl]-5-cyclopropyl-1,2-oxazol-4-yl]carbonyloxy)-8-azabicyclo[3.2.1]octane-8-carboxylate (15h)

To a 50 mL round-bottom flask was added a solution of 3-[2-chloro-6-(difluoromethoxy)phenyl]-5-cyclopropyl-1, 2-oxazole-4-carbonyl chloride 15g (480 mg, 1.38 mmol, 1.0 equiv.) in dichloromethane (10 mL), tert-butyl (1R,3R,5S)-3-hydroxy-8-azabicyclo[3.2.1]octane-8-carboxylate 1 h (469 mg, 2.06 mmol, 1.5 equiv.), 4-dimethylaminopyridine (68 mg, 0.56 mmol, 0.4 equiv.), and TEA (0.8 mL, 4.0 equiv.). The resulting mixture was stirred for 3 days at 30° C. The mixture was then diluted with 100 mL of dichloromethane, washed with water (100 mL) and brine (100 mL), dried over anhydrous sodium sulfate, filtered, and concentrated in vacuo. The residue was purified via silica gel chromatography eluting with ethyl acetate/petroleum ether (1:4) to afford tert-butyl (1R,3R,5S)-3-([3-[2-chloro-6-(difluoromethoxy)phenyl]-5-cyclopropyl-1,2-oxazol-4-yl]carbonyloxy)-8-azabicyclo[3.2.1]octane-8-carboxylate 15h (500 mg, 67%) as a light yellow oil.

Step 8. (1R,3R,5S)-8-Azabicyclo[3.2.1]octan-3-yl 3-[2-chloro-6-(difluoromethoxy)phenyl]-5-cyclopropyl-1,2-oxazole-4-carboxylate (15i)

To a 250 mL round-bottom flask was added tert-butyl (1R,3R,5S)-3-([3-[2-chloro-6-(difluoromethoxy)phenyl]-5-cyclopropyl-1,2-oxazol-4-yl]carbonyloxy)-8-azabicyclo [3.2.1]octane-8-carboxylate 15h (500 mg, 0.93 mmol, 1.0 equiv.), dichloromethane (10 mL), and trifluoroacetic acid (5 mL). The resulting mixture was stirred for 4 h at RT. The mixture was diluted with $H_2O$, the pH of the solution was adjusted to 7 using sodium bicarbonate, and the aqueous mixture was extracted with dichloromethane (40 mL×3). The combined organic layers were washed with brine (30 mL×2), dried over anhydrous sodium sulfate, filtered, and concentrated in vacuo to give (1R,3R,5S)-8-azabicyclo [3.2.1]octan-3-yl 3-[2-chloro-6-(difluoromethoxy)phenyl]-5-cyclopropyl-1,2-oxazole-4-carboxylate 15i (300 mg, 74%) as a white solid. The product was carried on to the next step without further purification.

Step 9. Methyl 2-[(1R,3R,5S)-3-([3-[2-chloro-6-(difluoromethoxy)phenyl]-5-cyclopropyl-1,2-oxazol-4-yl]carbonyloxy)-8-azabicyclo[3.2.1]octan-8-yl]-4-fluoro-1,3-benzothiazole-6-carboxylate (15j)

To a 50-mL round-bottom flask purged and maintained with an inert atmosphere of nitrogen, was added (1R,3R,5S)-8-azabicyclo[3.2.1]octan-3-yl 3-[2-chloro-6-(difluoromethoxy) phenyl]-5-cyclopropyl-1,2-oxazole-4-carboxylate 15i (200 mg, 0.46 mmol, 1.0 equiv.), methyl 2-bromo-4-fluoro-1,3-benzothiazole-6-carboxylate (160 mg, 0.55 mmol, 1.2 equiv.), DMA (10 mL), and $Cs_2CO_3$ (297 mg, 0.91 mmol, 2.0 equiv.) and the resulting mixture was stirred at 60° C. overnight. The reaction was quenched with water and the resulting aqueous mixture was extracted with ethyl acetate (30 mL×3). The combined organic layers were washed with brine (20 mL×2), dried over anhydrous sodium sulfate, filtered, and concentrated in vacuo. The residue was purified by silica gel column chromatography eluting with ethyl acetate/petroleum ether (1:4) to provide methyl 2-[(1R,3R,5S)-3-([3-[2-chloro-6-(difluoromethoxy)phenyl]-5-cyclopropyl-1,2-oxazol-4-yl]carbonyloxy)-8-azabicyclo [3.2.1]octan-8-yl]-4-fluoro-1,3-benzothiazole-6-carboxylate 15j (350 mg) as a white solid.

Step 10. 2-[(1R,3R,5S)-3-([3-[2-Chloro-6-(difluoromethoxy)phenyl]-5-cyclopropyl-1,2-oxazol-4-yl] carbonyloxy)-8-azabicyclo[3.2.1]octan-8-yl]-4-fluoro-1,3-benzothiazole-6-carboxylic acid (I-15)

To a 50 mL round-bottom flask purged and maintained with an inert atmosphere of nitrogen was added methyl 2-[(1R,3R,5S)-3-([3-[2-chloro-6-(difluoromethoxy)phenyl]-5-cyclopropyl-1,2-oxazol-4-yl]carbonyloxy)-8-azabicyclo[3.2.1]octan-8-yl]-4-fluoro-1,3-benzothiazole-6-carboxylate 15j (350 mg, 0.54 mmol, 1.0 equiv.), pyridine (5 mL), and LiI (725 mg, 5.41 mmol, 10.0 equiv.). The resulting mixture was stirred at 125° C. overnight. The reaction was quenched with water and the pH of the solution was adjusted to 7 using HCl. The aqueous mixture was extracted with ethyl acetate (30 mL×3), and the combined organic layers were washed with brine (20 mL×2), dried over anhydrous sodium sulfate, filtered, and concentrated in vacuo to give a crude product which was purified by Prep-HPLC using the following conditions: Column, XBridge C18 OBD Prep Column, 10 μm, 19 mm×250 mm; mobile phases, water (0.05% TFA) and ACN (55.0% ACN up to 76.0% in 8 min); Detector, UV 254 nm, to provide 2-[(1R,3R,5S)-3-([3-[2-chloro-6-(difluoromethoxy)phenyl]-5-cyclopropyl-1,2-oxazol-4-yl]carbonyloxy)-8-azabicyclo[3.2.1]octan-8-yl]-4-fluoro-1,3-benzothiazole-6-carboxylic acid I-15 (141.7 mg, 41%) as a white solid. $^1$HNMR (300 MHz, DMSO-$d_6$) δ: 1HNMR δ 12.98 (s, 1H), 8.23 (d, J=1.5 Hz, 1H), 7.74-7.50 (m, 3H), 7.41 (dd, J=8.4, 1.1 Hz, 2H), 5.07 (t, J=5.2 Hz, 1H), 4.25 (s, 2H), 3.01-2.85 (m, 1H), 2.28 (d, J=15.5 Hz, 2H), 1.89-1.64 (m, 4H), 1.49-1.21 (m, 6H). MS (ES, m/z): [M+1]=634.10.

Example 25: 2-[(1R,3R,5S)-3-[5-cyclopropyl-3-(2,6-difluorophenyl)-1,2-oxazole-4-carbonyloxy]-8-azabicyclo[3.2.1]octan-8-yl]-4-fluoro-1,3-benzothiazole-6-carboxylic acid (I-16)

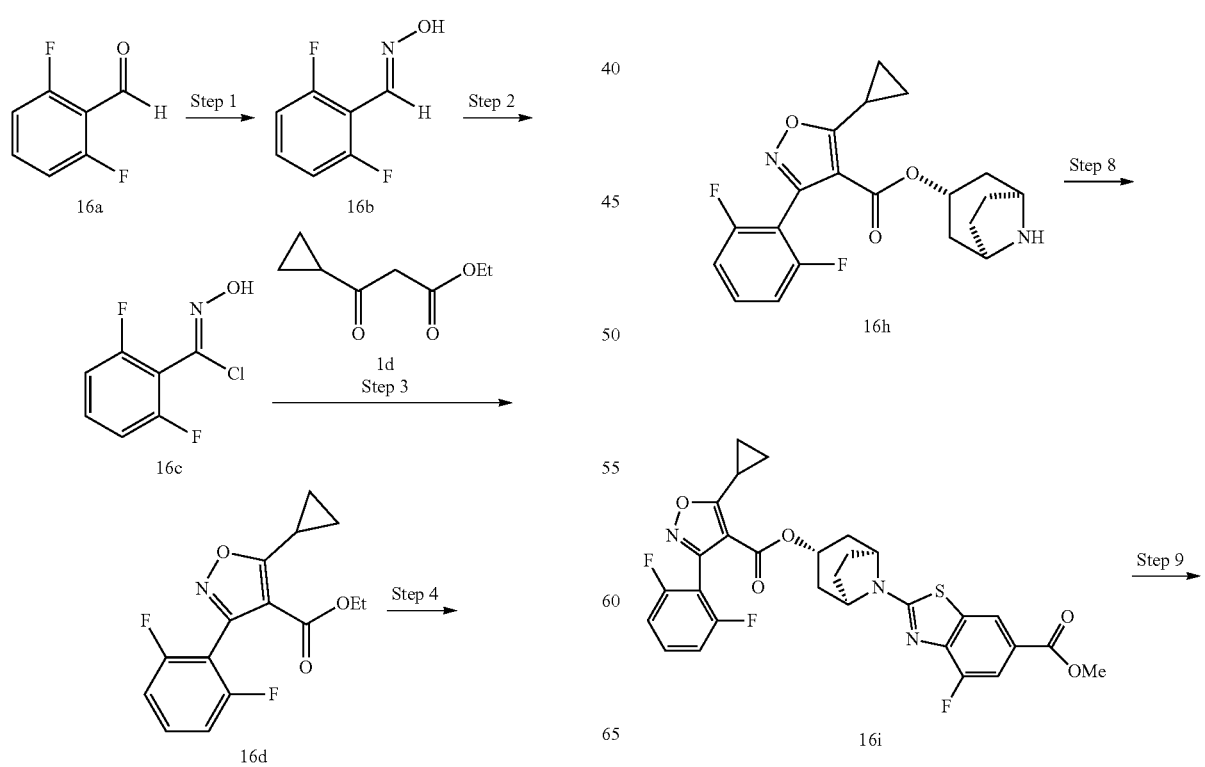

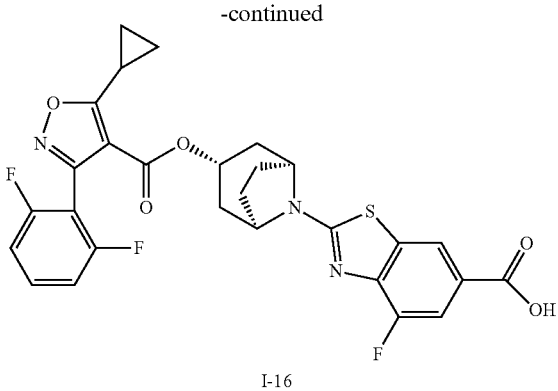

I-16

Step 1. (E)-N-[(2,6-Difluorophenyl)methylidene]-hydroxylamine (16b)

To a 500 mL round-bottom flask was added 2,6-difluorobenzaldehyde 16a (14.76 g, 103.87 mmol, 1.0 equiv.) in ethanol/H$_2$O (100/50 mL), followed by the batchwise addition of NH$_2$OH.HCl (8.75 g, 126.81 mmol, 1.2 equiv.) at 0° C. To the above mixture was added sodium carbonate (8.26 g, 77.93 mmol, 0.75 equiv.), batchwise at 0° C., followed by ethanol/H$_2$O (1:1, 100 mL). The resulting mixture was stirred for 2 h at RT, and diluted with EtOAc (500 mL). The mixture was washed with sodium bicarbonate (aq., 50 mL×3) and brine (50 mL×3), dried over anhydrous sodium sulfate, filtered, and concentrated in vacuo to give (E)-N-[(2,6-difluorophenyl)methylidene]-hydroxylamine 16b (15.56 g, 95%) as an off-white solid.

Step 2. 2,6-Difluoro-N-hydroxybenzene-1-carbonimidoyl chloride (16c)

To a 500 mL round-bottom flask was placed N-[(2,6-difluorophenyl)methylidene]-hydroxylamine 16b (15.56 g, 99.03 mmol, 1.0 equiv.) in N,N-dimethylformamide (300 mL), followed by the batchwise addition of NCS (13.28 g, 99.45 mmol, 1.0 equiv.) at 0° C. The resulting mixture was stirred for 2 h at RT, then diluted with EtOAc (500 mL). The mixture was washed with brine (50 mL×3), dried over anhydrous sodium sulfate, filtered, and concentrated in vacuo to provide 2,6-difluoro-N-hydroxybenzene-1-carbonimidoyl chloride 16c (19 g, 100%) as a colorless oil.

Step 3. Ethyl 5-cyclopropyl-3-(2,6-difluorophenyl)-1,2-oxazole-4-carboxylate (16d)

To a 500 mL round-bottom flask was added 2,6-difluoro-N-hydroxybenzene-1-carbonimidoyl chloride 16c (19 g, 99.18 mmol, 1.0 equiv.) in dichloromethane (300 mL) followed by TEA (200 mL), followed by the dropwise addition of ethyl 3-cyclopropyl-3-oxopropanoate 1d (23 g, 147.27 mmol, 1.5 equiv.) at 0° C. The resulting mixture was stirred overnight at 30° C. and concentrated in vacuo. 300 mL of EtOAc was added; the mixture was washed with HCl (1M, 50 mL×3) and brine (50 mL×3), and concentrated to a solid which was dried in an oven under reduced pressure to give ethyl 5-cyclopropyl-3-(2,6-difluorophenyl)-1,2-oxazole-4-carboxylate 16d (20 g, 69%) as an off-white solid.

Step 4. 5-Cyclopropyl-3-(2,6-difluorophenyl)-1,2-oxazole-4-carboxylic acid (16e)

To a 1000 mL round-bottom flask was added ethyl 5-cyclopropyl-3-(2,6-difluorophenyl)-1,2-oxazole-4-carboxylate 16d (20 g, 68.20 mmol, 1.0 equiv.) in ethanol/H$_2$O (500/50 mL) followed by LiOH.H$_2$O (28.7 g, 683.98 mmol, 10.0 equiv.). The resulting mixture was stirred overnight at 50° C., then concentrated in vacuo. The residue was diluted with 300 mL of H$_2$O, and the pH value of the solution was adjusted to 3-4 using HCl (1M). The aqueous mixture was extracted with ethyl acetate (200 mL×3), and the combined organic layers were washed with brine, dried over sodium sulfate, filtered, and concentrated in vacuo to give 5-cyclopropyl-3-(2,6-difluorophenyl)-1,2-oxazole-4-carboxylic acid 16e (16 g, (88%) as an off-white solid.

Step 5. 5-Cyclopropyl-3-(2,6-difluorophenyl)-1,2-oxazole-4-carbonyl chloride (16f)

To a 250 mL round-bottom flask was placed 5-cyclopropyl-3-(2,6-difluorophenyl)-1,2-oxazole-4-carboxylic acid (2 g, 7.54 mmol, 1.0 equiv.), thionyl chloride (20 mL), and N,N-dimethylformamide (a catalytic amount). The resulting mixture was stirred overnight at 60° C. and concentrated in vacuo to provide 5-cyclopropyl-3-(2,6-difluorophenyl)-1,2-oxazole-4-carbonyl chloride 16f (2 g, 93%) as a colorless oil.

Step 6. tert-butyl (1R,3R,5S)-3-[[5-Cyclopropyl-3-(2,6-difluorophenyl)-1,2-oxazol-4-yl]carbonyloxy]-8-azabicyclo[3.2.1]octane-8-carboxylate (16g)

To a 250 mL round-bottom flask was added a solution of tert-butyl (1R,3R,5S)-3-hydroxy-8-azabicyclo[3.2.1]octane-8-carboxylate 1h (1.2 g, 5.28 mmol, 1.5 equiv.) in dichloromethane (50 mL), 4-dimethylaminopyridine (170 mg, 1.39 mmol, 0.4 equiv.), and TEA (1.07 g, 10.57 mmol, 3.0 equiv.), followed by the dropwise addition of 5-cyclopropyl-3-(2,6-difluorophenyl)-1,2-oxazole-4-carbonyl chloride 16f (1 g, 3.53 mmol, 1.0 equiv.) in dichloromethane (5 mL) at 0° C. The resulting mixture was stirred for 3 h at 30° C. The reaction was quenched with H$_2$O (200 mL). The aqueous mixture was extracted with dichloromethane (50 mL×3), and the combined organic layers were dried over sodium sulfate, filtered, and concentrated in vacuo to a residue which was purified by silica gel column chromatography eluting with PE:EtOAc (1:1) to provide tert-butyl (1R,3R,5S)-3-[[5-cyclopropyl-3-(2,6-difluorophenyl)-1,2-oxazol-4-yl]carbonyloxy]-8-azabicyclo[3.2.1]octane-8-carboxylate 16g (1.1 g, 66%) as a colorless oil.

Step 7. (1R,3R,5S)-8-Azabicyclo[3.2.1]octan-3-yl 5-cyclopropyl-3-(2,6-difluorophenyl)-1,2-oxazole-4-carboxylate (16h)

To a 100 mL round-bottom flask was added a solution of tert-butyl (1R,3S,5S)-3-[[5-cyclopropyl-3-(2,6-difluorophenyl)-1,2-oxazol-4-yl]carbonyloxy]-8-azabicyclo[3.2.1]octane-8-carboxylate 16g (1.1 g, 2.32 mmol, 1.0 equiv.) in dichloromethane (10 mL) followed by trifluoroacetic acid (2 mL). The resulting mixture was stirred for 2 h at RT, then quenched with H$_2$O (50 mL). The pH value of the solution was adjusted to 9-10 using an aqueous solution of sodium bicarbonate. The resulting mixture was extracted with dichloromethane (50 mL×3). The combined organic layers were dried over sodium sulfate, filtered, and concentrated in vacuo to give crude (1R,3R,5S)-8-azabicyclo[3.2.1]octan-3-yl 5-cyclopropyl-3-(2,6-difluorophenyl)-1,2-oxazole-4-carboxylate 16h (1 g) as an off-white solid. The product was carried on to the next step without further purification.

Step 8. Methyl 2-[(1R,3R,5S)-3-[[5-cyclopropyl-3-(2,6-difluorophenyl)-1,2-oxazol-4-yl]carbonyloxy]-8-azabicyclo[3.2.1]octan-8-yl]-4-fluoro-1,3-benzothiazole-6-carboxylate (16i)

To a 100 mL round-bottom flask was added a solution of (1R,3S,5S)-8-azabicyclo[3.2.1]octan-3-yl 5-cyclopropyl-3-(2,6-difluorophenyl)-1,2-oxazole-4-carboxylate 16h (330 mg, 0.88 mmol, 1.0 equiv.) in DMSO (5 mL), methyl 2-bromo-4-fluoro-1,3-benzothiazole-6-carboxylate A1 (280 mg, 0.97 mmol, 1.1 equiv.), CsF (400 mg, 2.63 mmol, 3.0 equiv.). The resulting solution was stirred overnight at 115° C. The reaction was quenched by the addition of EtOAc (200 mL). The mixture was washed with brine (30 mL×3), dried over sodium sulfate, filtered, and concentrated in vacuo to a residue which was purified by silica gel column chromatography eluting with PE:EtOAc (1:1) to afford methyl 2-[(1R,3R,5S)-3-[[5-cyclopropyl-3-(2,6-difluorophenyl)-1,2-oxazol-4-yl]carbonyloxy]-8-azabicyclo[3.2.1]octan-8-yl]-4-fluoro-1,3-benzothiazole-6-carboxylate 16i (150 mg, 29%) as an off-white solid.

Step 9. 2-[(1R,3R,5S)-3-[[5-Cyclopropyl-3-(2,6-difluorophenyl)-1,2-oxazol-4-yl]carbonyloxy]-8-azabicyclo[3.2.1]octan-8-yl]-4-fluoro-1,3-benzothiazole-6-carboxylic acid (I-16)

To a 50 mL round-bottom flask was added a solution of methyl 2-[(1R,3S,5S)-3-[[5-cyclopropyl-3-(2,6-difluorophenyl)-1,2-oxazol-4-yl]carbonyloxy]-8-azabicyclo[3.2.1]octan-8-yl]-4-fluoro-1,3-benzothiazole-6-carboxylate 16i (150 mg, 0.26 mmol, 1.0 equiv.) in pyridine (10 mL) followed by LiI (345 mg, 2.57 mmol, 10.0 equiv.). The resulting mixture was stirred overnight at 125° C. The reaction was quenched by the addition of EtOAc (100 mL). The mixture was washed with brine (30 mL×3), dried over sodium sulfate, filtered, and concentrated in vacuo. The crude product was purified by Prep-HPLC using the following conditions: Column, XBridge C18 OBD Prep Column, 10 µm, 19 mm×250 mm; mobile phases, waters (0.05% TFA) and ACN (56% ACN up to 76% in 8 min); Detector, UV 220 nm. After purification, 2-[(1R,3R,5S)-3-[[5-cyclopropyl-3-(2,6-difluorophenyl)-1,2-oxazol-4-yl]carbonyloxy]-8-azabicyclo[3.2.1]octan-8-yl]-4-fluoro-1,3-benzothiazole-6-carboxylic acid I-16 (72.3 mg, 49%) was obtained as an off-white solid. $^1$HNMR (400 MHz, DMSO-$d_6$) δ: 12.96 (s, 1H), 8.22 (d, J=1.5 Hz, 1H), 7.69 (tt, J=8.4, 6.6 Hz, 1H), 7.58 (dd, J=11.5, 1.6 Hz, 1H), 7.34 (t, J=8.2 Hz, 2H), 5.09 (t, J=5.2 Hz, 1H), 4.24 (s, 2H), 2.88 (tt, J=8.0, 5.3 Hz, 1H), 2.27 (dt, J=15.5, 4.3 Hz, 2H), 1.87-1.71 (m, 4H), 1.44-1.25 (m, 6H). MS (ES, m/z): [M+1]=570.

Example 26: 2-[(1R,3R,5S)-3-[5-cyclopropyl-3-(2,6-difluorophenyl)-1,2-oxazole-4-carboxyloxy]-8-azabicyclo[3.2.1]octan-8-yl]-4-methoxy-1,3-benzothiazole-6-carboxylic acid (I-17)

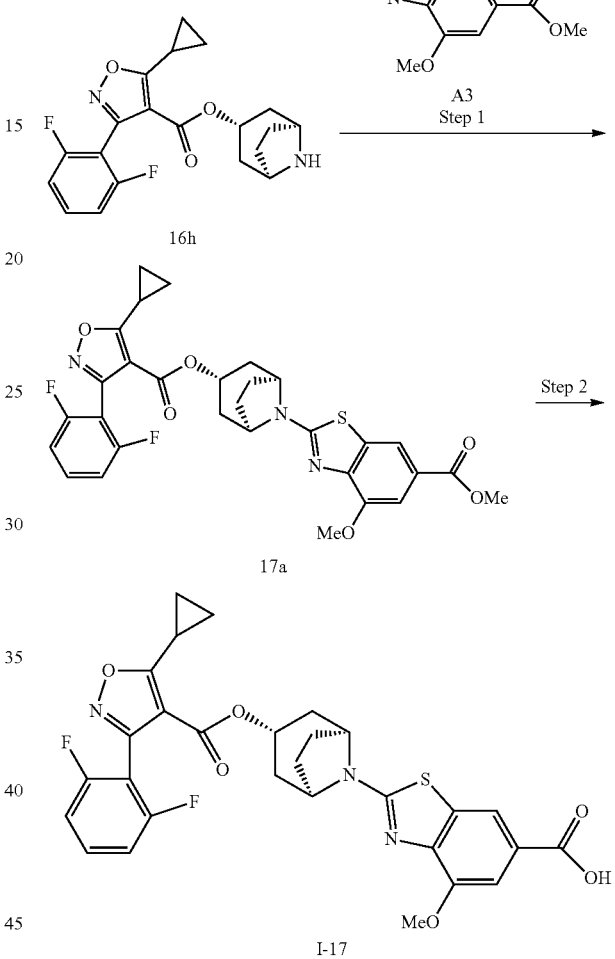

Step 1. Methyl 2-[(1R,3R,5S)-3-[[5-cyclopropyl-3-(2,6-difluorophenyl)-1,2-oxazol-4-yl]carbonyloxy]-8-azabicyclo[3.2.1]octan-8-yl]-4-methoxy-1,3-benzothiazole-6-carboxylate (17a)

Intermediate methyl 2-[(1R,3R,5S)-3-[[5-cyclopropyl-3-(2,6-difluorophenyl)-1,2-oxazol-4-yl]carbonyloxy]-8-azabicyclo[3.2.1]octan-8-yl]-4-methoxy-1,3-benzothiazole-6-carboxylate 17a (300 mg, 57%) was obtained as an off-white solid following the procedure outlined in Example 10, step 8, from intermediates (1R,3R,5S)-8-azabicyclo[3.2.1]octan-3-yl 5-cyclopropyl-3-(2,6-difluorophenyl)-1,2-oxazole-4-carboxylate 16h (330 mg, 0.88 mmol, 1.0 equiv.), methyl 2-bromo-4-methoxy-1,3-benzothiazole-6-carboxylate A3 (320 mg, 1.06 mmol, 1.1 equiv.), CsF (400 mg, 2.63 mmol, 3.0 equiv.) and DMSO (10 mL).

Step 2. 2-[(1R,3R,5S)-3-[[5-Cyclopropyl-3-(2,6-difluorophenyl)-1,2-oxazol-4-yl] carbonyloxy]-8-azabicyclo[3.2.1]octan-8-yl]-4-methoxy-1,3-benzothiazole-6-carboxylic acid (I-17)

2-[(1R,3R,5S)-3-[[5-cyclopropyl-3-(2,6-difluorophenyl)-1,2-oxazol-4-yl]carbonyloxy]-8-azabicyclo[3.2.1]octan-8-yl]-4-methoxy-1,3-benzothiazole-6-carboxylic acid I-17 (56.5 mg, 19%) was obtained as a colorless solid following the procedure outlined in Example 11, from intermediates intermediate 17a (300 mg, 0.50 mmol, 1.0 equiv.), pyridine (10 mL) and LiI (676 mg, 5.04 mmol, 10.0 equiv.). $^1$HNMR (400 MHz, DMSO-$d_6$) δ: 7.98 (d, J=1.5 Hz, 1H), 7.69 (tt, J=8.5, 6.6 Hz, 1H), 7.39-7.28 (m, 3H), 5.08 (t, J=5.3 Hz, 1H), 3.87 (s, 3H), 2.88 (tt, J=8.0, 5.3 Hz, 1H), 2.31-2.20 (m, 2H), 1.85-1.68 (m, 4H), 1.43-1.25 (m, 6H). MS (ES, m/z): [M+1]=582.

Example 27: 2-[(1R,3R,5S)-3-[5-cyclopropyl-3-(2,6-difluorophenyl)-1,2-oxazole-4-carbonyloxy]-8-azabicyclo[3.2.1]octan-8-yl]-5-methoxy-1,3-benzothiazole-6-carboxylic acid (I-18)

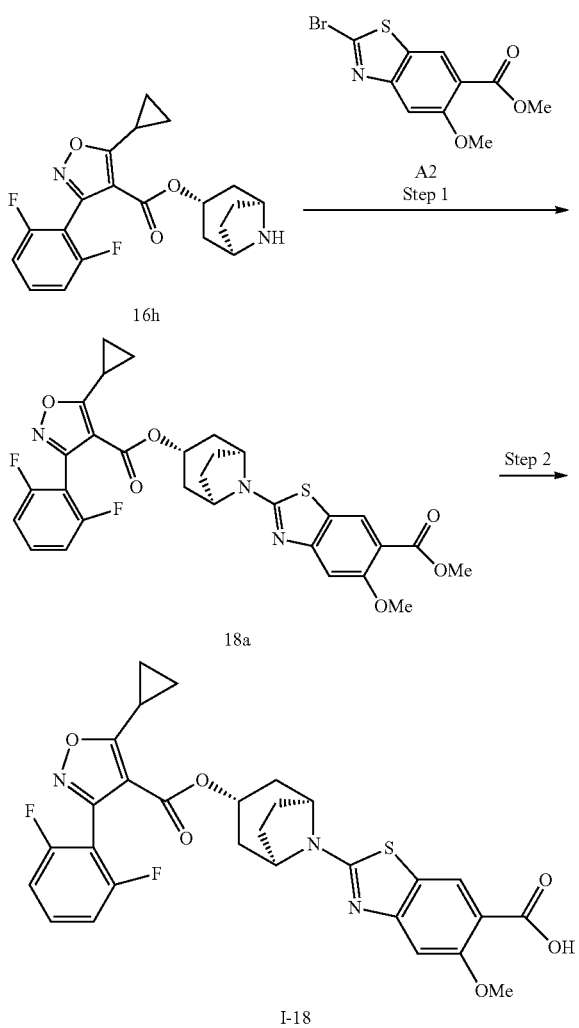

Step 1. Methyl 2-[(1R,3R,5S)-3-[[5-cyclopropyl-3-(2,6-difluorophenyl)-1,2-oxazol-4-yl]carbonyloxy]-8-azabicyclo[3.2.1]octan-8-yl]-5-methoxy-1,3-benzothiazole-6-carboxylate (18a)

Methyl 2-[(1R,3R,5S)-3-[[5-cyclopropyl-3-(2,6-difluorophenyl)-1,2-oxazol-4-yl]carbonyloxy]-8-azabicyclo[3.2.1]octan-8-yl]-5-methoxy-1,3-benzothiazole-6-carboxylate 18a was obtained as an off-white solid following the procedure outlined in Example 11, step 8, from intermediates (1R,3R,5S)-8-azabicyclo[3.2.1]octan-3-yl 5-cyclopropyl-3-(2,6-difluorophenyl)-1,2-oxazole-4-carboxylate 16h (330 mg, 0.88 mmol, 1.0 equiv.), methyl 2-bromo-5-methoxy-1,3-benzothiazole-6-carboxylate A2 (320 mg, 1.06 mmol, 1.1 equiv.), CsF (400 mg, 2.63 mmol, 3.0 equiv.) and DMSO (10 mL).

Step 2. 2-[(1R,3R,5S)-3-[[5-Cyclopropyl-3-(2,6-fluorophenyl)-1,2-oxazol-4-yl]carbonyloxy]-8-azabicyclo[3.2.1]octan-8-yl]-5-methoxy-1,3-benzothiazole-6-carboxylic acid (I-18)

Following the procedure outlined in Example 11, conversion of intermediate 18a (200 mg, 0.34 mmol, 1.0 equiv.) using pyridine (10 mL) and LiI (450 mg, 3.36 mmol, 10.0 equiv.), afforded the title compound 2-[(1R,3R,5S)-3-[[5-cyclopropyl-3-(2,6-fluorophenyl)-1,2-oxazol-4-yl]carbonyloxy]-8-azabicyclo[3.2.1]octan-8-yl]-5-methoxy-1,3-benzothiazole-6-carboxylic acid I-18 (38.7 mg, 20%) as an off-white solid. $^1$HNMR (400 MHz, DMSO-$d_6$) δ: 8.09 (s, 1H), 7.69 (tt, J=8.5, 6.6 Hz, 1H), 7.34 (t, J=8.2 Hz, 2H), 7.15 (s, 1H), 5.09 (t, J=5.3 Hz, 1H), 3.80 (s, 3H), 2.87 (tt, J=8.1, 5.3 Hz, 1H), 2.26 (dt, J=15.3, 4.6 Hz, 2H), 1.86-1.78 (m, 2H), 1.73 (d, J=15.2 Hz, 2H), 1.44-1.25 (m, 6H). MS (ES, m/z): [M+1]=582.

Example 28: 2-[(1R,3R,5S)-3-(5-cyclopropyl-3-{spiro[2.5]octan-6-yl}-1,2-oxazole-4-carbonyloxy)-8-azabicyclo[3.2.1]octan-8-yl]-4-fluoro-1,3-benzothiazole-6-carboxylic acid (I-19)

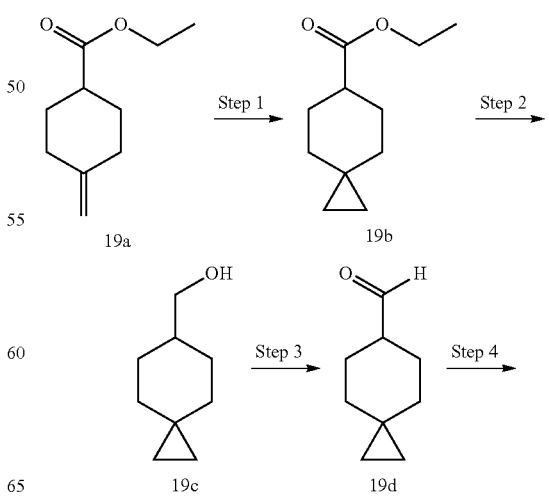

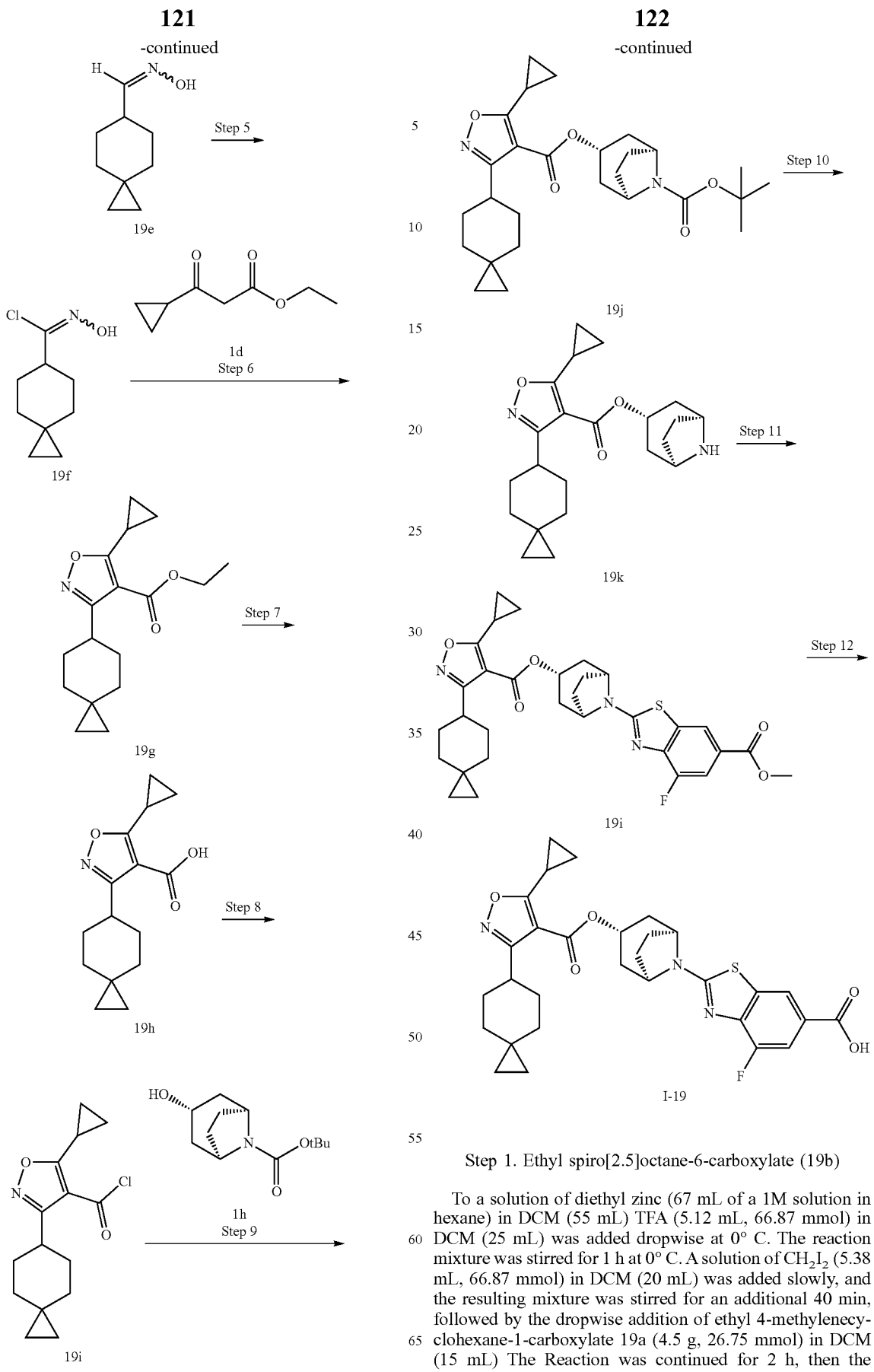

Step 1. Ethyl spiro[2.5]octane-6-carboxylate (19b)

To a solution of diethyl zinc (67 mL of a 1M solution in hexane) in DCM (55 mL) TFA (5.12 mL, 66.87 mmol) in DCM (25 mL) was added dropwise at 0° C. The reaction mixture was stirred for 1 h at 0° C. A solution of CH$_2$I$_2$ (5.38 mL, 66.87 mmol) in DCM (20 mL) was added slowly, and the resulting mixture was stirred for an additional 40 min, followed by the dropwise addition of ethyl 4-methylenecyclohexane-1-carboxylate 19a (4.5 g, 26.75 mmol) in DCM (15 mL) The Reaction was continued for 2 h, then the mixture was diluted with DCM (200 mL), washed with a saturated aqueous NH₄Cl solution and brine, dried over MgSO₄, and concentrated in vacuo to give ethyl spiro[2.5]octane-6-carboxylate 19b (4.9 g, 100%) as a clear oil.

Step 2. Spiro[2.5]octan-6-ylmethanol (19c)

To a solution of ethyl spiro[2.5]octane-6-carboxylate 19b (4.90 g, 26.74 mmol) in 50 mL of dry THF was added LAH solution (17.38 mL, 2 M in THF) at 0° C. The reaction mixture was stirred overnight while being allowed to come to RT. The mixture was cooled again to 0° C., quenched with water (1.5 mL), NaOH (1.5 mL, 1N in water), and a second batch of water (3.0 mL). The aqueous mixture was diluted with EtOAc (200 mL), dried over MgSO₄, filtered, and concentrated in vacuo to give spiro[2.5]octan-6-ylmethanol 19c (3.43 g, 91%) as a clear oil.

Step 3. Spiro[2.5]octane-6-carbaldehyde (19d)

To a solution of spiro[2.5]octan-6-ylmethanol 19c (3.43 g, 24.33 mmol) in DCM (50 mL) at 0° C. Dess-Martin reagent (10.32 g, 24.33 mmol) was added portionwise. The mixture was stirred for 2 h while gradually being warmed to RT. The mixture was diluted with DCM (200 mL), washed with brine, dried over MgSO₄, filtered, concentrated and purified with column chromatography to give spiro[2.5]octane-6-carbaldehyde 19d (1.61 g, 47.6%) as a clear oil.

Step 4. Spiro[2.5]octane-6-carbaldehyde oxime (19e)

To a solution of spiro[2.5]octane-6-carbaldehyde 19d (1.60 g, 11.51 mmol) in EtOH (30 mL) at 0° C. was added hydroxylamine hydrochloride (0.96 g, 13.81 mmol) and pyridine. The mixture was stirred at 0° C. for 3 h. EtOH was removed and the residue was partitioned between EtOAc and water. The organic layer was dried over MgSO₄, filtered and concentrated to give spiro[2.5]octane-6-carbaldehyde oxime 19e (1.77 g) as a sticky solid. The product was carried on to the next step without further purification.

Step 5. N-Hydroxyspiro[2.5]octane-6-carbimidoyl chloride (19f)

To a solution of spiro[2.5]octane-6-carbaldehyde oxime 19e (1.77 g, 11.49 mmol) in DMF (20 mL) at 0° C. was added N-chlorosuccinimide (1.69 g, 12.66 mmol). The reaction mixture was slowly warmed to RT and stirred overnight, then quenched with brine and extracted with Et₂O. The combined organic layers were washed with water and brine, dried over MgSO₄, filtered and concentrated in vacuo. The residue was purified via silica gel chromatography eluting with hexane-EtOAc (20% EtOAc) to give N-hydroxyspiro[2.5]octane-6-carbimidoyl chloride 19f (E22 g, 56%) as a clear oil.

Step 6. Ethyl 5-cyclopropyl-3-(spiro[2.5]octan-6-yl)isoxazole-4-carboxylate (19g)

A solution of ethyl 3-cyclopropyl-3-oxopropanoate 1d (E0 g, 6.40 mmol) in THF (20 mL) at 0° C. was treated with potassium tert-butoxide (7.59 mL, 1M in THF). After stirring for 30 minutes at 0° C., N-hydroxyspiro[2.5]octane-6-carbimidoyl chloride 19f (E10 g, 5.84 mmol) in THF (10 mL) was added dropwise. The reaction mixture was stirred for E5 h at 0° C., then quenched with water (5 mL) at 0° C. THF was removed and the residue was partitioned between EtOAc and water. The organic layer was dried over MgSO₄, filtered, concentrated and purified via silica gel chromatography to give ethyl 5-cyclopropyl-3-(spiro[2.5]octan-6-yl)isoxazole-4-carboxylate 19g (0.84 g, 50%) as a light oil. ¹HNMR (400 MHz, CDCl₃): δ 4.43-4.25 (m, 2H), 3.14 (tt, J=11.7, 3.2 Hz, 1H), 2.81 (tt, J=8.4, 5.1 Hz, 1H), 2.03-1.93 (m, 2H), 1.85 (tt, J=13.7, 7.0 Hz, 2H), 1.79-1.64 (m, 2H), 1.43-1.34 (m, 3H), 1.31-1.21 (m, 2H), 1.20-1.09 (m, 2H), 0.98 (d, J=13.2 Hz, 2H), 0.37-0.18 (m, 4H).

Step 7. 5-Cyclopropyl-3-(spiro[2.5]octan-6-yl)isoxazole-4-carboxylic acid (19h)

A mixture of ethyl 5-cyclopropyl-3-(spiro[2.5]octan-6-yl)isoxazole-4-carboxylate 19g (0.1 g, 0.34 mmol) in MeOH (3 mL), and NaOH (0.69 mL, 1M in H₂O). was stirred overnight at 50° C. After removal of MeOH the residue was acidified to pH 5-6 using HCl (aq., 1 M), and extracted twice with EtOAc. The combined organic layers were dried over MgSO₄, filtered and concentrated to give 5-cyclopropyl-3-(spiro[2.5]octan-6-yl)isoxazole-4-carboxylic acid 19h (0.086 g, 95%) as a light yellow solid. The product was carried on to the next step without further purification.

Steps 8 and 9. (1R,3R,5S)-8-(tert-Butoxycarbonyl)-8-azabicyclo[3.2.1]octan-3-yl 5-cyclopropyl-3-(spiro[2.5]octan-6-yl)isoxazole-4-carboxylate (19j)

To a mixture of oxalyl chloride (0.072 mL, 0.84 mmol), and 5-cyclopropyl-3-(spiro[2.5]octan-6-yl)isoxazole-4-carboxylic acid 19h (0.146 g, 0.56 mmol) in DCM (5 mL) were added two drops of DMF. The reaction mixture was stirred for 1 h at RT and was concentrated to dryness. The crude acid chloride 19i was dried in vacuo for 30 min and dissolved in DCM (8 mL). tert-Butyl (1R,3R,5S)-3-hydroxy-8-azabicyclo[3.2.1]octane-8-carboxylate 1 h (0.14 g, 0.62 mmol) was added, followed by Et₃N (0.22 mL, 1.56 mmol) and DMAP (6.8 mg, 0.056 mmol). The reaction mixture was continued overnight at 45° C. The mixture was concentrated in vacuo, and the residue was purified via silica gel chromatography eluting with hexane-EtOAc (20% EtOAc) to give (1R,3r,5S)-8-(7c/7-butoxycarbonyl)-8-azabicyclo[3,2,1]octan-3-yl 5-cyclopropyl-3-(spiro[2.5]octan-6-yl)isoxazole-4-carboxylate 19j (0.071 g, 26.9%) as a clear oil.

Step 10. (1R,3r,5S)-8-Azabicyclo[3.2.1]octan-3-yl 5-cyclopropyl-3-(spiro[2.5]octan-6-yl)isoxazole-4-carboxylate (19k)

To a solution of (1R,3r,5S)-8-(tert-butoxycarbonyl)-8-azabicyclo[3,2,1]octan-3-yl 5-cyclopropyl-3-(spiro[2.5]octan-6-yl)isoxazole-4-carboxylate 19j (0.065 g, 0.14 mmol) in DCM (2 mL) was added TFA (0.2 mL). The mixture was stirred for 30 minutes at RT. The solvent and TFA were removed in vacuo to give crude (1R,3R,5S)-8-azabicyclo[3.2.1]octan-3-yl 5-cyclopropyl-3-(spiro[2.5]octan-6-yl)isoxazole-4-carboxylate 19k (0.051 g) as a clear oil. The product was carried on to the next step without further purification. MS (ES, m/z): [M+1]=371.

Step 11. (1R,3r,5S)-8-(4-Fluoro-6-(methoxycarbonyl)benzo[d]thiazol-2-yl)-8-azabicyclo[3.2.1]octan-3-yl 5-cyclopropyl-3-(spiro[2.5]octan-6-yl)isoxazole-4-carboxylate (19l)

To a solution of (1R,3r,5S)-8-azabicyclo[3.2.1]octan-3-yl 5-cyclopropyl-3-(spiro[2.5]octan-6-yl)isoxazole-4-carboxylate 19k (0.04 g, 0.11 mmol) and methyl 2-bromo-4-fluorobenzo[d]thiazole-6-carboxylate A1 (0.052 g, 0.18 mmol) in DMA (2 mL) was added $Cs_2CO_3$ (0.056 g, 0.17 mmol). The mixture was stirred overnight at 100° C. The reaction mixture was cooled to RT and partitioned between EtOAc and water. The organic layer was washed with brine, dried over $MgSO_4$, filtered and concentrated. The residue was purified via silica gel chromatography hexane-EtOAc (EtOAc 20-30%) to give (1R,3r,5S)-8-(4-fluoro-6-(methoxycarbonyl)benzo[d]thiazol-2-yl)-8-azabicyclo[3.2.1]octan-3-yl 5-cyclopropyl-3-(spiro[2.5]octan-6-yl)isoxazole-4-carboxylate 19l (0.064 g) as a white foam. MS (ES, m z): [M+1]=580.

Step 12. 2-((1R,3r,5S)-3-((5-Cyclopropyl-3-(spiro[2.5]octan-6-yl)isoxazole-4-carbonyl)oxy)-8-azabicyclo[3.2.1]octan-8-yl)-4-fluorobenzo[d]thiazole-6-carboxylic acid (I-19)

A mixture of (1R,3r,5S)-8-(4-fluoro-6-(methoxycarbonyl)benzo[d]thiazol-2-yl)-8-azabicyclo[3.2.1]octan-3-yl 5-cyclopropyl-3-(spiro[2.5]octan-6-yl)isoxazole-4-carboxylate 19l (0.05 g, 0.086 mmol) and LiI (0.07 g, 0.52 mmol) in pyridine (1 mL) was stirred for 48 h at 100° C. After cooling to RT, the mixture was quenched with water (2 mL), and the pH value of the aqueous mixture was adjusted to pH 4-5 using HCl (aq., 1M). The acidic mixture was extracted with EtOAc (50 mL×2). The combined organic layers were washed with brine, dried over $MgSO_4$, filtered and concentrated. The residue was purified using reverse phase prep HPLC using gradient 40 to 90% acetonitrile/water with 0.1% TFA to yield the TFA salt of 2-((1R,3r,5S)-3-((5-cyclopropyl-3-(spiro[2.5]octan-6-yl)isoxazole-4-carbonyl)oxy)-8-azabicyclo[3.2.1]octan-8-yl)-4-fluorobenzo[d]thiazole-6-carboxylic acid I-19, (0.038 g) as an off white solid. $^1$HNMR (400 MHz, DMSO-cfc): δ 8.26 (d, J=1.4 Hz, 1H), 7.72-7.50 (m, 1H), 5.21 (s, 1H), 4.44 (s, 2H), 3.18 (t, J=11.6 Hz, 1H), 2.80 (d, J=5.3 Hz, 1H), 2.40 (d, J=15.3 Hz, 2H), 2.14 (s, 4H), 2.02 (d, J=15.3 Hz, 2H), 1.94 (d, J=10.80 Hz, 2H), 1.79 (t, J=14.1 Hz, 2H), 1.61 (t, J=10.5 Hz, 2H), 1.30-1.11 (m, 4H), 0.98 (d, J=13.4 Hz, 2H), 0.27 (td, J=14.4, 6.3 Hz, 4H). MS (ES, m/z): [M+1]=566.

Example 29: 2-[(1R,3R,5S)-3-(3-{Bicyclo[2.2.2]octan-1-yl}-5-cyclopropyl-1,2-oxazole-4-carbonyloxy)-8-azabicyclo[3.2.1]octan-8-yl]-4-fluoro-1,3-benzothiazole-6-carboxylic acid (I-20)

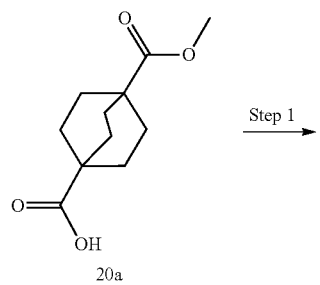

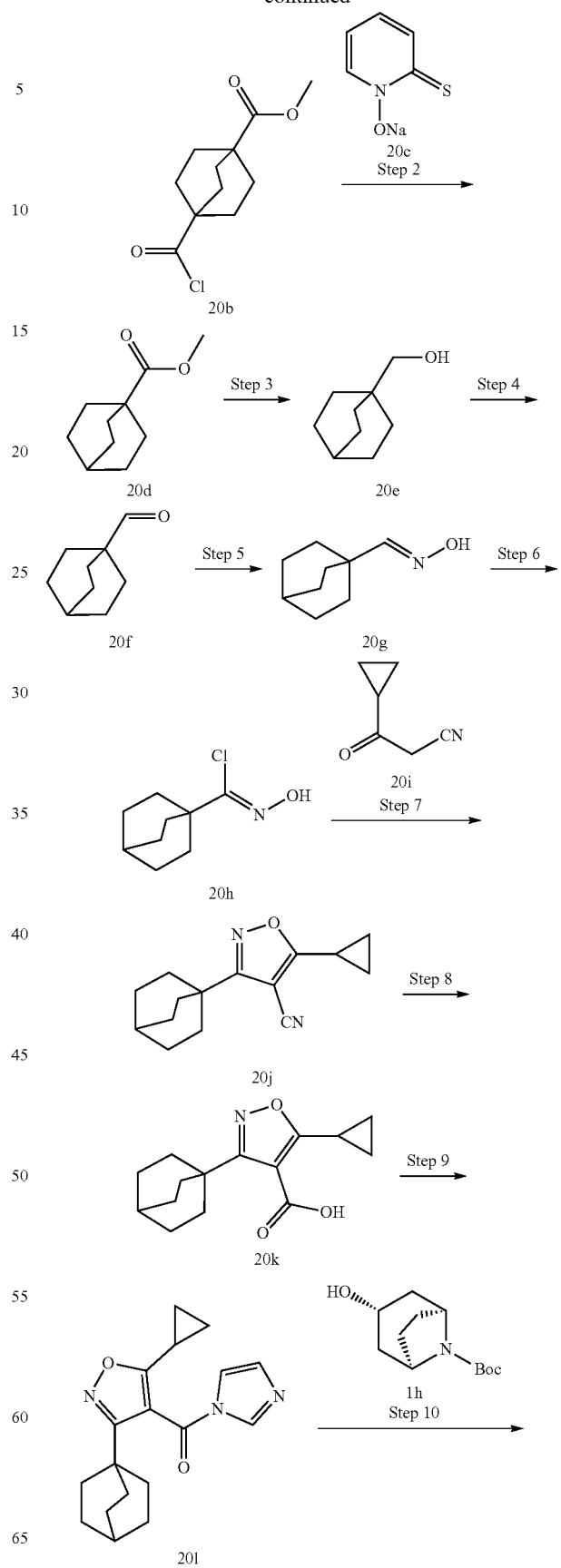

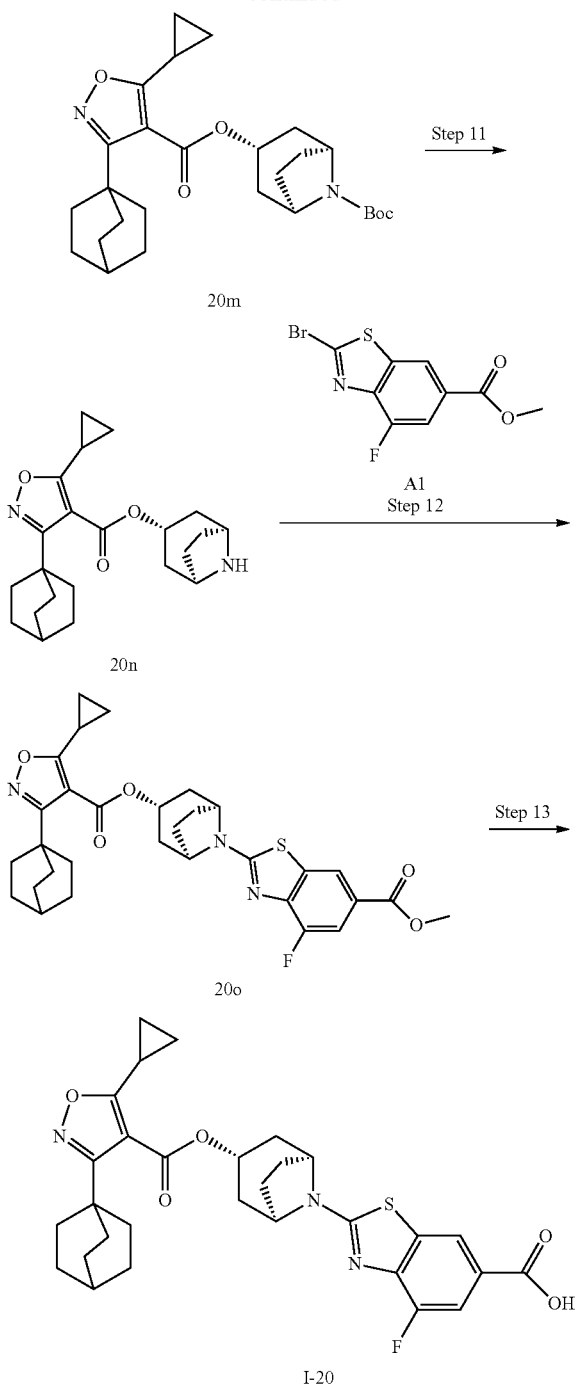

Step 2. Methyl bicyclo[2.2.2]octane-1-carboxylate (20d)

To a 500 mL 3-necked round-bottom flask was added 1-(sodiooxy)-1,2-dihydropyridine-2-thione 20c (16.3 g, 109.29 mmol, 1.2 equiv.), chloroform (150 mL), and 4-dimethylaminopyridine (112 mg, 0.92 mmol, 0.01 equiv.), followed by the dropwise addition of methyl 4-(carbonochloridoyl)bicyclo[2.2.2]-octane-1-carboxylate 20b (21 g, 91.03 mmol, 1.0 equiv.) in chloroform (50 mL) over a 30 min period, under concomitant irradiation from a tungsten lamp (120 V, 150 W). The resulting mixture was stirred for 120 min at 80° C., then cooled to RT. HCl (1M, 300 mL) was added and the aqueous mixture was extracted with dichloromethane (300 mL×3). The combined organic layers were dried over anhydrous sodium sulfate, filtered, and concentrated in vacuo to give a crude product (15 g), which was purified by Flash-Prep-HPLC using the following conditions: Column, silica gel; mobile phase, PE:EtOAc=100:0 increasing to PE:EtOAc=100:10 within 20 min; Detector, UV 254 nm. Removal of solvents gave methyl bicyclo[2.2.2]octane-1-carboxylate 20d (13 g, 85%) as a light yellow oil.

Step 3. Bicyclo[2.2.2]octan-1-ylmethanol (20e)

To a 500 mL round-bottom flask was added methyl bicyclo[2.2.2]octane-1-carboxylate 20d (13 g, 77.27 mmol, 1.0 equiv.), tetrahydrofuran (150 mL) lithium aluminum hydride (5.9 g, 155.47 mmol, 2.0 equiv.) was added at 0° C. After 5 min, the cooling bath was removed and reaction was continued for 1 h at RT, then quenched with $H_2O$ (300 mL). The resulting mixture was extracted with ethyl acetate (500 mL×3) and the combined organic layers were concentrated to a crude product (12 g) which was purified by Flash-Prep-HPLC using the following conditions: Column, silica gel; mobile phase, PE:EtOAc=100:0 increasing to PE:EtOAc=90:10 within 30 min; Detector, UV 254 nm. Bicyclo[2.2.2]octan-1-ylmethanol 20e (8.0 g, 74%) was obtained as a colorless oil.

Step 4. Bicyclo[2.2.2]octane-1-carbaldehyde (20f)

To a 500 mL round-bottom flask was added bicyclo[2.2.2]octan-1-ylmethanol 20e (8.0 g, 57.05 mmol, 1.0 equiv.), dichloromethane (240 mL), and Dess-Martin periodinate (37 g, 87.26 mmol, 1.5 equiv.). The resulting mixture was stirred overnight at RT. The solvent was removed in vacuo, and the residue was purified via silica gel column chromatography eluting with ethyl acetate/petroleum ether (10%-90%) to give bicyclo[2.2.2]octane-1-carbaldehyde 20f (5.6 g, 71%) as a light yellow oil.

Step 5. N-[Bicyclo[2.2.2]octan-1-ylmethylidene]hydroxylamine (20g)

To a 250 mL vial was added $NH_2OH \cdot HCl$ (4.2 g, 60.87 mmol, 1.5 equiv.), water (60 mL), sodium carbonate (2.2 g, 20.76 mmol, 0.5 equiv.), and bicyclo[2.2.2]octane-1-carbaldehyde 20f (5.6 g, 40.52 mmol, 1.0 equiv.) in ethanol (30 mL). The resulting mixture was stirred for 2 h at RT, then extracted with ethyl acetate (600 mL). The organic layer was washed with brine (300 mL×3), dried over anhydrous sodium sulfate, filtered, and concentrated in vacuo. The residue was purified via silica gel column chromatography

Step 1. Methyl 4-(carbonochloridoyl)bicyclo[2.2.2]octane-1-carboxylate (20b)

To a 250 mL round-bottom flask was added 4-(methoxycarbonyl)bicyclo[2.2.2]octane-1-carboxylic acid 20a (20 g, 94.23 mmol, 1.0 equiv.) and thionyl chloride (100 mL). The resulting mixture was stirred overnight at RT and concentrated in vacuo to give methyl 4-(carbonochloridoyl)bicyclo[2.2.2]octane-1-carboxylate 20b (21 g, 97%) as a white solid.

eluting with PE:EtOAc (90:10) to give N-[bicyclo[2.2.2]octan-1-ylmethylidene]hydroxylamine 20g (4.3 g, 69%) as a white solid.

Step 6. N-Hydroxybicyclo[2.2.2]oct-1-carbonimidoyl (20h)

To a 50 mL round-bottom flask was added N-[bicyclo[2.2.2]octan-1-ylmethylidene]-hydroxylamine 20g (2.3 g, 15.01 mmol, 1.0 equiv.) and N,N-dimethylformamide (20 mL). NCS (3.1 g, 23.13 mmol, 1.5 equiv.) was added. The resulting mixture was stirred at RT for 2 h. Ethyl acetate (300 mL) was added. The mixture was washed with brine (200 mL×3), dried over anhydrous sodium sulfate, filtered, and concentrated in vacuo to provide N-hydroxybicyclo[2.2.2]oct-1-carbonimidoyl chloride 20h (2.8 g, 99%) as a white solid.

Step 7. 3-[Bicyclo[2.2.2]octan-1-yl]-5-cyclopropyl (20j)

To a 50 mL round-bottom flask containing 3-cyclopropyl-3-oxopropanenitrile 20i (1.63 g, 14.94 mmol, 1.0 equiv.), ethanol (20 mL), and TEA (1.51 g, 14.92 mmol, 1.0 equiv.), N-hydroxybicyclo[2.2.2]oct-1-carbonimidoyl chloride 20h (2.8 g, 14.92 mmol, 1.0 equiv.) was added. The reaction mixture was stirred for 5 min at 0° C. and then for 2 h at RT. The resulting mixture was diluted with EtOAc (300 mL), washed with brine (100 mL×2), dried over anhydrous sodium sulfate, filtered, and concentrated in vacuo. The crude product was purified by Flash-Prep-HPLC using the following conditions: Column, silica gel; mobile phase, PE:EtOAc=100:0 increasing to PE:EtOAc=80:20 within 30 min; Detector, UV 254 nm. Removal of solvents provided 3-[bicyclo[2.2.2]octan-1-yl]-5-cyclopropyl-1,2-oxazole-4-carbonitrile 20j (1.7 g, 47%) as a light yellow oil.

Step 8. 3-[Bicyclo[2.2.2]octan-1-yl]-5-cyclopropyl-1,2-oxazole-4-carboxylic (20k)

To a 25 mL round-bottom flask purged with nitrogen was added 3-[bicyclo[2.2.2]octan-1-yl]-5-cyclopropyl-1,2-oxazole-4-carbonitrile 20j (200 mg, 0.83 mmol, 1.0 equiv.), ethylene glycol (2 mL), and potassium hydroxide (462 mg, 8.23 mmol, 10.0 equiv.). The resulting mixture was stirred overnight at 140° C. The mixture was diluted with H$_2$O (100 mL) and the pH value of the solution was adjusted to 3-4 using a HCl (aq., 1M). The aqueous mixture was extracted with ethyl acetate (200 mL). The organic layer was washed with brine (50 mL×2), and concentrated to a residue which was purified via silica gel column chromatography eluting with dichloromethane/methanol (10:1) to afford 3-[bicyclo[2.2.2]octan-1-yl]-5-cyclopropyl-1,2-oxazole-4-carboxylic acid 20k (150 mg, 70%) as a light yellow solid.

Step 9. 3-[Bicyclo[2.2.2]octan-1-yl]-5-cyclopropyl-4-[(1H-imidazol-1-yl)carbonyl]-1,2-oxazole (20l)

To a 50 mL round-bottom flask purged with nitrogen was added 3-[bicyclo[2.2.2]octan-1-yl]-5-cyclopropyl-1,2-oxazole-4-carboxylic acid 20k (100 mg, 0.38 mmol, 1.0 equiv.), N,N-dimethylformamide (1 mL), and CDI (75 mg, 0.46 mmol, 1.2 equiv.). The resulting mixture was stirred for 2 h at 40° C., then concentrated in vacuo to give 3-[bicyclo[2.2.2]octan-1-yl]-5-cyclopropyl-4-[(1H-imidazol-1-yl)carbonyl]-1,2-oxazole 20l (100 mg, 84%) as a yellow oil.

Step 10. (1R,3r,5S)-8-(tert-butoxycarbonyl)-8-azabicyclo[3.2.1]octan-3-yl 3-(bicyclo[2.2.2]octan-1-yl)-5-cyclopropylisoxazole-4-carboxylate (20m)

To a 50 mL round-bottom flask purged with nitrogen was added 3-[bicyclo[2.2.2]octan-1-yl]-5-cyclopropyl-4-[(1H-imidazol-1-yl)carbonyl]-1,2-oxazole 20l (100 mg, 0.32 mmol, 1.0 equiv.), N,N-dimethylformamide (2 mL), (1R,3r,5S)-tert-butyl 3-hydroxy-8-azabicyclo[3.2.1]octane-8-carboxylate 1h (173 mg, 0.76 mmol, 1.2 equiv.), and DBU (58 mg, 0.38 mmol, 1.0 equiv.). The resulting mixture was stirred overnight at 50° C. After cooling to RT, ethyl acetate (200 mL) was added and the mixture was washed with brine (50 mL×4), dried over anhydrous sodium sulfate, filtered, and concentrated in vacuo. The residue was purified by a silica gel chromatography eluting with ethyl acetate/petroleum ether (1:5) to give (1R,3r,5S)-8-(tert-butoxycarbonyl)-8-azabicyclo[3.2.1]octan-3-yl-3-(bicyclo[2.2.2]octan-1-yl)-5 cyclopropylisoxazole-4-carboxylate 20m (60 mg, 40%) as a light yellow oil.

Step 11. (1R,3R,5S)-8-azabicyclo[3.2.1]octan-3-yl 3-[bicyclo[2.2.2]octan-1-yl]-5-cyclopropyl-1,2-oxazole-4-carboxylate (20n)

To a 25-mL round-bottom flask was added tert-butyl (1R,3R,5S)-3-[(3-[bicyclo[2.2.2]octan-1-yl]-5-cyclopropyl-1,2-oxazol-4-yl)carbonyloxy]-8-azabicyclo[3.2.1]octane-8-carboxylate 20m (35 mg, 0.07 mmol, 1.0 equiv.), dichloromethane (1 mL), and trifluoroacetic acid (1 mL). The resulting mixture was stirred for 2 h at RT and quenched with H$_2$O. The pH value of the mixture was adjusted to 10 using sodium bicarbonate (aq., 1 M). The mixture was extracted with ethyl acetate (30 mL×4), and the combined organic layers were washed with of brine (30 mL), dried over anhydrous sodium sulfate, filtered, and concentrated in vacuo to afford (1R,3R,5S)-8-azabicyclo[3.2.1]octan-3-yl 3-[bicyclo[2.2.2]octan-1-yl]-5-cyclopropyl-1,2-oxazole-4-carboxylate 20n (27 mg, 98%) as a light yellow oil.

Step 12. Methyl 2-[(1R,3R,5S)-3-[(3-[bicyclo[2.2.2]octan-1-yl]-5-cyclopropyl-1,2-oxazol-4-yl)carbonyloxy]-8-azabicyclo[3.2.1]octan-8-yl]-4-fluoro-1,3-benzothiazole-6-carboxylate (20o)

To a 25-mL round-bottom flask purged with nitrogen was added (1R,3R,5S)-8-azabicyclo[3.2.1]octan-3-yl 3-[bicyclo[2.2.2]octan-1-yl]-5-cyclopropyl-1,2-oxazole-4-carboxylate 20n (27 mg, 0.09 mmol, 1.0 equiv.), methyl 2-bromo-4-fluoro-1,3-benzothiazole-6-carboxylate A1 (29 mg, 0.09 mmol, 1.0 equiv.), DMA (1 mL), and Cs$_2$CO$_3$ (55 mg, 0.17 mmol, 2.0 equiv.). The reaction mixture was stirred overnight at 60° C., cooled to RT and diluted with H$_2$O. The aqueous mixture was extracted with ethyl acetate (50 mL×3). The combined organic layers were washed with brine (50 mL), dried over anhydrous sodium sulfate, filtered, and concentrated in vacuo. The residue was purified by silica gel column chromatography eluting with PE:EtOAc (5:1) to provide methyl 2-[(1R,3R,5S)-3-[(3-[bicyclo[2.2.2]octan-1-yl]-5-cyclopropyl-1,2-oxazol-4-yl)carbonyloxy]-8-azabicyclo[3.2.1]octan-8-yl]-4-fluoro-1,3-benzothiazole-6-carboxylate 20o (27 mg, 54%) as a light yellow oil.

Step 13. 2-[(1R,3R,5S)-3-[(3-[Bicyclo[2.2.2]octan-1-yl]-5-cyclopropyl-1,2-oxazol-4-yl)carbonyloxy]-8-azabicyclo[3.2.1]octan-8-yl]-4-fluoro-1,3-benzothiazole-6-carboxylic acid (I-20)

To a 25 mL round-bottom flask purged with nitrogen was added methyl 2-[(1R,3R,5S)-3-[(3-[bicyclo[2.2.2]octan-1- yl]-5-cyclopropyl-1,2-oxazol-4-yl)carbonyloxy]-8-azabicyclo[3.2.1]octan-8-yl]-4-fluoro-1,3-benzothiazole-6-carboxylate 20o (50 mg, 0.09 mmol, 1.0 equiv.), LiI (115 mg, 10.0 equiv.) and pyridine (2 mL). The resulting mixture was stirred overnight at 125° C. H₂O was added, the pH value of the solution was adjusted to 5 using HCl (aq., 1 M). The aqueous mixture was extracted with ethyl acetate (100 mL×3), the combined organic layers were washed with brine (50 mL×1), and concentrated in vacuo. The crude product was purified by Prep-HPLC using the following conditions: Column, XBridge C18 OBD Prep Column, 5 μm, 19 mm×250 mm; mobile phase, water (0.05% TFA) and ACN (80.0% ACN up to 92.0% in 8 min); Detector, UV 220 nm. After purification, 2-[(1R,3R,5S)-3-[(3-[bicyclo[2.2.2]octan-1-yl]-5-cyclopropyl-1,2-oxazol-4-yl)carbonyloxy]-8-azabicyclo[3.2.1]octan-8-yl]-4-fluoro-1,3-benzothiazole-6-carboxylic acid I-20 (21 mg, 43%) was obtained as a colorless solid. ¹HNMR (400 MHz, CD₃OD) δ: 8.17 (d, J=1.5 Hz, 1H), 7.68 (dd, J=11.5, 1.5 Hz, 1H), 5.26 (t, J=5.1 Hz, 1H), 4.52 (s, 2H), 2.67 (tt, J=8.2, 5.2 Hz, 1H), 2.51 (dt, J=15.7, 4.5 Hz, 2H), 2.21 (d, J=2.6 Hz, 4H), 2.14-1.94 (m, 8H), 1.73-1.64 (m, 7H), 1.31-1.14 (m, 4H). MS (ES, m/z): [M+1]=566.25.

Example 30: 2-[(1R,3R,5S)-3-(3-{bicyclo[2.2.2]octan-1-yl}-5-cyclopropyl-1,2-oxazole-4-carbonyloxy)-8-azabicyclo[3.2.1]octan-8-yl]-4-methoxy-1,3-benzothiazole-6-carboxylic acid (I-21)

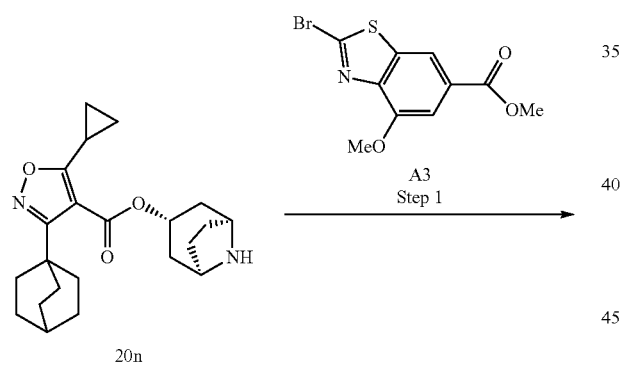

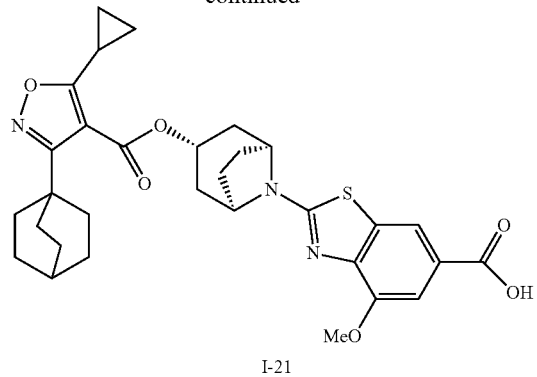

Step 1. (1R,3r,5S)-8-(4-Methoxy-6-(methoxycarbonyl)benzo[d]thiazol-2-yl)-8-azabicyclo[3.2.1]octan-3-yl 3-(bicyclo[2.2.2]octan-1-yl)-5-cyclopropylisoxazole-4-carboxylate (21a)

Following the procedure outlined in Example 10, step 8, using intermediates (1R,3R,5S)-8-azabicyclo[3.2.1]octan-3-yl 3-[bicyclo[2.2.2]octan-1-yl]-5-cyclopropyl-1,2-oxazole-4-carboxylate 20n (80 mg, 0.22 mmol, 1.0 equiv.) and methyl 2-bromo-4-methoxy-1,3-benzothiazole-6-carboxylate A3 (65 mg, 0.22 mmol, 1.0 equiv.) with DMA (2 mL) and Cs₂CO₃ (143 mg, 0.44 mmol, 2.0 equiv.) at 60° C., (1R,3R,5S)-8-(4-Methoxy-6-(methoxycarbonyl)benzo[d]thiazol-2-yl)-8-azabicyclo[3.2.1]octan-3-yl 3-(bicyclo[2.2.2]octan-1-yl)-5-cyclopropylisoxazole-4-carboxylate 21a (52 mg, 41%) was obtained as a light yellow oil.

Step 2. [(1R,3R,5S)-3-[(3-[bicyclo[2.2.2]octan-1-yl]-5-cyclopropyl-1,2-oxazol-4-yl)carbonyloxy]-8-azabicyclo[3.2.1]octan-8-yl]-4-methoxy-1,3-benzothiazole-6-carboxylic acid (I-21)

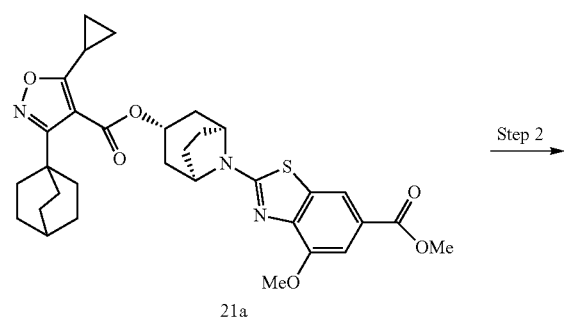

Following the procedure outlined in the preparative example 2, intermediate 21a (52 mg, 0.09 mmol, 1.0 equiv.) from step 1 above, under the conditions of pyridine (2 mL) and LiI (108 mg, 10.0 equiv.), was converted to the title compound 2-[(1R,3R,5S)-3-[(3-[bicyclo[2.2.2]octan-1-yl]-5-cyclopropyl-1,2-oxazol-4-yl)carbonyloxy]-8-azabicyclo[3.2.1]octan-8-yl]-4-methoxy-1,3-benzothiazole-6-carboxylic acid I-21 (18.3 mg (36%) as an off-white solid. ¹HNMR (400 MHz, CD₃OD) δ: 8.02 (d, J=1.4 Hz, 1H), 7.58 (d, J=1.4 Hz, 1H), 5.25 (t, J=5.1 Hz, 1H), 4.56 (s, 2H), 4.02 (s, 3H), 2.67 (tt, J=8.2, 5.2 Hz, 1H), 2.52 (dt, J=15.8, 4.6 Hz, 2H), 2.21 (d, J=2.5 Hz, 4H), 2.15-2.05 (m, 2H), 2.03-1.94 (m, 6H), 1.74-1.64 (m, 7H), 1.35-1.14 (m, 5H). MS (ES, m/z): [M+1]=578.25.

Example 31: 2-[(1R,3R,5S)-3-(3-{bicyclo[2.2.2]octan-1-yl}-5-cyclopropyl-1,2-oxazole-4-carbonyloxy)-8-azabicyclo[3.2.1]octan-8-yl]-5-methoxy-1,3-benzothiazole-6-carboxylic acid (I-22)

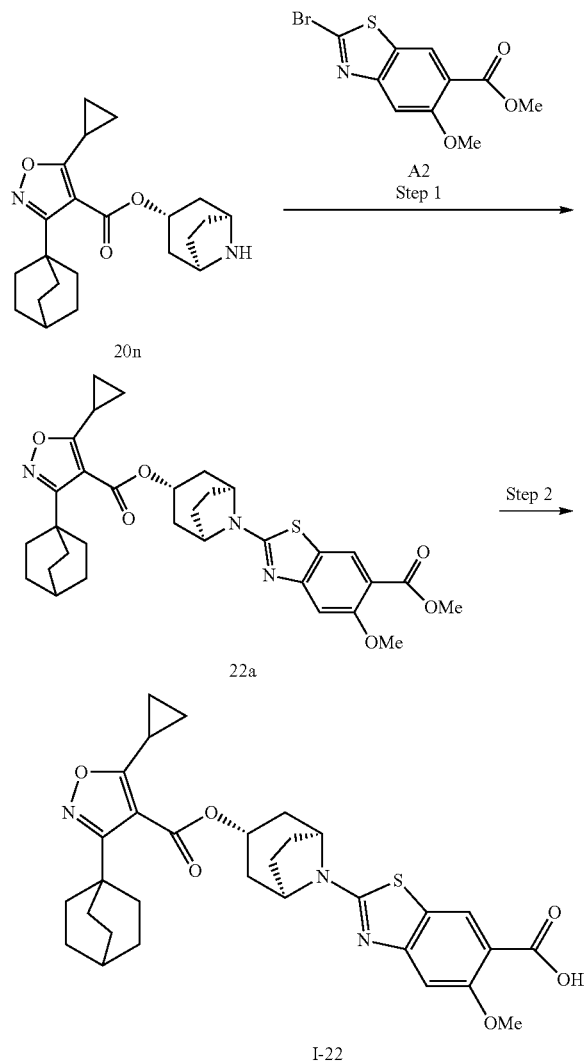

Step 1. (1R,3r,5S)-8-(5-methoxy-6-(methoxycarbonyl)benzo[d]thiazol-2-yl)-8-azabicyclo[3.2.1]octan-3-yl 3-(bicyclo[2.2.2]octan-1-yl)-5-cyclopropylisoxazole-4-carboxylate (22a)

Following the procedure outlined in Example 10, step 8, conversion of intermediates (1R,3R,5S)-8-azabicyclo[3.2.1]octan-3-yl 3-[bicyclo[2.2.2]octan-1-yl]-5-cyclopropyl-1,2-oxazole-4-carboxylate 20n (80 mg, 0.22 mmol, 1.0 equiv.) and methyl 2-bromo-5-methoxy-1,3-benzothiazole-6-carboxylate A3 (65 mg, 0.22 mmol, 1.0 equiv.) with DMA (2 mL), Cs$_2$CO$_3$ (143 mg, 0.44 mmol, 2.0 equiv.) at 60° C., afforded (1R,3r,5S)-8-(5-methoxy-6-(methoxycarbonyl)benzo[d]thiazol-2-yl)-8-azabicyclo[3.2.1]octan-3-yl 3-(bicyclo[2.2.2]octan-1-yl)-5-cyclopropylisoxazole-4-carboxylate 22a (50 mg, 39%) as a light yellow oil.

Step 2. 2-[(1R,3R,5S)-3-[(3-[bicyclo[2.2.2]octan-1-yl]-5-cyclopropyl-1,2-oxazol-4-yl)carbonyloxy]-8-azabicyclo[3.2.1]octan-8-yl]-5-methoxy-1,3-benzothiazole-6-carboxylic (I-22)

Following the procedure outlined in Example 11, conversion of intermediate 22a (50 mg, 0.08 mmol, 1.0 equiv.) obtained in step 1 above, with pyridine (2 mL) and LiI (108 mg, 10.0 equiv.), afforded the title compound 2-[(1R,3R,5S)-3-[(3-[bicyclo[2.2.2]octan-1-yl]-5-cyclopropyl-1,2-oxazol-4-yl)carbonyloxy]-8-azabicyclo[3.2.1]octan-8-yl]-5-methoxy-1,3-benzothiazole-6-carboxylic acid I-22 (21 mg, 41%) as an off-white solid. $^1$HNMR (300 MHz, DMSO-d$_6$) δ: 12.28 (s, 1H), 8.12 (s, 1H), 7.21 (s, 1H), 5.20 (s, 1H), 4.38 (s, 2H), 3.85 (s, 3H), 2.72-2.60 (m, 1H), 2.40 (d, J=15.3 Hz, 2H), 2.13-1.86 (m, 12H), 1.68-1.56 (m, 7H), 1.28-1.10 (m, 4H). MS (ES, m/z): [M+1]=578.25.

Example 32: 2-[(1R,3S,5S)-3-[3-(2,6-dichlorophenyl)-5-methyl-1,2-oxazole-4-carbonyloxy]-8-azabicyclo[3.2.1]octan-8-yl]-4-fluoro-1,3-benzothiazole-6-carboxylic acid (I-23)

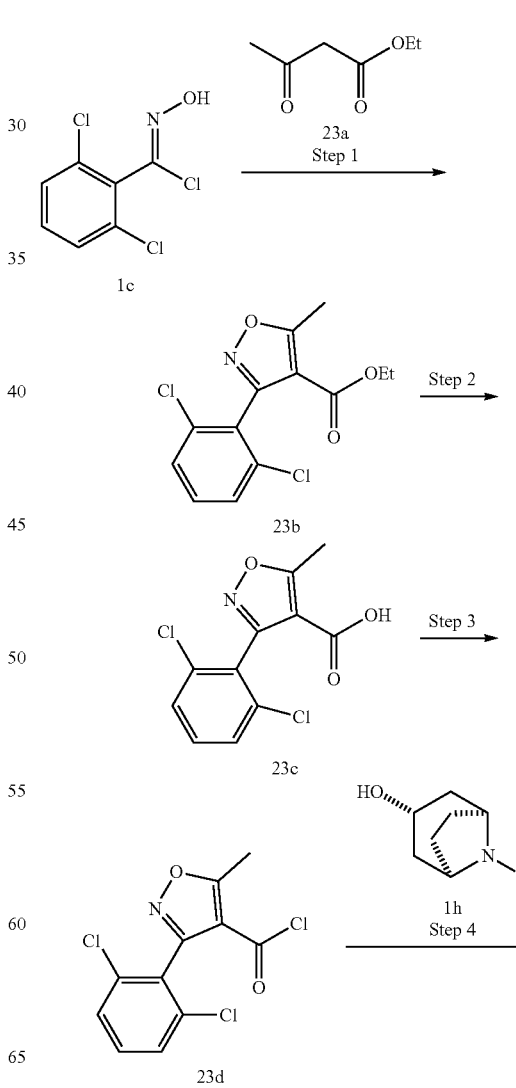

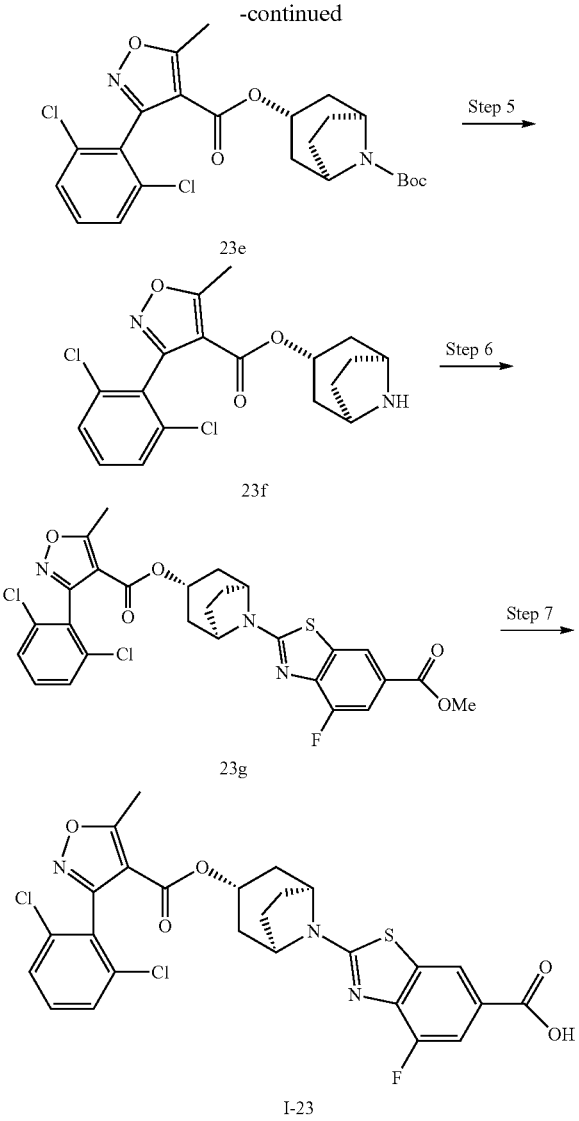

Step 1. Ethyl 3-(2,6-dichlorophenyl)-5-methyl-1,2-oxazole-4-carboxylate (23b)

To a 500 mL round-bottom flask was added 1-ethyl 3-methyl propanedioate 23a (5.70 g, 39.0 mmol, 1.5 equiv.) in dichloromethane (50 mL) and TEA (50 mL), followed by dropwise addition of 2,6-dichloro-N-hydroxybenzene-1-carbonimidoyl chloride 1c (5.8 g, 25.84 mmol, 1.0 equiv.) in dichloromethane (20 mL) at 0° C. The resulting mixture was stirred overnight at RT and concentrated in vacuo. The residue was diluted with EtOAc (300 mL). The mixture was washed with HCl (3 M, 30 mL×3)) and brine (30 mL×3). The organic layer was dried over anhydrous sodium sulfate, filtered, and concentrated in vacuo to give ethyl 3-(2,6-dichlorophenyl)-5-methyl-1,2-oxazole-4-carboxylate 23b (5 g, 64%) as light yellow oil.

Step 2. 3-(2,6-Dichlorophenyl)-5-methyl-1,2-oxazole-4-carboxylic acid (23c)

To a 500 mL round-bottom flask was added ethyl 3-(2,6-dichlorophenyl)-5-methyl-1,2-oxazole-4-carboxylate 23b (5 g, 16.66 mmol, 1.0 equiv.) in ethanol/$H_2O$ (300/30 mL) and $LiOH \cdot H_2O$ (7 g, 166.83 mmol, 10.0 equiv.). The resulting mixture was stirred overnight at 50° C. and concentrated in vacuo. $H_2O$ (300 mL) was added and the pH value of the solution was adjusted to 4-5 using HCl (aq., 1M). The aqueous mixture was extracted with ethyl acetate (300 mL×3), and the combined organic layers were dried over anhydrous sodium sulfate, filtered, and concentrated in vacuo to a residue which was purified via silica gel column chromatography eluting with PE:EtOAc (1:1) to provide 3-(2,6-dichlorophenyl)-5-methyl-1,2-oxazole-4-carboxylic acid 23c (3 g, 66%) as a light-yellow solid.

Step 3. 3-(2,6-dichlorophenyl)-5-methyl-1,2-oxazole-4-carbonyl chloride (23d)

To a 50 mL round-bottom flask was added 3-(2,6-dichlorophenyl)-5-methyl-1,2-oxazole-4-carboxylic acid 23c (600 mg, 2.21 mmol, 1.0 equiv.), thionyl chloride (10 mL), and a catalytic amount of N,N-dimethylformamide. The resulting mixture was stirred overnight at 60° C. and concentrated in vacuo to give 3-(2,6-dichlorophenyl)-5-methyl-1,2-oxazole-4-carbonyl chloride 23d (600 mg, 94%) as colorless oil.

Step 4. tert-butyl (1R,3R,5S)-3-[[3-(2,6-dichlorophenyl)-5-methyl-1,2-oxazol-4-yl]carbonyloxy]-8-azabicyclo[3.2.1]octane-8-carboxylate (23e)

To a 100 mL round-bottom flask was added tert-butyl (1R,3R,5S)-3-hydroxy-8-azabicyclo[3.2.1]octane-8-carboxylate 1 h (700 mg, 3.08 mmol, 1.5 equiv.) in dichloromethane (30 mL), 4-dimethylaminopyridine (100 mg, 0.82 mmol, 0.4 equiv.), and TEA (630 mg, 6.23 mmol, 3.0 equiv.), followed by the dropwise addition of 3-(2,6-dichlorophenyl)-5-methyl-1,2-oxazole-4-carbonyl chloride 23d (600 mg, 2.07 mmol, 1.0 equiv.) in dichloromethane (5 mL) at 0° C. The resulting mixture was stirred overnight at 30° C. The reaction was quenched by the addition with $H_2O$ (50 mL). The aqueous mixture was extracted with dichloromethane (30 mL×3), and the combined organic layers were dried over sodium sulfate, filtered, and concentrated in vacuo to a residue which was purified by a silica gel column chromatography eluting with PE:EtOAc (5:1) to provide tert-butyl (1R,3R,5S)-3-[[3-(2,6-dichlorophenyl)-5-methyl-1,2-oxazol-4-yl]carbonyloxy]-8-azabicyclo[3.2.1]octane-8-carboxylate 23e (0.41 g, 41%) as a light yellow oil.

Step 5. (1R,3R,5S)-8-Azabicyclo[3.2.1]octan-3-yl 3-(2,6-dichlorophenyl)-5-methyl-1,2-oxazole-4-carboxylate (23f)

To a 50 mL round-bottom flask was added a solution of tert-butyl (1R,3S,5S)-3-[[3-(2,6-dichlorophenyl)-5-methyl-1,2-oxazol-4-yl]carbonyloxy]-8-azabicyclo[3.2.1]octane-8-carboxylate 23e (450 mg, 0.93 mmol, 1.0 equiv.) in dichloromethane (10 mL) and trifluoroacetic acid (2 g, 17.69 mmol, 18.93 equiv.). The resulting mixture was stirred for 2 h at room temperature. The reaction was quenched by the addition of 50 mL of $H_2O$. The pH value of the solution was adjusted to 9-10 with a sodium bicarbonate aqueous solution, and the aqueous mixture was extracted with ethyl acetate (30 mL×3). The combined organic layers were dried over sodium sulfate, filtered, and concentrated in vacuo to give (1R,3R,5S)-8-azabicyclo[3.2.1]octan-3-yl 3-(2,6-dichlorophenyl)-5-methyl-1,2-oxazole-4-carboxylate 23f (300 mg, 84%) as a light brown solid.

Step 6. Methyl 2-[(1R,3R,5S)-3-[[3-(2,6-dichlorophenyl)-5-methyl-1,2-oxazol-4-yl]carbonyloxy]-8-azabicyclo[3.2.1]octan-8-yl]-4-fluoro-1,3-benzothiazole-6-carboxylate (23g)

To a 100-mL round-bottom flask purged with nitrogen, was added (1R,3R,5S)-8-azabicyclo[3.2.1]octan-3-yl 3-(2,6-dichlorophenyl)-5-methyl-1,2-oxazole-4-carboxylate 23f (522 mg, 1.37 mmol, 1.0 equiv.) in DMA (10 mL), methyl 2-bromo-4-fluoro-1,3-benzothiazole-6-carboxylate A1 (400 mg, 1.38 mmol, 1.0 equiv.), and $Cs_2CO_3$ (896 mg, 2.75 mmol, 2.0 equiv.). The resulting mixture was stirred overnight at 60° C. The mixture was diluted with EtOAc (100 mL), washed with brine (30 mL×3), dried over anhydrous sodium sulfate, filtered, and concentrated in vacuo to a residue which was purified via silica gel column chromatography eluting with ethyl acetate/petroleum ether (1:3) to yield methyl 2-[(1R,3R,5S)-3-[[3-(2,6-dichlorophenyl)-5-methyl-1,2-oxazol-4-yl]carbonyloxy]-8-azabicyclo[3.2.1]octan-8-yl]-4-fluoro-1,3-benzothiazole-6-carboxylate 23g (220 mg, 27%) as a light yellow solid.

Step 7. 2-[(1R,3R,5S)-3-[[3-(2,6-Dichlorophenyl)-5-methyl-1,2-oxazol-4-yl]carbonyloxy]-8-azabicyclo[3.2.1]octan-8-yl]-4-fluoro-1,3-benzothiazole-6-carboxylic acid (I-23)

To a 100 mL round-bottom flask purged with nitrogen was added a solution of methyl 2-[(1R,3S,5S)-3-[[3-(2,6-dichlorophenyl)-5-methyl-1,2-oxazol-4-yl]carbonyloxy]-8-azabicyclo[3.2.1]octan-8-yl]-4-fluoro-1,3-benzothiazole-6-carboxylate (220 mg, 0.37 mmol, 1.0 equiv.) 23g in pyridine (10 mL) followed by LiI (500 mg, 3.73 mmol, 10.0 equiv.). The resulting mixture was stirred overnight at 125° C., upon cooling diluted with 100 mL of EtOAc. The mixture was washed with HCl (aq., 1M, 30 mL×3) and brine (30 mL×3), dried over anhydrous sodium sulfate, filtered, and concentrated in vacuo. The crude product was purified by Prep-HPLC using following conditions: Column, XBridge C18 OBD Prep Column, 19 mm×250 mm; mobile phase, water (0.05% TFA) and ACN (60% ACN to 80% over min); Detector, UV 254 nm. After purification 2-[(1R,3R,5S)-3-[[3-(2,6-dichlorophenyl)-5-methyl-1,2-oxazol-4-yl]carbonyloxy]-8-azabicyclo[3.2.1]octan-8-yl]-4-fluoro-1,3-benzothiazole-6-carboxylic acid I-23 (68.8 mg, 32%) was obtained as an off-white solid. $^1$HNMR (300 MHz, DMSO-$d_6$) δ: 12.94 (s, 1H), 8.23 (d, J=1.5 Hz, 1H), 7.75-7.54 (m, 4H), 5.08 (t, J=5.3 Hz, 1H), 4.26 (s, 2H), 2.84 (s, 3H), 2.29 (dt, J=15.6, 4.7 Hz, 2H), 1.90-1.79 (m, 2H), 1.69 (d, J=15.4 Hz, 2H), 1.38 (q, J=6.4 Hz, 2H). MS (ES, m/z): [M+1]=576.10.

Example 33: 2-[(1R,3R,5S)-3-[5-cyclobutyl-3-(2,6-dichlorophenyl)-1,2-oxazole-4-carbonyloxy]-8-azabicyclo[3.2.1]octan-8-yl]-4-fluoro-1,3-benzothiazole-6-carboxylic acid (I-24)

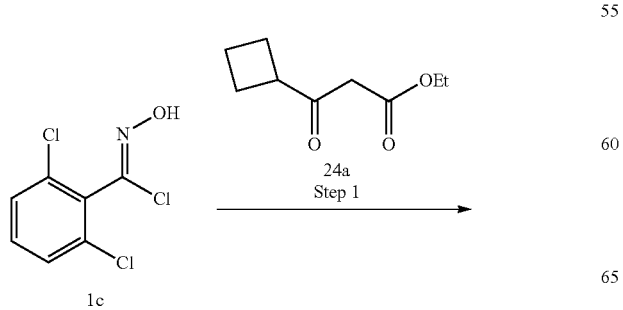

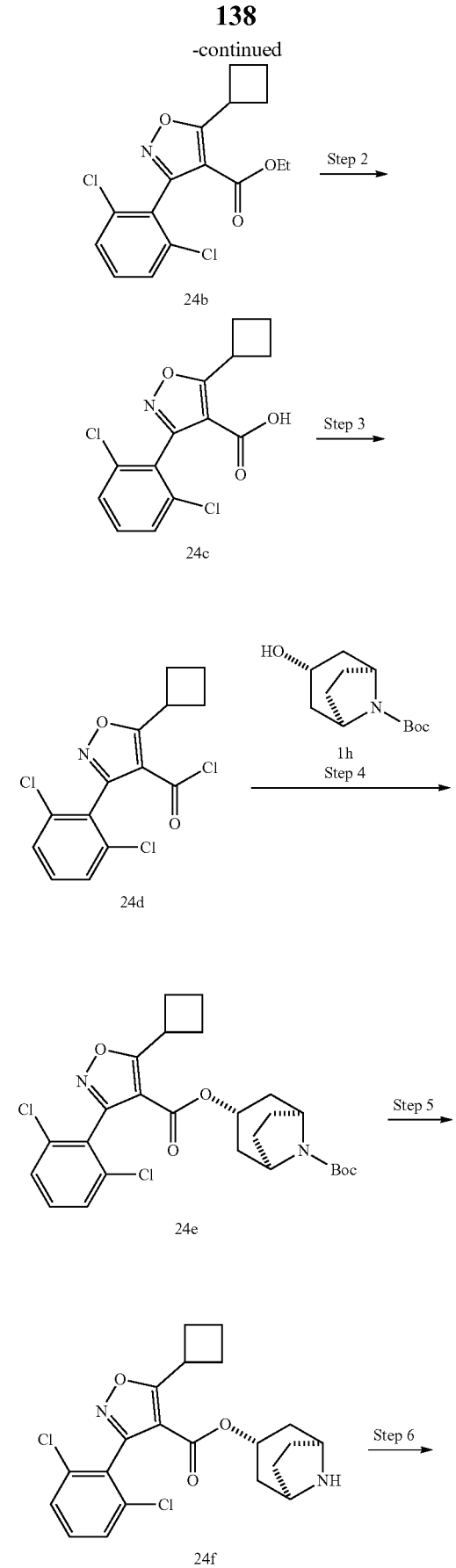

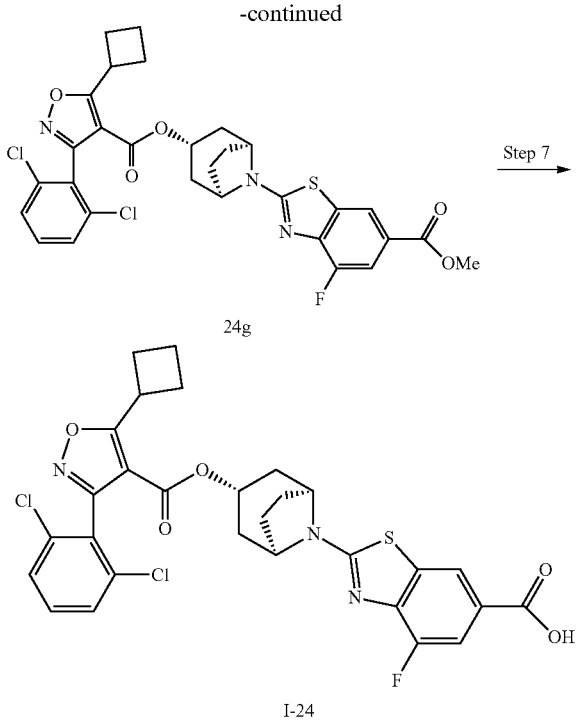

Step 1. Ethyl 5-cyclobutyl-3-(2,6-dichlorophenyl)-1, 2-oxazole-4-carboxylate (24b)

To a 100 mL round-bottom flask was added ethyl 3-cyclobutyl-3-oxopropanoate 24a (1.5 g, 8.81 mmol, 1.0 equiv.) in tetrahydrofuran (10 mL). t-BuOK (1 g, 8.91 mmol, 1.0 equiv.) was added over the course of 5 min at 0° C., followed by the addition of 2,6-dichloro-N-hydroxybenzene-1-carbonimidoyl chloride 1c (2 g, 8.91 mmol, 1.0 equiv.) in tetrahydrofuran (16 mL) at 0° C. The resulting mixture was stirred for 2 h at RT and extracted with ethyl acetate (30 mL×3). The combined organic layers were washed with brine (30 mL), dried over anhydrous sodium sulfate, and concentrated in vacuo. The residue was purified via silica gel column chromatography eluting with ethyl acetate/petroleum ether (1:10) to give ethyl 5-cyclobutyl-3-(2,6-dichlorophenyl)-1,2-oxazole-4-carboxylate 24b (2.3 g, 76%) as a light yellow oil.

Step 2. 5-Cyclobutyl-3-(2,6-dichlorophenyl)-1,2-oxazole-4-carboxylic acid (24c)

To a 50 mL round-bottom flask was added a solution of ethyl 5-cyclobutyl-3-(2,6-dichlorophenyl)-1,2-oxazole-4-carboxylate 24b (600 mg, 1.76 mmol, 1.0 equiv.) in ethanol (6 mL), LiOH (741 mg, 30.94 mmol, 10.0 equiv.) and water (1 mL). The resulting mixture was stirred for at 50° C. overnight. The pH value of the solution was adjusted to 5 using a 1M hydrogen chloride solution. The aqueous mixture was extracted with ethyl acetate (30 mL×3); and the combined organic layers were washed with brine (30 mL), dried over anhydrous sodium sulfate, filtered, and concentrated in vacuo. The residue was purified by silica gel column chromatography eluting with dichloromethane/methanol (10:1) to provide 5-cyclobutyl-3-(2,6-dichlorophenyl)-1,2-oxazole-4-carboxylic acid 24c (450 mg, 82%) as a light yellow oil.

Steps 3 to 7. 2-[(1R,3R,5S)-3-[[5-Cyclobutyl-3-(2,6-dichlorophenyl)-1,2-oxazol-4-yl]carbonyloxy]-8-azabicyclo[3.2.1]octan-8-yl]-4-fluoro-1,3-benzothiazole-6-carboxylic acid (I-24)

Following the procedure outlined in Example 32 steps 3 to 7, conversion of the intermediate 5-cyclobutyl-3-(2,6-dichlorophenyl)-1,2-oxazole-4-carboxylic acid 24c (450 mg, 1.44 mmol, 1.0 equiv.), obtained in step 2 above, afforded the title compound, 2-[(1R,3R,5S)-3-[[5-cyclobutyl-3-(2,6-dichlorophenyl)-1,2-oxazol-4-yl]carbonyloxy]-8-azabicyclo[3.2.1]octan-8-yl]-4-fluoro-1,3-benzothiazole-6-carboxylic acid I-24 (40.2 mg) as a light yellow solid. $^1$HNMR (300 MHz, DMSO-$d_6$) δ: 12.93 (s, 1H), 8.20 (d, J=1.5 Hz, 1H), 7.73-7.51 (m, 4H), 5.04 (t, J=5.2 Hz, 1H), 4.33 (p, J=8.8 Hz, 1H), 3.29 (s, 2H), 2.42 (td, J=8.6, 8.1, 5.4 Hz, 4H), 2.34-1.91 (m, 5H), 1.80 (dd, J=7.6, 4.0 Hz, 2H), 1.64 (d, J=15.4 Hz, 2H), 1.37-1.18 (m, 2H). MS (ES, m/z): [M+1]=615.90.

Example 34: 2-[(1R,3S,5S)-3-[5-tert-butyl-3-(2,6-dichlorophenyl)-1,2-oxazole-4-carbonyloxy]-8-azabicyclo[3.2.1]octan-8-yl]-4-fluoro-1,3-benzothiazole-6-carboxylic acid (I-25)

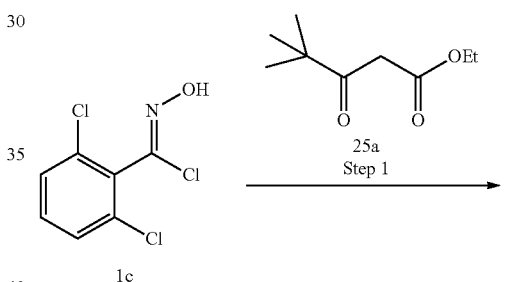

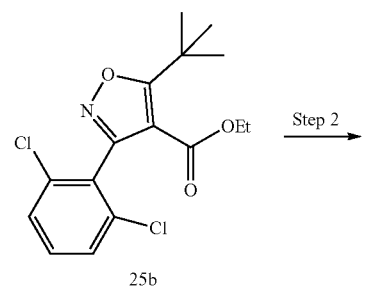

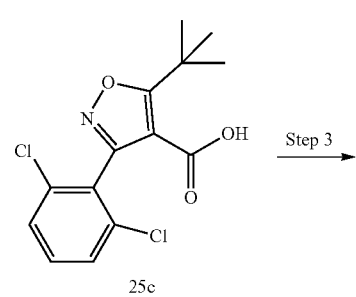

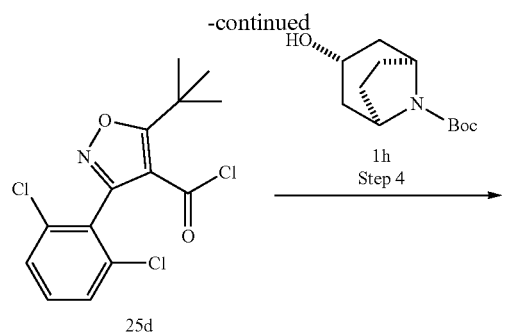

25d

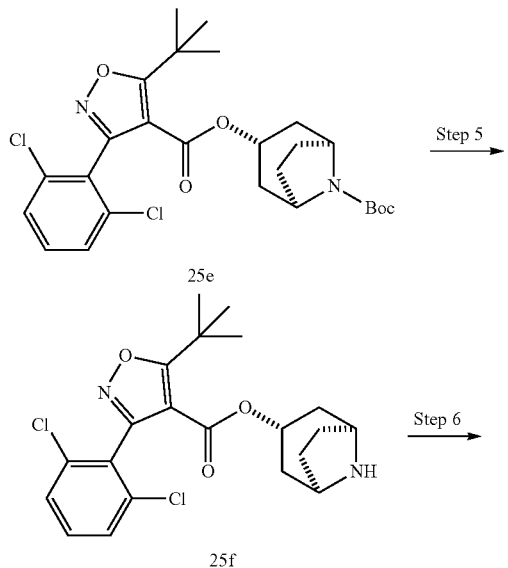

25e

25f

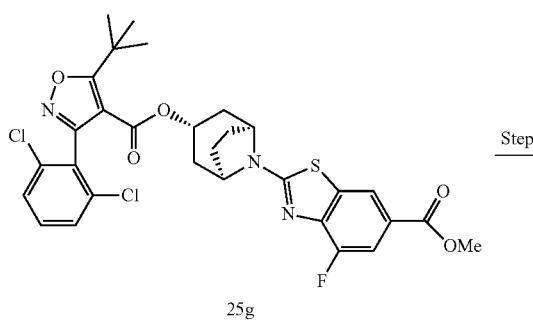

25g

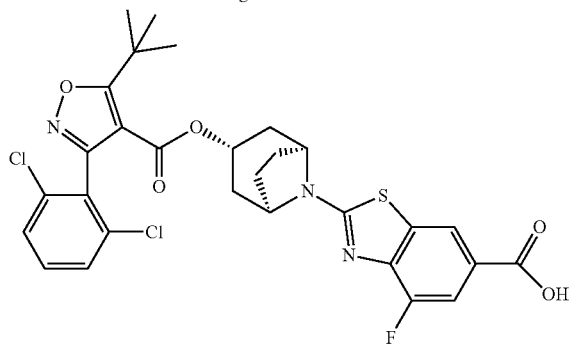

I-25

Step 1. Ethyl 5-tert-butyl-3-(2,6-dichlorophenyl)-1,2-oxazole-4-carboxylate (25b)

To a 500 mL round-bottom flask, was added 2,6-dichloro-N-hydroxybenzene-1-carbonimidoyl chloride 1c (9 g, 40.09 mmol, 1.0 equiv.), TEA (100 mL), and ethyl 4,4-dimethyl-3-oxopentanoate 25a (10.4 g, 60.39 mmol, 1.5 equiv.). The resulting mixture was stirred overnight at RT and then concentrated in vacuo. The residue was purified via silica gel column chromatography eluting with ethyl acetate/petroleum ether (0-10%), providing ethyl 5-tert-butyl-3-(2,6-dichlorophenyl)-1,2-oxazole-4-carboxylate 25b (7 g, 51%) as a yellow solid.

Step 2. 5-tert-Butyl-3-(2,6-dichlorophenyl)-1,2-oxazole-4-carboxylic acid (25c)

To a 250 mL round-bottom flask was added ethyl 5-tert-butyl-3-(2,6-dichlorophenyl)-1,2-oxazole-4-carboxylate 25b (2 g, 5.84 mmol, 1.0 equiv.), ethanol (40 mL) and water (4 mL) followed by the portionwise addition of potassium hydroxide (1.65 g, 29.41 mmol, 5.0 equiv.) at 0° C. The resulting mixture was stirred overnight at 60° C. The reaction was quenched with water and the pH value of the solution was adjusted to 4 using HCl (aq. 2 M). The aqueous mixture was extracted with ethyl acetate (50 mL×3), and the combined organic layers were washed brine (30 mL×2), dried over anhydrous sodium sulfate, filtered, and concentrated to a residue which was purified via silica gel column chromatography eluting with ethyl acetate/petroleum ether (15%-20%) to give 5-tert-butyl-3-(2,6-dichlorophenyl)-1,2-oxazole-4-carboxylic acid 25c (1.8 g, 98%) as an off-white solid.

Steps 3 to 7. 2-[(1R,3R,5S)-3-[[5-tert-Butyl-3-(2,6-dichlorophenyl)-1,2-oxazol-4-yl]carbonyloxy]-8-azabicyclo[3.2.1]octan-8-yl]-4-fluoro-1,3-benzothiazole-6-carboxylic acid (I-25)

Following the procedure outlined in Example 32, steps 3 to 7, converting the intermediate 5-tert butyl-3-(2,6-dichlorophenyl)-1,2-oxazole-4-carboxylic acid 25c (500 mg, 1.59 mmol, 1.0 equiv.) obtained in step 2 above afforded the title compound, 2-[(1R,3R,5S)-3-[[5-tert-butyl-3-(2,6-dichlorophenyl)-1,2-oxazol-4-yl]carbonyloxy]-8-azabicyclo[3.2.1]octan-8-yl]-4-fluoro-1,3-benzothiazole-6-carboxylic acid as a white solid I-25 (62.5 mg). $^1$HNMR (300 MHz, DMSO-$d_6$) δ: 12.98 (s, 300 M, 1H), 8.23 (d, J=1.5 Hz, 1H), 7.77-7.54 (m, 4H), 4.98 (t, J=5.2 Hz, 1H), 3.33 (s, 2H), 2.31-2.18 (m, 2H), 2.08 (s, 1H), 1.83 (d, J=6.5 Hz, 2H), 1.52 (s, 13H); MS (ES, m/z): [M+1]=618.15.

Example 35: 2-[(1R,3S,5S)-3-[3-(2,6-dichlorophenyl)-5-(1-methylcyclopropyl)-1,2-oxazole-4-carbonyloxy]-8-azabicyclo[3.2.1]octan-8-yl]-4-fluoro-1,3-benzothiazole-6-carboxylic acid (I-26)

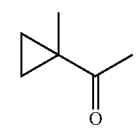

26a

Step 1

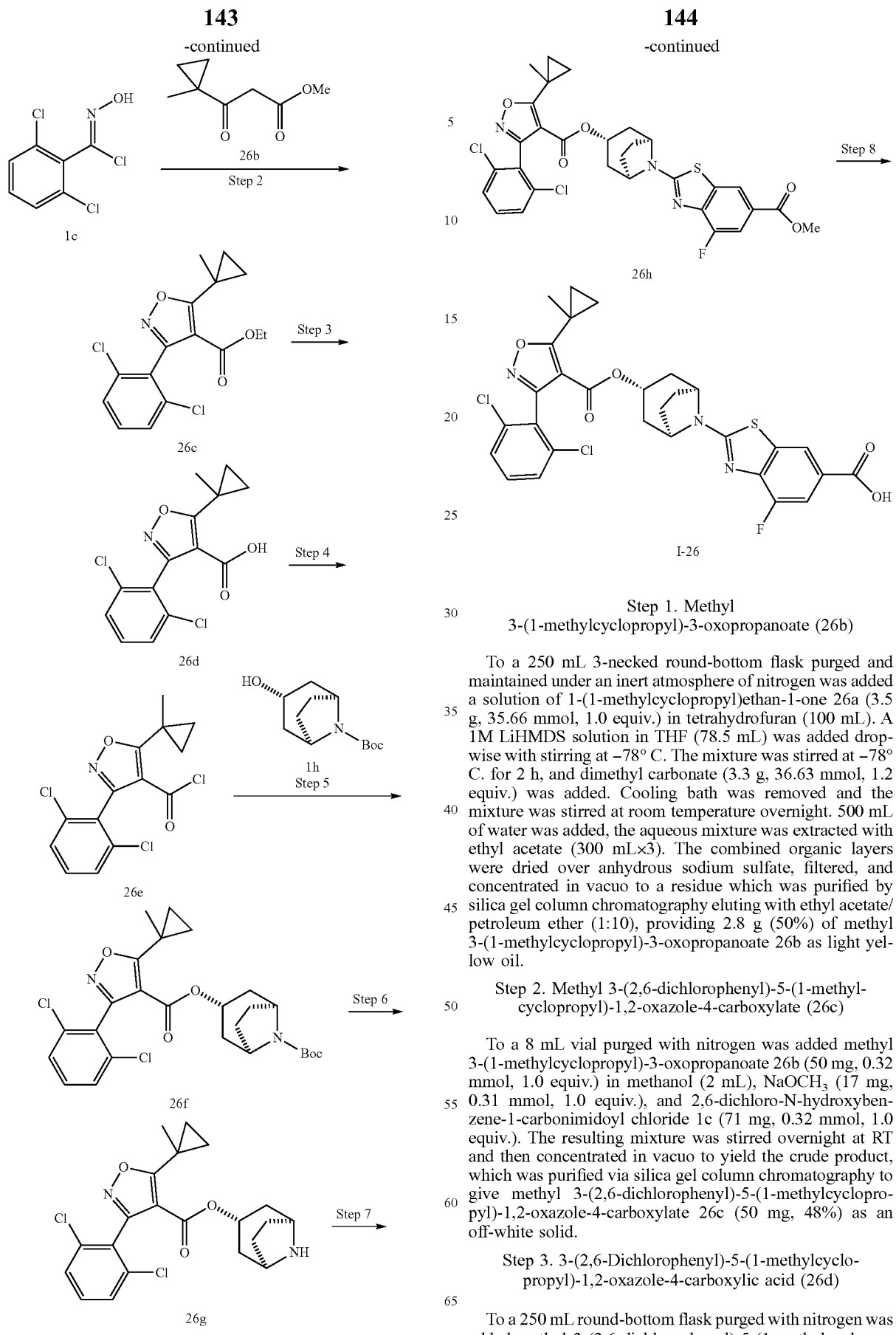

Step 1. Methyl 3-(1-methylcyclopropyl)-3-oxopropanoate (26b)

To a 250 mL 3-necked round-bottom flask purged and maintained under an inert atmosphere of nitrogen was added a solution of 1-(1-methylcyclopropyl)ethan-1-one 26a (3.5 g, 35.66 mmol, 1.0 equiv.) in tetrahydrofuran (100 mL). A 1M LiHMDS solution in THF (78.5 mL) was added dropwise with stirring at −78° C. The mixture was stirred at −78° C. for 2 h, and dimethyl carbonate (3.3 g, 36.63 mmol, 1.2 equiv.) was added. Cooling bath was removed and the mixture was stirred at room temperature overnight. 500 mL of water was added, the aqueous mixture was extracted with ethyl acetate (300 mL×3). The combined organic layers were dried over anhydrous sodium sulfate, filtered, and concentrated in vacuo to a residue which was purified by silica gel column chromatography eluting with ethyl acetate/petroleum ether (1:10), providing 2.8 g (50%) of methyl 3-(1-methylcyclopropyl)-3-oxopropanoate 26b as light yellow oil.

Step 2. Methyl 3-(2,6-dichlorophenyl)-5-(1-methylcyclopropyl)-1,2-oxazole-4-carboxylate (26c)

To a 8 mL vial purged with nitrogen was added methyl 3-(1-methylcyclopropyl)-3-oxopropanoate 26b (50 mg, 0.32 mmol, 1.0 equiv.) in methanol (2 mL), NaOCH₃ (17 mg, 0.31 mmol, 1.0 equiv.), and 2,6-dichloro-N-hydroxybenzene-1-carbonimidoyl chloride 1c (71 mg, 0.32 mmol, 1.0 equiv.). The resulting mixture was stirred overnight at RT and then concentrated in vacuo to yield the crude product, which was purified via silica gel column chromatography to give methyl 3-(2,6-dichlorophenyl)-5-(1-methylcyclopropyl)-1,2-oxazole-4-carboxylate 26c (50 mg, 48%) as an off-white solid.

Step 3. 3-(2,6-Dichlorophenyl)-5-(1-methylcyclopropyl)-1,2-oxazole-4-carboxylic acid (26d)

To a 250 mL round-bottom flask purged with nitrogen was added methyl 3-(2,6-dichlorophenyl)-5-(1-methylcyclopropyl)-1,2-oxazole-4-carboxylate 26c (3.5 g, 10.73 mmol, 1.0 equiv.) in methanol/H₂O (50/5 mL) and LiOH.H₂O (4.51 g, 107.48 mmol, 10.0 equiv.). The resulting mixture was stirred for 1 h at 50° C. Water was added (100 mL), and the pH value of the solution was adjusted to 3-4 using HCl (aq., 1 M). The aqueous mixture was extracted with ethyl acetate (50 mL×3) and the organic layers were combined, dried over anhydrous sodium sulfate, filtered, and concentrated in vacuo. The residue was purified via silica gel column chromatography eluting with ethyl acetate/petroleum ether (1:5) to afford 3-(2,6-dichlorophenyl)-5-(1-methylcyclopropyl)-1,2-oxazole-4-carboxylic acid 26d (2.5 g, 75%) as a pink solid.

Steps 4 to 8. 2-[(1R,3R,5S)-3-[[3-(2,6-dichlorophenyl)-5-(1-methylcyclopropyl)-1,2-oxazol-4-yl]carbonyloxy]-8-azabicyclo[3.2.1]octan-8-yl]-4-fluoro-1,3-benzothiazole-6-carboxylic acid (I-26)

Following the procedure of Example 32 steps 3 to 7, conversion of the intermediate 3-(2,6-dichlorophenyl)-5-(1-methylcyclopropyl)-1,2-oxazole-4-carboxylic acid 26d from Step 3 above afforded the title compound, 2-[(1R,3R,5S)-3-[[3-(2,6-dichlorophenyl)-5-(1-methylcyclopropyl)-1,2-oxazol-4-yl]carbonyloxy]-8-azabicyclo[3.2.1]octan-8-yl]-4-fluoro-1,3-benzothiazole-6-carboxylic acid as an off-white solid I-26. ¹HNMR (400 MHz, DMSO-d₆) δ: 12.99 (s, 1H), 8.23 (d, J=1.5 Hz, 1H), 7.74-7.55 (m, 4H), 5.05 (t, J=5.3 Hz, 1H), 4.25 (s, 2H), 2.28 (dt, J=15.5, 4.8 Hz, 2H), 1.83 (dt, J=6.6, 2.9 Hz, 2H), 1.60 (d, J=15.4 Hz, 2H), 1.54-1.33 (m, 5H), 1.28-1.20 (m, 2H), 1.06-0.99 (m, 2H), 0.94 (s, 2H). MS (ES, m/z): [M+1]=616.0.

Example 36: 2-[(1R,3R,5S)-3-[3-(2,6-dichlorophenyl)-5-(1-fluorocyclopropyl)-1,2-oxazole-4-carbonyloxy]-8-azabicyclo[3.2.1]octan-8-yl]-4-fluoro-1,3-benzothiazole-6-carboxylic acid (I-27)

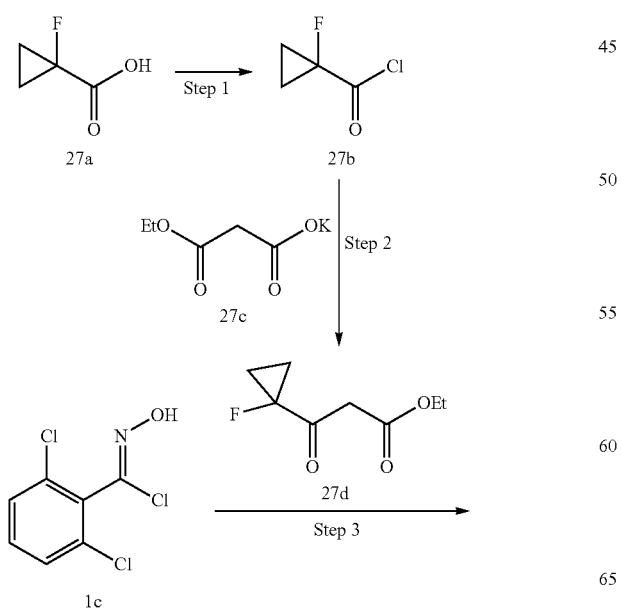

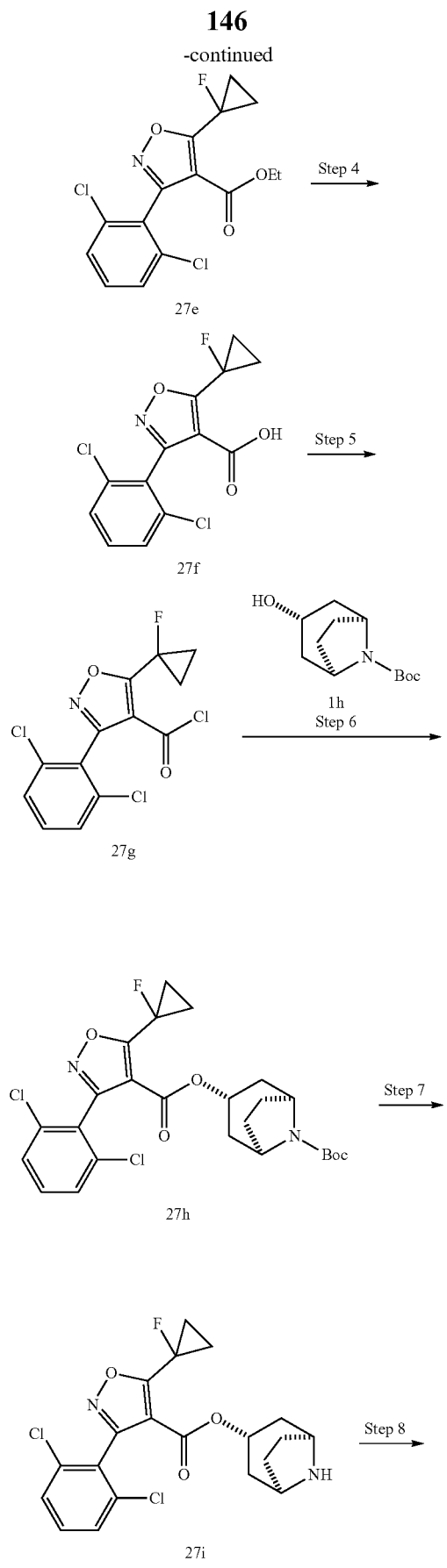

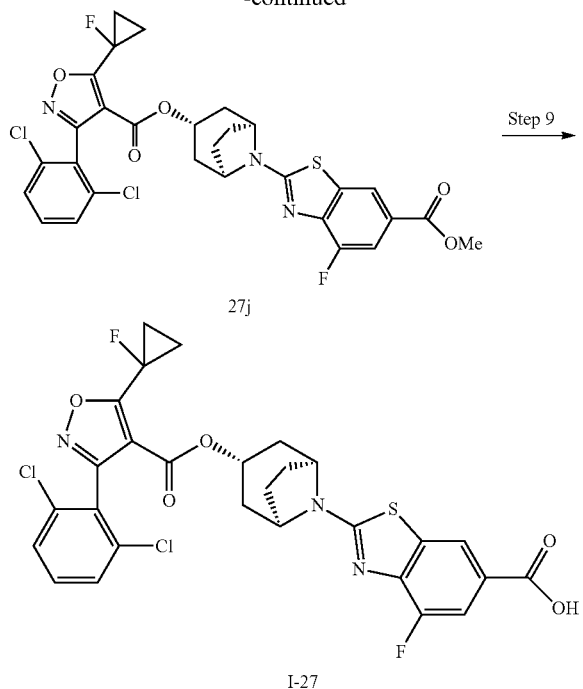

Step 9 →

I-27

Step 1. 1-Fluorocyclopropane-1-carbonyl chloride (27b)

To a 50 mL round-bottom flask purged with nitrogen was added 1-fluorocyclopropane-1-carboxylic acid 27a (2.96 g, 28.48 mmol, 1.0 equiv.), THF (30 mL), and oxalylchloride (2.52 mL, 1.0 equiv.), followed by the addition of a catalytic amount of DMF (2 mg, 0.03 mmol) at 0° C. The reaction was continued for 1 h at 0° C. then at RT for 1 h to afford 1-fluorocyclopropane-1-carbonyl chloride 27b. The product was carried on to the next step without further purification.

Step 2. Ethyl 3-(1-fluorocyclopropyl)-3-oxopropanoate (27d)

To a 250 mL round-bottom flask purged with nitrogen was added 1-ethyl 3-potassium propanedioate 27c (9.81 g, 57.64 mmol, 2.0 equiv.) in ethyl acetate (60 mL) MgCl$_2$ (8.13 g, 3.0 equiv.) was added at 0° C., followed by TEA (14.6 g, 144.28 mmol, 5.0 equiv.). The mixture was stirred overnight at 40° C. then cooled to 0° C. A solution of 1-fluorocyclopropane-1-carbonyl chloride 27b (3.49 g, 28.48 mmol, 1.0 equiv.) in THF (30 mL) was added and the resulting mixture was stirred overnight at 25° C. The reaction was quenched with citric acid (aq. 300 mL, 10%). The aqueous mixture was extracted with dichloromethane (500 mL×2). The combined organic layers were washed with a sodium bicarbonate (aq., 100 mL×2) and brine (200 mL×2), dried over anhydrous sodium sulfate, and concentrated in vacuo. The residue was purified by silica gel column chromatography eluting with PE:EtOAc (0%-5%). Removal of solvent provided ethyl 3-(1-fluorocyclopropyl)-3-oxopropanoate 27d (3.7 g, 75%) as a volatile yellow oil. The product was carried on to the next step without further purification.

Step 3. Ethyl 3-(2,6-dichlorophenyl)-5-(1-fluorocyclopropyl)-1,2-oxazole-4-carboxylate (27e)

To a 100-mL round-bottom flask was added a solution of ethyl 3-(1-fluorocyclopropyl)-3-oxopropanoate 27d (380 mg, 2.18 mmol, 1.0 equiv.) in tetrahydrofuran (10 mL), KO/Bu (290 mg, 2.59 mmol, 1.2 equiv.), and a solution of 2,6-dichloro-N-hydroxybenzene-1-carbonimidoyl chloride 1c (580 mg, 2.58 mmol, 1.2 equiv.) in tetrahydrofuran (5 mL). The resulting mixture was stirred overnight at RT. The mixture was diluted with 100 mL of EtOAc and washed with brine (30 mL×3). The organic layer was dried over sodium sulfate, filtered, and concentrated in vacuo to give ethyl 3-(2,6-dichlorophenyl)-5-(1-fluorocyclopropyl)-1,2-oxazole-4-carboxylate 27e (700 mg, 93%) as a pale-yellow oil.

Step 4. 3-(2,6-Dichlorophenyl)-5-(1-fluorocyclopropyl)-1,2-oxazole-4-carboxylic acid (27f)

To a 25 mL round-bottom flask was added a solution of ethyl 3-(2,6-dichlorophenyl)-5-(1-fluorocyclopropyl)-1,2-oxazole-4-carboxylate 27e (700 mg, 2.03 mmol, 1.0 equiv.) in ethanol/H$_2$O (20/2 mL), followed by LiOH.H$_2$O (860 mg, 20.50 mmol, 10.0 equiv.). The resulting mixture was stirred for 2 h at 50° C., then quenched with H$_2$O (50 mL). The pH value of the solution was adjusted to 3-4 using HCl (aq., 1M). The aqueous mixture was extracted with ethyl acetate (30 mL×3), and the combined organic layers were dried over sodium sulfate, filtered, and concentrated in vacuo. The residue was purified via silica gel column chromatography eluting with PE:EtOAc (5:1) to give 3-(2,6-dichlorophenyl)-5-(1-fluorocyclopropyl)-1,2-oxazole-4-carboxylic acid 27f (200 mg, 31%) as a pale-yellow solid.

Step 5. 3-(2,6-dichlorophenyl)-5-(1-fluorocyclopropyl)-1,2-oxazole-4-carbonyl chloride (27g)

To a 250 mL round-bottom flask was added 3-(2,6-dichlorophenyl)-5-(1-fluorocyclopropyl)-1,2-oxazole-4-carboxylic acid 27f (200 mg, 0.63 mmol, 1.0 equiv.) and thionyl chloride (10 mL). The resulting mixture was stirred overnight at 80° C., then concentrated in vacuo to provide 3-(2,6-dichlorophenyl)-5-(1-fluorocyclopropyl)-1,2-oxazole-4-carbonyl chloride 27g (200 mg, 94%) as a light yellow oil.

Step 6. tert-Butyl (1R,3R,5S)-3-[[3-(2,6-dichlorophenyl)-5-(1-fluorocyclopropyl)-1,2-oxazol-4-yl]carbonyloxy]-8-azabicyclo[3.2.1]octane-8-carboxylate (27h)

To a 250 mL round-bottom flask was added tert-butyl (1R,3R,5S)-3-hydroxy-8-azabicyclo[3.2.1]octane-8-carboxylate 1 h (205 mg, 0.90 mmol, 1.5 equiv.) in dichloromethane (10 mL), 4-dimethylaminopyridine (29 mg, 0.24 mmol, 0.4 equiv.), and TEA (182 mg, 1.80 mmol, 3.0 equiv.), Followed by the dropwise addition of 3-(2,6-dichlorophenyl)-5-(1-fluorocyclopropyl)-1,2-oxazole-4-carbonyl chloride 27g (200 mg, 0.60 mmol, 1.0 equiv.) in dichloromethane (5 mL) at 0° C. with stirring. The reaction was continued overnight at 30° C., then quenched with H$_2$O (50 mL). The aqueous mixture was extracted with dichloromethane (30 mL×3) and the combined organic layers were dried over sodium sulfate, filtered, and concentrated in vacuo. The residue was purified via silica gel column chromatography eluting with PE:EtOAc (5:1) to give tert-butyl (1R,3R,5S)-3-[[3-(2,6-dichlorophenyl)-5-(1-fluorocyclopropyl)-1,2- oxazol-4-yl]carbonyloxy]-8-azabicyclo[3.2.1]octane-8-carboxylate 27h (220 mg, 70%) as a light yellow oil.

Step 7. (1R,3R,5S)-8-Azabicyclo[3.2.1]octan-3-yl 3-(2,6-dichlorophenyl)-5-(1-fluorocyclopropyl)-1,2-oxazole-4-carboxylate (27i)

To a 100 mL round-bottom flask was added tert-butyl (1R,3S,5S)-3-[[3-(2,6-dichlorophenyl)-5-(1-fluorocyclopropyl)-1,2-oxazol-4-yl]carbonyloxy]-8-azabicyclo[3.2.1]octane-8-carboxylate 27h (220 mg, 0.42 mmol, 1.0 equiv.) in dichloromethane (10 mL) and trifluoroacetic acid (5 mL). The resulting mixture was stirred for 2 h at RT, them quenched with $H_2O$ (50 mL). The pH value of the solution was adjusted to 9-10 using sodium bicarbonate (aq.). The aqueous mixture was extracted with dichloromethane (30 mL×3) and the combined organic layers were dried over sodium sulfate, filtered, and concentrated in vacuo to give (1R,3R,5S)-8-azabicyclo[3.2.1]octan-3-yl 3-(2,6-dichlorophenyl)-5-(1-fluorocyclopropyl)-1,2-oxazole-4-carboxylate 27i (170 mg, 95%) as a light yellow oil.

Step 8. Methyl 2-[(1R,3R,5S)-3-[[3-(2,6-dichlorophenyl)-5-(1-fluorocyclopropyl)-1,2-oxazol-4-yl]carbonyloxy]-8-azabicyclo[3.2.1]octan-8-yl]-4-fluoro-1,3-benzothiazole-6-carboxylate (27j)

To a 100 mL round-bottom flask was added (1R,3S,5S)-8-azabicyclo[3.2.1]octan-3-yl 3-(2,6-dichlorophenyl)-5-(1-fluorocyclopropyl)-1,2-oxazole-4-carboxylate 27i (170 mg, 0.40 mmol, 1.0 equiv.) in DMSO (15 mL), methyl 2-bromo-4-fluoro-1,3-benzothiazole-6-carboxylate A1 (128 mg, 0.44 mmol, 1.1 equiv.) and CsF (183 mg, 1.20 mmol, 3.0 equiv.). The resulting mixture was stirred overnight at 115° C. After cooling to RT, the mixture was diluted with EtOAc (200 mL), washed with brine (30 mL×3), dried over sodium sulfate, filtered, and concentrated in vacuo. The residue was purified via silica gel column chromatography eluting with PE:EtOAc (5:1) to afford methyl 2-[(1R,3R,5S)-3-[[3-(2,6-dichlorophenyl)-5-(1-fluorocyclopropyl)-1,2-oxazol-4-yl]carbonyloxy]-8-azabicyclo[3.2.1]octan-8-yl]-4-fluoro-1,3-benzothiazole-6-carboxylate 27j (200 mg, 79%) as an off-white solid.

Step 9. 2-[(1R,3R,5S)-3-[[3-(2,6-dichlorophenyl)-5-(1-fluorocyclopropyl)-1,2-oxazol-4-yl]carbonyloxy]-8-azabicyclo[3.2.1]octan-8-yl]-4-fluoro-1,3-benzothiazole-6-carboxylic acid (I-27)

To a 50 mL round-bottom flask was added a solution of methyl 2-[(1R,3R,5S)-3-[[3-(2,6-dichlorophenyl)-5-(1-fluorocyclopropyl)-1,2-oxazol-4-yl]carbonyloxy]-8-azabicyclo[3.2.1]octan-8-yl]-4-fluoro-1,3-benzothiazole-6-carboxylate 27j (200 mg, 0.32 mmol, 1.0 equiv.) in pyridine (5 mL) and LiI (423 mg, 3.16 mmol, 10.0 equiv.). The resulting mixture was stirred overnight at 125° C., then concentrated in vacuo. The crude product was purified via Prep-HPLC using the following conditions: Column, XBridge C18 OBD Prep Column, 5 μm, 19 mm×250 mm; mobile phase, Water (0.05% TFA) and ACN (62.0% ACN up to 85.0% in 8 min); Detector, UV 254 nm. After purification, 2-[(1R,3R,5S)-3-[[3-(2,6-dichlorophenyl)-5-(1-fluorocyclopropyl)-1,2-oxazol-4-yl]carbonyloxy]-8-azabicyclo[3.2.1] octan-8-yl]-4-fluoro-1,3-benzothiazole-6-carboxylic acid I-27 (68.8 mg, 35%) was obtained as an off-white solid. $^1$HNMR (300 MHz, DMSO-$d_6$) δ: 12.97 (s, 1H), 8.23 (d, J=1.5 Hz, 1H), 7.77-7.53 (m, 4H), 5.08 (t, J=5.2 Hz, 1H), 3.32 (s, 1H), 2.29 (dt, J=15.5, 4.3 Hz, 2H), 2.07 (s, 1H), 1.88 (dd, J=8.6, 4.4 Hz, 2H), 1.82-1.48 (m, 8H). MS (ES, m/z): [M+1]=620.0.

Example 37: 6-[(1R,3R,5S)-3-[5-cyclopropyl-3-(2,6-dichlorophenyl)-1,2-oxazole-4-carbonyloxy]-8-azabicyclo[3.2.1]octan-8-yl]-1-methyl-1H-indole-3-carboxylic acid (I-28)

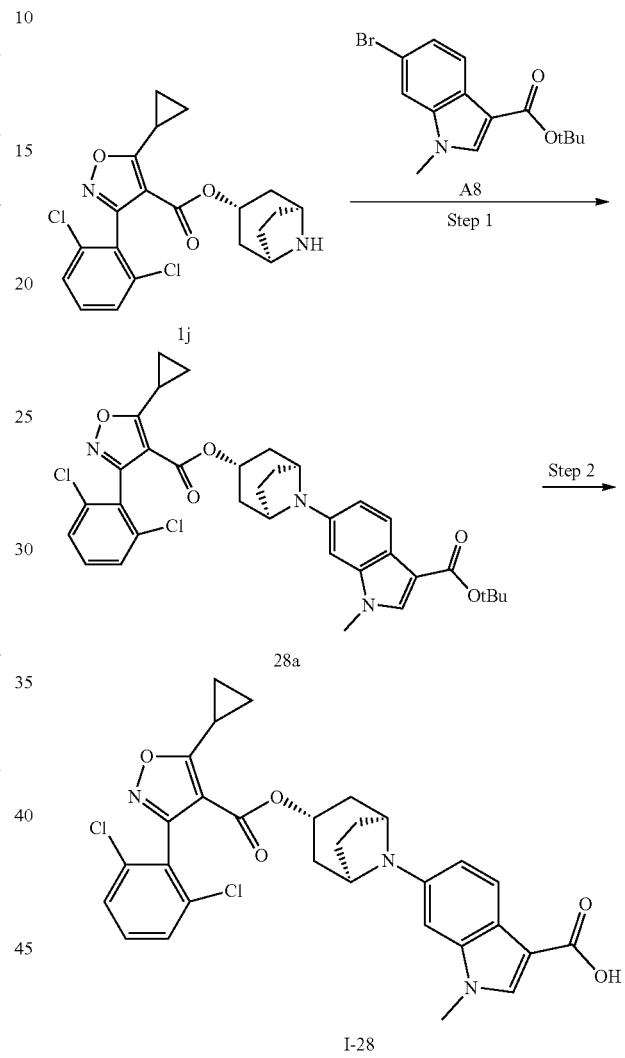

Step 1. tert-butyl 6-[(1R,3R,5S)-3-[[5-cyclopropyl-3-(2,6-dichlorophenyl)-1,2-oxazol-4-yl]carbonyloxy]-8-azabicyclo[3.2.1] octan-8-yl]-1-methyl-1H-indole-3-carboxylate (28a)

To a 50 mL round-bottom flask purged with nitrogen was added (1R,3R,5S)-8-azabicyclo[3.2.1]octan-3-yl 5-cyclopropyl-3-(2,6-dichlorophenyl)-1,2-oxazole-4-carboxylate 1j (150 mg, 0.37 mmol, 1.0 equiv.), toluene (30 mL), tert-butyl 6-bromo-1-methyl-1H-indole-3-carboxylate A8 (171.35 mg, 0.55 mmol, 1.5 equiv.), $Cs_2CO_3$ (168 mg, 0.52 mmol, 1.4 equiv.), BINAP (23 mg, 0.04 mmol, 0.1 equiv.), and $Pd_2(dba)_3$ (33.7 mg, 0.04 mmol, 0.1 equiv.). The resulting mixture was stirred overnight at 110° C. The reaction mixture was cooled to RT, quenched with $H_2O$, and extracted with ethyl acetate. The organic layers were washed with brine, dried over sodium sulfate, and concentrated in vacuo to a residue which was purified via silica gel column chromatography to give tert-butyl 6-[(1R,3R,5S)-3-[[5-cyclopropyl-3-(2,6-dichlorophenyl)-1,2-oxazol-4-yl]carbonyloxy]-8-azabicyclo[3.2.1] octan-8-yl]-1-methyl-1H-indole-3-carboxylate 28a (150 mg, 64%) as a light yellow solid.

Step 2. 6-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-1-methyl-1H-indole-3-carboxylic acid (I-28)

To a 50 mL round-bottom flask was added tert-butyl 6-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-1-methyl-1H-indole-3-carboxylate 28a (150 mg, 0.24 mmol, 1.0 equiv.), dichloromethane (5 mL), and trifluoroacetic acid (1.5 mL). The resulting mixture was stirred for 2 h at 25° C., then quenched with water (100 mL). The aqueous mixture was extracted with dichloromethane (30 mL×3), and the combined organic layers were dried over anhydrous sodium sulfate, then concentrated in vacuo. The crude product was purified via Prep-HPLC using the following conditions: Column, XBridge C18 OBD Prep Column, 10 μm, 19 mm×250 mm; mobile phase, water (0.05% TFA) and ACN (48.0% ACN up to 56.0% in 10 min); Detector, UV 254 nm. After purification, 6-[(1R,3R,5S)-3-[[5-cyclopropyl-3-(2,6-dichlorophenyl)-1,2-oxazol-4-yl] carbonyloxy]-8-azabicyclo[3.2.1]octan-8-yl]-1-methyl-1H-indole-3-carboxylic acid I-28 (57.5 mg, 42%) of was obtained as a light yellow solid. $^1$HNMR (400 MHz, DMSO-$d_6$) δ: 7.79-7.58 (m, 5H), 6.76 (d, J=8.3 Hz, 2H), 4.93 (t, J=5.6 Hz, 1H), 4.14 (s, 2H), 3.73 (s, 3H), 3.00-2.91 (m, 1H), 2.19 (s, 2H), 1.73 (s, 2H), 1.44 (d, J=15.1 Hz, 2H), 1.41-1.28 (m, 6H), 1.24 (s, 1H), 1.15 (s, 2H). MS (ES, m/z): [M+1]=580.0.

Example 38: 6-[(1R,3R,5S)-3-[5-cyclopropyl-3-(2,6-dichlorophenyl)-1,2-oxazole-4-carbonyloxy]-8-azabicyclo[3.2.1]octan-8-yl]-1,2-benzoxazole-3-carboxylic acid (I-29)

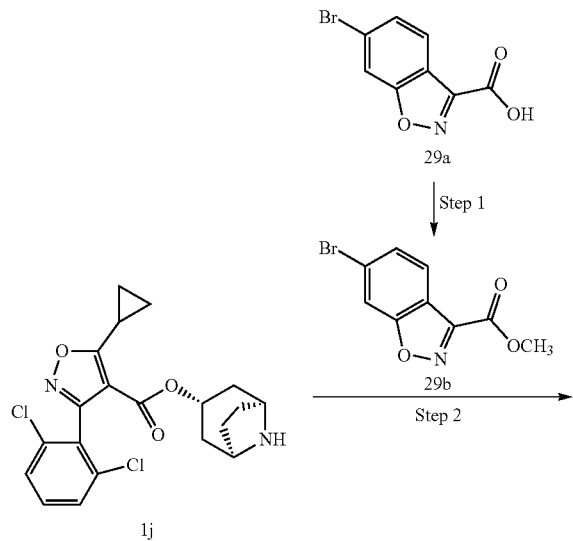

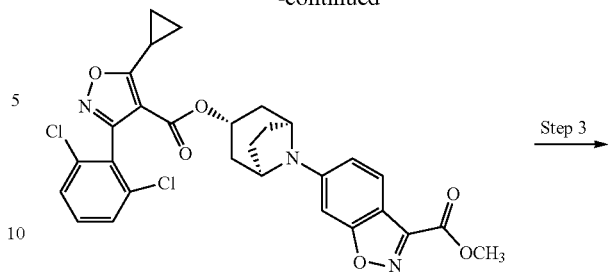

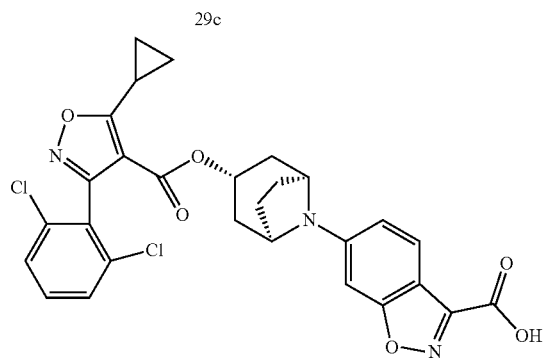

Step 1. Methyl 6-bromo-1,2-benzoxazole-3-carboxylate (29b)

To a 100-mL round-bottom flask was added a solution of 6-bromo-1,2-benzoxazole-3-carboxylic acid 29a (400 mg, 1.65 mmol, 1.0 equiv.) in tetrahydrofuran/MeOH (10/10 mL), followed by the dropwise addition of TMSCHN$_2$ (1.65 mL, 2.0 equiv.) at 0° C. The resulting mixture was stirred for 30 min at RT and then concentrated in vacuo. The residue was purified via silica gel column chromatography eluting with ethyl acetate/petroleum ether (1:5) to give of methyl 6-bromo-1,2-benzoxazole-3-carboxylate 29b (180 mg, 43%) as an off-white solid.

Step 2. Methyl 6-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-1,2-benzoxazole-3-carboxylate (29c)

To a 50 mL round-bottom flask purged with nitrogen was added methyl 6-bromo-1,2-benzoxazole-3-carboxylate 29b (20 mg, 0.08 mmol, 1.2 equiv.) in toluene (2 mL), (1R,3R,5S)-8-azabicyclo[3.2.1]octan-3-yl 5-cyclopropyl-3-(2,6-dichlorophenyl)-1,2-oxazole-4-carboxylate 1j (26 mg, 0.06 mmol, 1.0 equiv.), BINAP (8 mg, 0.01 mmol, 0.2 equiv.), Cs$_2$CO$_3$ (52 mg, 0.16 mmol, 2.5 equiv.), and Pd$_2$(dba)$_3$ (13 mg, 0.01 mmol, 0.2 equiv.). The resulting solution was stirred at 110° C. overnight. The resulting mixture was concentrated in vacuo. The residue was purified via silica gel column chromatography eluting with ethyl acetate/petroleum ether (1:5) to give methyl 6-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-1,2-benzoxazole-3-carboxylate 29c (10 mg, 27%) as a yellow solid.

Step 3. 6-[(1R,3R,5S)-3-[[5-Cyclopropyl-3-(2,6-dichlorophenyl)-1,2-oxazol-4-yl]carbonyloxy]-8-azabicyclo[3.2.1]octan-8-yl]-1,2-benzoxazole-3-carboxylic acid (I-29)

To a 25 mL round-bottom flask was added methyl 6-[(1R,3S,5S)-3-[[5-cyclopropyl-3-(2,6-dichlorophenyl)-1,2-oxazol-4-yl]carbonyloxy]-8-azabicyclo[3.2.1]octan-8-yl]-1,2-benzoxazole-3-carboxylate 29c (100 mg, 0.17 mmol, 1.0 equiv.) and tetrahydrofuran (1 mL), followed by the batchwise addition of KOt-Bu (10 mg). The resulting mixture was stirred for 3 h at RT, and quenched with H$_2$O. The pH value of the solution was adjusted to 3-4 using HCl (aq.). The aqueous mixture was extracted with ethyl acetate (20 mL×3). The combined organic layers were dried over anhydrous sodium sulfate, filtered, and concentrated in vacuo to give a crude product which was purified by Prep-HPLC using the following conditions: Column, XBridge C18 OBD Prep Column, 19 mm×250 mm; mobile phase, Water (0.05% TFA) and ACN (70.0% ACN up to 84.0% in 6 min); Detector, UV 254 nm, giving 6-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-1,2-benzoxazole-3-carboxylic acid I-29 (31.6 mg, 32%) as a yellow greenish solid. $^1$HNMR (300 MHz, CD$_3$OD) δ: 7.86 (d, J=9.0 Hz, 1H), 7.67-7.50 (m, 3H), 7.06-6.97 (m, 1H), 6.92 (d, J=1.8 Hz, 1H), 5.04 (d, J=5.4 Hz, 1H), 4.25 (s, 2H), 3.06 (dd, J=8.1, 5.5 Hz, 1H), 2.27 (d, J=15.5 Hz, 2H), 1.66 (d, J=15.3 Hz, 2H), 1.53-1.32 (m, 7H), 1.25 (s, 3H). MS (ES, m/z): [M+1]=568.0.

Example 39: (1R,3R,5S)-8-(2,2-difluoro-1-methyl-3-oxo-2,3-dihydro-1H-indol-6-yl)-8-azabicyclo[3.2.1]octan-3-yl 5-cyclopropyl-3-(2,6-dichlorophenyl)-1,2-oxazole-4-carboxylate (I-30)

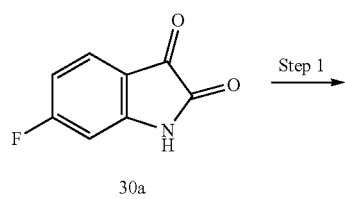

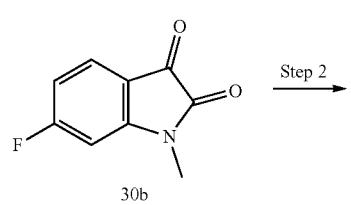

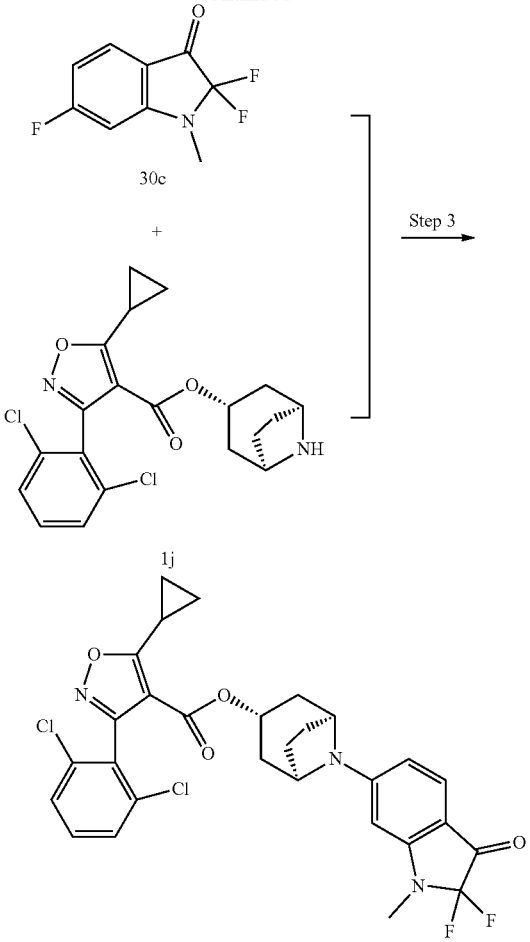

Step 1. 6-Fluoro-1-methyl-2,3-dihydro-1H-indole-2,3-dione (30b)

To a 250 mL round-bottom flask was added 6-fluoro-2,3-dihydro-1H-indole-2,3-dione (8 g, 48.45 mmol, 1.0 equiv.), iodomethane (15.1 g, 106.38 mmol, 2.2 equiv.), potassium carbonate (26.7 g, 193.18 mmol, 4.0 equiv.), and CH$_3$CN (150 mL). The resulting mixture was stirred overnight at 60° C. The reaction was quenched with water. The resulting solution was extracted with ethyl acetate (100 mL×3); and the combined organic layers were washed with brine (50 mL×2), dried over anhydrous sodium sulfate, and concentrated in vacuo. The residue was purified via silica gel column chromatography eluting with ethyl acetate/petroleum ether (20%-40%) to give 6-fluoro-1-methyl-2,3-dihydro-1H-indole-2,3-dione 30b (7 g, 81%) as a red solid.

Step 2. 2,2,6-trifluoro-1-methyl-2,3-dihydro-1H-indol-3-one (30c)

To a 30 mL plastic bottle was added 6-fluoro-1-methyl-2,3-dihydro-1H-indole-2,3-dione 30b (2 g, 11.16 mmol, 1.0 equiv.) and dichloromethane (15 mL), followed by the dropwise addition of DAST (5.40 g, 33.50 mmol, 3.0 equiv.). The resulting mixture was stirred overnight at RT. The mixture was diluted with EtOAc, washed with sodium carbonate (aq., 50 mL×3) and brine (30 mL×2), dried over anhydrous sodium sulfate, and concentrated in vacuo. The residue was purified via silica gel column chromatography eluting with ethyl acetate/petroleum ether (0%-10%) to give 2,2,6-trifluoro-1-methyl-2,3-dihydro-1H-indol-3-one 30c (1.9 g, 85%) as a pink solid.

Step 3. (1R,3R,5S)-8-(2,2-difluoro-1-methyl-3-oxo-2,3-dihydro-1H-indol-6-yl)-8-azabicyclo[3.2.1]octan-3-yl 5-cyclopropyl-3-(2,6-dichlorophenyl)-1,2-oxazole-4-carboxylate (I-30)

To a 100 mL round-bottom flask purged with nitrogen was added 2,2,6-trifluoro-1-methyl-2,3-dihydro-1H-indol-3-one 30c (400 mg, 1.99 mmol, 1.2 equiv.), (1R,3R,5S)-8-azabicyclo[3.2.1]octan-3-yl 5-cyclopropyl-3-(2,6-dichlorophenyl)-1,2-oxazole-4-carboxylate 1j (673 mg, 1.65 mmol, 1.0 equiv.), CsF (756 mg, 4.97 mmol, 3.0 equiv.), and DMSO (2 mL). The resulting mixture was stirred overnight at 140° C. The reaction was quenched with H₂O and the aqueous mixture was extracted with ethyl acetate (30 mL×3). The combined organic layers were washed with brine (20 mL×3), dried over anhydrous sodium sulfate, and concentrated in vacuo. The crude product was purified via Prep-HPLC using the following conditions: Column, XBridge C18 OBD Prep Column, 10 μm, 19 mm×250 mm; mobile phase, water (0.05% TFA) and ACN (60.0% ACN to 80.0% over 8 min); Detector, UV 254 nm. After purification, (1R,3R,5S)-8-(2,2-difluoro-1-methyl-3-oxo-2,3-dihydro-1H-indol-6-yl)-8-azabicyclo[3.2.1]octan-3-yl 5-cyclopropyl-3-(2,6-dichlorophenyl)-1,2-oxazole-4-carboxylate (I-30) (30.3 mg, 3%) was obtained as a red solid. $^1$HNMR (300 MHz, CDCl$_3$) δ: 7.48-7.30 (m, 4H), 6.17 (dd, J=8.7, 2.0 Hz, 1H), 5.92 (d, J=2.0 Hz, 1H), 5.15-5.04 (m, 1H), 4.18 (s, 2H), 3.13 (s, 3H), 2.97 (tt, J=8.4, 5.1 Hz, 1H), 2.24-2.09 (m, 2H), 1.98 (s, 1H), 1.92-1.55 (m, 4H), 1.47-1.19 (m, 7H). MS (ES, m/z): [M+1]=588.

Example 40: 2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1-methyl-1H-1,3-benzodiazole-6-carboxylic acid (I-31)

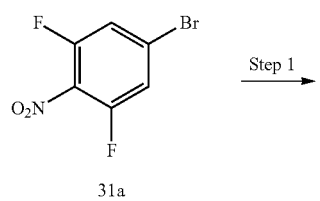

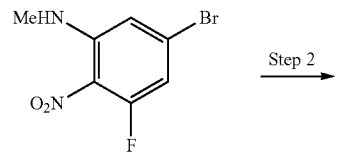

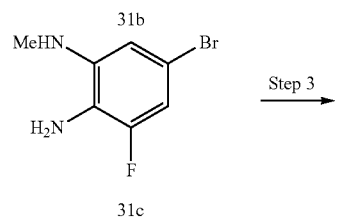

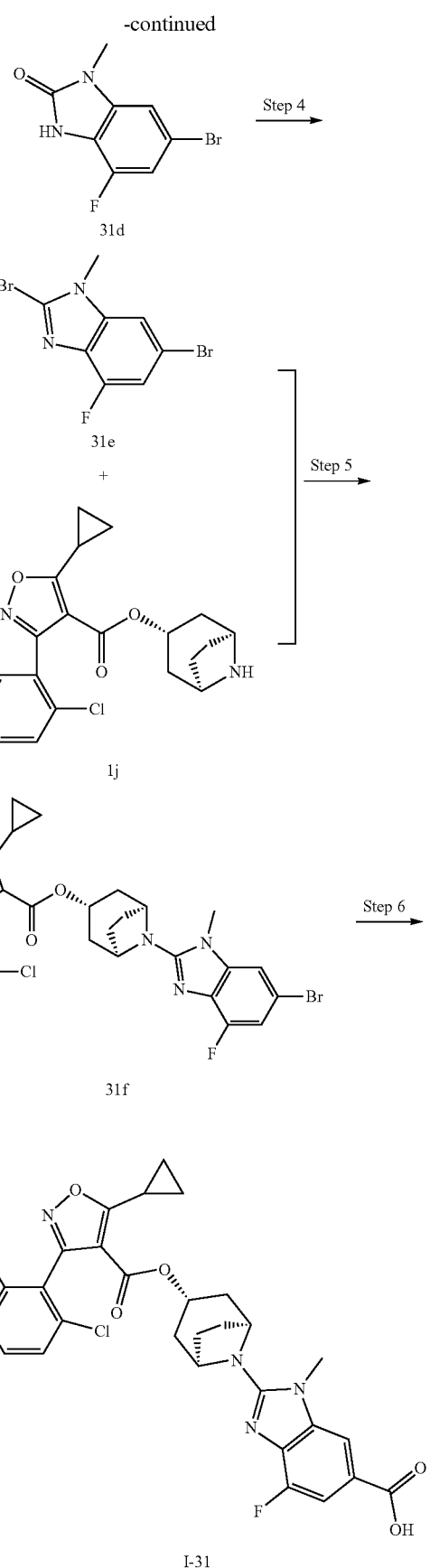

Step 1. 5-Bromo-3-fluoro-N-methyl-2-nitroaniline (31b)

To a 250 mL round-bottom flask was added 5-bromo-1,3-difluoro-2-nitrobenzene 31a (7.5 g, 31.51 mmol, 1.0 equiv.) in tetrahydrofuran (100 mL), followed by the batchwise addition of cesium carbonate (12.4 g, 37.94 mmol, 1.2 equiv.). The mixture was cooled to 0° C., and methylamine (2 M, 15.8 mL, 1.0 equiv.) was added dropwise. The resulting mixture was stirred overnight at RT, then quenched with $H_2O$ (100 mL). The aqueous mixture was extracted with ethyl acetate (80 mL×2). The combined organic layers were washed with brine (100 mL), dried over anhydrous sodium sulfate, filtered, and concentrated in vacuo. The residue was purified by silica gel column chromatography eluting with ethyl acetate/petroleum ether (0-30%) to give 5-bromo-3-fluoro-N-methyl-2-nitroaniline 31b (6 g, 76%) as a red solid.

Step 2. 5-Bromo-3-fluoro-1-N-methylbenzene-1,2-diamine (31c)

To a 500 mL round-bottom flask was added 5-bromo-3-fluoro-N-methyl-2-nitroaniline 31b (5 g, 20.08 mmol, 1.0 equiv.) in ethanol/$H_2O$ (100/25 mL) and AcOH (17 mL), followed by the batchwise addition of Fe (8.26 g, 147.50 mmol, 7.32 equiv.) at RT. The resulting mixture was stirred for 2 h at 50° C. The solids were filtered out and the filtrate was concentrated in vacuo, then diluted with $H_2O$ (80 mL). The aqueous mixture was extracted with ethyl acetate (50 mL×2); and the combined organic layers were washed with brine (100 mL), dried over anhydrous sodium sulfate, filtered, and concentrated in vacuo. The residue was purified by silica gel column chromatography eluting with ethyl acetate/petroleum ether (0-30%) to provide 5-bromo-3-fluoro-1-N-methylbenzene-1,2-diamine 31c (3 g, 68%) as yellow oil.

Step 3. 6-Bromo-4-fluoro-1-methyl-2,3-dihydro-1H-1,3-benzodiazol-2-one (31d)

To a 250 mL round-bottom flask was added a solution of 5-bromo-3-fluoro-1-N-methylbenzene-1,2-diamine 31c (2 g, 9.13 mmol, 1.0 equiv.) in tetrahydrofuran (60 mL), CDI (2.97 g, 18.32 mmol, 2.0 equiv.), and pyridine (1.45 g, 18.33 mmol, 2.0 equiv.). The resulting mixture was stirred overnight at 65° C. After cooling to RT, the mixture was diluted with $H_2O$ (200 mL) and extracted with ethyl acetate (100 mL×2). The combined organic layers were washed with brine (150 mL), dried over anhydrous sodium sulfate, filtered, and concentrated in vacuo. The residue was purified via silica gel column chromatography eluting with ethyl acetate/petroleum ether (0-80%) to give 6-bromo-4-fluoro-1-methyl-2,3-dihydro-1H-1,3-benzodiazol-2-one 31d (1.3 g, 58%) as a white solid.

Step 4. 2,6-Dibromo-4-fluoro-1-methyl-1H-1,3-benzodiazole (31e)

To a 25 mL round-bottom flask was added 6-bromo-4-fluoro-1-methyl-2,3-dihydro-1H-1,3-benzodiazol-2-one 31d (300 mg, 1.22 mmol, 1.0 equiv.), and $POBr_3$ (7 g, 24.65 mmol, 20.0 equiv.). The resulting mixture was stirred overnight at 95° C. After cooling to RT, the reaction was quenched using sodium bicarbonate (aq., 100 mL) and ice. The aqueous mixture was extracted with ethyl acetate (50 mL×2). The combined organic layers were washed with brine (100 mL), dried over anhydrous sodium sulfate, and concentrated in vacuo. The residue was purified by silica gel column chromatography eluting with ethyl acetate/petroleum ether (1:4) to give 2,6-dibromo-4-fluoro-1-methyl-1H-1,3-benzodiazole 31e (300 mg, 80%) as a white solid.

Step 5. (1R,3R,5S)-8-(6-bromo-4-fluoro-1-methyl-1H-1,3-benzodiazol-2-yl)-8-azabicyclo[3.2.1]octan-3-yl 5-cyclopropyl-3-(2,6-dichlorophenyl)-1,2-oxazole-4-carboxylate (31f)

To a 25 mL round-bottom flask purged with nitrogen was added (1R,3R,5S)-8-azabicyclo[3.2.1]octan-3-yl 5-cyclopropyl-3-(2,6-dichlorophenyl)-1,2-oxazole-4-carboxylate 1j (50 mg, 0.12 mmol, 1.0 equiv.), a 2,6-dibromo-4-fluoro-1-methyl-1H-1,3-benzodiazole 31e (45 mg, 0.15 mmol, 1.2 equiv.) in DMSO (0.5 mL), and CsF (26 mg, 0.17 mmol, 1.4 equiv.). The resulting mixture was stirred overnight at 115° C. After cooling to RT, $H_2O$ (10 mL) was added. The aqueous mixture was extracted with ethyl acetate (10 mL×2); and the combined organic layers were washed with brine (20 mL), dried over anhydrous sodium sulfate, filtered, and concentrated in vacuo. The residue was purified via silica gel column chromatography eluting with ethyl acetate/petroleum ether (1:4) to provide (1R,3R,5S)-8-(6-bromo-4-fluoro-1-methyl-1H-1,3-benzodiazol-2-yl)-8-azabicyclo[3.2.1]octan-3-yl 5-cyclopropyl-3-(2,6-dichlorophenyl)-1,2-oxazole-4-carboxylate 31f (50 mg, 64%) as a white solid.

Step 6. 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-fluoro-1-methyl-1H-1,3-benzodiazole-6-carboxylic acid (I-31)

To a 50 mL round-bottom flask was added lithium formate (31 mg, 0.60 mmol, 3.0 equiv.), DIEA (52 mg, 0.40 mmol, 2.0 equiv.) in N,N-dimethylformamide (0.5 mL), (1R,3R,5S)-8-(6-bromo-4-fluoro-1-methyl-1H-1,3-benzodiazol-2-yl)-8-azabicyclo[3.2.1]octan-3-yl 5-cyclopropyl-3-(2,6-dichlorophenyl)-1,2-oxazole-4-carboxylate 31f (290 mg, 0.46 mmol, 1.0 equiv.), palladium acetate (3 mg, 0.01 mmol, 0.05 equiv.), dppf (6 mg, 0.01 mmol, 0.05 equiv.), and acetic anhydride (41 mg, 0.40 mmol, 2.0 equiv.). The resulting mixture was stirred overnight at 120° C. After cooling to RT, the mixture was diluted EtOAc (30 mL), washed with brine (30 mL×3), dried over anhydrous sodium sulfate, and concentrated in vacuo. The residue was purified via silica gel column chromatography eluting with ethyl acetate/petroleum ether (1:1) to give a relatively pure product. This product was further purified by Prep-HPLC using the following conditions: Column, Gemini-NX C18 AXAI Packed, 21.2*150 mm 5 μm; mobile phase, Water (0.05% TFA) and ACN (43.0% ACN up to 46.0% in 13 min); Detector, UV 254 nm, to afford 26.3 mg (10%) of 2-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-4-fluoro-1-methyl-1H-1,3-benzodiazole-6-carboxylic acid I-31 as a colorless solid. $^1$HNMR (300 MHz, $CD_3OD$) δ: 7.93 (d, J=1.2 Hz, 1H), 7.70 (d, J=11.1 Hz, 1H), 7.59 (d, J=0.7 Hz, 3H), 5.23 (t, J=5.4 Hz, 1H), 4.46 (d, J=4.1 Hz, 2H), 3.79 (s, 3H), 3.14-2.00 (m, 5H), 1.80-2.00 (dt, J=15.4, 4.6 Hz, 4H), 1.22-1.54 (m, 8H), 0.92 (m, 1H). MS (ES, m/z): [M+1]=599.0.

Example 41: 2-[(1R,3R,5S)-3-({2-[5-cyclopropyl-3-(2,6-dichlorophenyl)-1,2-oxazol-4-yl]acetyl}oxy)-8-azabicyclo[3.2.1]octan-8-yl]-4-fluoro-1,3-benzothiazole-6-carboxylic acid (I-32)
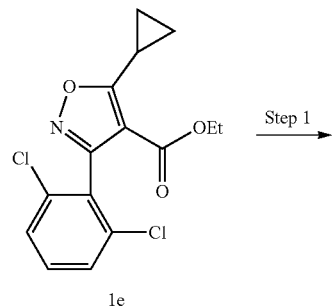
1e
Step 1
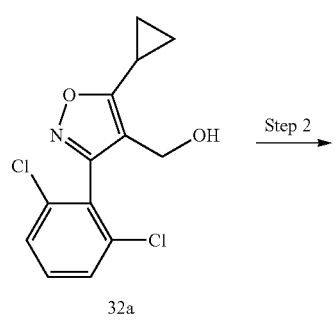
32a
Step 2
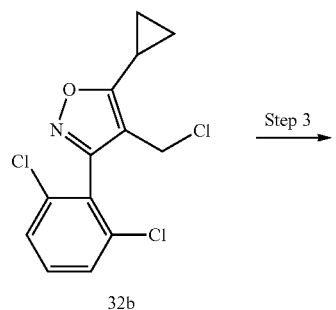
32b
Step 3
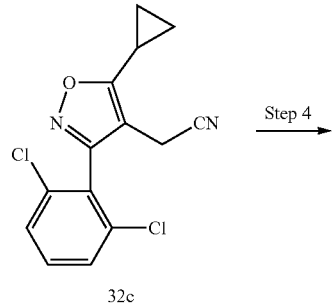
32c
Step 4
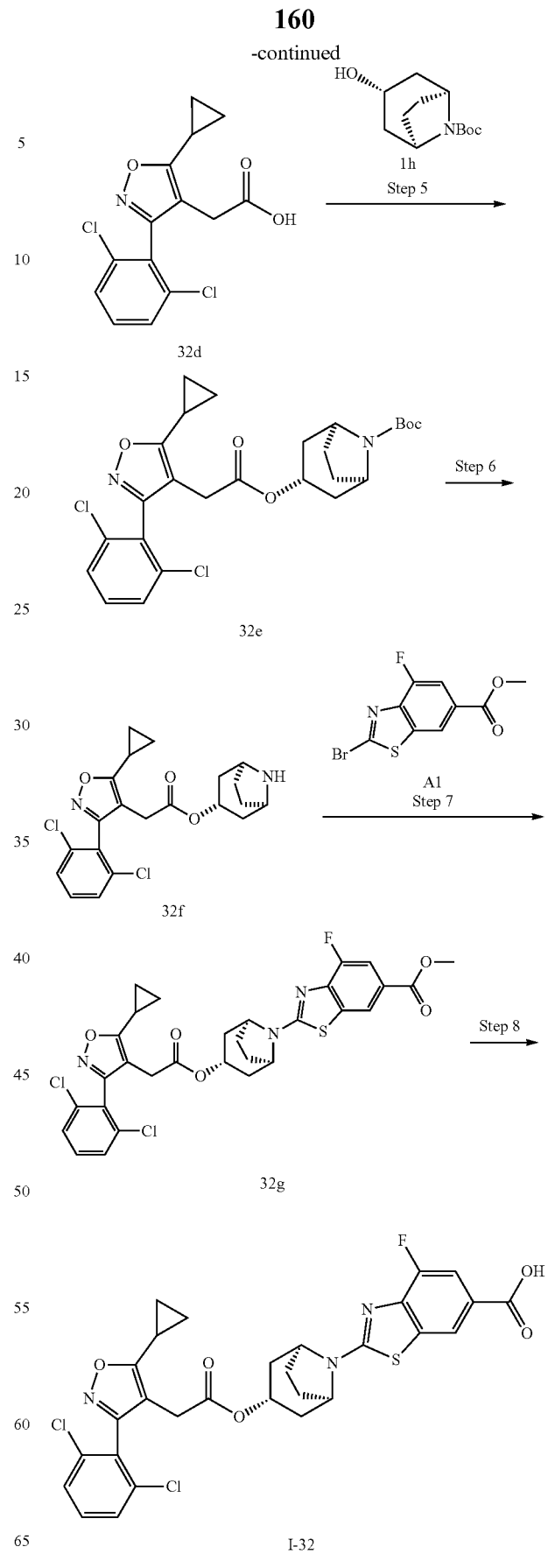

Step 1. [5-Cyclopropyl-3-(2,6-dichlorophenyl)-1,2-oxazol-4-yl]methanol (32a)

To a 100 mL round-bottom flask was added ethyl 5-cyclopropyl-3-(2,6-dichlorophenyl)-1,2-oxazole-4-carboxylate 1e (12.5 g, 38.32 mmol, 1.0 equiv.) and tetrahydrofuran (100 mL), followed by the batchwise addition of LiAlH$_4$ (2.9 g, 76.42 mmol, 2.0 equiv.) at 0° C. The resulting mixture was stirred for 2 h at RT and quenched by the addition of H$_2$O/ice (50 mL). The aqueous mixture was extracted with ethyl acetate (200 mL×2), and the combined organic layers were washed with brine (200 mL×2), then concentrated in vacuo. The crude product was purified by Flash-Prep-HPLC using the following conditions: Column, silica gel; mobile phase, PE:EtOAc=100:0 increasing to PE:EtOAc=70:30 within 35 min; Detector, UV 254 nm. Removal of the solvents provided [5-cyclopropyl-3-(2,6-dichlorophenyl)-1,2-oxazol-4-yl]methanol 32a (3.9 g, 36%) as a light yellow oil. $^1$HNMR (400 MHz, CD$_3$OD) δ: 7.56-7.42 (m, 3H), 4.36 (s, 2H), 2.36-2.25 (m, 1H), 1.21-1.10 (m, 4H). MS (ES, m/z): [M+1]=284.05.

Step 2. 4-(Chloromethyl)-5-cyclopropyl-3-(2,6-dichlorophenyl)-1,2-oxazole (32b)

To a 250 mL round-bottom flask was added a solution of 1H-1,2,3-benzotriazole (1 g, 8.39 mmol, 1.0 equiv.) in dichloromethane (50 mL), followed by the dropwise addition of SOCl$_2$ (1 g, 8.41 mmol, 1.0 equiv.) at 0° C. After 1 h, [5-cyclopropyl-3-(2,6-dichlorophenyl)-1,2-oxazol-4-yl]methanol 32a (2.5 g, 8.80 mmol, 1.0 equiv.) in dichloromethane (50 mL) was added dropwise at 0° C. Reaction was continued at overnight at RT, and quenched with 50 mL of H$_2$O/ice (50 mL). The aqueous mixture was extracted with dichloromethane (100 mL). The organic layer was washed with brine (100 mL), dried over anhydrous sodium sulfate, and concentrated in vacuo. The residue was purified via silica gel column chromatography eluting with ethyl acetate/petroleum ether (0-10%) to give 4-(chloromethyl)-5-cyclopropyl-3-(2,6-dichlorophenyl)-1,2-oxazole 32b (2.11 g, 79%) as an off-white solid. $^1$HNMR (300 MHz, CDCl$_3$) δ: 7.46-7.28 (m, 3H), 4.33 (s, 2H), 2.11 (tt, J=8.3, 5.1 Hz, 1H), 1.32-1.08 (m, 4H). MS (ES, m/z): [M+1]=301.75.

Step 3. 2-[5-Cyclopropyl-3-(2,6-dichlorophenyl)-1,2-oxazol-4-yl]acetonitrile (32c)

To a 250 mL round-bottom flask was added 4-(chloromethyl)-5-cyclopropyl-3-(2,6-dichlorophenyl)-1,2-oxazole 32b (5 g, 16.52 mmol, 1.0 equiv.) in acetone (100 mL), followed by addition of potassium cyanate (2.2 g, 33.79 mmol, 2.0 equiv.) in water (10 mL) at RT. The resulting mixture was stirred overnight at 65° C. After cooling to RT, H$_2$O (100 mL) was added. The aqueous mixture was extracted with ethyl acetate (100 mL×2). The combined organic layers were washed with brine (100 mL×3), dried over anhydrous sodium sulfate, filtered, and concentrated in vacuo to give 2-[5-cyclopropyl-3-(2,6-dichlorophenyl)-1,2-oxazol-4-yl]acetonitrile 32c (4.5 g, 93%) as a brownish oil. The product was carried on to the next step without further purification.

Step 4. 2-[5-Cyclopropyl-3-(2,6-dichlorophenyl)-1,2-oxazol-4-yl]acetic acid (32d)

To a 250 mL round-bottom flask was added 2-[5-cyclopropyl-3-(2,6-dichlorophenyl)-1,2-oxazol-4-yl]acetonitrile 32c (2.6 g, 8.87 mmol, 1.0 equiv.) in ethanol (20 mL), Followed by the dropwise addition of sodium hydroxide (aq., 4M, 8.9 mL, 4.0 equiv.). The resulting mixture was stirred overnight at 75° C. The pH value of the solution was adjusted to 1 using HCl (aq., 2M). The aqueous mixture was extracted with ethyl acetate (50 mL×2) and the combined organic layers were washed with brine (100 mL), dried over anhydrous sodium sulfate, filtered, and concentrated in vacuo. The residue was purified by silica gel column chromatography eluting with ethyl acetate/petroleum ether (0-50%) to give 2-[5-cyclopropyl-3-(2,6-dichlorophenyl)-1,2-oxazol-4-yl]acetic acid 32d as a white solid (2 g, 72%).

Step 5. tert-Butyl (1R,3R,5S)-3-([2-[5-cyclopropyl-3-(2,6-dichlorophenyl)-1,2-oxazol-4-yl]acetyl]oxy)-8-azabicyclo[3.2.1]octane-8-carboxylate (32e)

To a 100 mL round-bottom flask was added a solution of 2-[5-cyclopropyl-3-(2,6-dichlorophenyl)-1,2-oxazol-4-yl] acetic acid 32d (300 mg, 0.96 mmol, 1.0 equiv.) in dichloromethane (15 mL), tert-butyl (1R,3R,5S)-3-hydroxy-8-azabicyclo[3.2.1]octane-8-carboxylate 1 h (219 mg, 0.96 mmol, 1.0 equiv.), 4-dimethylaminopyridine (12 mg, 0.10 mmol, 0.1 equiv.), and EDCI (204 mg, 1.06 mmol, 1.1 equiv.). The resulting mixture was stirred overnight at 35° C. The mixture was diluted with 30 mL of DCM, washed with water (20 mL) and brine (20 mL), dried over anhydrous sodium sulfate, and concentrated. The residue was purified via silica gel column chromatography eluting with ethyl acetate/petroleum ether (1:3) to give tert-butyl (1R,3R,5S)-3-([2-[5-cyclopropyl-3-(2,6-dichlorophenyl)-1,2-oxazol-4-yl]acetyl]oxy)-8-azabicyclo[3.2.1]octane-8-carboxylate 32e (230 mg, 46%) as a white solid.

Step 6. (1R,3R,5S)-8-Azabicyclo[3.2.1]octan-3-yl 2-[5-cyclopropyl-3-(2,6-dichlorophenyl)-1,2-oxazol-4-yl]acetate (32f)

To a 50 mL round-bottom flask was added a solution of tert-butyl (1R,3R,5S)-3-([2-[5-cyclopropyl-3-(2,6-dichlorophenyl)-1,2-oxazol-4-yl]acetyl]oxy)-8-azabicyclo[3.2.1]octane-8-carboxylate 32e (230 mg, 0.44 mmol, 1.0 equiv.) in dichloromethane (5 mL), followed by the dropwise addition of trifluoroacetic acid (5 mL) in dichloromethane (5 mL) at 0° C. The resulting mixture was stirred for 1 h at RT. The pH value of the solution was adjusted to 8 using sodium bicarbonate (aq., 2M). The aqueous mixture was extracted with ethyl acetate (20 mL×2). The combined organic layers were washed with brine (30 mL), dried over anhydrous sodium sulfate, filtered, and concentrated in vacuo to give (1R,3R,5S)-8-azabicyclo[3.2.1]octan-3-yl 2-[5-cyclopropyl-3-(2,6-dichlorophenyl)-1,2-oxazol-4-yl]acetate 32f (160 mg, 86%) as light yellow oil.

Step 7. Methyl 2-[(1R,3S,5S)-3-([2-[5-cyclopropyl-3-(2,6-dichlorophenyl)-1,2-oxazol-4-yl]acetyl]oxy)-8-azabicyclo[3.2.1]octan-8-yl]-4-fluoro-1,3-benzothiazole-6-carboxylate (32g)

To a 25 mL round-bottom flask purged with nitrogen was added (1R,3R,5S)-8-azabicyclo[3.2.1]octan-3-yl 2-[5-cyclopropyl-3-(2,6-dichlorophenyl)-1,2-oxazol-4-yl]acetate 32f (160 mg, 0.38 mmol, 1.0 equiv.), a solution of methyl 2-bromo-4-fluoro-1,3-benzothiazole-6-carboxylate A1 (132 mg, 0.46 mmol, 1.2 equiv.) in DMA (8 mL), and Cs$_2$CO$_3$ (248 mg, 0.76 mmol, 2.0 equiv.). The resulting solution was stirred overnight at 60° C., then quenched with H$_2$O (30 mL). The aqueous mixture was extracted with ethyl acetate (15 mL×3); and the combined organic layers were washed with brine (20 mL×2), dried over anhydrous sodium sulfate, and concentrated in vacuo. The residue was purified via silica gel column chromatography eluting with ethyl acetate/petroleum ether (1:3) to give methyl 2-[(1R,3S,5S)-3-([2-[5-cyclopropyl-3-(2,6-dichlorophenyl)-1,2-oxazol-4-yl]acetyl]oxy)-8-azabicyclo[3.2.1]octan-8-yl]-4-fluoro-1,3-benzothiazole-6-carboxylate 32g (170 mg, 71%) as a yellow oil.

Step 8. 2-[(1R,3R,5S)-3-([2-[5-Cyclopropyl-3-(2,6-dichlorophenyl)-1,2-oxazol-4-yl]acetyl]oxy)-8-azabicyclo[3.2.1]octan-8-yl]-4-fluoro-1,3-benzothiazole-6-carboxylic acid (I-32)

To a 50 mL round-bottom flask purged with nitrogen was added a solution of methyl 2-[(1R,3R,5S)-3-([2-[5-cyclopropyl-3-(2,6-dichlorophenyl)-1,2-oxazol-4-yl]acetyl]oxy)-8-azabicyclo[3.2.1]octan-8-yl]-4-fluoro-1,3-benzothiazole-6-carboxylate 32g (170 mg, 0.27 mmol, 1.0 equiv.) in pyridine (4 mL), followed by the portionwise addition of lithium iodide (362 mg, 2.7 mmol, 10.0 equiv.). The resulting mixture was stirred overnight at 125° C. After cooling to RT, 20 mL of H₂O was added; the pH value of the solution was adjusted to 2 using HCl (2M, aq.). The aqueous mixture was extracted with ethyl acetate (30 mL×3). The combined organic layers were washed with brine (20 mL×2), dried over anhydrous sodium sulfate, filtered, and concentrated. The crude product was purified by Prep-HPLC using the following conditions: Column, XBridge Shield RP18 OBD Column, 5 μm, 19×150 mm; mobile phase, Water (0.05% TFA) and ACN (56.0% ACN up to 78.0% in 8 min); Detector, UV 254 nm, to afford 2-[(1R,3R,5S)-3-([2-[5-cyclopropyl-3-(2,6-dichlorophenyl)-1,2-oxazol-4-yl]acetyl]oxy)-8-azabicyclo[3.2.1]octan-8-yl]-4-fluoro-1,3-benzothiazole-6-carboxylic acid I-32 (19.7 mg, 12%) as a light yellow solid. ¹HNMR (300 MHz, CD₃OD) δ: 8.12 (d, J=1.5 Hz, 1H), 7.63 (dd, J=11.5, 1.5 Hz, 1H), 7.53 (s, 3H), 4.94 (t, J=4.9 Hz, 1H), 4.38 (d, J=4.9 Hz, 2H), 3.44 (s, 2H), 2.34-2.18 (m, 3H), 2.11-1.97 (m, 4H), 1.76 (d, J=15.4 Hz, 2H), 1.26 (s, 1H), 1.16 (d, J=6.7 Hz, 4H). MS (ES, m/z): [M+1]=614.00.

Example 42: 2-[(1R,3R,5S)-3-({2-[5-cyclopropyl-3-(2,6-dichlorophenyl)-1,2-oxazol-4-yl]acetyl}oxy)-8-azabicyclo[3.2.1]octan-8-yl]-4-fluoro-1-methyl-1H-1,3-benzodiazole-6-carboxylic acid (I-33)

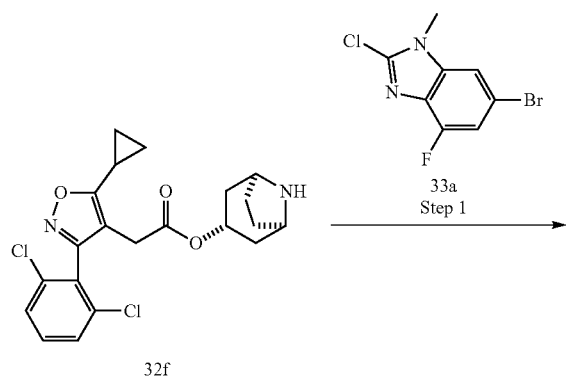

32f

33a
Step 1

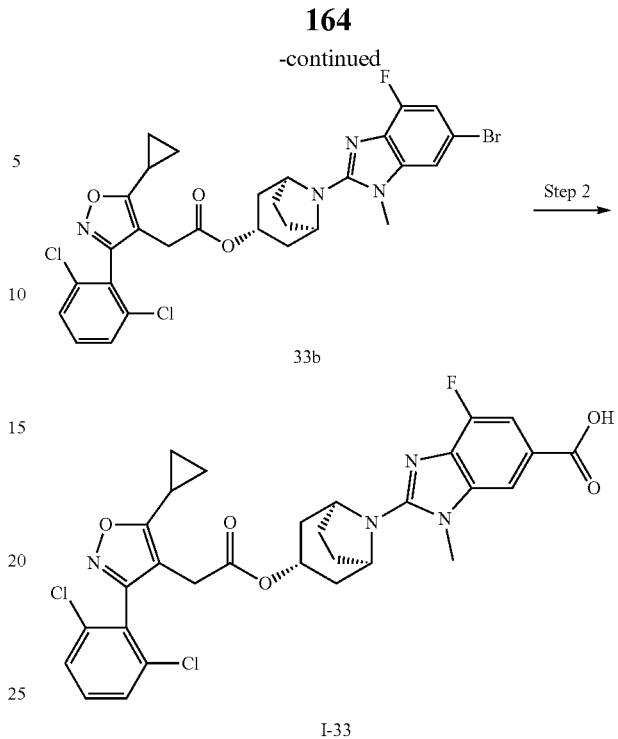

33b

I-33

Step 1. (1R,3S,5S)-8-(6-bromo-4-fluoro-1-methyl-1H-1,3-benzodiazol-2-yl)-8-azabicyclo[3.2.1]octan-3-yl-2-[5-cyclopropyl-3-(2,6-dichlorophenyl)-1,2-oxazol-4-yl]acetate (33b)

To a 25 mL round-bottom flask purged and maintained under an inert atmosphere of nitrogen was added (1R,3S,5S)-8-azabicyclo[3.2.1]octan-3-yl 2-[5-cyclopropyl-3-(2,6-dichlorophenyl)-1,2-oxazol-4-yl]acetate 32f (300 mg, 0.71 mmol, 2.0 equiv.), a solution of 6-bromo-2-chloro-4-fluoro-1-methyl-1H-1,3-benzodiazole 33a (94 mg, 0.36 mmol, 1.0 equiv.), which was prepared according to the procedure outlined for 31e in Example 40, in DMSO (3 mL), and CsF (163 mg, 1.07 mmol, 3.0 equiv.). The resulting mixture was stirred at 115° C. overnight. After cooling to RT, 20 mL of H₂O was added. The aqueous mixture was extracted with ethyl acetate (20 mL×2), and the combined organic layers were washed with brine (50 mL), dried over anhydrous sodium sulfate, filtered, and concentrated in vacuo. The residue was purified by silica gel column chromatography eluting with ethyl acetate/petroleum ether (1:4) to give (1R,3S,5S)-8-(6-bromo-4-fluoro-1-methyl-1H-1,3-benzodiazol-2-yl)-8-azabicyclo[3.2.1] octan-3-yl-2-[5-cyclopropyl-3-(2,6-dichlorophenyl)-1,2-oxazol-4-yl]acetate 33b (160 mg, 69%) as a white solid.

Step 2. 2-[(1R,3S,5S)-3-([2-[5-cyclopropyl-3-(2,6-dichlorophenyl)-1,2-oxazol-4-yl]acetyl]oxy)-8-azabicyclo[3.2.1]octan-8-yl]-4-fluoro-1-methyl-1H-1,3-benzodiazole-6-carboxylic (I-33)

Into a 25 mL round-bottom flask purged with nitrogen was placed lithium formate (31 mg, 0.60 mmol, 3.0 equiv.) and DIEA (52 mg, 0.40 mmol, 2.0 equiv.). The mixture was stirred for 10 min at RT, then acetic anhydride (41 mg, 0.40 mmol, 2.0 equiv.) in N,N-dimethylformamide (0.5 mL), (1R,3S,5S)-8-(6-bromo-4-fluoro-1-methyl-1H-1,3-benzodiazol-2-yl)-8-azabicyclo[3.2.1]octan-3-yl-2-[5-cyclopropyl- 3-(2,6-dichlorophenyl)-1,2-oxazol-4-yl]acetate 33b (130 mg, 0.20 mmol, 1.0 equiv.), palladium acetate (3 mg, 0.01 mmol, 0.05 equiv.), and dppf (6 mg, 0.01 mmol, 0.05 equiv.) were added. The resulting solution was stirred overnight at 120° C. Upon cooling to RT, the mixture was diluted with EtOAc (20 mL). The solids were removed by filtration and the organic layer was washed with brine (30 mL), dried over anhydrous sodium sulfate, and concentrated in vacuo. The residue was purified by silica gel column chromatography eluting with ethyl acetate/petroleum ether (1:1) to give a relatively pure product which was purified via Prep-HPLC with the following conditions: Column, XBridge C18 OBD Prep Column, 19 mm×250 mm; mobile phase, waters (0.05% TFA) and ACN (40% ACN up to 58% in 8 min); Detector, UV 254 nm, providing 2-[(1R,3S,5S)-3-([2-[5-cyclopropyl-3-(2,6-dichlorophenyl)-1,2-oxazol-4-yl]acetyl]oxy)-8-azabicyclo[3.2.1]octan-8-yl]-4-fluoro-1-methyl-1H-1,3-benzodiazole-6-carboxylic acid I-33 (23.2 mg, 19%) as a light yellow solid. $^1$HNMR (300 MHz, CD$_3$OD) δ: 7.93 (t, J=1.2 Hz, 1H), 7.74-7.48 (m, 4H), 5.05 (t, J=4.9 Hz, 1H), 4.77 (s, 2H), 4.52 (s, 2H), 3.81 (d, J=1.3 Hz, 3H), 3.49 (d, J=1.3 Hz, 2H), 3.12 (s, 2H), 2.44-2.24 (m, 3H), 2.09 (dd, J=10.2, 7.0 Hz, 5H), 1.89 (d, J=15.2 Hz, 2H), 1.33 (d, J=11.6 Hz, 1H), 1.26-1.17 (m, 4H). MS (ES, m/z): [M+1]=613.0.

Example 43: 4-[(1R,3R,5S)-3-[5-Cyclopropyl-3-(2,6-dichlorophenyl)-1,2-oxazole-4-carbonyloxy]-8-azabicyclo[3.2.1]octan-8-yl]benzoic acid (I-34)

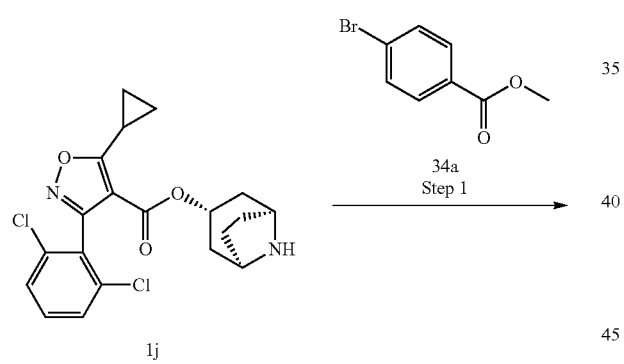

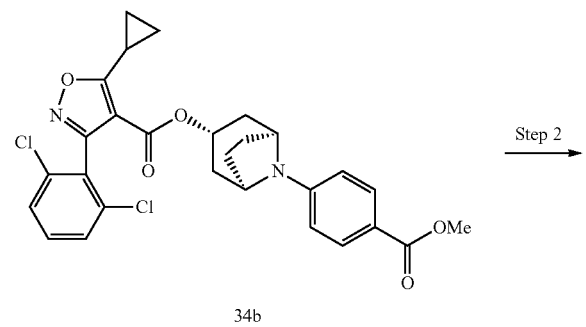

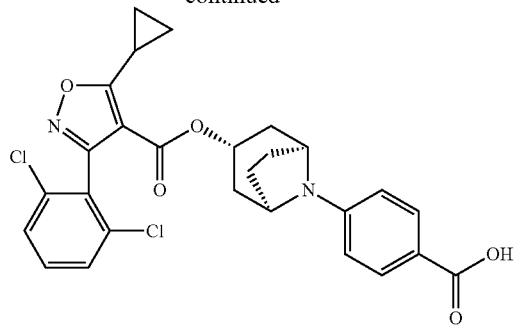

I-34

Step 1. (1R,3R,5S)-8-[4-(methoxycarbonyl)phenyl]-8-azabicyclo[3.2.1]octan-3-yl 5-cyclopropyl-3-(2,6-dichlorophenyl)-1,2-oxazole-4-carboxylate (34b)

To a 100 mL round-bottom flask purged with nitrogen was added (1R,3R,5S)-8-azabicyclo[3.2.1]octan-3-yl 5-cyclopropyl-3-(2,6-dichlorophenyl)-1,2-oxazole-4-carboxylate 1j (300 mg, 0.74 mmol, 1.0 equiv.), toluene (60 mL), methyl 4-bromobenzoate 34a (237.6 mg, 1.10 mmol, 1.5 equiv.), Cs$_2$CO$_3$ (336 mg, 1.03 mmol, 1.4 equiv.), BINAP (45.8 mg, 0.07 mmol, 0.1 equiv.), and Pd$_2$(dba)$_3$ (67.4 mg, 0.07 mmol, 0.1 equiv.). The resulting mixture was stirred overnight at 110° C. The solids were removed by filtration. The filtrate was concentrated in vacuo and the residue was purified via silica gel column chromatography eluting with ethyl acetate/petroleum ether (1:10-1:5) to give (1R,3R,5S)-8-[4-(methoxycarbonyl)phenyl]-8-azabicyclo[3.2.1]octan-3-yl 5-cyclopropyl-3-(2,6-dichlorophenyl)-1,2-oxazole-4-carboxylate 34b (300 mg, 75%) as a light yellow oil.

Step 2. 4-[(1R,3R,5S)-3-[[5-Cyclopropyl-3-(2,6-dichlorophenyl)-1,2-oxazol-4-yl]carbonyloxy]-8-azabicyclo[3.2.1]octan-8-yl]benzoic acid (I-34)

To a 50-mL round-bottom flask purged with nitrogen was added (1R,3R,5S)-8-[4-(methoxycarbonyl)phenyl]-8-azabicyclo[3.2.1]octan-3-yl 5-cyclopropyl-3-(2,6-dichlorophenyl)-1,2-oxazole-4-carboxylate 34b (300 mg, 0.55 mmol, 1.0 equiv.), pyridine (5 mL) and LiI (1 g). The resulting mixture was stirred at 125° C. for 3d. The mixture was concentrated in vacuo, and diluted with 50 mL of H$_2$O. The aqueous mixture was extracted with ethyl acetate (30 mL×2). The aqueous mixture was adjusted to pH 5-6 using HCL (aq.). The precipitated solids were collected by filtration, and the filtrate was purified by Prep-HPLC using the following conditions: Column, XBridge C18 OBD Prep Column, 10 μm, 19 mm×250 mm; mobile phase, Waters (0.05% TFA) and ACN (60.0% ACM to 70.0% over 8 min); Detector, UV 254 nm, resulting 4-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]benzoic acid I-34 (150 mg, 51%) as a light yellow solid. $^1$HNMR (400 MHz, DMSO-d$_6$) δ: 12.16 (d, J=13.0 Hz, 1H), 7.76-7.58 (m, 5H), 6.77 (d, J=8.9 Hz, 2H), 4.96 (t, J=5.4 Hz, 1H), 4.19 (s, 2H), 2.95 (ddd, J=13.4, 8.4, 5.2 Hz, 1H), 2.07 (dt, J=16.3, 4.5 Hz, 2H), 1.76-1.68 (m, 2H), 1.49 (d, J=15.3 Hz, 2H), 1.41-1.22 (m, 6H), 1.15 (s, 1H). MS (ES, m/z): [M+1]=527.

Example 44: 4-[(1R,3R,5S)-3-[5-Cyclopropyl-3-(2,6-dichlorophenyl)-1,2-oxazole-4-carbonyloxy]-8-azabicyclo[3.2.1]octan-8-yl]-3-fluorobenzoic acid (I-35)

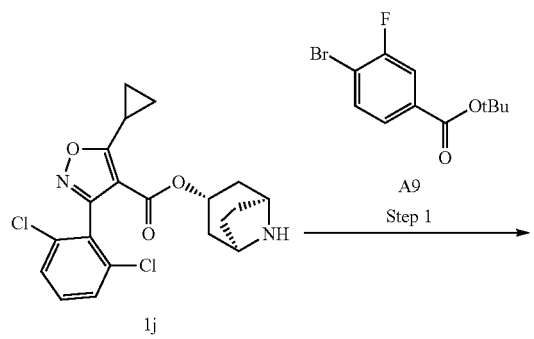

Step 1. (1R,3S,5S)-8-[4-[(tert-butoxy)carbonyl]-2-fluorophenyl]-8-azabicyclo[3.2.1]octan-3-yl-5-cyclopropyl-3-(2,6-dichlorophenyl)-1,2-oxazole-4-carboxylate (35a)

To a 100 mL round-bottom flask was added (1R,3R,5S)-8-azabicyclo[3.2.1]octan-3-yl 5-cyclopropyl-3-(2,6-dichlorophenyl)-1,2-oxazole-4-carboxylate 1j (600 mg, 1.47 mmol, 1.0 equiv.), Pd$_2$(dba)$_3$ (67 mg, 0.07 mmol, 0.05 equiv.), BINAP (46 mg, 0.07 mmol, 0.05 equiv.), Cs$_2$CO$_3$ (674 mg, 2.07 mmol, 1.4 equiv.), tert-butyl 4-bromo-3-fluorobenzoate A9 (486 mg, 1.77 mmol, 1.2 equiv.), and toluene (30 mL). The resulting mixture was stirred at 110° C. overnight. The mixture was cooled to RT and diluted H$_2$O (50 mL), then extracted with ethyl acetate (100 mL×2). The combined organic layers were washed with brine (100 mL×2), dried over anhydrous sodium sulfate, filtered, and concentrated in vacuo. The residue was purified by silica gel column chromatography eluting with ethyl acetate/petroleum ether (1:6) to give of (1R,3S,5S)-8-[4-[(tert-butoxy)carbonyl]-2-fluorophenyl]-8-azabicyclo[3.2.1]octan-3-yl-5-cyclopropyl-3-(2,6-dichlorophenyl)-1,2-oxazole-4-carboxylate 35a (0.52 g, 59%) as a greenish oil.

Step 2. 4-[(1R,3R,5S)-3-[[5-cyclopropyl-3-(2,6-dichlorophenyl)-1,2-oxazol-4-yl]carbonyloxy]-8-azabicyclo[3.2.1] octan-8-yl]-3-fluorobenzoic acid (I-35)

To a 50 mL round-bottom flask was added (1R,3R,5S)-8-[4-[(tert-butoxy)carbonyl]-2-fluorophenyl]-8-azabicyclo[3.2.1]octan-3-yl-5-cyclopropyl-3-(2,6-dichlorophenyl)-1,2-oxazole-4-carboxylate 35a (300 mg, 0.50 mmol, 1.0 equiv.), dichloromethane (10 mL), and trifluoroacetic acid (5 mL). The resulting mixture was stirred for 30 min at RT, then diluted with H$_2$O (100 mL). The aqueous mixture was extracted with dichloromethane (100 mL×3); the combined organic layers were washed with brine (100 mL×2), and concentrated in vacuo to a crude product which was purified by Prep-HPLC using the following conditions: Column, XBridge C18 OBD Prep Column, 10 μm, 19 mm×250 mm; mobile phase, water (0.05% TFA) and ACN (60.0% ACN up to 75.0% in 8 min); Detector, UV 254 nm, providing 4-[(1R,3R,5S)-3-[[5-cyclopropyl-3-(2,6-dichlorophenyl)-1,2-oxazol-4-yl]carbonyloxy]-8-azabicyclo[3.2.1] octan-8-yl]-3-fluorobenzoic acid I-35 (150.0 mg, 55%) as an off-white solid. $^1$HNMR (400 MHz, DMSO-d$_6$) δ: 12.33 (s, 1H), 7.71-7.55 (m, 4H), 6.61-6.51 (m, 2H), 4.96 (t, J=5.4 Hz, 1H), 4.16 (d, J=4.9 Hz, 2H), 2.93 (tt, J=8.2, 5.2 Hz, 1H), 2.04 (dt, J=15.5, 4.8 Hz, 2H), 1.69 (dd, J=7.5, 3.6 Hz, 2H), 1.47 (d, J=15.3 Hz, 2H), 1.39-1.19 (m, 7H); MS (ES, m/z): [M+1]=545.

The compounds in Table 2 below (I-36 to I-42) were synthesized according to the procedure outlined in Example 44, using 1j, and the appropriate precursor Ax in step 1.

Scheme: 1. Ax, Pd$_2$(dba)$_3$, BINAP, Cs$_2$CO$_3$, toluene, 110° C., overnight; 2. TFA, DCM, RT.

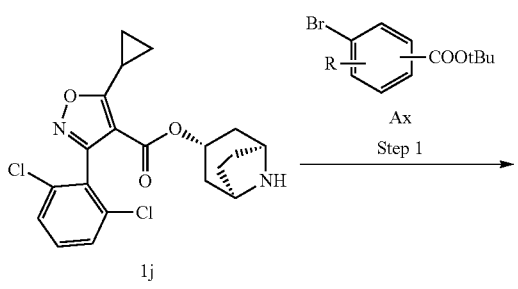

169

-continued

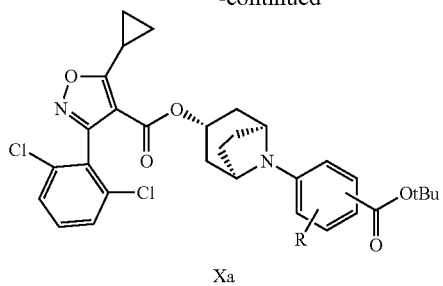

Xa

Step 2 →

170

-continued

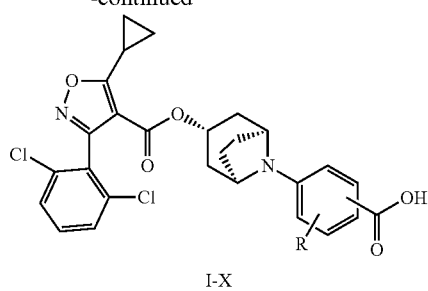

I-X

TABLE 2

Preparation of compounds I-36 to I-42.

| Compound No and Structure | MS/$^1$HNMR |
|---|---|
| I-36 | MS (ES, m/z): [M + 1] = 561.<br>$^1$HNMR (300 MHz, Methanol-d$_4$) δ: 7.95 (d, J = 2.0 Hz, 1H), 7.79 (dd, J = 8.5, 1.9 Hz, 1H), 7.64-7.47 (m, 3H), 6.97 (d, J = 8.5 Hz, 1H), 5.21 (t, J = 5.7 Hz, 1H), 4.01 (s, 2H), 3.39 (s, 2H), 3.10-2.99 (m, 1H), 2.44-2.32 (m, 2H), 1.86-1.70 (m, 4H), 1.46-1.29 (m, 6H). |
| I-37 | MS (ES, m/z): [M + 1] = 595.<br>$^1$HNMR (300 MHz, DMSO-d$_6$) δ: 12.70 (s, 1H), 7.80-7.56 (m, 4H), 7.06-6.94 (m, 2H), 4.98 (t, J = 5.2 Hz, 1H), 3.33 (s, 1H), 2.95 (tt, J = 7.9, 5.2 Hz, 1H), 2.13-1.98 (m, 2H), 1.78-1.68 (m, 2H), 1.52 (d, J = 15.4 Hz, 2H), 1.43-1.21 (m, 6H). |
| I-38 | MS (ES, m/z): [M + 1] = 595.<br>$^1$HNMR (300 MHz, DMSO-d$_6$) δ: 12.95 (s, 1H), 8.05 (d, J = 2.1 Hz, 1H), 7.93 (dd, J = 8.8, 2.1 Hz, 1H), 7.71-7.52 (m, 3H), 7.12 (d, J = 8.8 Hz, 1H), 5.07 (t, J = 5.4 Hz, 1H), 3.32 (s, 1H), 2.93 (ddd, J = 13.3, 8.3, 5.4 Hz, 1H), 2.17 (dt, J = 15.3, 4.4 Hz, 2H), 1.64 (d, J = 14.0 Hz, 4H), 1.30 (ddt, J = 16.3, 13.5, 5.3 Hz, 6H). |

TABLE 2-continued

Preparation of compounds I-36 to I-42.

| Compound No and Structure | MS/¹HNMR |
|---|---|
| I-39 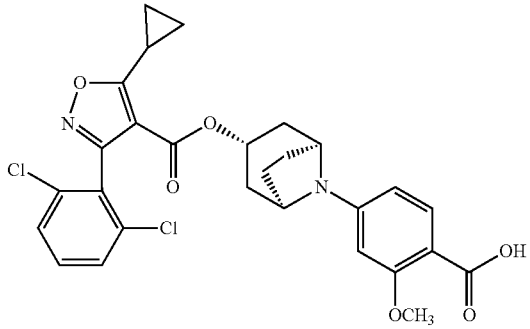 [SMILES: COc1cc(N2[C@@H]3CC[C@H]2C[C@@H](OC(=O)c2c(-c4c(Cl)cccc4Cl)noc2C2CC2)C3)ccc1C(=O)O] | MS (ES, m/z): [M + 1] = 557.<br>¹HNMR (300 MHz, DMSO-d$_6$) δ: 11.59 (s, 1H), 7.72-7.53 (m, 4H), 6.37-6.24 (m, 2H), 4.95 (t, J = 5.4 Hz, 1H), 4.17 (s, 2H), 3.76 (s, 3H), 2.94 (td, J = 8.2, 4.0 Hz, 1H), 2.16-2.02 (m, 2H), 1.69 (d, J = 8.2 Hz, 2H), 1.52-1.40 (m, 2H), 1.41-1.22 (m, 6H). |
| I-40 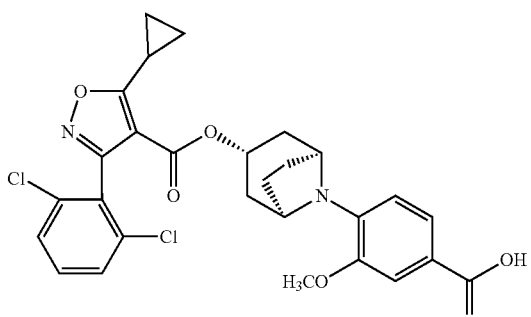 | MS (ES, m/z): [M + 1] = 557.<br>¹HNMR (300 MHz, DMSO-d$_6$) δ: 7.71-7.52 (m, 3H), 7.45-7.30 (m, 2H), 6.77 (d, J = 8.5 Hz, 1H), 4.99 (t, J = 5.5 Hz, 1H), 4.23 (d, J = 4.6 Hz, 2H), 2.92 (td, J = 8.2, 4.2 Hz, 1H), 2.09 (dd, J = 16.2, 5.2 Hz, 2H), 1.61 (d, J = 7.5 Hz, 2H), 1.50 (d, J = 15.3 Hz, 2H), 1.41-1.17 (m, 6H). |
| I-41 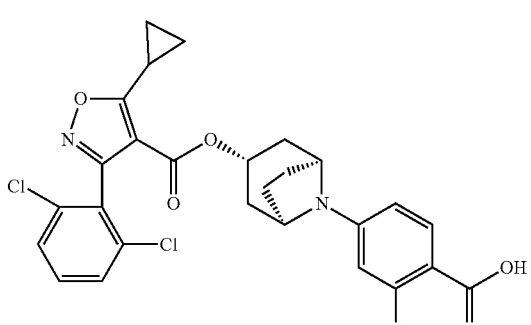 | MS (ES, m/z): [M + 1] = 545.<br>¹HNMR (300 MHz, DMSO-d$_6$) δ: 12.70 (s, 1H), 7.80-7.56 (m, 4H), 7.06-6.94 (m, 2H), 4.98 (t, J = 5.2 Hz, 1H), 3.33 (s, 1H), 2.95 (tt, J = 7.9, 5.2 Hz, 1H), 2.13-1.98 (m, 2H), 1.78-1.68 (m, 2H), 1.52 (d, J = 15.4 Hz, 2H), 1.43-1.21 (m, 6H). |
| I-42 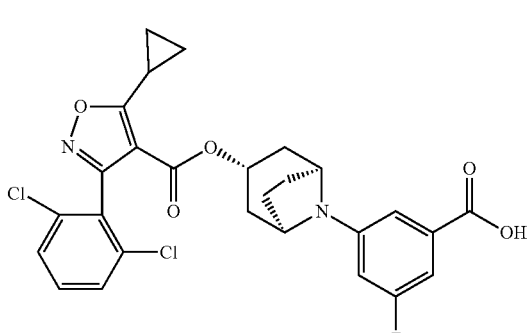 | MS (ES, m/z): [M + 1] = 545.<br>¹HNMR (300 MHz, DMSO-d$_6$) δ: 13.03 (s, 1H), 7.72-7.53 (m, 3H), 7.04 (s, 1H), 6.88-6.77 (m, 2H), 4.94 (t, J = 5.2 Hz, 1H), 4.10 (s, 2H), 2.93 (p, J = 7.9, 7.0 Hz, 1H), 2.02 (dt, J = 21.1, 7.1 Hz, 3H), 1.74-1.64 (m, 2H), 1.51-1.39 (m, 2H), 1.41-1.19 (m, 8H). |

Example 45: 4-[(1R,3R,5S)-3-{3-[2-chloro-6-(difluoromethoxy)phenyl]-5-cyclopropyl-1,2-oxazole-4-carbonyloxy}-8-azabicyclo[3.2.1]octan-8-yl]-3-fluorobenzoic acid (I-43)

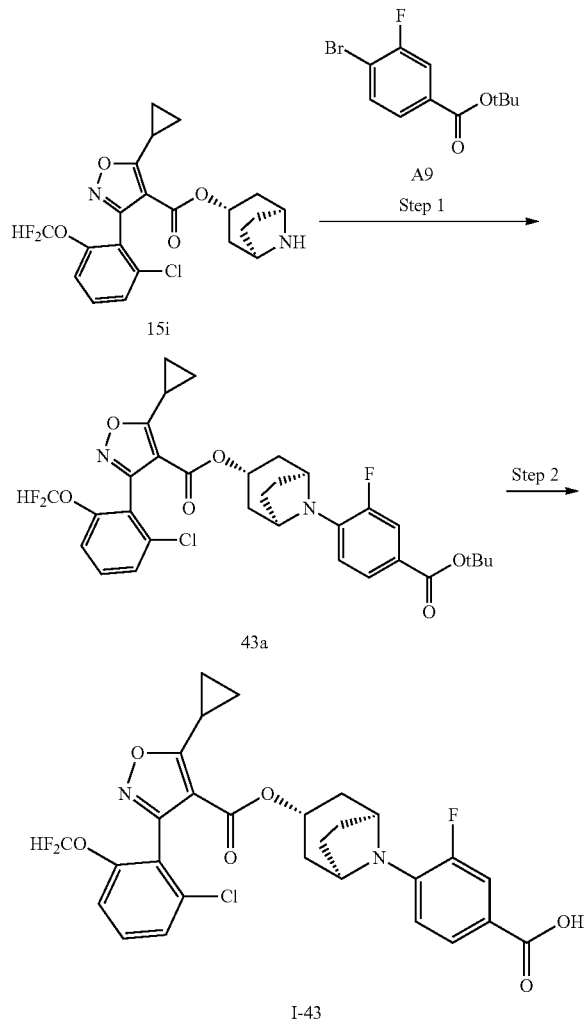

Step 1. (1R,3R,5S)-8-[4-(2,2-dimethylpropanoyl)-2-fluorophenyl]-8-azabicyclo[3.2.1]octan-3-yl 3-[2-chloro-6-(difluoromethoxy)phenyl]-5-cyclopropyl-1,2-oxazole-4-carboxylate (43a)

Following the procedure in Example 44, Step 1, conversion of (1R,3R,5S)-8-azabicyclo[3.2.1]octan-3-yl-3-[2-chloro-6-(difluoromethoxy)phenyl]-5-cyclopropyl-1,2-oxazole-4-carboxylate 15i (150 mg, 0.34 mmol, 1.0 equiv.) 43a under the conditions of tert-butyl 4-bromo-3-fluorobenzoate A9 (141 mg, 0.51 mmol, 1.5 equiv.), toluene (5 mL), BINAP (21 mg, 0.03 mmol, 0.1 equiv.), Pd$_2$(dba)$_3$ (31 mg, 0.03 mmol, 0.1 equiv.), and Cs$_2$CO$_3$ (156 mg, 0.48 mmol, 1.4 equiv.) afforded (1R,3R,5S)-8-[4-(2,2-dimethylpropanoyl)-2-fluorophenyl]-8-azabicyclo[3.2.1]octan-3-yl-3-[2-chloro-6-(difluoromethoxy)phenyl]-5-cyclopropyl-1,2-oxazole-4-carboxylate 43a (200 mg, 95%) as a light yellow solid.

Step 2. 4-[(1R,3R,5S)-3-([3-[2-chloro-6-(difluoromethoxy)phenyl]-5-cyclopropyl-1,2-oxazol-4-yl]carbonyloxy)-8-azabicyclo[3.2.1]octan-8-yl]-3-fluorobenzoic acid (I-43)

Following the procedure outlined in Example 44, Step 2, conversion of (1R,3R,5S)-8-[4-[(tert-butoxy)carbonyl]-2-fluorophenyl]-8-azabicyclo[3.2.1]octan-3-yl-3-[2-chloro-6-(difluoromethoxy)phenyl]-5-cyclopropyl-1,2-oxazole-4-carboxylate 43a (200 mg, 0.32 mmol, 1.0 equiv.) afforded the title product 4-[(1R,3R,5S)-3-([3-[2-chloro-6-(difluoromethoxy) phenyl]-5-cyclopropyl-1,2-oxazol-4-yl]carbonyloxy)-8-azabicyclo[3.2.1]octan-8-yl]-3-fluorobenzoic acid I-43 (61.9 mg, 34%) as a colorless solid. $^1$HNMR (300 MHz, DMSO-d$_6$) δ: 12.34 (s, 1H), 7.73-7.49 (m, 3H), 7.41 (dd, J=8.3, 1.1 Hz, 1H), 6.65-6.51 (m, 2H), 4.96 (t, J=5.2 Hz, 1H), 3.33 (s, 2H), 2.99-2.85 (m, 1H), 2.03 (s, 1H), 1.74 (d, J=7.3 Hz, 2H), 1.52 (t, J=14.4 Hz, 2H), 1.42-1.21 (m, 6H); MS (ES, m/z): [M+1]=577.15.

Example 46—(I-44): (1R,3R,5S)-8-[4-(methanesulfonylcarbamoyl)phenyl]-8-azabicyclo[3.2.1]octan-3-yl 5-cyclopropyl-3-(2,6-dichlorophenyl)-1,2-oxazole-4-carboxylate

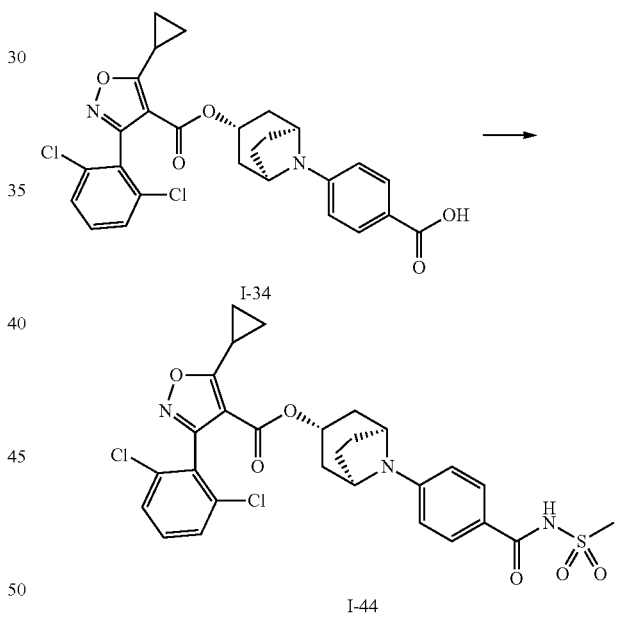

To a 100 mL round-bottom flask was added 4-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]benzoic acid I-34 (120 mg, 0.23 mmol, 1.0 equiv.), N,N-dimethylformamide (20 mL), methanesulfonamide (65 mg, 0.68 mmol, 3.0 equiv.), EDCI (152.6 mg, 0.80 mmol, 3.5 equiv.), and 4-dimethylaminopyridine (97.3 mg, 0.80 mmol, 3.5 equiv.). The resulting mixture was stirred overnight at RT. The solids were removed by filtration and the filtrate was concentrated in vacuo. The residue was diluted with ethyl acetate (5 mL), washed with, citric acid (aq., 5%) and brine, dried over anhydrous Na$_2$SO$_4$, filtered and concentrated under reduced pressure. The crude product was purified by Prep-HPLC using the following conditions: Column, XBridge C18 OBD Prep Column, 19 mm×250 mm; mobile phase, water (0.05% TFA) and ACN (55% ACN up to 74% in 8 min); Detector, UV 254 nm, affording (1R,3R,5S)-8-[4-(methanesulfonylcarbamoyl)phenyl]-8-azabicyclo[3.2.1]octan-3-yl 5-cyclopropyl-3-(2,6-dichlorophenyl)-1,2-oxazole-4-carboxylate I-44 (35 mg, 25%) as a colorless solid. $^1$HNMR (400 MHz, DMSO-d$_6$) δ: 11.61 (s, 1H), 7.80 (d, J=8.8 Hz, 3H), 7.73-7.58 (m, 3H), 6.80 (d, J=8.7 Hz, 2H), 4.97 (t, J=5.4 Hz, 1H), 4.23 (s, 2H), 2.95 (ddd, J=13.4, 8.3, 5.2 Hz, 1H), 2.54 (s, 3H), 2.06 (dt, J=15.7, 4.1 Hz, 2H), 1.77-1.69 (m, 2H), 1.51 (d, J=15.2 Hz, 2H), 1.41-1.27 (m, 6H), 1.15 (s, 1H). MS (ES, m/z): [M+1]=604.

Example 46a: Synthesis of Compounds I-45 to I-49

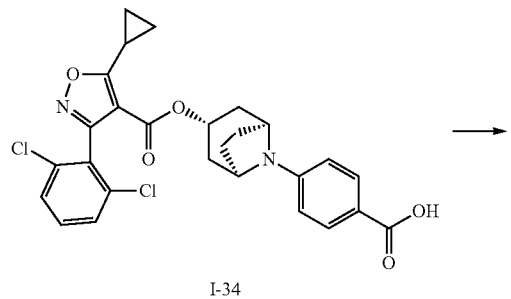

I-34

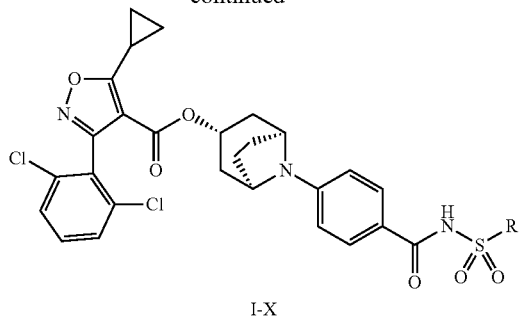

I-X

The compounds in Table 3 below (I-45 to I-49) were synthesized according to the following general procedure: To a mixture of I-34 (0.1 mmol, 1 equiv.) and the appropriate alkylsulfonamide RSO$_2$NH$_2$ (0.15 mmol; 1.5 equiv.) in CH$_2$Cl$_2$ (5 ml) was added triethylamine (0.3 mmol; 3 equiv.), EDCI (0.15 mmol; 1.5 equiv.) and N,N-dimethylaminopyridine (0.15 mmol; 1.5 equiv.). The mixture was stirred for 16 h at RT. The solvents were removed under reduced pressure and resulting residue was suspended in ethyl acetate. The organic layer was washed with citric acid (aq., 5%) and brine, dried over anhydrous Na$_2$SO$_4$, filtered, and concentrated under reduced pressure. The crude material was purified via reverse phase chromatography on Semi-prep HPLC using 40 to 95% acetonitrile containing 0.1% TFA (30 min. method). Fractions were collected monitoring UV absorbance at 215 nm and lyophilized to give the desired compound.

TABLE 3

Preparation of compounds I-45 to I-49.

| Cmpd No. | $^1$HNMR | MS (ESI, m/z) [M + H] |
|---|---|---|
| I-45 | $^1$HNMR (400 MHz, DMSO-d$_6$) δ: 11.53 (s, 1H), 7.80 (d, J = 9.0 Hz, 2H), 7.74-7.56 (m, 3H), 6.79 (d, J = 9.1 Hz, 2H), 4.97 (t, J = 5.4 Hz, 1H), 3.51-3.38 (m, 3H), 3.05-2.83 (m, 1H), 2.05 (d, J = 15.1 Hz, 1H), 1.73-1.68 (m, 4H), 1.50 (d, J = 15.4 Hz, 2H), 1.41-1.26 (m, 4H), 0.98 (t, J = 7.4 Hz, 3H). | 632.13 |
| I-46 | $^1$HNMR (400 MHz, DMSO-d$_6$) δ: 11.51 (s, 1H), 7.78 (d, J = 8.6 Hz, 2H), 7.68-7.55 (m, 3H), 6.79 (d, J = 8.8 Hz, 2H), 4.96 (t, J = 5.4 Hz, 1H), 3.53-3.36 (m, 3H), 2.94-2.89 (m, 1H), 2.05 (d, J = 15.5 Hz, 1H), 1.71-1.67 (m, 4H), 1.50 (d, J = 15.4 Hz, 2H), 1.41-1.15(m, 12H), 0.83 (t, J = 7.1 Hz, 3H). | 660.07 |
| I-47 | $^1$HNMR (400 MHz, DMSO-d$_6$) δ: 11.43 (s, 1H), 7.78 (d, J = 8.9 Hz, 2H), 7.71-7.53 (m, 3H), 6.78 (d, J = 9.1 Hz, 2H), 4.95 (t, J = 5.4 Hz, 1H), 3.88-3.72 (m, 2H), 3.02-2.85 (m, 1H), 2.04 (d, J = 15.5 Hz, 1H), 1.74-1.70 (m, 2H), 1.49 (d, J = 15.3 Hz, 2H), 1.39-1.23 (m, 14H). | 632.16 |
| I-48 | $^1$HNMR (400 MHz, DMSO-d$_6$) δ: 11.55 (s, 1H), 7.79 (d, J = 8.9 Hz, 2H), 7.74-7.58 (m, 3H), 6.80 (d, J = 9.1 Hz, 2H), 4.96 (t, J = 5.4 Hz, 1H), 3.18-3.04 (m, 1H), 2.96-2.93 (m, 1H), 2.06 (d, J = 15.5 Hz, 2H), 1.76-1.73 (m, 2H), 1.50 (d, J = 15.2 Hz, 2H), 1.37-1.31 (m, 8H), 1.17-0.99 (m, 4H). | 630.14 |
| I-49 | $^1$HNMR (400 MHz, DMSO-d$_6$) δ: 11.61 (s, 1H), 7.81 (d, J = 7.4 Hz, 2H), 7.70-7.63 (m, 3H), 6.79 (d, J = 7.5 Hz, 2H), 4.97 (t, J = 5.4 Hz, 1H), 3.33-3.41 (m, 3H), 2.96-2.94 (m, 1H), 2.06 (d, J = 14.5 Hz, 2H), 1.71 (bs, 2H), 1.51 (d, J = 15.3 Hz, 2H), 1.34-1.32 (m, 8H), 0.58-0.56 (m, 2H), 0.31-0.29 (m, 2H). | 644.08 |

Example 47: (1R,3R,5S)-8-{4-[(3-hydroxypropane-sulfonyl)carbamoyl]phenyl}-8-azabicyclo[3.2.1]octan-3-yl 5-cyclopropyl-3-(2,6-dichlorophenyl)-1,2-oxazole-4-carboxylate (I-50)

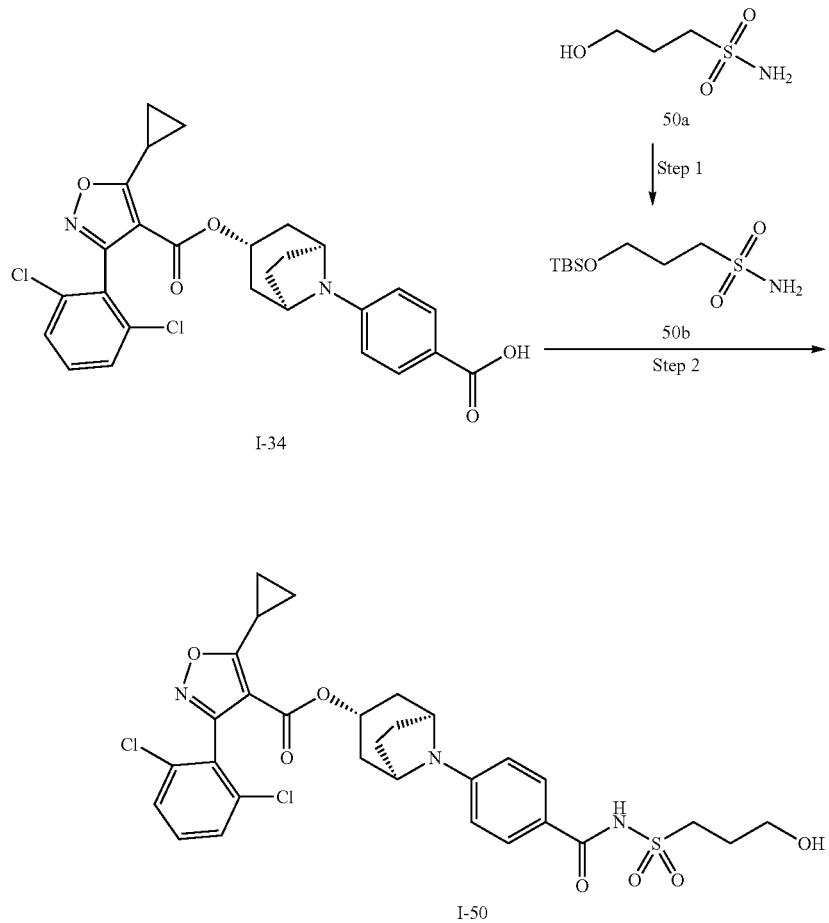

Step 1. 3-(tert-Butyldimethylsilyloxy)propane-1-sulfonamide (50b)

To a solution of 3-hydroxypropane-1-sulfonamide 50a (1.0 g, 7.2 mmol) and imidazole (0.83 g, 12.5 mmol) in DMF (15 ml) was added tert-butyldimethylchlorosilane at 0° C., then stirred for 4 h at RT, then, ammonium chloride (aq., sat.) and ethyl acetate were added to the reaction mixture. The organic layer was washed with sodium chloride (aq., sat.) and. The solvent was evaporated under reduced pressure. The residue was dried over anhydrous sodium sulfate, filtered and concentrated in vacuo. The crude material was purified by silica gel chromatography eluting with 10-15% ethyl acetate in hexane to give 3-(7c/7-butyl dimethyl silyloxy)propane-1-sulfonamide 50b (1.5 g) as a white amorphous solid. ¹HNMR (400 MHz, DMSO-d₆) δ: 6.78 (d, J=4.9 Hz, 2H), 3.67 (q, J=5.9 Hz, 2H), 2.99 (dt, J=7.4& 5.7 Hz, 2H), 1.96-1.79 (m, 2H), 0.88-0.86 (bs, 9H), 0.05-0.03 (s, 6H).

Step 2. (1R,3R,5S)-8-{4-[(3-hydroxypropanesulfonyl)carbamoyl]phenyl}-8-azabicyclo[3.2.1]octan-3-yl 5-cyclopropyl-3-(2,6-dichlorophenyl)-1,2-oxazole-4-carboxylate (I-50)

Following the general procedure outlined for the preparation of compounds I-45 to I-49, 4-((1R,3R,5S)-3-(5-cyclopropyl-3-(2,6-dichlorophenyl)isoxazole-4-carbonyloxy)-8-azabicyclo[3.2.1]octan-8-yl)benzoic acid trifluoroacetic acid salt I-34 (64 mg; 0.1 mmol) was reacted with 3-(tert-butyldimethylsilyloxy)propane-1-sulfonamide 50b (37.5 mg; 0.15 mmol) to give the desired acylsulfonamide. Removal of O-silyl protecting group with HCl in dioxane, followed by purification via semi-prep HPLC gave the title product (1R,3R,5S)-8-{4-[(3-hydroxypropanesulfonyl)carbamoyl]phenyl}-8-azabicyclo[3.2.1]octan-3-yl 5-cyclopropyl-3-(2,6-dichlorophenyl)-1,2-oxazole-4-carboxylate I-50 (trifluoroacetate salt, 34 mg) as an off-white solid. ¹H-NMR (400 MHz, DMSO-d₆) δ: 11.52 (s, 1H), 7.78 (d, J=8.4 Hz, 2H), 7.70-7.53 (m, 3H), 6.78 (d, J=8.6 Hz, 2H), 4.95 (t, J=5.4 Hz, 1H), 4.66-4.65 (bs, 1H), 4.22-4.21 (bs, 2H), 4.74-4.72 (m, 4H), 3.05-2.86 (m, 1H), 2.05 (d, J=15.1 Hz, 2H), 1.82-1.71 (m, 4H), 1.49 (d, J=15.4 Hz, 2H), 1.47-1.23 (m, 6H). MS (ES, m/z): 647.83 [M+H]⁺.

Example 48: (1R,3R,5S)-8-[2-fluoro-4-(methanesulfonylcarbamoyl)phenyl]-8-azabicyclo[3.2.1]octan-3-yl 5-cyclopropyl-3-(2,6-dichlorophenyl)-1,2-oxazole-4-carboxylate (I-51)

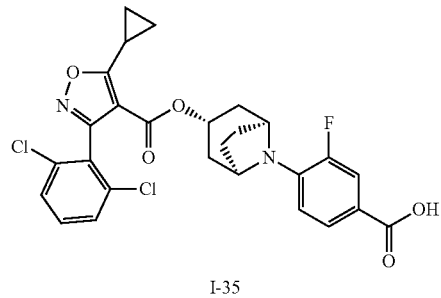

I-35

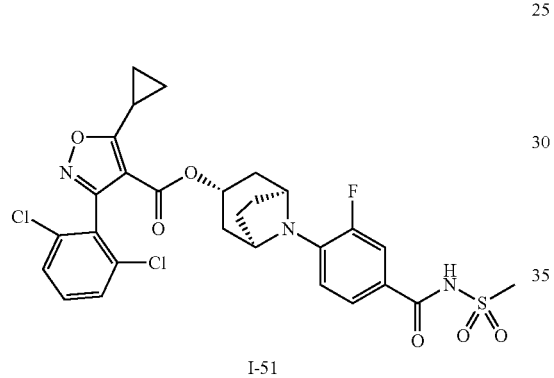

I-51

Example 49: (1R,3R,5S)-8-[2-chloro-4-(methanesulfonylcarbamoyl)phenyl]-8-azabicyclo[3.2.1]octan-3-yl 5-cyclopropyl-3-(2,6-dichlorophenyl)-1,2-oxazole-4-carboxylate

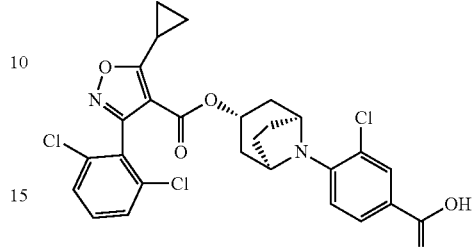

I-36

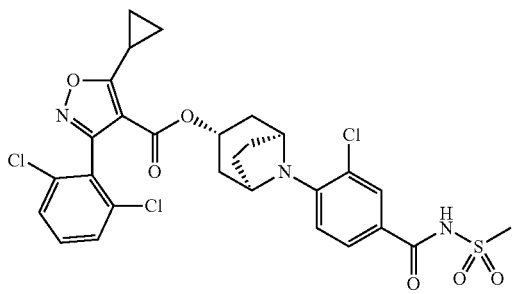

I-52

To a 25 mL round-bottom flask, was added 4-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-3-fluorobenzoic acid I-35 (400 mg, 0.73 mmol, 1.0 equiv.), EDCI (212 mg, 1.11 mmol, 1.5 equiv.), 4-dimethylaminopyridine (134 mg, 1.10 mmol, 1.5 equiv.), N,N-dimethylformamide (6 mL), and methanesulfonamide (84 mg, 0.88 mmol, 1.2 equiv.). The resulting solution was stirred overnight at RT. The resulting mixture was concentrated in vacuo. The crude product was purified via Prep-HPLC using the following conditions: Column, XSelect CSH Prep C18 OBD Column, 5 μm, 19×150 mm; mobile phase, waters (0.05% TFA) and ACN (55.0% ACN to 71.0% over 10 min); Detector, ETV 254 nm, yielding (1R,3R,5S)-8-[2-fluoro-4-(methanesulfonylcarbamoyl)phenyl]-8-azabicyclo[3.2.1]octan-3-yl-5-cyclopropyl-3-(2,6-dichlorophenyl)-1,2-oxazole-4-carboxylate I-51 (108.1 mg, 24%) as a white solid. $^{1}$HNMR (300 MHz, Methanol-$d_4$) δ: 7.69-7.48 (m, 5H), 6.96 (t, J=8.9 Hz, 1H), 5.08 (s, 1H), 4.31 (s, 2H), 3.05 (t, J=6.7 Hz, 1H), 2.23 (d, J=15.3 Hz, 2H), 1.80 (s, 2H), 1.68 (d, J=15.2 Hz, 2H), 1.46-1.32 (m, 6H); MS (ES, m/z): [M+1]=622.

To a 25-mL round-bottom flask, was placed 3-chloro-4-[(1R,3R,5S)-3-[[5-cyclopropyl-3-(2,6-dichlorophenyl)-1,2-oxazol-4-yl]carbonyloxy]-8-azabicyclo[3.2.1]octan-8-yl] benzoic acid I-36 (400 mg, 0.71 mmol, 1.0 equiv.), methanesulfonamide (100 mg, 1.05 mmol, 1.2 equiv.), 4-dimethylaminopyridine (87 mg, 0.71 mmol, 1.5 equiv.), EDCI (200 mg, 1.04 mmol, 1.5 equiv.), and N,N-dimethylformamide (6 mL). The resulting mixture was stirred overnight at RT and concentrated in vacuo. The crude product was purified by Prep-HPLC using the following conditions: Column, XSelect CSH Prep C18 OBD Column, 5 μm, 19×150 mm; mobile phase, waters (0.05% TFA) and ACN (45.0% ACN up to 85.0% in 10 min); Detector, UV 254 nm, yielding (1R,3R,5S)-8-[2-chloro-4-(methanesulfonylcarbamoyl)phenyl]-8-azabicyclo[3.2.1]octan-3-yl 5-cyclopropyl-3-(2,6-dichlorophenyl)-1,2-oxazole-4-carboxylate I-52 (9.7 mg, 2%) as an off-white solid. $^{1}$HNMR (300 MHz, Methanol-$d_4$) δ: 7.91 (d, J=2.2 Hz, 1H), 7.73 (dd, J=8.7, 2.2 Hz, 1H), 7.64-7.46 (m, 3H), 7.03 (d, J=8.7 Hz, 1H), 5.20 (t, J=5.6 Hz, 1H), 4.09 (s, 3H), 2.36 (d, J=14.7 Hz, 3H), 1.86-1.70 (m, 5H), 1.44-1.32 (m, 7H); MS (ES, m/z): [M+1]=638.

Example 50: (1R,3R,5S)-8-(4-cyano-3-hydroxyphenyl)-8-azabicyclo[3.2.1]octan-3-yl 5-cyclopropyl-3-(2,6-dichlorophenyl)-1,2-oxazole-4-carboxylate (I-53)

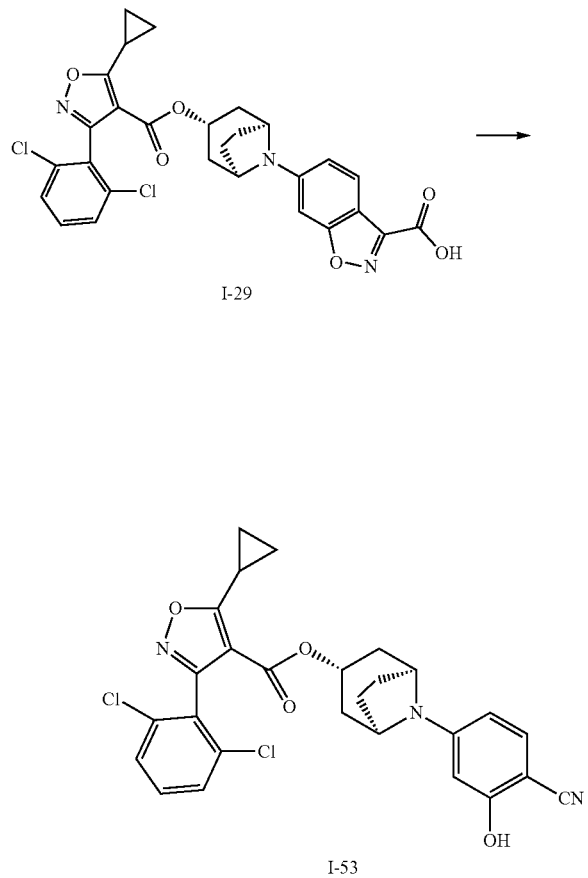

Example 51: 5-[(1R,3R,5S)-3-[5-Cyclopropyl-3-(2,6-dichlorophenyl)-1,2-oxazole-4-carbonyloxy]-8-azabicyclo[3.2.1]octan-8-yl]pyrimidine-2-carboxylic acid (I-54)

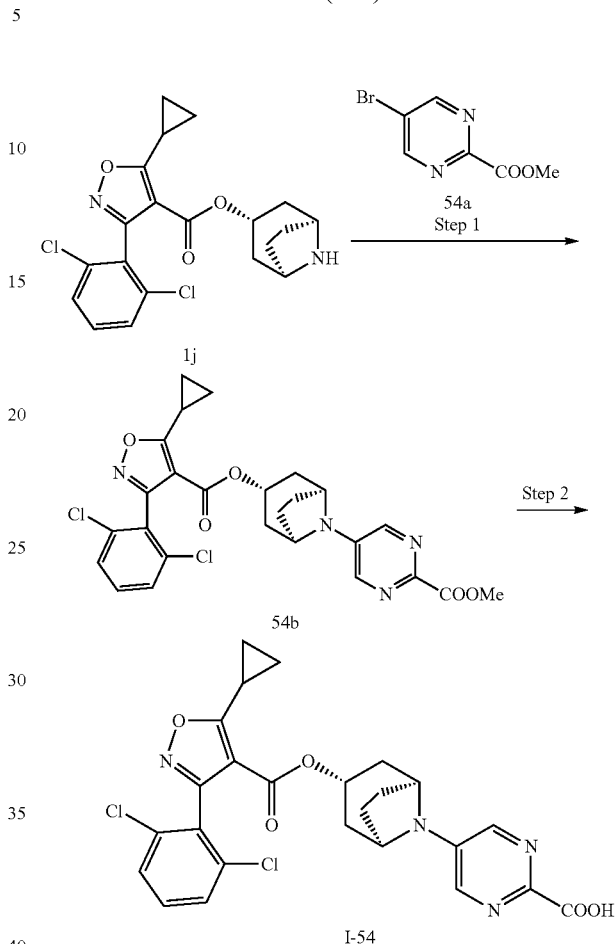

To a 8 mL sealed tube was added 6-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]-1,2-benzoxazole-3-carboxylic acid I-29 (100 mg, 0.18 mmol, 1.0 equiv.) and N,N-dimethylformamide (3 mL). The resulting mixture was stirred for 10 min at RT. The crude product was purified by Prep-HPLC with the following conditions: Column, XBridge C18 OBD Prep Column, 19 mm×250 mm; mobile phase, water (0.05% TFA) and ACN (70.0% ACN to 84.0% over 6 min); Detector, UV 254 nm, providing 27.9 mg (30%) of (1R,3R,5S)-8-(4-cyano-3-hydroxyphenyl)-8-azabicyclo[3.2.1]octan-3-yl-5-cyclopropyl-3-(2,6-dichlorophenyl)-1,2-oxazole-4-carboxylate I-53 as an off-white solid. $^1$HNMR (300 MHz, DMSO-$d_6$) δ: 10.51 (s, 1H), 7.74-7.56 (m, 3H), 7.29 (d, J=8.7 Hz, 1H), 6.33 (dd, J=8.8, 2.0 Hz, 1H), 6.19 (d, J=2.1 Hz, 1H), 4.99 (s, 1H), 4.05 (s, 2H), 3.00-2.86 (m, 1H), 2.06 (d, J=15.2 Hz, 2H), 1.71 (s, 1H), 1.56-1.21 (m, 8H); MS (ES, m/z): [M+1]=524.

Step 1. Methyl 5-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]pyrimidine-2-carboxylate (54b)

To a 250 mL round-bottom flask was added (1R,3S,5S)-8-azabicyclo[3.2.1]octan-3-yl 5-cyclopropyl-3-(2,6-dichlorophenyl)-1,2-oxazole-4-carboxylate 1j (500 mg, 1.23 mmol, 1.0 equiv.), methyl 5-bromopyrimidine-2-carboxylate 54a (320 mg, 1.47 mmol, 1.2 equiv.), $Cs_2CO_3$ (560 mg, 1.72 mmol, 1.4 equiv.), BINAP (38 mg, 0.06 mmol, 0.05 equiv.), $Pd_2(dba)_3$ (56 mg, 0.06 mmol, 0.05 equiv.), and toluene (50 mL). The resulting mixture was stirred at 110° C. overnight. The mixture was diluted with 50 mL of $H_2O$ and extracted with ethyl acetate (100 mL×2). The combined organic layers were washed with brine (100 mL×2), dried over anhydrous sodium sulfate, filtered, and concentrated in vacuo. The residue was purified by silica gel column chromatography eluting with dichloromethane/methanol (10:1) to give methyl 5-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]pyrimidine-2-carboxylate 54b (0.127 g, 19%) as a yellow oil.

Step 2. 5-[(1R,3S,5S)-3-[[5-cyclopropyl-3-(2,6-dichlorophenyl)-1,2-oxazol-4-yl]carbonyloxy]-8-azabicyclo[3.2.1]octan-8-yl]pyrimidine-2-carboxylic acid (I-54)

To a 25 mL round-bottom flask was added methyl 5-[(1R,3R,5S)-3-[[5-cyclopropyl-3-(2,6-dichlorophenyl)-1,2-oxazol-4-yl]carbonyloxy]-8-azabicyclo[3.2.1]octan-8-yl]pyrimidine-2-carboxylate 54b (180 mg, 0.33 mmol, 1.0 equiv.), pyridine (4 mL), and LiI (0.44 g, 10.0 equiv.). The resulting mixture was stirred at 125° C. overnight. The reaction was quenched with H$_2$O/ice (20 mL). The aqueous mixture was extracted ethyl acetate (100 mL). The organic layer was washed with brine (100 mL×2), and concentrated. The crude product was purified by Prep-HPLC using the following conditions: Column, XBridge C18 OBD Prep Column, 10 μm, 19 mm×250 mm; mobile phase, water (0.05% TFA) and ACN (48.0% ACN up to 63.0% in 6 min); Detector, UV 254 nm, affording 5-[(1R,3S,5S)-3-[[5-cyclopropyl-3-(2,6-dichlorophenyl)-1,2-oxazol-4-yl]carbonyloxy]-8-azabicyclo[3.2.1]octan-8-yl]pyrimidine-2-carboxylic acid I-54 (7.9 mg, 5%) as a light yellow solid. $^1$HNMR (300 MHz, DMSO-d$_6$) δ: 8.35 (s, 2H), 7.58 (q, J=5.9 Hz, 3H), 4.89 (s, 1H), 4.35 (s, 2H), 2.19 (d, J=15.1 Hz, 1H), 1.83 (s, 2H), 1.72 (d, J=15.7 Hz, 2H), 1.46 (d, J=7.6 Hz, 2H), 1.41-1.28 (m, 5H); MS (ES, m/z): [M+1]=529.

Example 52: 3-{[(1R,3R,5S)-3-[5-cyclopropyl-3-(2,6-dichlorophenyl)-1,2-oxazole-4-carbonyloxy]-8-azabicyclo[3.2.1]octan-8-yl]sulfonyl}benzoic acid (I-55)

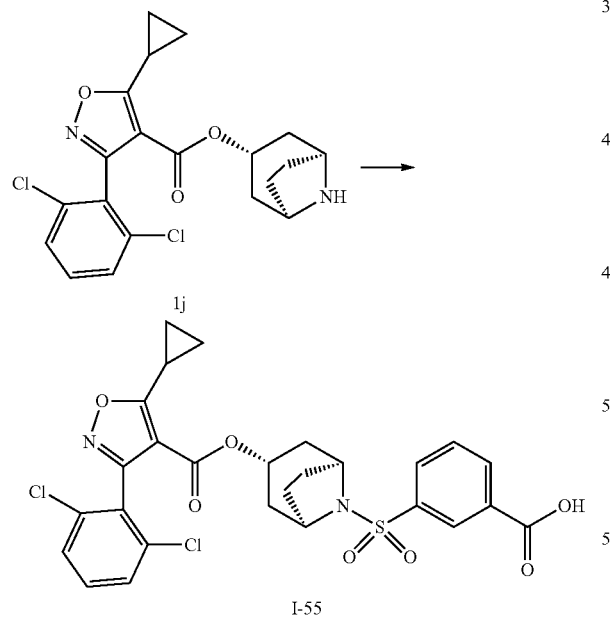

To a 25 mL round-bottom flask was added (1R,3R,5S)-8-azabicyclo[3.2.1]octan-3-yl 5-cyclopropyl-3-(2,6-dichlorophenyl)-1,2-oxazole-4-carboxylate 1j (100 mg, 0.25 mmol, 1.0 equiv.), dichloromethane (4 mL), 3-(chlorosulfonyl)benzoic acid (54 mg, 0.24 mmol, 1.0 equiv.), and DIEA (96 mg, 0.74 mmol, 3.0 equiv.). The resulting mixture was stirred for 30 min at RT and then concentrated in vacuo. The residue was dissolved in 2 mL of DMF. The crude product was purified by Prep-HPLC using the following conditions: Column, XSelect CSH Prep C18 OBD Column, 5 μm, 19×150 mm; mobile phase, water (0.05% TFA) and ACN (55.0% ACN up to 75.0% in 8 min); Detector, UV 254 nm, providing 3-[(1R,3R,5S)-3-[[5-cyclopropyl-3-(2,6-dichlorophenyl)-1,2-oxazol-4-yl]carbonyloxy]-8-azabicyclo[3.2.1]octane-8-sulfonyl]benzoic acid I-55 (65.8 mg, 45%) as a white solid. $^1$HNMR (400 MHz, DMSO-d$_6$) δ: 13.58 (s, 1H), 8.31-8.17 (m, 2H), 8.08 (dt, J=7.8, 1.4 Hz, 1H), 7.73 (t, J=7.8 Hz, 1H), 7.66-7.58 (m, 2H), 7.54 (dd, J=9.2, 6.9 Hz, 1H), 5.06 (t, J=5.5 Hz, 1H), 4.19-4.01 (m, 2H), 2.87 (tt, J=8.3, 5.2 Hz, 1H), 2.13 (t, J=4.9 Hz, 1H), 2.11-2.09 (m, 1H), 1.75-1.61 (m, 2H), 1.29 (dddd, J=15.4, 12.9, 9.1, 4.9 Hz, 4H), 1.14-0.97 (m, 4H); MS (ES, m/z): [M+1]=591.0.

Example 5:3 3-{[(1R,3R,5S)-3-[5-cyclopropyl-3-(2,6-dichlorophenyl)-1,2-oxazole-4-carbonyloxy]-8-azabicyclo[3.2.1]octan-8-yl]sulfonyl}-5-fluorobenzoic acid (I-56)

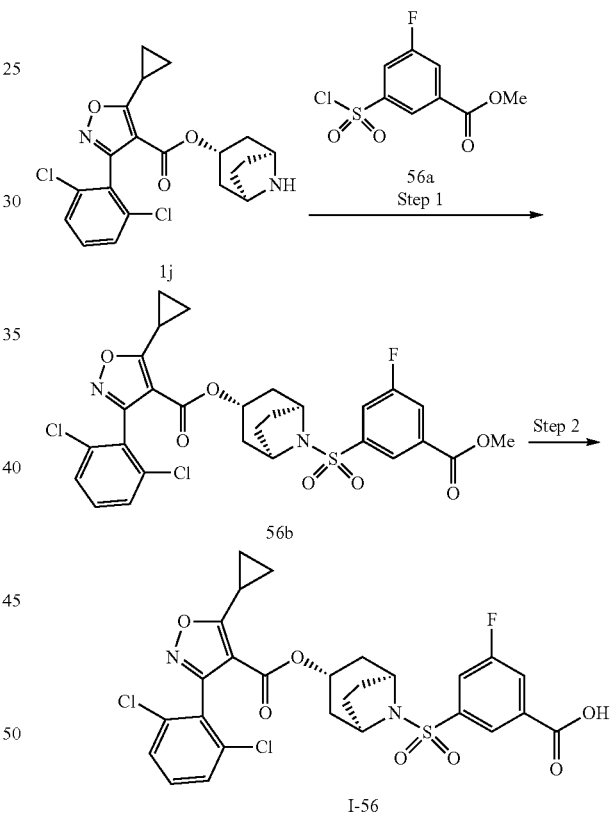

Step 1. (1R,3R,5S)-8-[[3-fluoro-5-(methoxycarbonyl)benzene]sulfonyl]-8-azabicyclo[3.2.1]octan-3-yl 5-cyclopropyl-3-(2,6-dichlorophenyl)-1,2-oxazole-4-carboxylate (56b)

To a 25 mL round-bottom flask was added (1R,3R,5S)-8-azabicyclo[3.2.1]octan-3-yl 5-cyclopropyl-3-(2,6-dichlorophenyl)-1,2-oxazole-4-carboxylate 1j (200 mg, 0.49 mmol, 1.0 equiv.), methyl 3-(chlorosulfonyl)-5-fluorobenzoate 56a (124 mg, 0.49 mmol, 1.00 equiv.), DIEA (143 mg, 1.11 mmol, 3.0 equiv.), and dichloromethane (2 mL). The resulting mixture was stirred for 30 min at 0° C., and quenched with H₂O. The aqueous mixture was extracted with ethyl acetate (30 mL×3); the combined organic layers were dried over anhydrous sodium sulfate, and concentrated in vacuo. The residue was purified via silica gel column chromatography eluting with ethyl acetate/petroleum ether (1:2) to give (1R,3R,5S)-8-[[3-fluoro-5-(methoxycarbonyl)benzene]sulfonyl]-8-azabicyclo[3.2.1]octan-3-yl 5-cyclopropyl-3-(2,6-dichlorophenyl)-1,2-oxazole-4-carboxylate 56b (0.25 g, 82%) as a white solid.

Step 2. 3-[(1R,3R,5S)-3-[[5-cyclopropyl-3-(2,6-dichlorophenyl)-1,2-oxazol-4-yl]carbonyloxy]-8-azabicyclo[3.2.1]octane-8-sulfonyl]-5-fluorobenzoic acid (I-56)

To a 50 mL round-bottom flask was added (1R,3R,5S)-8-[[3-fluoro-5-(methoxycarbonyl)benzene]sulfonyl]-8-azabicyclo[3.2.1]octan-3-yl 5-cyclopropyl-3-(2,6-dichlorophenyl)-1,2-oxazole-4-carboxylate 56b (300 mg, 0.48 mmol, 1.0 equiv.), LiI (646 mg, 4.82 mmol, 10.0 equiv.), and pyridine (3 mL). The resulting mixture was stirred at 125° C. for 12 h and then concentrated in vacuo. H₂O was added, and the aqueous mixture was extracted with ethyl acetate (30 mL×2). The combined organic layers were dried over anhydrous sodium sulfate, concentrated in vacuo to a residue which was purified via Prep-HPLC using the following conditions: Column, XBridge C18 OBD Prep Column, 19 mm×250 mm; mobile phase, Waters (0.05% TFA) and ACN (55% ACN to 73% over 8 min); Detector, UV 254 nm, providing 3-[(1R,3R,5S)-3-[[5-cyclopropyl-3-(2,6-dichlorophenyl)-1,2-oxazol-4-yl]carbonyloxy]-8-azabicyclo[3.2.1]octane-8-sulfonyl]-5-fluorobenzoic acid I-56 (0.1127 g, 38%) as an off-white solid. ¹HNMR (300 MHz, DMSO-d₆) δ: 13.91-13.84 (m, 1H), 8.13-7.94 (m, 3H), 7.69-7.49 (m, 3H), 5.08 (t, J=5.5 Hz, 1H), 3.34 (s, 1H), 2.88 (t, J=7.0 Hz, 1H), 2.21-2.05 (m, 2H), 1.75-1.63 (m, 2H), 1.31 (ddd, J=14.0, 6.9, 3.0 Hz, 4H), 1.12 (s, 4H); MS (ES, m/z): [M+1]=606.90.

Example 54: (I-57): 2-[(1R,3R,5S)-3-(3-{bicyclo[2.2.2]octan-1-yl}-5-cyclopropyl-1,2-oxazole-4-carbonyloxy)-8-azabicyclo[3.2.1]octan-8-yl]-4-(trifluoromethoxy)-1,3-benzothiazole-6-carboxylic acid (I-57)

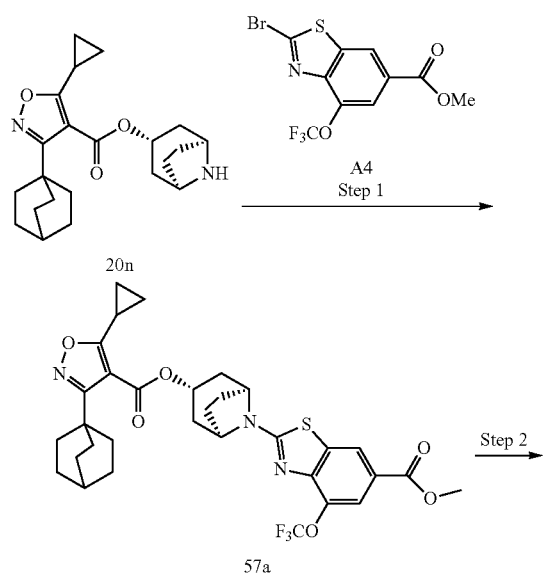

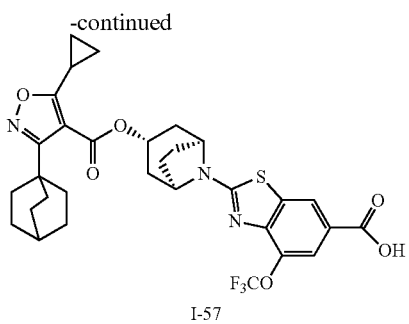

Step 1. Methyl 2-[(1R,3R,5S)-3-[(3-[bicyclo[2.2.2]octan-1-yl]-5-cyclopropyl-1,2-oxazol-4-yl)carbonyloxy]-8-azabicyclo[3.2.1]octan-8-yl]-4-(trifluoromethoxy)-1,3-benzothiazole-6-carboxylate (57a)

To a 25 mL round-bottom flask purged with nitrogen was added (1R,3R,5S)-8-azabicyclo[3.2.1]octan-3-yl 3-[bicyclo[2.2.2]octan-1-yl]-5-cyclopropyl-1,2-oxazole-4-carboxylate 20n (60 mg, 0.16 mmol, 1.0 equiv.), methyl 2-bromo-4-(trifluoromethoxy)-1,3-benzothiazole-6-carboxylate A4 (53 mg, 0.15 mmol, 1.0 equiv.), DMA (1 mL), and Cs₂CO₃ (97 mg, 0.3 mmol, 2.0 equiv.). The resulting mixture was stirred at 60° C. overnight. H₂O was added, the aqueous mixture was extracted with ethyl acetate (150 mL), and the organic layer was washed with brine (20 mL×4), then dried over anhydrous sodium sulfate. Removal of the solvents gave a residue which was purified via silica gel column chromatography eluting with ethyl acetate/petroleum ether (1:5) to give methyl 2-[(1R,3R,5S)-3-[(3-[bicyclo[2.2.2]octan-1-yl]-5-cyclopropyl-1,2-oxazol-4-yl)carbonyloxy]-8-azabicyclo[3.2.1]octan-8-yl]-4-(trifluoromethoxy)-1,3-benzothiazole-6-carboxylate 57a (60 mg, 57%) as a light yellow oil.

Step 2. 2-[(1R,3R,5S)-3-[(3-[bicyclo[2.2.2]octan-1-yl]-5-cyclopropyl-1,2-oxazol-4-yl)carbonyloxy]-8-azabicyclo[3.2.1]octan-8-yl]-4-(trifluoromethoxy)-1,3-benzothiazole-6-carboxylic acid (I-57)

To a 25 mL round-bottom flask purged and maintained under an inert atmosphere of nitrogen was added methyl 2-[(1R,3R,5S)-3-[(3-[bicyclo[2.2.2]octan-1-yl]-5-cyclopropyl-1,2-oxazol-4-yl)carbonyloxy]-8-azabicyclo[3.2.1]octan-8-yl]-4-(trifluoromethoxy)-1,3-benzothiazole-6-carboxylate 57a (40 mg, 0.06 mmol, 1.0 equiv.), pyridine (2 mL) and LiI (83 mg, 10.0 equiv.). The resulting mixture was stirred overnight at 125° C. H₂O was added, and the aqueous mixture was extracted with ethyl acetate (100 mL). The organic layer was washed with HCl (1 M, 50 mL×2) and brine (50 mL×2). Removal of solvents gave a crude product which was purified via Prep-HPLC using the following conditions: Column, XBridge C18 OBD Prep Column, 5 μm, 19 mm×250 mm; mobile phase, water (0.05% TFA) and ACN (88.0% ACN to 90.0% over 9 min); Detector, UV 254 nm, yielding of 2-[(1R,3R,5S)-3-[(3-[bicyclo[2.2.2]octan-1-yl]-5-cyclopropyl-1,2-oxazol-4-yl)carbonyloxy]-8-azabicyclo[3.2.1]octan-8-yl]-4-(trifluoromethoxy)-1,3-benzothiazole-6-carboxylic acid I-57 (24.2 mg, 62%) as an off-white solid. ¹HNMR (300 MHz, CD₃OD) δ: 8.34 (d, J=1.5 Hz, 1H), 7.90-7.82 (m, 1H), 5.28 (t, J=5.1 Hz, 1H), 4.56 (s, 2H), 2.75-2.61 (m, 1H), 2.54 (dt, J=15.8, 4.7 Hz, 2H), 2.23 (d, J=2.5 Hz, 4H), 2.18-1.95 (m, 8H), 1.77-1.65 (m, 7H), 1.34-1.16 (m, 4H), 0.93 (s, 1H); MS (ES, m/z): [M+1]=632.25.

Example 55: 2-[(1R,3S,5S)-3-(5-cyclopropyl-3-{4-methoxybicyclo[2.2.2]octan-1-yl}-1,2-oxazole-4-carbonyloxy)-8-azabicyclo[3.2.1]octan-8-yl]-4-(trifluoromethoxy)-1,3-benzothiazole-6-carboxylic acid (I-58)
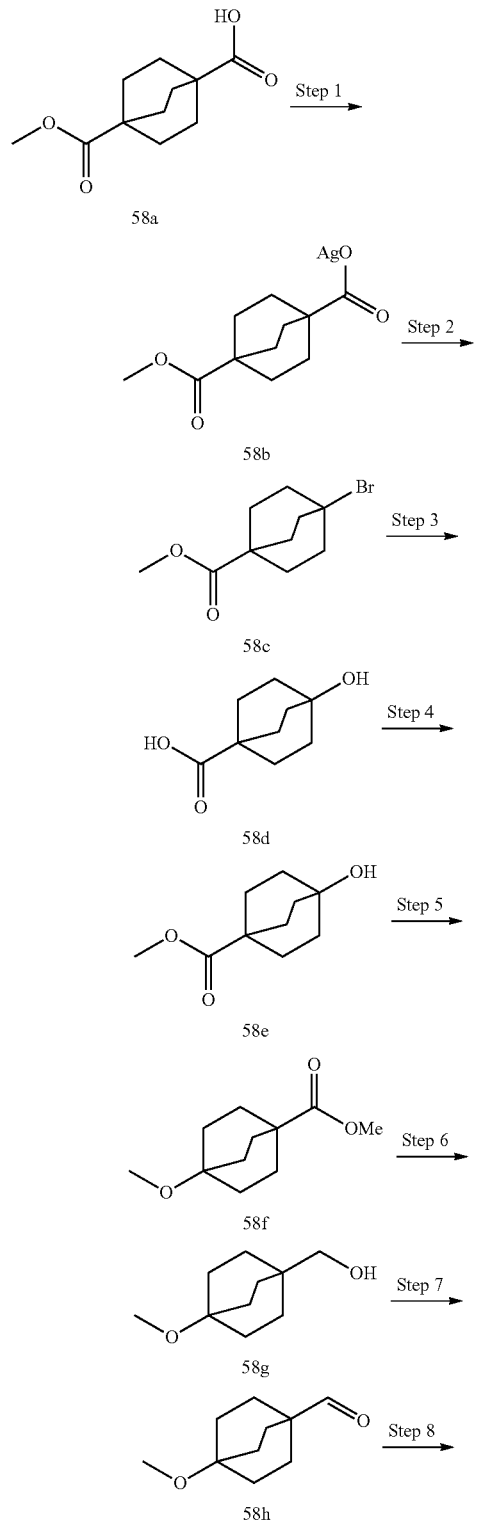
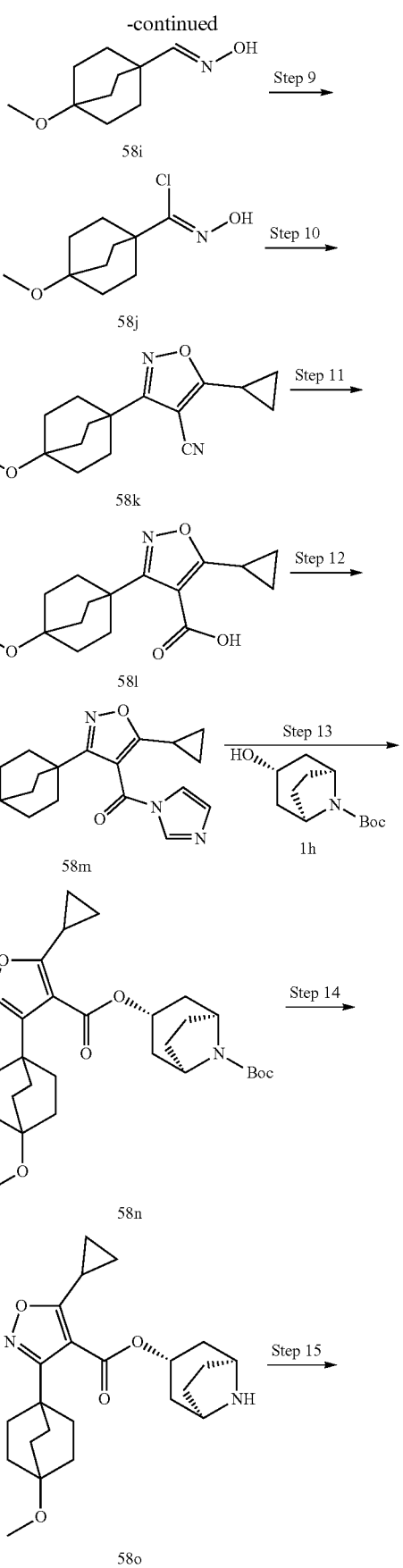

-continued

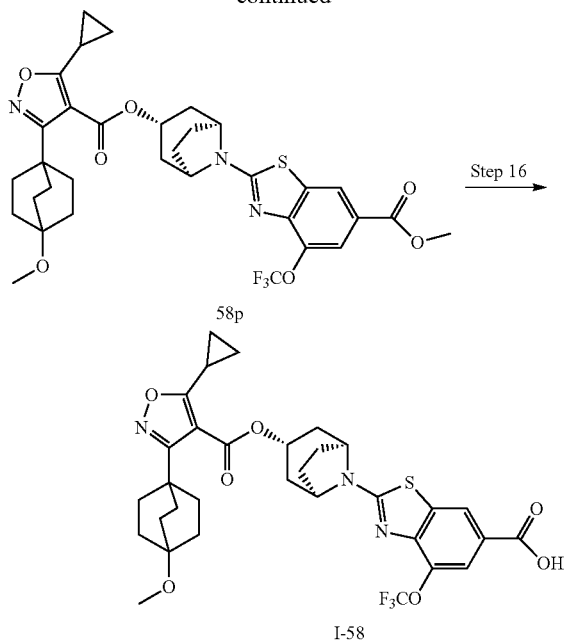

58p

I-58

Step 1. ((4-(Methoxycarbonyl)bicyclo[2.2.2]octane-1-carbonyl)oxy)silver (58b)

To a 1000 mL round-bottom flask was added 4-(methoxycarbonyl)bicyclo[2.2.2]octane-1-carboxylic acid 58a (30 g, 141.35 mmol, 1.0 equiv.), acetone (300 mL), sodium hydroxide (143 mL, 1.01 equiv, 1M), and AgNO$_3$ (38 mL, 1.06 equiv.). The resulting mixture was stirred for 1 h at RT. The solids were collected by filtration, and further dried in an oven under reduced pressure to give ((4-(methoxycarbonyl) bicyclo[2.2.2]octane-1-carbonyl)oxy)silver 58b (42 g, 93%) as a yellow solid.

Step 2. Methyl 4-bromobicyclo[2.2.2]octane-1-carboxylate (58c)

To a 500 mL 1-necked round-bottom flask was added ((4-(methoxycarbonyl)bicyclo[2.2.2]octane-1-carbonyl)oxy)silver 58b (42 g, 131.62 mmol, 1.0 equiv.), petroleum ether (250 mL), and Br$_2$ (6.8 mL, 1.0 equiv.). The resulting mixture was stirred for 30 min at RT, then stirred for 40 min at 60° C. Solids were filtered out; the filtrate was washed with 500 ml of a 1M sodium carbonate aqueous solution, dried over anhydrous sodium sulfate, and concentrated in vacuo to give methyl 4-bromobicyclo[2.2.2]octane-1-carboxylate 58c (24.7 g, 76%) as a white solid.

Step 3. 4-Hydroxybicyclo[2.2.2]octane-1-carboxylic acid (58d)

To a 500-mL round-bottom flask was added methyl 4-bromobicyclo[2.2.2]octane-1-carboxylate 58c (24.7 g, 99.95 mmol, 1.0 equiv.) and HCl (aq., 10%, 250 mL). The resulting mixture was stirred for 24h at 100° C. After cooling to RT, the pH value of the solution was adjusted to 3.0 using a HCl (6 M) solution. The aqueous mixture was extracted with ethyl acetate (400 mL×3); and the combined organic layers were dried over anhydrous sodium sulfate, concentrated in vacuo to afford 4-hydroxybicyclo[2.2.2]octane-1-carboxylic acid 58d (15.5 g, 91%) as a light yellow solid.

Step 4. Methyl 4-hydroxybicyclo[2.2.2]octane-1-carboxylate (58e)

To a 500 mL round-bottom flask was added 4-hydroxybicyclo[2.2.2]octane-1-carboxylic acid 58d (15.5 g, 91.07 mmol, 1.0 equiv.), dichloromethane (85 mL), methanol (45 mL), and TMSCHN$_2$ (85 mL, 2.0 equiv.). The resulting mixture was stirred overnight at RT, then concentrated in vacuo. The crude product was purified by Flash-Prep-HPLC using the following conditions: Column, silica gel; mobile phase, PE:EtOAc=100:0 increasing to PE:EtOAc=90:10 within 20 min; Detector, UV 254 nm, yielding methyl 4-hydroxybicyclo[2.2.2]octane-1-carboxylate 58e (15 g, 89%) as a white solid.

Step 5. Methyl 4-methoxybicyclo[2.2.2]octane-1-carboxylate (58o)

To a 250 mL round-bottom flask was added methyl 4-hydroxybicyclo[2.2.2]octane-1-carboxylate 58e (15 g, 81.42 mmol, 1.0 equiv.), iodomethane (96 g, 676.35 mmol, 8.0 equiv.), and N,N-dimethylformamide (120 mL). The mixture was cooled to 0° C. Sodium hydride (5.0 g, 208.33 mmol, 1.5 equiv.) was added and the reaction was continued for 1 h at RT. EtOAc (500 mL) was added and the mixture was washed with brine (300 mL×3), dried over anhydrous sodium sulfate, and concentrated in vacuo to give crude methyl 4-methoxybicyclo[2.2.2]octane-1-carboxylate 58f (18 g) as a light yellow oil. The product was carried on to the next step without further purification Step 6. [4-Methoxybicyclo[2.2.2]octan-1-yl]methanol (58g)

To a 1000 mL round-bottom flask was added methyl 4-methoxybicyclo[2.2.2]octane-1-carboxylate 58f (27 g, 108.95 mmol, 1.0 equiv., 80% purity) and tetrahydrofuran (400 mL), followed by the portionwise addition of 0° C. LiAlH$_4$ (11 g, 289.86 mmol, 2.0 equiv.). The reaction mixture was stirred for 10 min at 0° C., and then continued for 1 h at RT. HCl (aq., 1 N, 300 ml) was added and the aqueous mixture was extracted with dichloromethane (500 mL×3). The combined organic layers were dried over anhydrous sodium sulfate, filtered, and concentrated in vacuo. The crude product was purified via Flash-Prep-HPLC using the following conditions (IntelFlash-1): Column, silica gel; mobile phase, PE:EtOAc=100:0 increasing to PE:EtOAc=50:50 within 30 min; Detector, UV 254 nm, providing [4-methoxybicyclo[2.2.2]octan-1-yl]methanol 58g (13.5 g, 73%) as a light yellow oil.

Step 7. 4-Methoxybicyclo[2.2.2]octane-1-carbaldehyde (58h)

To a 1000 mL round-bottom flask was added [4-methoxybicyclo[2.2.2]octan-1-yl]methanol 58g (13.5 g, 79.30 mmol, 1.0 equiv.), dichloromethane (600 mL), and Dess-Martin periodinate (51 g, 120.28 mmol, 1.5 equiv.). The resulting mixture was stirred overnight at RT and concentrated in vacuo. The residue was purified via silica gel column chromatography eluting with ethyl acetate/petroleum ether (5:95) to give 4-methoxybicyclo[2.2.2]octane-1-carbaldehyde 58h (7.0 g, 52%) as a white solid.

Step 8. N-([4-methoxybicyclo[2.2.2]octan-1-yl]methylidene)hydroxylamine (58i)

To a 250 mL round-bottom flask was placed NH$_2$OH·HCl (4.4 g, 63.77 mmol, 1.5 equiv.), water (70 mL), and sodium carbonate (2.21 g, 20.85 mmol, 0.5 equiv.). A solution of 4-methoxybicyclo[2.2.2]octane-1-carbaldehyde 58h (7.0 g, 41.61 mmol, 1.0 equiv.) in ethanol (70 mL) was added dropwise with stirring. Reaction continued for 2 h at RT. The mixture was diluted with FLO (100 mL) and extracted with ethyl acetate (300 mL×3). The combined organic layers were dried over sodium sulfate, filtered, and concentrated in vacuo to a residue which was purified via silica gel column chromatography eluting with ethyl acetate/petroleum ether (10:1) to give N-([4-methoxybicyclo[2.2.2]octan-1-yl]methylidene)hydroxylamine 58i (5.9 g, 77%) as a white solid.

Step 9. N-Hydroxy-4-methoxybicyclo[2.2.2]oct-1-carbonimidoyl chloride (58j)

To a 1000 mL round bottle flask was added N-([4-methoxybicyclo[2.2.2]octan-1-yl]methylidene)hydroxylamine 58i (2.9 g, 15.83 mmol, 1.0 equiv.), N,N-dimethylformamide (30 mL), and NCS (3.2 g, 23.96 mmol, 1.5 equiv.). The resulting mixture was stirred for 1 h at RT, then diluted with EtOAc (300 mL) and washed with H$_2$O (200 mL×3). The organic layer was dried over anhydrous sodium sulfate, filtered, and concentrated in vacuo to give crude N-hydroxy-4-methoxybicyclo[2.2.2]oct-1-carbonimidoyl chloride 58j (3.5 g) as a white solid.

Step 10. 5-Cyclopropyl-3-[4-methoxybicyclo[2.2.2]octan-1-yl]-1,2-oxazole-4-carbonitrile (58k)

To a 50 mL round-bottom flask was added 3-cyclopropyl-3-oxopropanenitrile (1.76 g, 16.13 mmol, 1.0 equiv.), ethanol (10 mL), and TEA (1.63 g, 16.11 mmol, 1.0 equiv.), followed by the dropwise addition of N-hydroxy-4-methoxybicyclo[2.2.2]oct-1-carbonimidoyl chloride 58j (3.5 g, 16.08 mmol, 1.0 equiv.) in ethanol (10 mL). The resulting mixture was stirred overnight at −5° C. The mixture was diluted with H$_2$O (100 mL) and extracted with ethyl acetate (200 mL×3). The combined organic layers were dried and concentrated in vacuo. The residue was purified via silica gel column chromatography eluting with ethyl acetate/petroleum ether (1:3) to give 5-cyclopropyl-3-[4-methoxybicyclo[2.2.2]octan-1-yl]-1,2-oxazole-4-carbonitrile 58k (1.05 g, 24%) as a colorless oil.

Step 11. 5-Cyclopropyl-3-[4-methoxybicyclo[2.2.2]octan-1-yl]-1,2-oxazole-4-carboxylic acid (58l)

To a 50 mL round-bottom flask was added 5-cyclopropyl-3-[4-methoxybicyclo[2.2.2]octan-1-yl]-1,2-oxazole-4-carbonitrile 58k (2.2 g, 8.08 mmol, 1.0 equiv.), ethylene glycol (13 mL), and potassium hydroxide (4.53 g, 80.73 mmol, 10.0 equiv.). The resulting mixture was stirred for 24 h at 140° C. H$_2$O was added, and the pH value of the solution was adjusted to 3.0 using HCl (1M). The aqueous mixture was extracted with ethyl acetate (200 mL×3). The combined organic layers were dried over anhydrous sodium sulfate, filtered, and concentrated in vacuo. The residue was purified via silica gel column chromatography eluting with dichloromethane/methanol (10:1) to give 5-cyclopropyl-3-[4-methoxybicyclo[2.2.2]octan-1-yl]-1,2-oxazole-4-carboxylic acid 58l (1.3 g, 55%) as a brown oil.

Step 12. 5-Cyclopropyl-4-[(1H-imidazol-1-yl)carbonyl]-3-[4-methoxybicyclo[2.2.2]octan-1-yl]-1,2-oxazole (58m)

To a 25 mL round-bottom flask was added 5-cyclopropyl-3-[4-methoxybicyclo[2.2.2]octan-1-yl]-1,2-oxazole-4-carboxylic acid 58l (180 mg, 0.62 mmol, 1.0 equiv.), N,N-dimethylformamide (1.5 mL) and CDI (120 mg, 0.74 mmol, 1.2 equiv.). The resulting mixture was stirred for 5 h at 40° C. Removal of solvent gave crude 5-cyclopropyl-4-[(1H-imidazol-1-yl)carbonyl]-3-[4-methoxybicyclo[2.2.2]octan-1-yl]-1,2-oxazole 58m (180 mg, 85%) as a colorless oil. The product was carried on to the next step without further purification.

Step 13. tert-butyl (1R,3R,5S)-3-[(5-cyclopropyl-3-[4-methoxybicyclo[2.2.2]octan-1-yl]-1,2-oxazol-4-yl)carbonyloxy]-8-azabicyclo[3.2.1]octane-8-carboxylate (58n)

To a 25 mL round-bottom flask was added 5-cyclopropyl-4-[(1H-imidazol-1-yl)carbonyl]-3-[4-methoxybicyclo[2.2.2]octan-1-yl]-1,2-oxazole 58m (180 mg, 0.53 mmol, 1.0 equiv.), N,N-dimethylformamide (2.5 mL), tert-butyl (1R,3R,5S)-3-hydroxy-8-azabicyclo[3.2.1]octane-8-carboxylate 1 h (360 mg, 1.58 mmol, 3.0 equiv.), and DBU (80 mg, 0.53 mmol, 1.0 equiv.). The resulting mixture was stirred overnight at 50° C. The mixture was diluted with H$_2$O (30 mL) and extracted with ethyl acetate (50 mL×3). The combined organic layers were dried over anhydrous sodium sulfate, filtered, and concentrated in vacuo. The residue was purified via silica gel column chromatography eluting with ethyl acetate/petroleum ether (1:10) to give tert-butyl (1R,3R,5S)-3-[(5-cyclopropyl-3-[4-methoxybicyclo[2.2.2]octan-1-yl]-1,2-oxazol-4-yl)carbonyloxy]-8-azabicyclo[3.2.1]octane-8-carboxylate 58n (70 mg, 27%) as a light yellow oil.

Step 14. (1R,3R,5S)-8-azabicyclo[3.2.1]octan-3-yl 5-cyclopropyl-3-[4-methoxybicyclo[2.2.2]octan-1-yl]-1,2-oxazole-4-carboxylate (58o)

To a 25 mL round-bottom flask was added tert-butyl (1R,3R,5S)-3-[(5-cyclopropyl-3-[4-methoxybicyclo[2.2.2]octan-1-yl]-1,2-oxazol-4-yl)carbonyloxy]-8-azabicyclo[3.2.1]octane-8-carboxylate 58n (70 mg, 0.14 mmol, 1.0 equiv.), dichloromethane (1 mL), and trifluoroacetic acid (0.5 mL). The resulting mixture was stirred for 30 min at RT and concentrated in vacuo. H$_2$O was added, and the pH value of the solution was adjusted to 10.0 using sodium bicarbonate (aq., 1 M). The mixture was extracted with dichloromethane (50 mL×3); and the combined organic layers were dried over anhydrous sodium sulfate, filtered, and concentrated in vacuo to provide (1R,3R,5S)-8-azabicyclo[3.2.1]octan-3-yl 5-cyclopropyl-3-[4-methoxybicyclo[2.2.2]octan-1-yl]-1,2-oxazole-4-carboxylate 58o (60 mg, crude yield 107%) as a light yellow oil. The product was carried on to the next step without further purification.

Step 15. Methyl 2-[(1R,3R,5S)-3-[(5-cyclopropyl-3-[4-methoxybicyclo[2.2.2]octan-1-yl]-1,2-oxazol-4-yl)carbonyloxy]-8-azabicyclo[3.2.1]octan-8-yl]-4-(trifluoromethoxy)-1,3-benzothiazole-6-carboxylate (58p)

To a 25 mL round-bottom flask was added (1R,3R,5S)-8-azabicyclo[3.2.1]octan-3-yl 5-cyclopropyl-3-[4- methoxybicyclo[2.2.2]octan-1-yl]-1,2-oxazole-4-carboxylate 58o (60 mg, 0.15 mmol, 1.0 equiv.), DMA (2 mL), methyl 2-bromo-4-(trifluoromethoxy)-1,3-benzothiazole-6-carboxylate A4 (65 mg, 0.18 mmol, 1.2 equiv.), and Cs$_2$CO$_3$ (98 mg, 0.30 mmol, 2.0 equiv.). The resulting mixture was stirred overnight at 60° C. H$_2$O (20 mL) was added and the aqueous mixture was extracted with ethyl acetate (50 mL×3). The combined organic layers were dried over anhydrous sodium sulfate, filtered, and concentrated in vacuo. The residue was purified via silica gel column chromatography eluting with ethyl acetate/petroleum ether (1:2) to give methyl 2-[(1R,3R,5S)-3-[(5-cyclopropyl-3-[4-methoxybicyclo[2.2.2]octan-1-yl]-1,2-oxazol-4-yl)carbonyloxy]-8-azabicyclo[3.2.1]octan-8-yl]-4-(trifluoromethoxy)-1,3-benzothiazole-6-carboxylate 58p (70 mg, 69%) as a white solid.

Step 16. 2-[(1R,3S,5S)-3-[(5-Cyclopropyl-3-[4-methoxybicyclo[2.2.2]octan-1-yl]-1,2-oxazol-4-yl)carbonyloxy]-8-azabicyclo[3.2.1]octan-8-yl]-4-(trifluoromethoxy)-1,3-benzothiazole-6-carboxylic acid (I-58)

To a 25 mL round-bottom flask was added methyl 2-[(1R,3R,5S)-3-[(5-cyclopropyl-3-[4-methoxybicyclo[2.2.2]octan-1-yl]-1,2-oxazol-4-yl)carbonyloxy]-8-azabicyclo[3.2.1]octan-8-yl]-4-(trifluoromethoxy)-1,3-benzothiazole-6-carboxylate 58p (70 mg, 0.10 mmol, 1.0 equiv.), pyridine (1.5 mL), and LiI (140 mg, 1.04 mmol, 10.0 equiv.). The resulting mixture was stirred overnight at 120° C. overnight and concentrated in vacuo. H$_2$O was added and the pH value of the solution was adjusted to 3.0 using a HCl (aq., 1M). The aqueous mixture was extracted with dichloromethane (50 mL×3), the combined organic layers were dried and concentrated in vacuo. The crude product was purified by Prep-HPLC using the following conditions: Column, XSelect CSH Prep C18 OBD Column, 5 μm, 19×150 mm; mobile phase, Waters (0.05% TFA) and ACN (43.0% ACN up to 63.0% in 8 min); Detector, UV 254 nm, yielding 2-[(1R,3S,5S)-3-[(5-cyclopropyl-3-[4-methoxybicyclo[2.2.2]octan-1-yl]-1,2-oxazol-4-yl)carbonyloxy]-8-azabicyclo[3.2.1]octan-8-yl]-4-(trifluoromethoxy)-1,3-benzothiazole-6-carboxylic acid I-58 (30 mg, 44%) as a colorless solid. $^1$HNMR (300 MHz, CD$_3$OD) δ: 8.30 (d, J=1.5 Hz, 1H), 7.82 (p, J=1.4 Hz, 1H), 5.24 (d, J=5.4 Hz, 1H), 4.51 (s, 2H), 3.17 (s, 3H), 2.74-2.60 (m, 1H), 2.49 (dt, J=15.9, 4.6 Hz, 2H), 2.21-2.02 (m, 12H), 1.73 (dd, J=10.0, 5.8 Hz, 6H), 1.19 (tt, J=7.7, 2.6 Hz, 4H). MS (ES, m/z): [M+1]=659.9.

Example 56: 2-[(1R,3R,5S)-3-[3-(2,6-dichlorophenyl)-5-(1-fluorocyclopropyl)-1,2-oxazole-4-carbonyloxy]-8-azabicyclo[3.2.1]octan-8-yl]-4-methyl-1,3-benzothiazole-6-carboxylic acid (I-59)

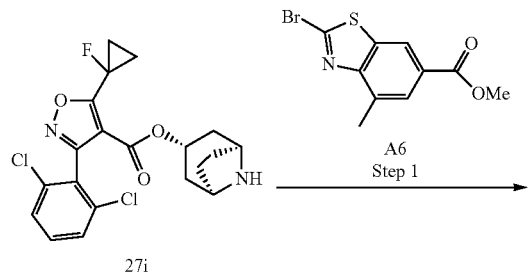

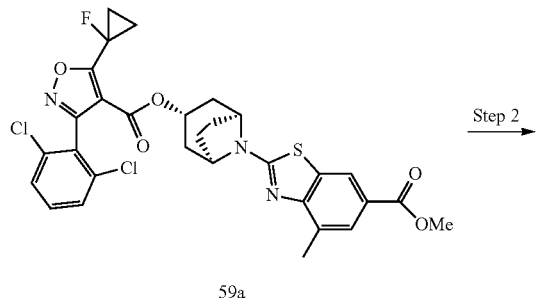

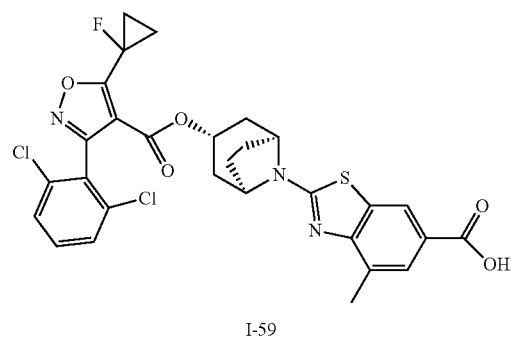

Step 1. Methyl 2-[(1R,3R,5S)-3-[[5-(1-fluorocyclopropyl)-3-(2,6-dichlorophenyl)-1,2-oxazol-4-yl]carbonyloxy]-8-azabicyclo[3.2.1]octan-8-yl]-4-methyl-1,3-benzothiazole-6-carboxylate (59a)

Following the procedure outlined in Example 10, step 8, using intermediates (1R,3R,5S)-8-azabicyclo[3.2.1]octan-3-yl 5-(1-fluorocyclopropyl)-3-(2,6-dichlorophenyl)-1,2-oxazole-4-carboxylate 27i (1.1 equiv.) and methyl 2-bromo-4-methyl-1,3-benzothiazole-6-carboxylate A6 (1.0 equiv.) affords methyl 2-[(1R,3R,5S)-3-[[5-(1-fluorocyclopropyl)-3-(2,6-dichlorophenyl)-1,2-oxazol-4-yl]carbonyloxy]-8-azabicyclo[3.2.1]octan-8-yl]-4-methyl-1,3-benzothiazole-6-carboxylate 59a.

Step 2. 2-[(1R,3S,5S)-3-[[5-(1-Fluorocyclopropyl)-3-(2,6-dichlorophenyl)-1,2-oxazol-4-yl]carbonyloxy]-8-azabicyclo[3.2.1]octan-8-yl]-4-methyl-1,3-benzothiazole-6-carboxylic acid (I-59)

2-[(1R,3S,5S)-3-[[5-(1-fluorocyclopropyl)-3-(2,6-dichlorophenyl)-1,2-oxazol-4-yl]carbonyloxy]-8-azabicyclo[3.2.1]octan-8-yl]-4-methyl-1,3-benzothiazole-6-carboxylic acid I-59 was obtained following the procedure outlined in Example 11 from intermediate 59a.

Example 57: 2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-ethyl-1,3-benzothiazole-6-carboxylic acid (I-60)

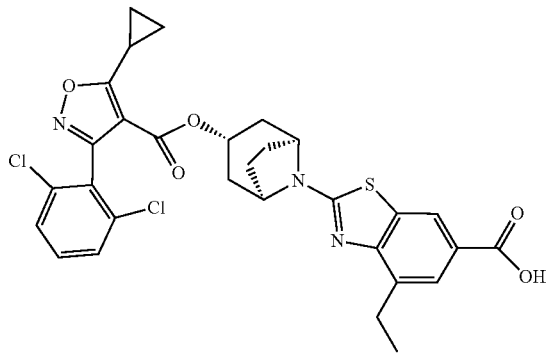 [SMILES: CCc1cc(C(=O)O)cc2sc(N3[C@@H]4CC[C@H]3C[C@@H](OC(=O)c3c(-c5c(Cl)cccc5Cl)noc3C3CC3)C4)nc12]

Example 58: 2-[(1R,3R,5S)-3-{5-cyclopropyl-3-[2-(trifluoromethyl)phenyl]-1,2-oxazole-4-carbonyloxy}-8-azabicyclo[3.2.1]octan-8-yl]-4-methyl-1,3-benzothiazole-6-carboxylic acid (I-61)

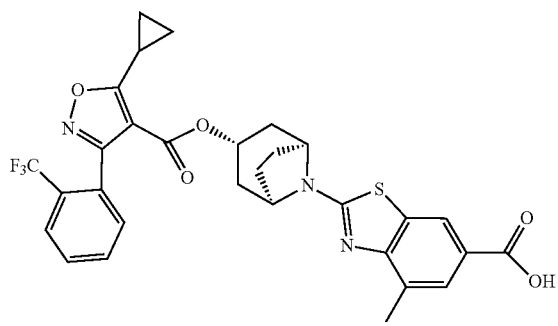 [SMILES: Cc1cc(C(=O)O)cc2sc(N3[C@@H]4CC[C@H]3C[C@@H](OC(=O)c3c(-c5ccccc5C(F)(F)F)noc3C3CC3)C4)nc12]

Example 59: (1R,3R,5S)-8-{4-fluoro-6-[(propane-1-sulfonyl)carbamoyl]-1,3-benzothiazol-2-yl}-8-azabicyclo[3.2.1]octan-3-yl 3-(2,6-dichlorophenyl)-5-(1-fluorocyclopropyl)-1,2-oxazole-4-carboxylate (I-62)

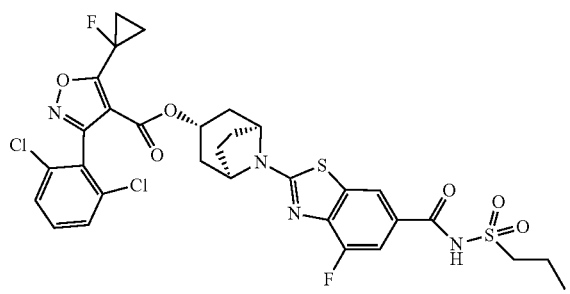 [SMILES: CCCS(=O)(=O)NC(=O)c1cc(F)c2nc(N3[C@@H]4CC[C@H]3C[C@@H](OC(=O)c3c(-c5c(Cl)cccc5Cl)noc3C3(F)CC3)C4)sc2c1]

Example 60: 2-[bis(2-hydroxyethyl)amino]ethyl 2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1,3-benzothiazole-6-carboxylate (I-63)

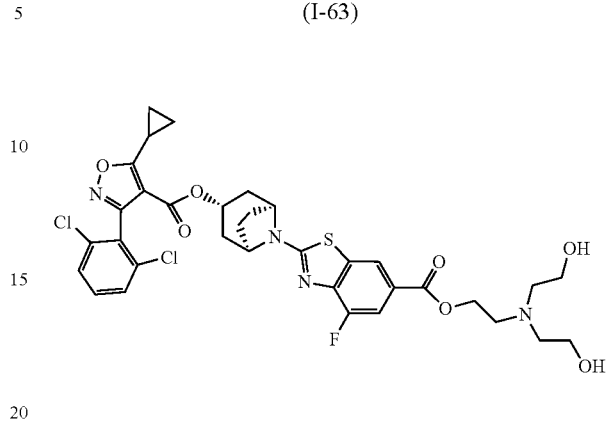

Example 61: [bis(2-hydroxyethyl)carbamoyl]methyl 2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1,3-benzothiazole-6-carboxylate (I-64)

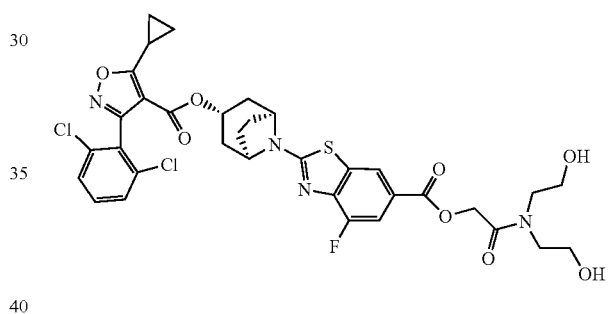

Example 62: FXR Ligand Binding Assay

The affinity of FXR ligands for the ligand binding domain of FXR was determined using a commercially available human FXR ligand binding assay (LanthaScreen, Thermofisher Cat #PV4833). The purified ligand binding domain of human FXR tagged with GST (glutathiones-S-transferase) is incubated with a terbium labelled anti-GLT antibody and a fluorescein-labelled SRC2-2 peptide (LKEKHKILHRLLQDSSSPV (SEQ ID No.: 1)). Binding of FXR ligands to the FXR ligand binding domain promotes binding of the fluorescein-labelled SRC2-2 peptide. This causes a FRET signal between the terbium-labelled anti-GST antibody and the fluorescein-labelled SRC peptide which are both bound to the FXR ligand binding domain.

Test compounds are dissolved in DMSO and a 3-fold serial dilution series is generated, then further diluted into assay buffer. The compounds are mixed with 5 nM GST-tagged FXR ligand binding domain, 5 nM Tb-labelled anti-GST antibody and 500 nM fluorescein-labelled SRC2-2 peptide in a pH 7.4 buffer. The reaction is incubated at room temperature for 1 hour, then the FRET signal is measured as the ratio of the 520 nm/495 nm emission following excitation at 340 nm. The change in FRET signal is plotted against the test article concentration and fit to a 3-parameter logistical equation. The concentration required to produce 50% activation is expressed as pEC$_{50}$ (−log EC$_{50}$), and the extent of activation is expressed relative to GW4064 as % activation. The data for the compounds of the disclosure in the ligand binding assay are shown in Table 4.

TABLE 4

FXR activity of compounds of the present disclosure in the FXR ligand binding assay

| Cmpd No. | FXR pEC$_{50}$ | % Efficacy |
| --- | --- | --- |
| I-1 | 6.5 | 40 |
| I-2 | 7.7 | 96 |
| I-3 | 6.9 | 60 |
| I-4 | 7.4 | 76 |
| I-5 | 6.9 | 77 |
| I-6 | 7.7 | 110 |
| I-7 | 7.1 | 125 |
| I-8 | 8 | 105 |
| I-9 | 7.9 | 136 |
| I-10 | 7.4 | 102 |
| I-11 | 7.6 | 110 |
| I-12 | 7.4 | 125 |
| I-13 | 6.7 | 40 |
| I-14 | 7.6 | 147 |
| I-15 | 7.4 | 71 |
| I-16 | 7.4 | 47 |
| I-17 | 7.5 | 44 |
| I-18 | 6.7 | 66 |
| I-19 | 7.2 | 55 |
| I-20 | >4.5 | |
| I-21 | >4.5 | |
| I-22 | >4.5 | |
| I-23 | 7.1 | 37 |
| I-24 | 7.9 | 64 |
| I-25 | 7.2 | 56 |
| I-26 | 7.4 | 75 |
| I-27 | 8.2 | 107 |
| I-28 | 6.7 | 94 |
| I-29 | 6.5 | 98 |
| I-30 | 6.6 | 40 |
| I-31 | 6.6 | 63 |
| I-32 | 7.4 | 34 |
| I-33 | <4.5 | |
| I-34 | 7.6 | 79 |
| I-35 | 7.8 | 92 |
| I-36 | 7.3 | 106 |
| I-37 | 7.7 | 50 |
| I-38 | 6.6 | 80 |
| I-39 | 6.8 | 64 |
| I-40 | 7.2 | 103 |
| I-41 | 7.7 | 92 |
| I-42 | 8 | 38 |
| I-43 | 7.3 | 72 |
| I-44 | 7.9 | 124 |
| I-45 | 8.3 | 130 |
| I-46 | 8.2 | 146 |
| I-47 | 7.8 | 168 |
| I-48 | 8.2 | 124 |
| I-49 | 8 | 128 |
| I-51 | 7.7 | 139 |
| I-52 | 7.3 | 110 |
| I-53 | 6.9 | 58 |
| I-54 | 6.2 | 46 |
| I-55 | >4.5 | |
| I-56 | 6.6 | 56 |
| I-57 | 6 | 26 |
| I-58 | >4.4 | 22 |
| I-59 | 7.4 | 95 |
| I-60 | 7 | 119 |
| I-61 | 7.1 | 139 |
| I-62 | 7.4 | 145 |
| I-63 | >6.5 | |
| I-64 | 6.6 | 32 |

Example 63: Cell-Based Assay of FXR Activation

FXR activation was measured using a cell line and procedure obtained from Life Technologies (Cat #K1691). FXR-UAS-&/a HEK 293T cells contain a human Farnesoid X receptor ligand-binding domain/Gal4 DNA binding domain chimera stably integrated into the CellSensor® UAS-bla HEK293T cell line. The CellSensor® UAS-bla HEK293T contains a beta-lactamase reporter gene under control of a UAS response element stably integrated into HEK 293T cells. Activation of FXR by bound ligands results in transcriptional activation of the beta-lactamase reporter gene, which is detected via assay of beta-lactamase activity.

Cells are harvested and diluted into assay medium containing phenol red-free DMEM supplemented with 2% Charcoal-stripped FBS, pyruvate, non-essential amino acids. Cells are then transferred to a 384 well assay plate. Test compounds are dissolved in DMSO and a 3-fold serial dilution series is generated, then further diluted into assay medium. Compounds in assay medium are added to cells in the 384 well plate and allowed to incubate 16 h at 37 C in the presence of 5% $CO_2$.

Following incubation, FXR activity is detected via measurement of beta-lactamase that is produced under its transcriptional control. A FRET-based beta-lactamase (CCF4) is loaded into cells as its acetomethoxy ester. Intracellular esterases liberate free CCF4, a cephalosporin core linking 7-hydroxycoumarin to fluorescein. In the presence of beta-lactamase activity produced in the presence of FXR agonists, cleavage of CCF4 spatially separates the two dyes and disrupts FRET, so that exciting the coumarin at 409 nm now produces a blue fluorescence signal at 447 nm. The change in FRET signal is plotted against the test compound concentration and fit to a 3-parameter logistical equation. The concentration required to produce 50% activation is expressed as pEC$_{50}$ (−log EC$_{50}$), and the extent of activation is expressed relative to GW4064 as % activation. The data for the compounds of the disclosure in the cell-based assay are shown in Table 5.

TABLE 5

The activity of compounds of the present disclosure in the cellular FXR beta-lactamase reporter assay

| Cmpd No. | FXR pEC$_{50}$ | % Efficacy |
| --- | --- | --- |
| I-1 | 6.5 | 76 |
| I-2 | 8.1 | 112 |
| I-3 | 7.6 | 64 |
| I-4 | 6.1 | 109 |
| I-5 | 5.6 | 72 |
| I-6 | 7.8 | 109 |
| I-7 | 8.1 | 110 |
| I-8 | 8.4 | 114 |
| I-9 | 8.5 | 119 |
| I-10 | 7.6 | 104 |
| I-11 | 8.6 | 121 |
| I-12 | 8.1 | 112 |
| I-13 | 6 | 93 |
| I-14 | 8.1 | 116 |
| I-15 | 7.4 | 108 |
| I-16 | 6.7 | 110 |
| I-17 | 6.9 | 112 |
| I-18 | 6.6 | 99 |
| I-19 | 6.8 | 79 |
| I-20 | 6.6 | 22 |
| I-21 | 6.2 | 44 |
| I-22 | 6.4 | 44 |
| I-23 | 6.8 | 100 |

TABLE 5-continued

The activity of compounds of the present disclosure in the cellular FXR beta-lactamase reporter assay

| Cmpd No. | FXR pEC$_{50}$ | % Efficacy |
|---|---|---|
| I-24 | 7.5 | 98 |
| I-25 | 7.6 | 100 |
| I-26 | 7.5 | 106 |
| I-27 | 8.4 | 108 |
| I-28 | 7.6 | 117 |
| I-29 | 6.6 | 124 |
| I-30 | 7 | 82 |
| I-31 | 6.4 | 100 |
| I-32 | 6.4 | 86 |
| I-33 | 5.8 | 72 |
| I-34 | 7.7 | 107 |
| I-35 | 7.5 | 116 |
| I-36 | 6.8 | 99 |
| I-37 | 7 | 93 |
| I-38 | 7.1 | 112 |
| I-39 | 7 | 114 |
| I-40 | 7.4 | 117 |
| I-41 | 7.7 | 117 |
| I-42 | 7.1 | 85 |
| I-43 | 7.4 | 108 |
| I-44 | 8.2 | 117 |
| I-45 | 8.6 | 128 |
| I-46 | 8.5 | 110 |
| I-47 | 8.5 | 124 |
| I-48 | 8.6 | 130 |
| I-49 | 8.1 | 107 |
| I-50 | 6.8 | 102 |
| I-51 | 8.3 | 105 |
| I-52 | 7.8 | 109 |
| I-53 | 6.6 | 81 |
| I-54 | <4.7 | 115 |
| I-55 | 6 | 96 |
| I-56 | 6.2 | 78 |
| I-57 | 6.4 | 33 |
| I-58 | >4.5 | |
| I-59 | 7.4 | 105 |
| I-60 | 8.2 | 104 |
| I-61 | 8 | 102 |
| I-62 | 7.7 | 107 |
| I-63 | 5 | 112 |
| I-64 | >7.5 | |

Example 64: Pharmacokinetic (PK) Studies

Plasma, bile, stool and distal ileum were collected for analysis at various time points after intravenous (IV) or oral (PO) dosing of Compound I-2 to bile-duct-, jugular-vein- and portal-vein-cannulated Sprague-Dawley rats and C57BL/6 mice. Rats were treated IV with 0.5 mg/kg or PO with 10 mg/kg in these studies while mice were dosed at 30 mg/Kg. Blood samples were collected via the jugular vein at various time points up to 24 h after dosing. Compound concentration was measured using a LC-MS/MS system. Data are presented as: $C_{max}$ for bile duct, portal vein and jugular vein; $C_{6h}$ for ileum; recovery (%) from stool after 48 h.

Figure 1B:
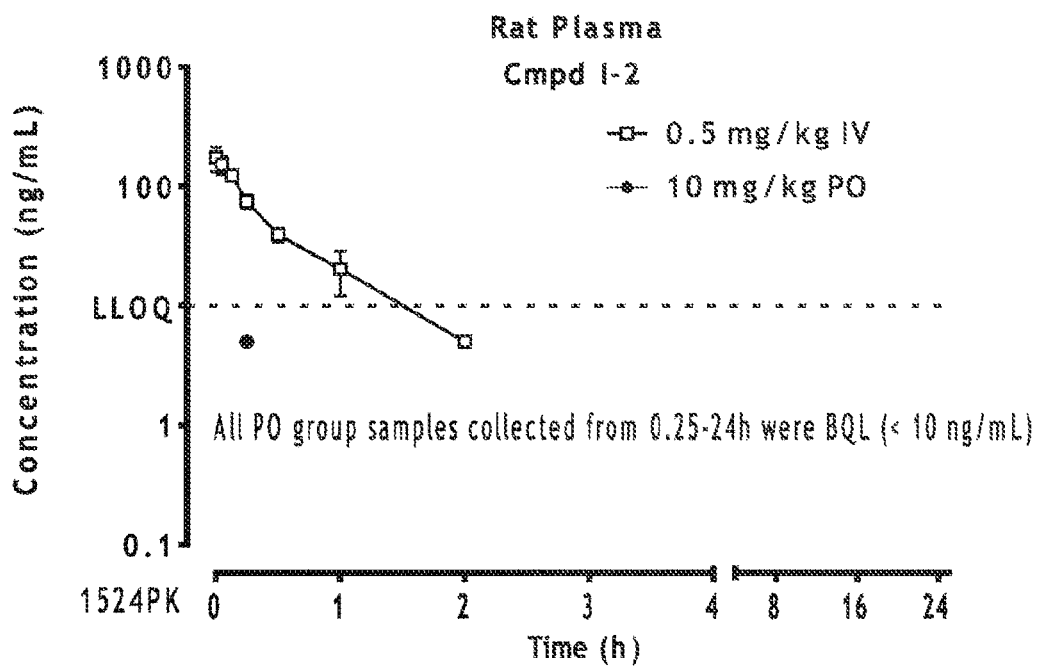
FIG. 1B is a graph showing the concentration of Compound I-2 in Sprague-Dawley rats when dosed intravenously (IV) with 0.5 mg/kg of Compound I-2 and orally (PO) with 10 mg/kg of Compound I-2. The results show high gastrointestinal exposure, high stool recovery and low systemic exposure in both mice and rats.
Figure 2A:
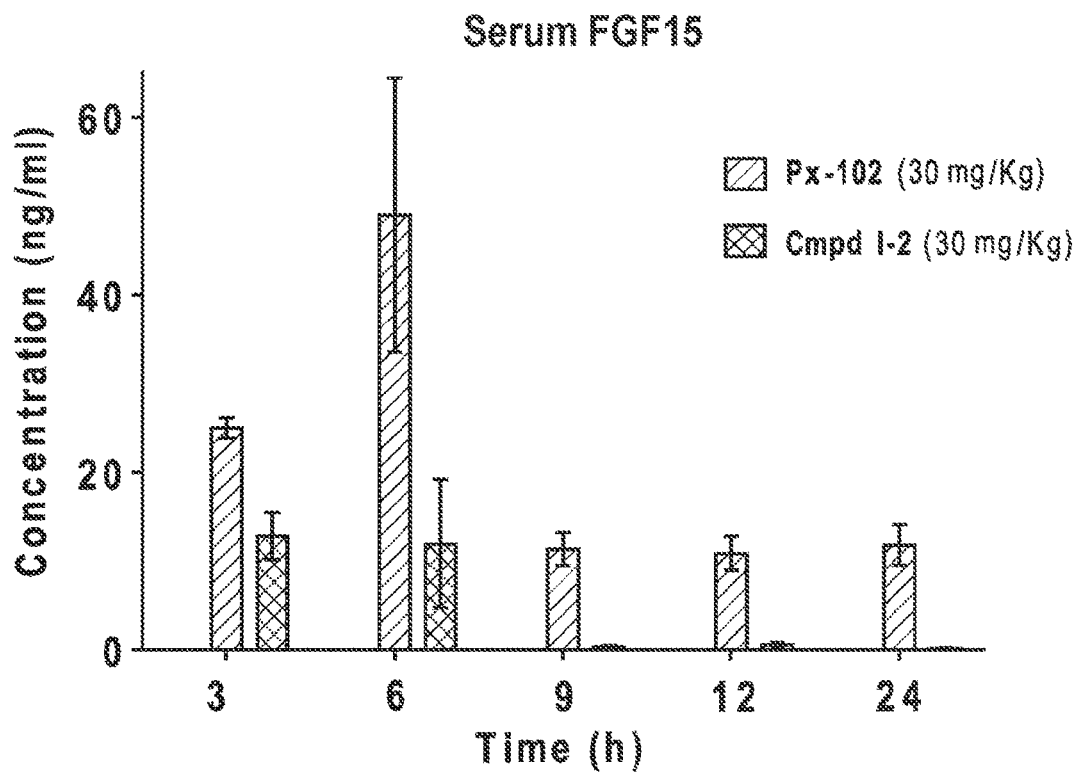
FIG. 2A is a graph showing the concentration of serum Fibroblast Growth Factor 15 (FGF15) at various time points over 24 h after a single dose in mice with vehicle (1% methyl cellulose), 30 mg/kg of Px-102, or 30 mg/kg of Compound I-2.
Figure 2B:
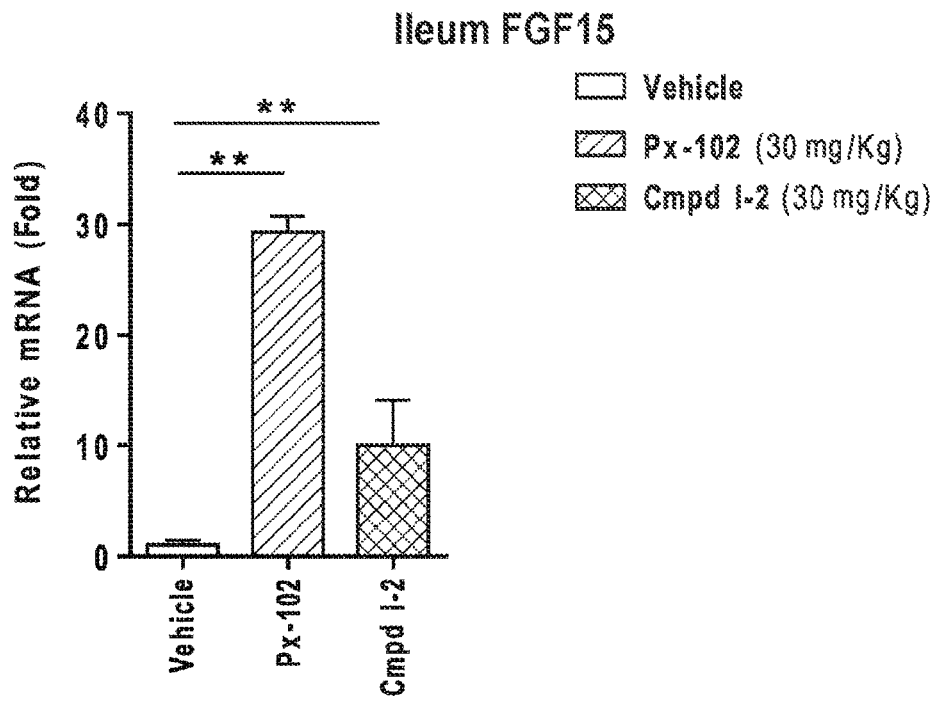
FIGS. 2B-2G are graphs showing the relative mRNA expression of Ileum FGF15, liver Cyp7a1, liver Scl51b/Ostβ, liver Alpl, liver Cyp2c53-ps and liver Akr1b7 in mice after a single dose with vehicle, 30 mg/kg of Px-102, or 30 mg/kg of Compound I-2. In mice administered a single dose of Compound I-2, expression of FXR target genes, including FGF15, was activated in the ileum 6 h after dosing, while minimal effect on the expression of selected FXR target genes were observed in the liver.
Figure 2C:
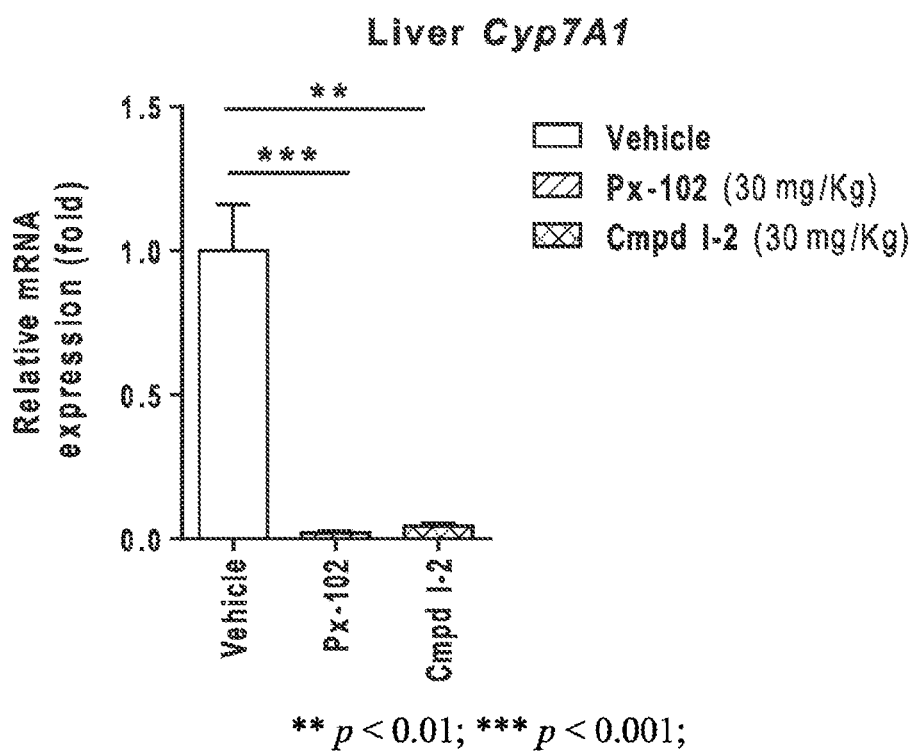
Figure 2D:
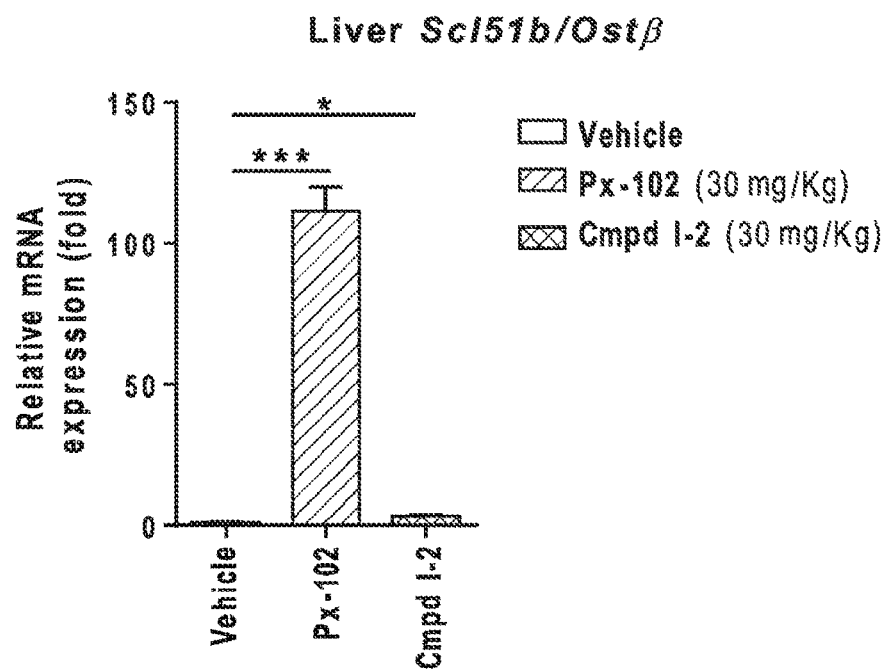
Figure 2E:
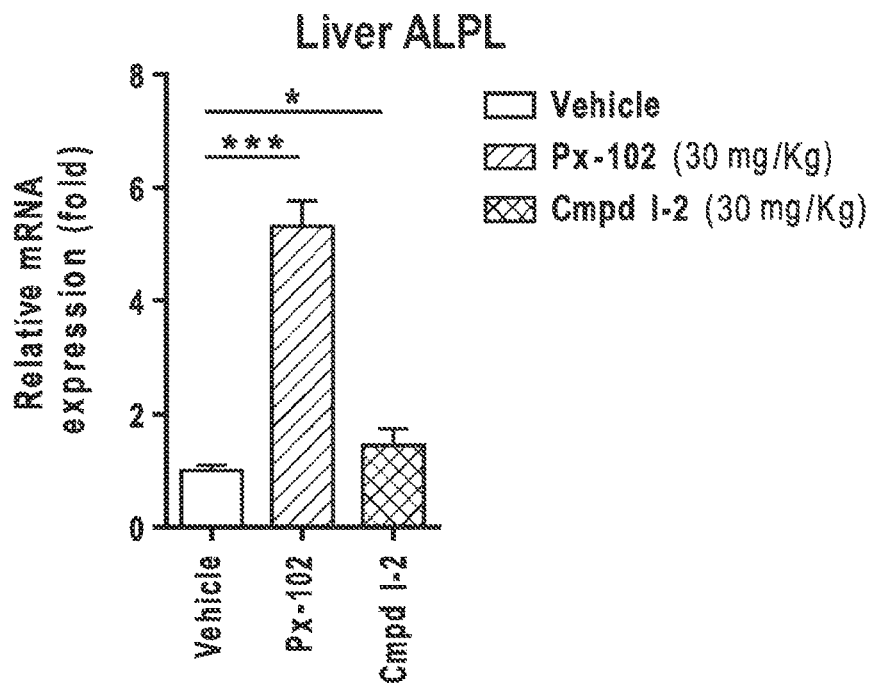
Figure 2F:
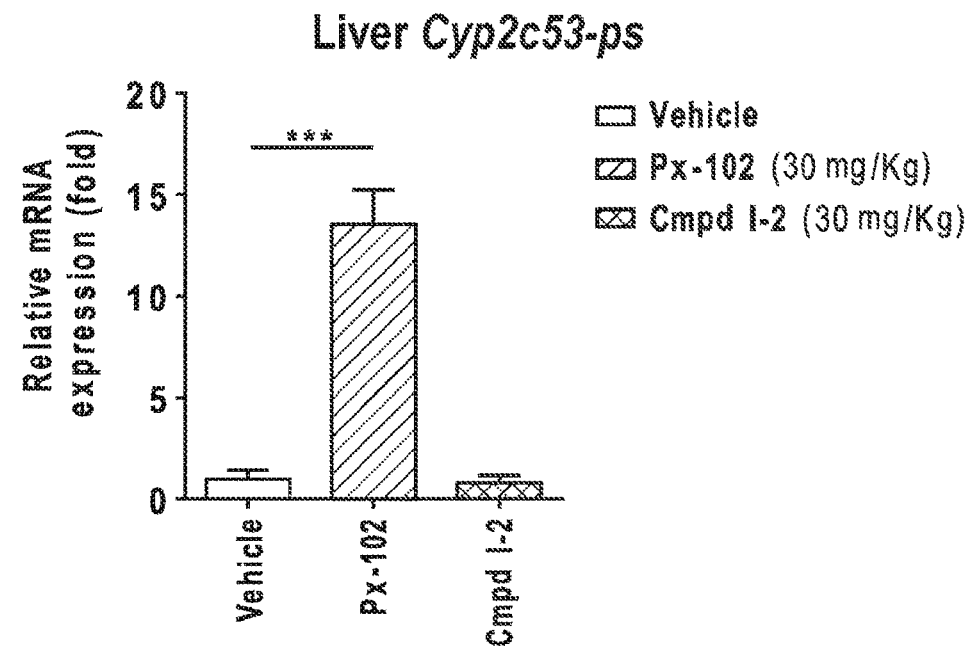
Figure 2G:
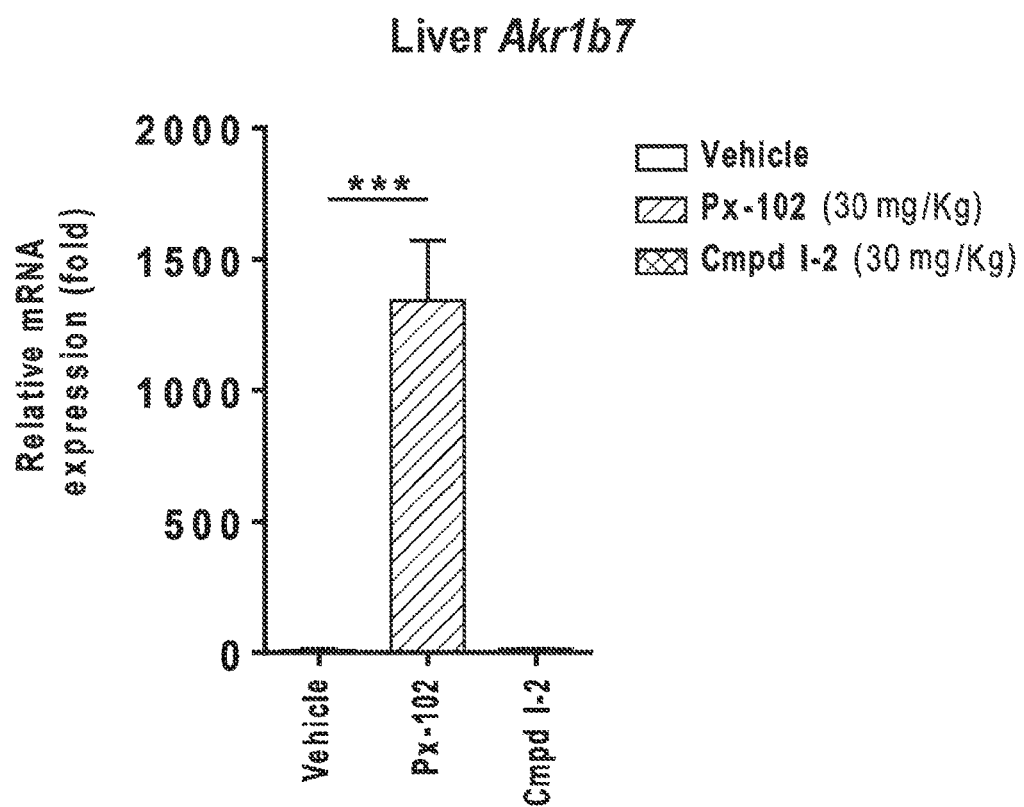

PK measurements demonstrate high gastrointestinal exposure, high stool recovery and low systemic exposure of mice and rats treated with Compound I-2. Low oral bioavailability was observed in rat pk study (rats were treated with 0.5 mg/kg IV or 10 mg/kg PO, F %<<3). (FIG. 1A and FIG. 1B)

Example 65: In Vitro Pharmacology Assays

FXR ligand-binding domain affinity, FXR activation in FXR-UAS-bla HEK 293T cells, and fibroblast growth factor 19 (FGF19) secretion in human ileum were assessed for Compound I-2 and FXR known agonists, GW4064, Obeticholic acid (OCA), and Px-102.

The concentration required to produce 50% activation was calculated as −log $E_{C50}$ (pEC$_{50}$), and the extent of activation was calculated relative to a potent FXR agonist, GW40644 (activity, %). Biochemical and cellular assays confirmed that Compound I-2 has FXR agonist activity similar to that of other potent FXR agonists. The results are shown in Table 6 below.

TABLE 6

| Assay | GW4064 | OCA | Px-102 | Cmpd I-2 |
|---|---|---|---|---|
| Human FXR Binding (FRET) | | | | |
| pEC$_{50}$ (n) | 7.1 ± 0.4 (216) | 7.4 ± 0.5 (32) | 8.0 ± 0.1 (3) | 7.7 ± 0.4 (5) |
| Activity, % (n) | 99 ± 10 (216) | 148 ± 13 (32) | 90 ± 15 (3) | 96 ± 16 (5) |
| Human FXR Cell (Gal4) | | | | |
| pEC$_{50}$ (n) | 7.6 ± 0.4 (218) | 6.8 ± 0.6 (23) | 6.8 (1) | 8.2 ± 0.4 (10) |
| Activity, % (n) | 99 ± 5 (218) | 107 ± 14 (23) | 108 (1) | 117 ± 7 (10) |
| Human Ileum APECCS (FGF19) | | | | |
| pEC$_{50}$ (n) | 6.5 ± 0.3 (154) | 6.3 ± 0.1 (8) | 6.48 ± 0.2 (4) | 7.25 ± 0.2 (15) |
| Activity, % (n) | 100 ± 0 (154) | 82.6 ± 19 (8) | 96.5 ± 25 (4) | 81.4 ± 17 (15) |

Example 66: Western Diet Study

Six-week-old C57BL/6 male mice were fed a Western diet (WD) (62% fat/0.2% cholesterol). After 8 weeks of preconditioning to the WD, 70% of the mice with the highest serum lipid concentration were selected and randomized into groups (n=10 per group), with each group receiving a different treatment: untreated control (WD control), vehicle (1% methylcellulose, q.d. or b.i.d.), 30 mg/kg (q.d. or b.i.d.) of Compound I-2, 30 mg/kg (q.d.) of Px-102 or FGF15-AAV (single IV dose of 3×10$^{10}$ plaque-forming units [pfu]). An additional control group (lean) was fed a standard rodent chow throughout the study. Body weight measurements and serum samples (tail bleed) were taken weekly. After 6 weeks of treatment, all animals were sacrificed and hepatosteatosis-related endpoints and other liver markers were measured.

Total RNA from mouse tissues was isolated and used for library preparation. Library samples were multiplexed ahead of mRNA sequencing. Compound I-2 and Px-102 measurements were performed by liquid chromatography tandem mass spectrometry.

In mice administered a single dose of Compound I-2, expression of FXR target genes, including FGF15, was activated in the ileum 6 h after dosing, but there was minimal effect on the expression of selected FXR target genes in the liver. In contrast, the systemic FXR agonist Px-102 activated the expression of FXR target genes in both the ileum and liver. (FIGS. 2A-2G).

Figure 3A:
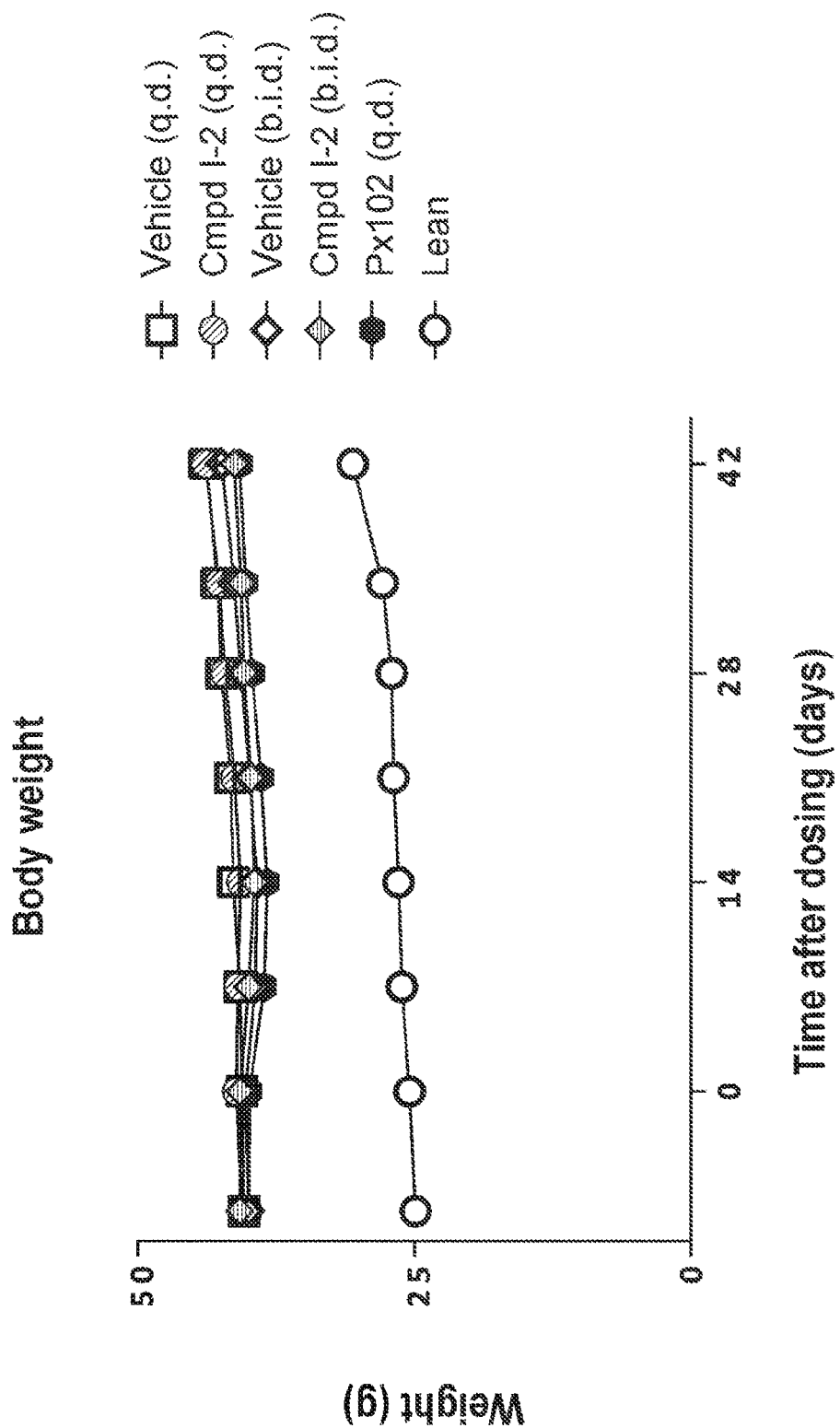
FIG. 3A is a graph showing the change in body weight in C57BL/6 mice fed a western diet when treated with vehicle once daily (q.d.), vehicle twice daily (b.i.d), Compound I-2 once daily, Compound I-2 twice daily, or Px-102 once daily over six weeks.
Figure 3B:
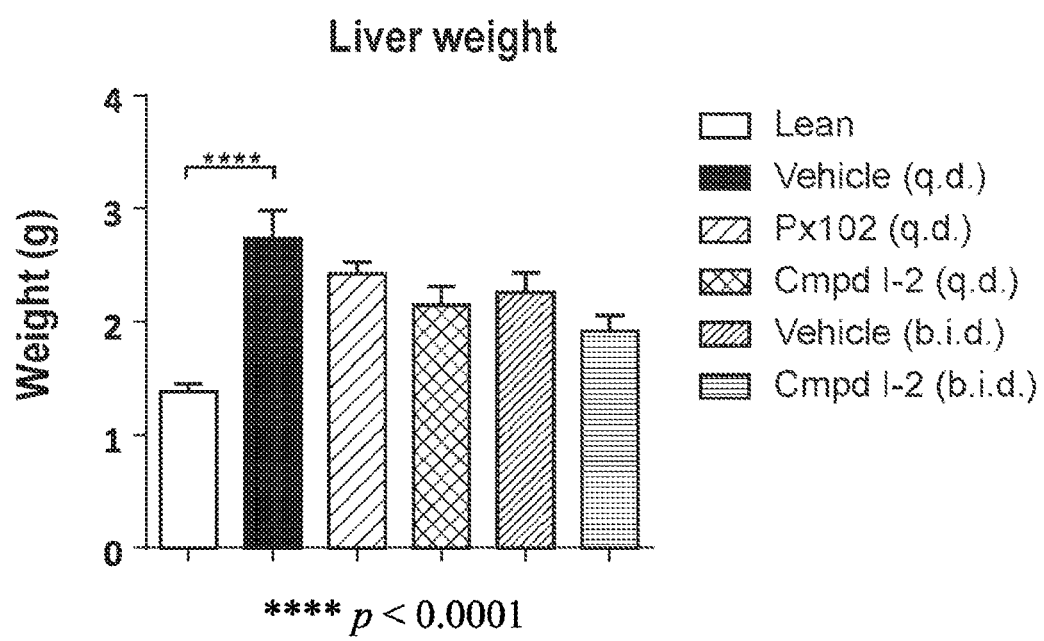
FIG. 3B is a graph showing the change in liver weight in C57BL/6 mice fed a western diet when treated with vehicle once daily (q.d.), vehicle twice daily (b.i.d), Compound I-2 once daily, Compound I-2 twice daily, or Px-102 once daily over six weeks.
Figure 3C:
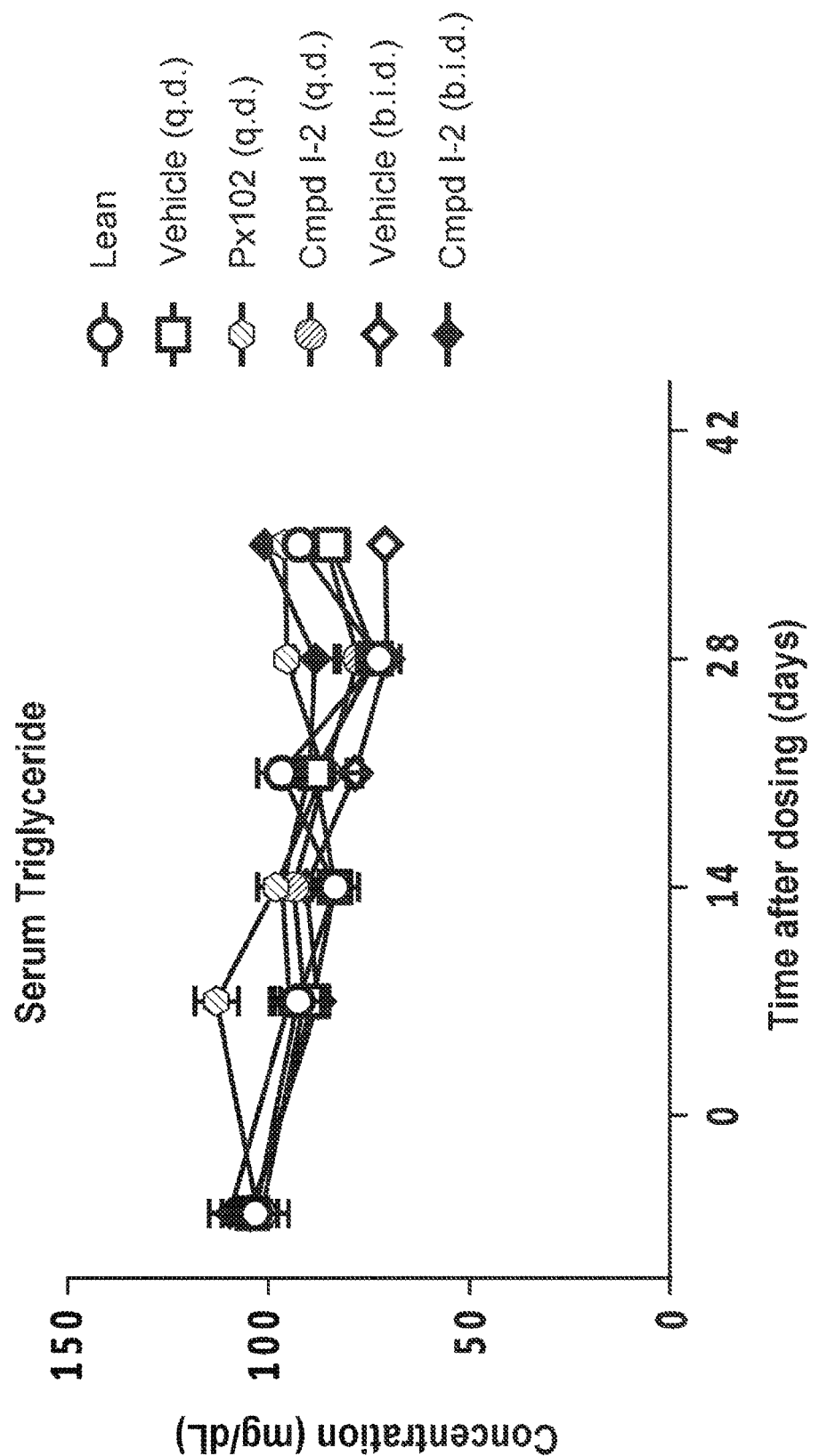
FIGS. 3C and 3D are graphs showing the change in concentration of serum triglycerides and serum cholesterol over six weeks in C57BL/6 mice fed a western diet when treated with vehicle once daily (q.d.), vehicle twice daily (b.i.d), Compound I-2 once daily, Compound I-2 twice daily, or Px-102 once daily.
Figure 3D:
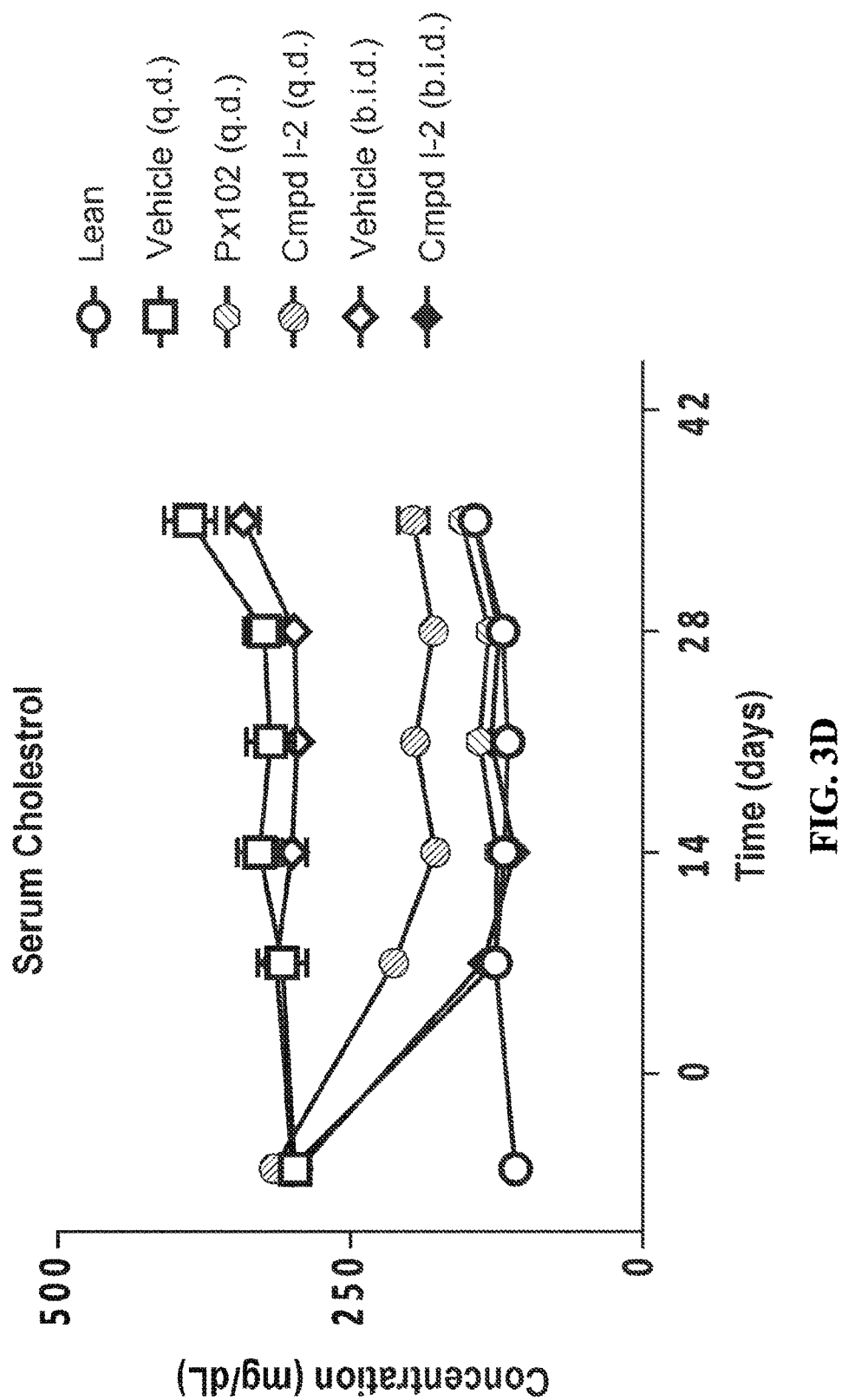
Figure 3E:
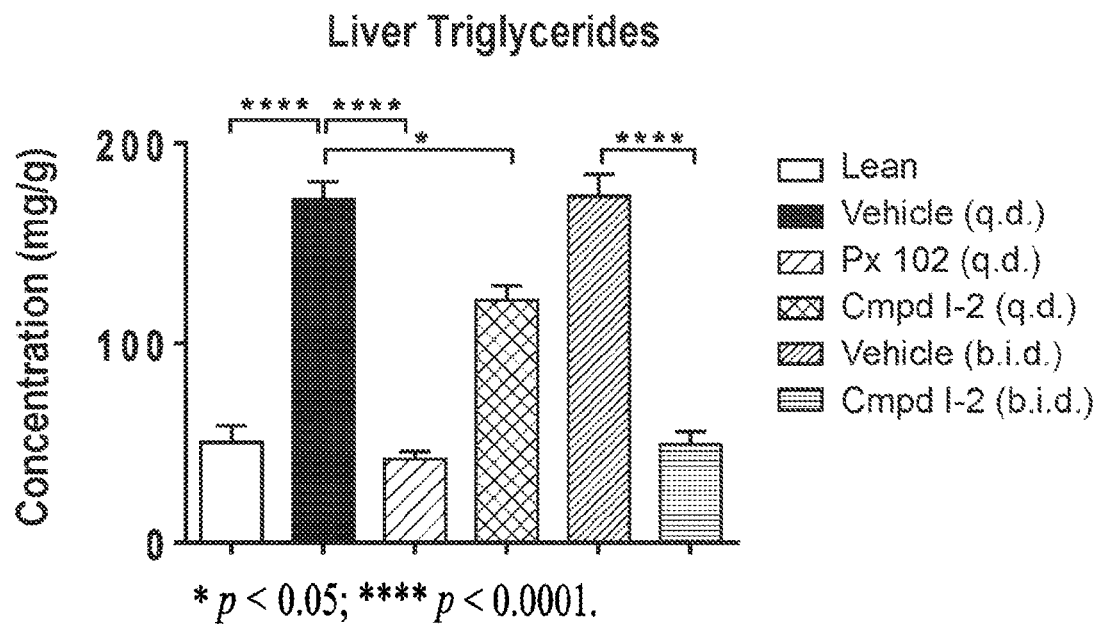
FIGS. 3E-3J are graphs showing the concentration of liver triglycerides, liver cholesterol, serum bile acids, liver aspartate transaminase (AST), liver alanine aminotransferase (ALT), and serum alkaline phosphatase (ALP) in C57BL/6 mice fed a western diet when treated with vehicle once daily (q.d.), vehicle twice daily (b.i.d), Compound I-2 once daily, Compound I-2 twice daily, or Px-102 once daily over six weeks.
Figure 3F:
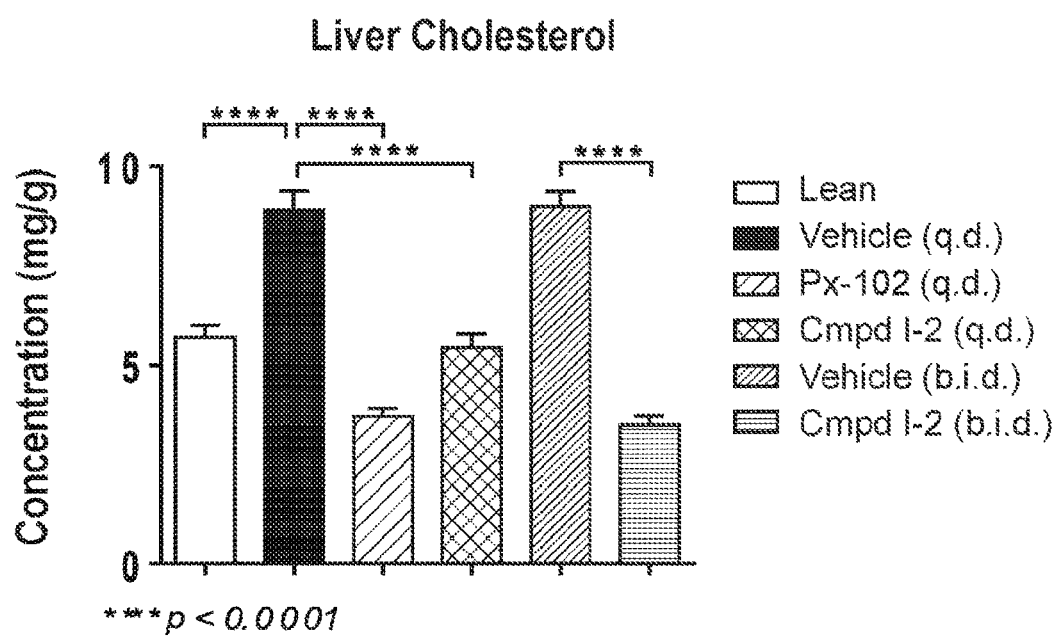
Figure 3G:
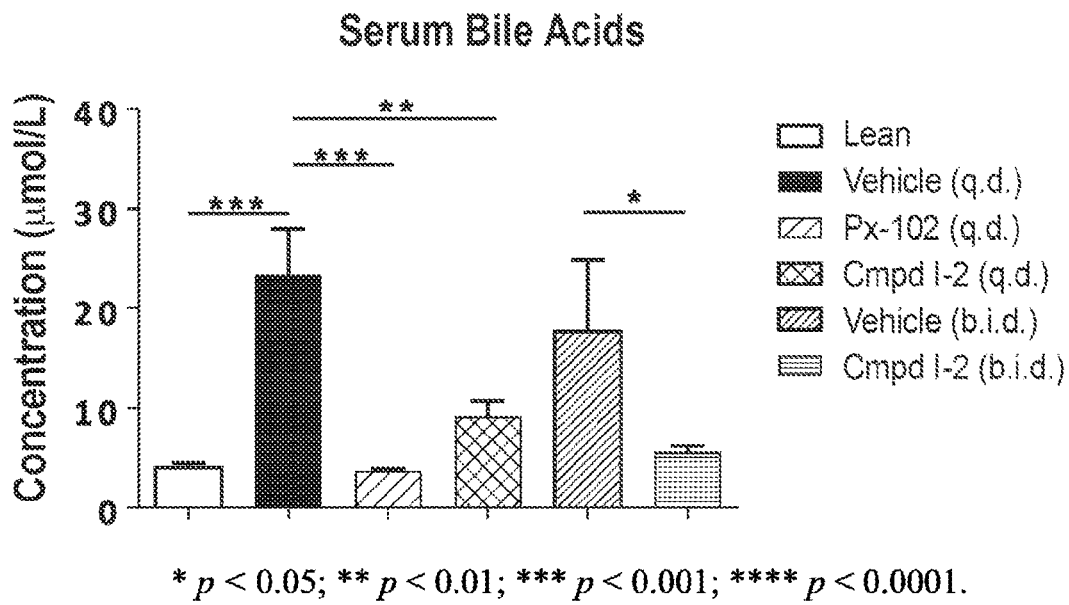
Figure 3H:
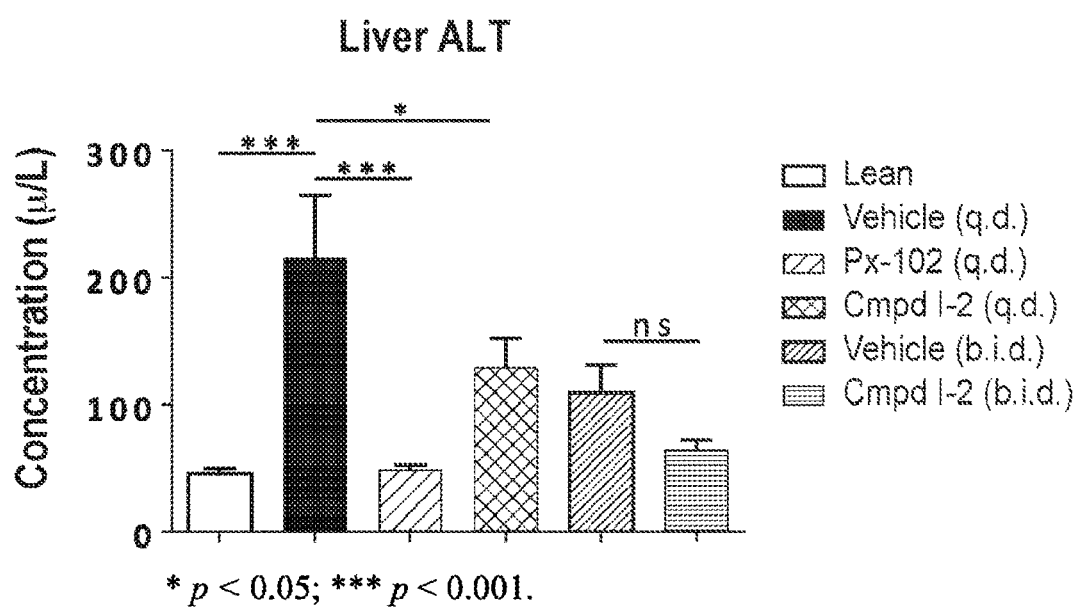
Figure 3I:
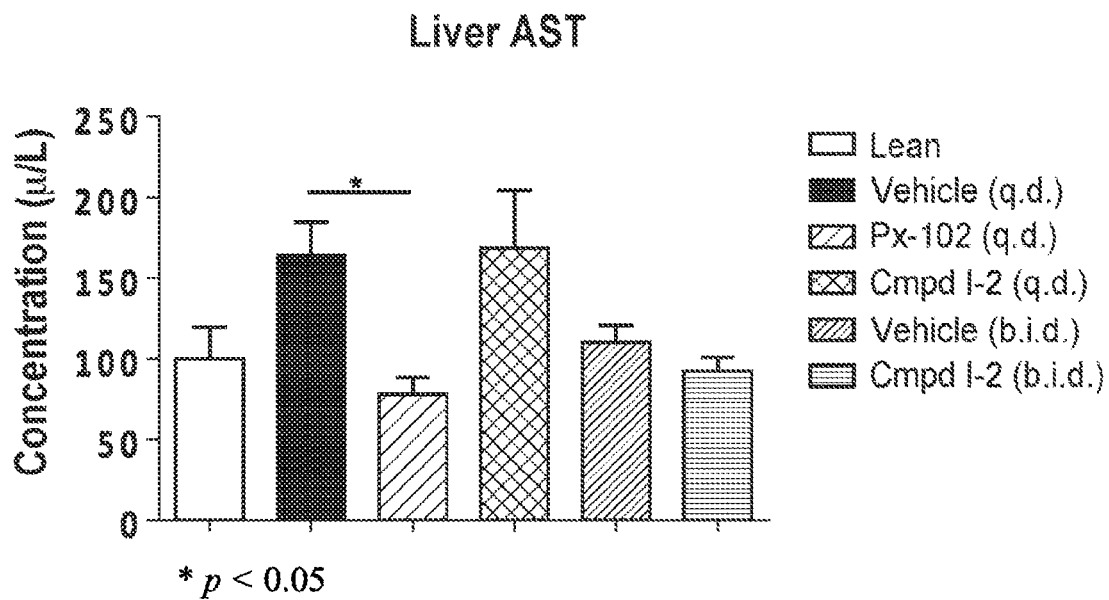
Figure 3J:
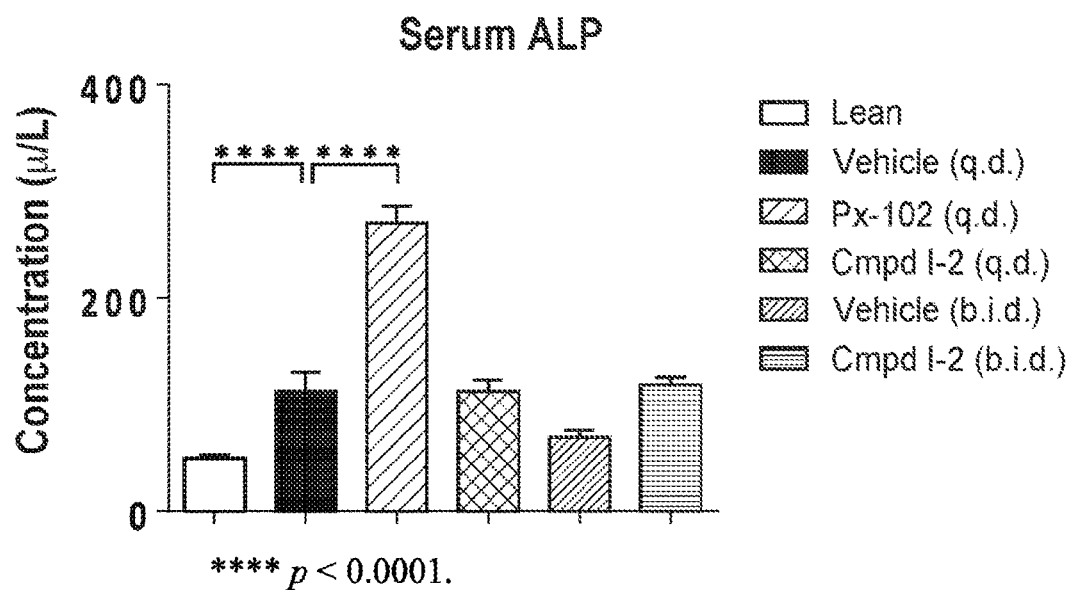
Figure 3K:
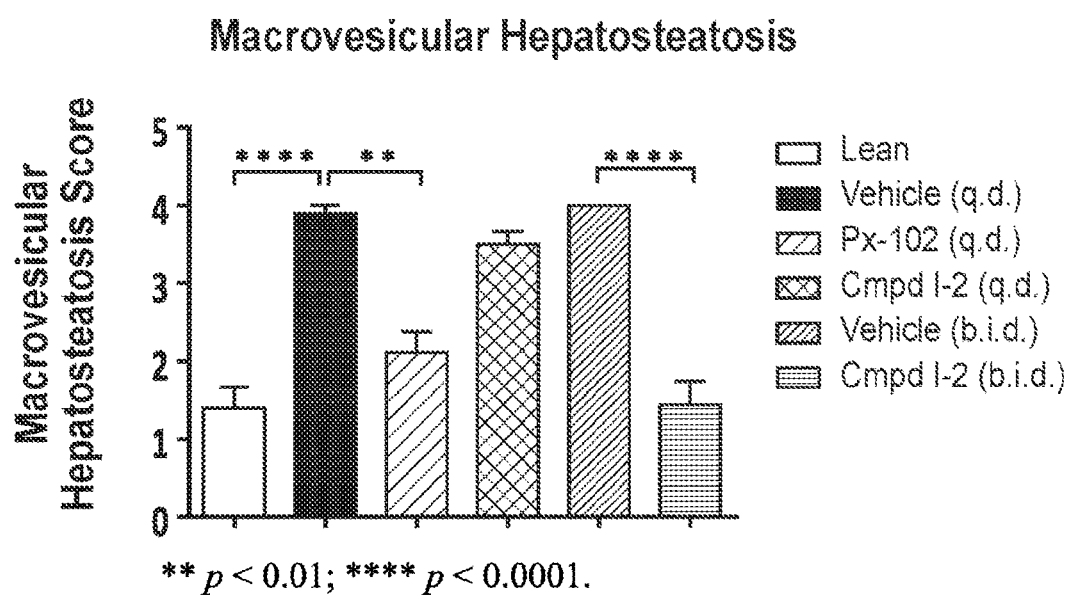
FIG. 3K is a graph showing the macrovesicular hepatosteatosis score of C57BL/6 mice fed a western diet when treated with vehicle once daily (q.d.), vehicle twice daily (b.i.d), Compound I-2 once daily, Compound I-2 twice daily, or Px-102 once daily over six weeks. Treatment with Compound I-2 reverses the effects of a Western diet on hepatosteatosis-related end points.

WD feeding caused body and liver weight increases. The Compound I-2 and Px-102 treatments did not affect body or liver weight significantly (FIG. 3A and FIG. 3B). Compound I-2 and Px-102 reduced serum cholesterol, normalized hepatosteatosis related endpoints (including liver triglycerides and liver cholesterol) and reduced macrovesicular steatosis (FIGS. 3C-3F and 3K). Compound I-2 treatment reduced serum bile acid and liver alanine aminotransferase concentrations (FIGS. 3G-3I). The effects of Compound I-2 appeared to be mediated primarily via the intestine, as indicated by minimal increases in serum alkaline phosphatase concentration compared with Px-102 treatment. (FIG. 3J)

Figure 4:
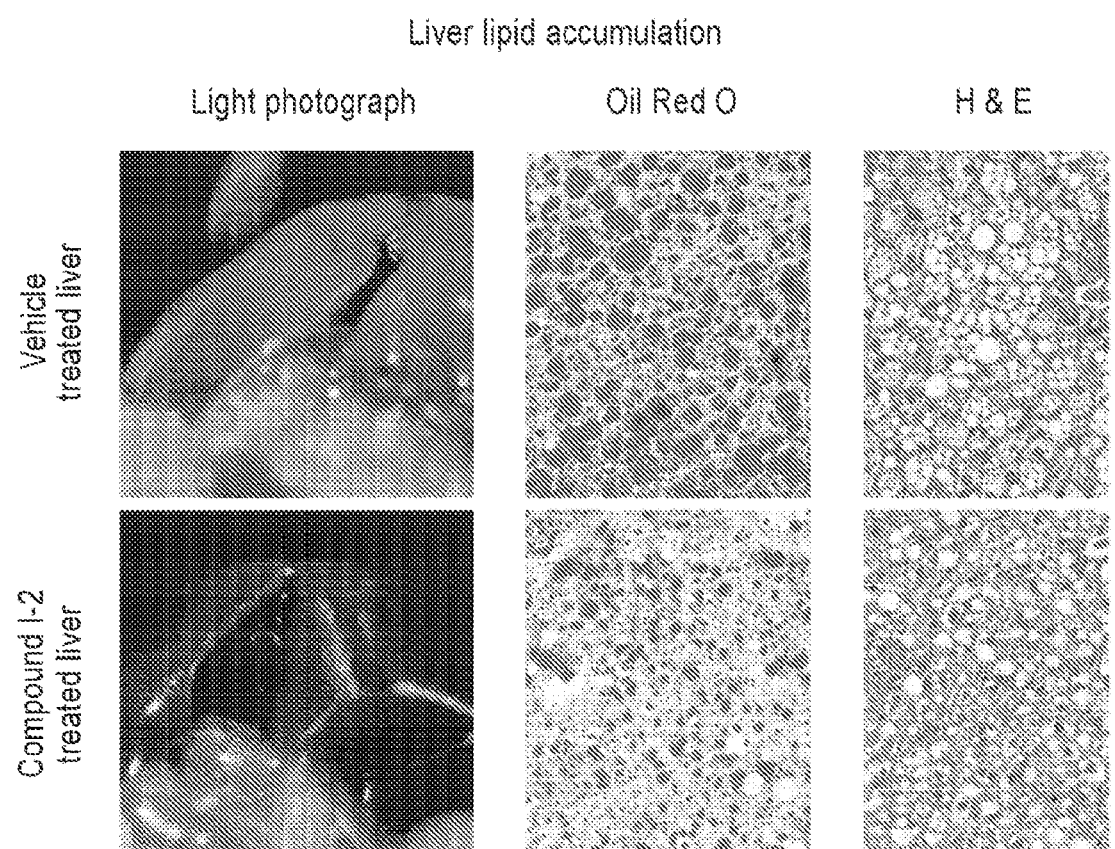
FIG. 4 shows images of liver lipid accumulation in C57BL/6 mice fed a western diet when treated with vehicle or Compound I-2. Mice treated with Compound I-2 show a reduction in liver lipid accumulation.

Compound I-2 b.i.d. treatment reversed liver lipid accumulation significantly, as indicated by reduced Oil Red O and H&E staining compared with vehicle in Compound I-2-treated livers. (FIG. 4)

After 2 weeks of treatment, serum FXR agonist concentrations (measured 2 hours after the last dose) were: Px-102, 475 ng/mL; Compound I-2 q.d., 71 ng/mL; Compound I-2 b.i.d., 76 ng/mL.

Figure 5A:
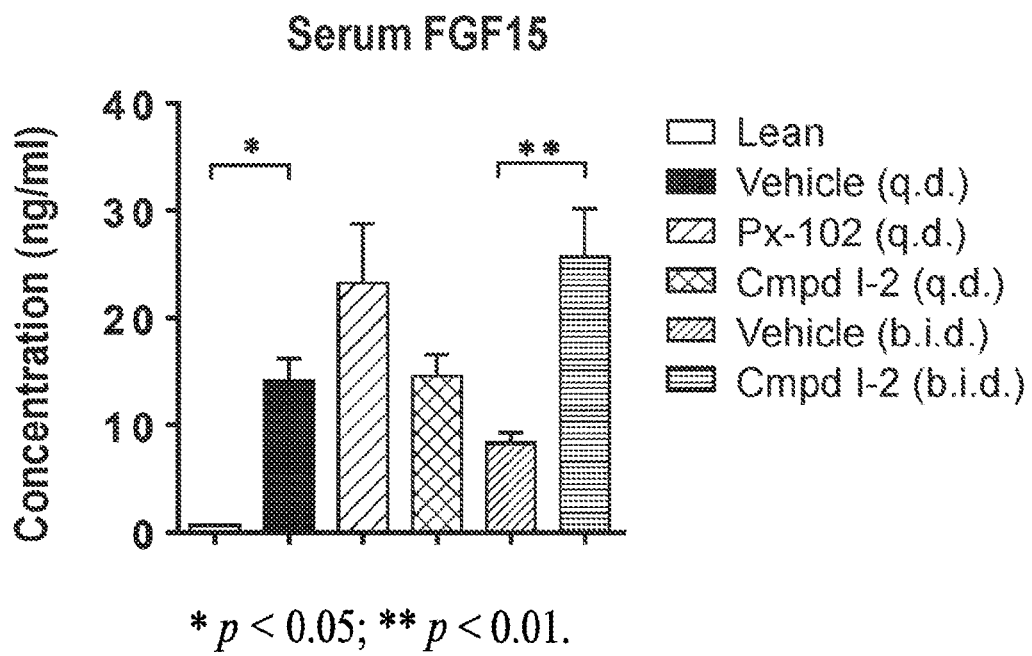
FIG. 5A is a graph showing the concentration of serum Fibroblast Growth Factor 15 (FGF15) in C57BL/6 mice fed a western diet when treated with vehicle once daily (q.d.), vehicle twice daily (b.i.d), Compound I-2 once daily, Compound I-2 twice daily, or Px-102 once daily over six weeks.
Figure 5B:
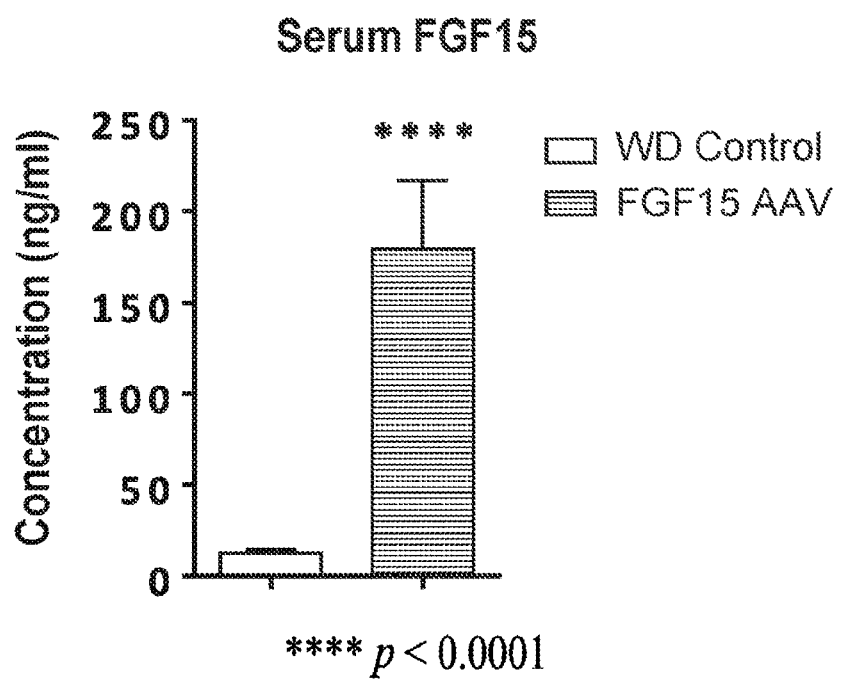
FIGS. 5B and 5E-5G are graphs showing the concentration of serum Fibroblast Growth Factor 15 (FGF15), liver triglycerides, liver cholesterol, and serum bile acids in untreated C57BL/6 mice or C57BL/6 mice treated with a single IV dose of FGF15-AAV.
Figure 5C:
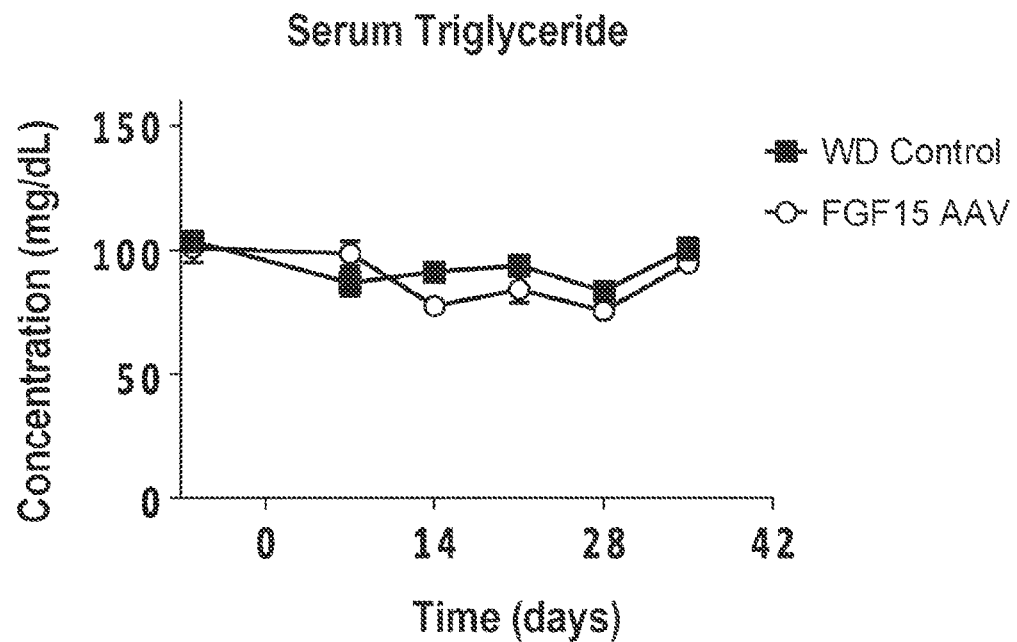
FIGS. 5C and 5D are graphs showing the concentration of serum triglycerides and serum cholesterol over six weeks in untreated C57BL/6 mice or C57BL/6 mice treated with a single IV dose of FGF15-AAV.
Figure 5D:
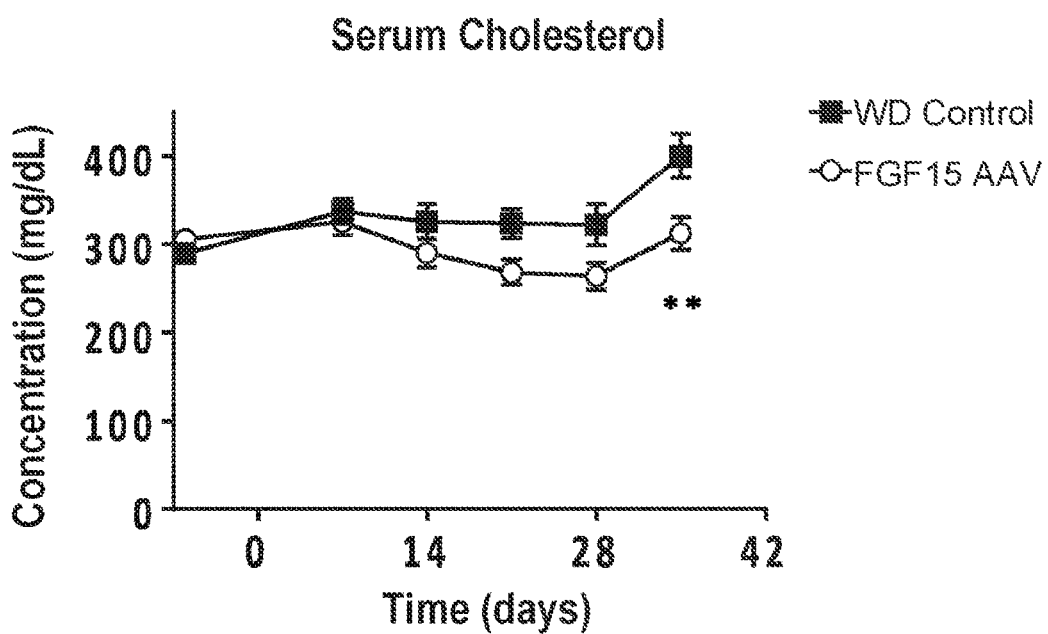
Figure 5E:
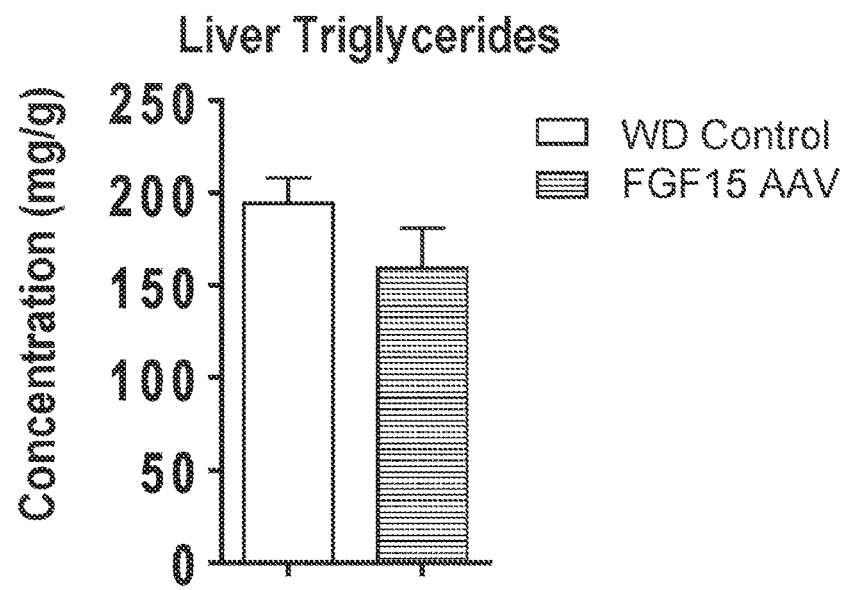
Figure 5F:
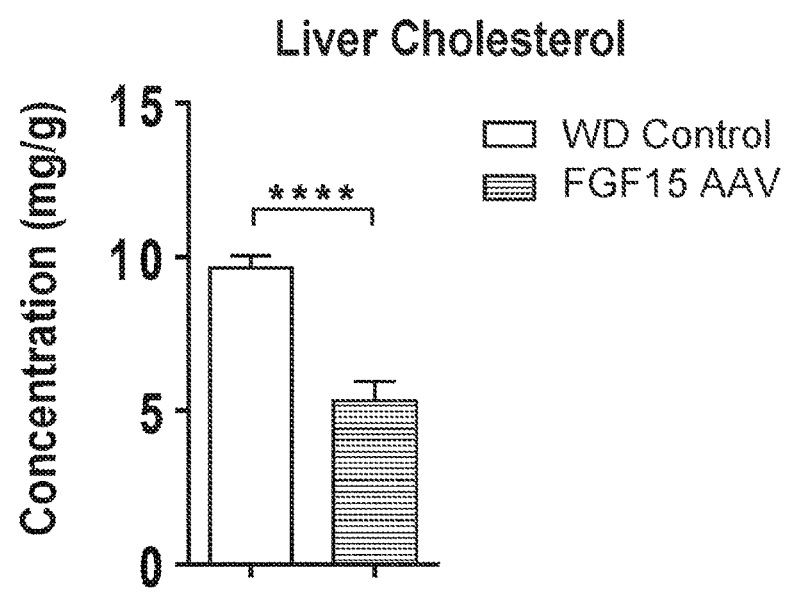
Figure 5G:
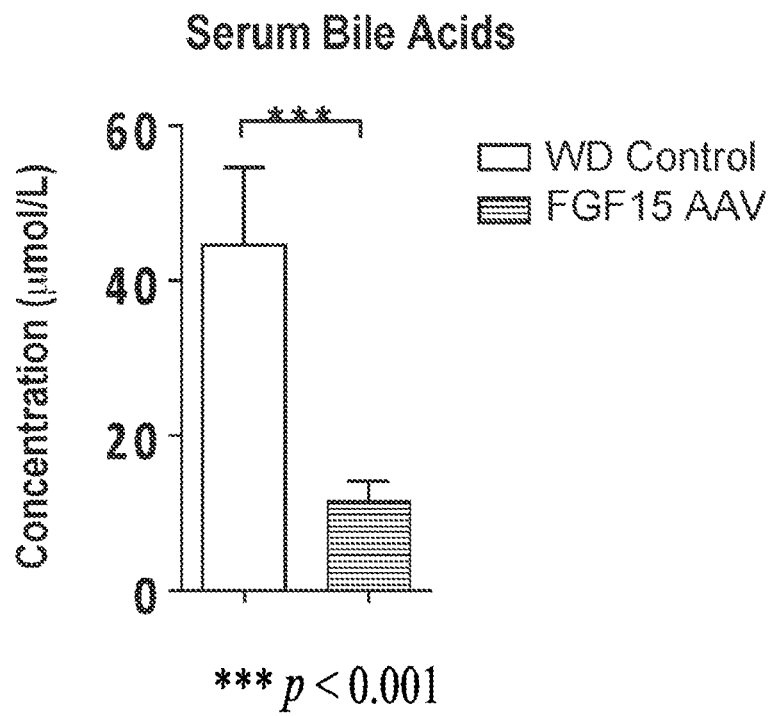
Figure 5H:
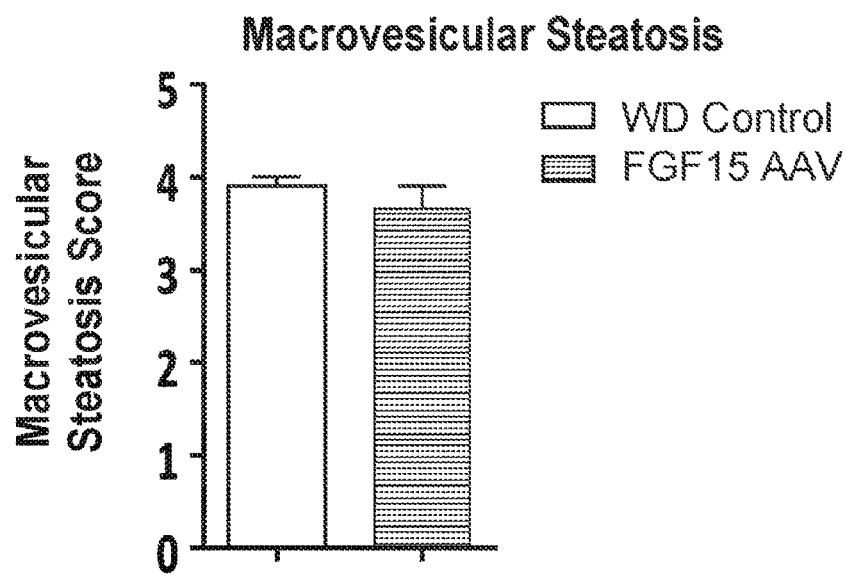
FIG. 5H is a graph showing the macrovesicular hepatosteatosis score of untreated C57BL/6 mice or C57BL/6 mice treated with a single IV dose of FGF15-AAV.
Figure 6A:
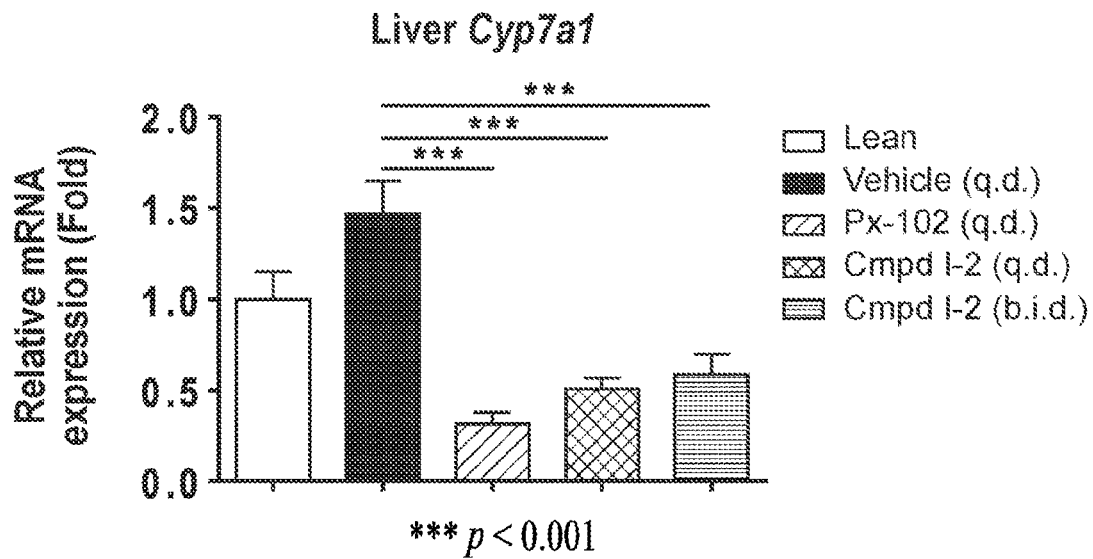
FIGS. 6A-6E are graphs showing the relative mRNA expression of liver Cyp7a1, Scl51b/Ostβ, liver Alpl, liver Cyp2c53-ps, and liver Akr1b7 in C57BL/6 mice fed a western diet when treated with vehicle once daily (q.d.), Compound I-2 once daily, Compound I-2 twice daily, or Px-102 once daily.
Figure 6B:
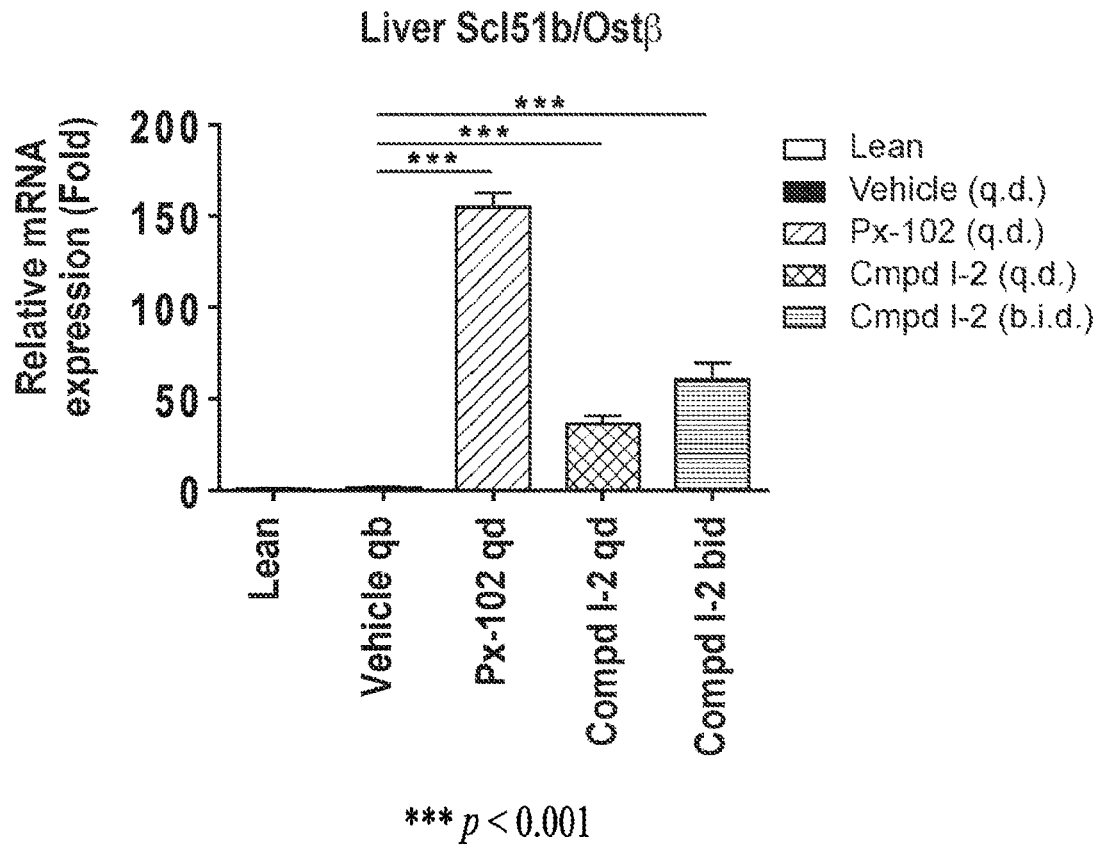
Figure 6C:
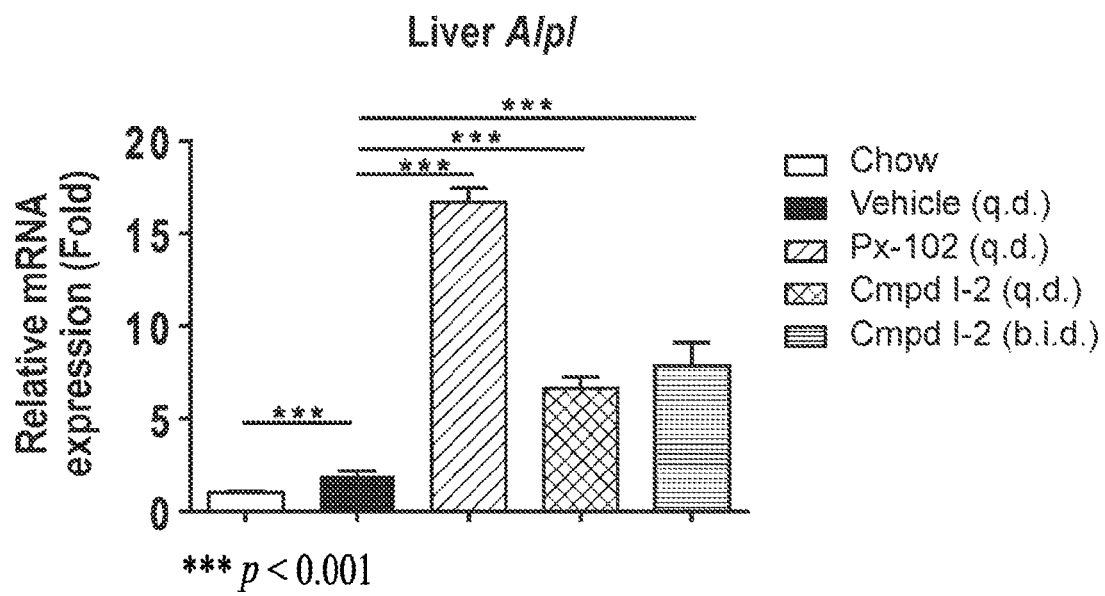
Figure 6D:
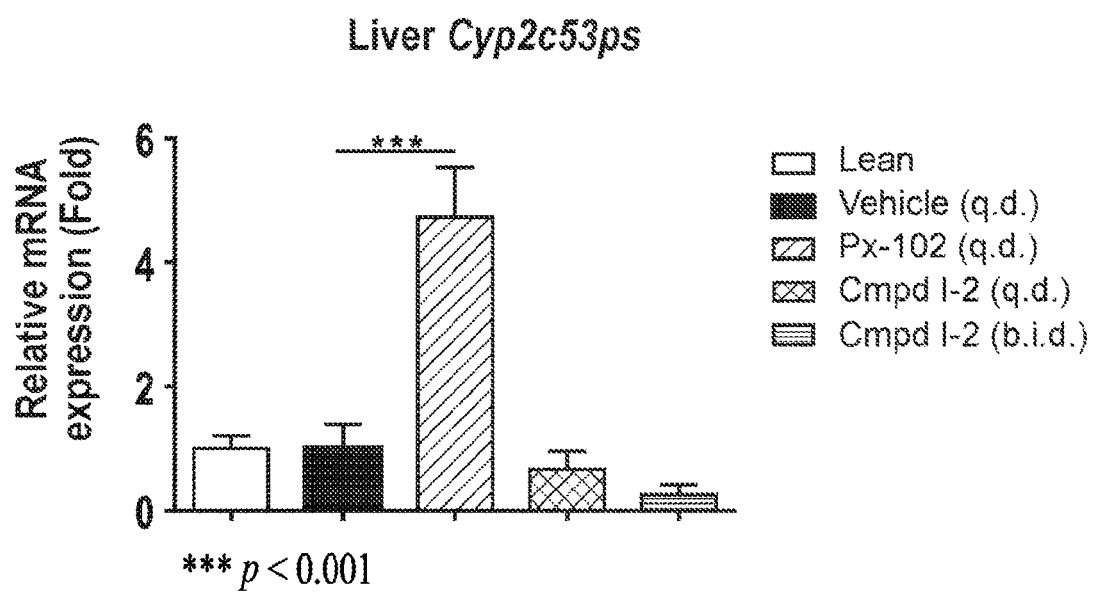
Figure 6E:
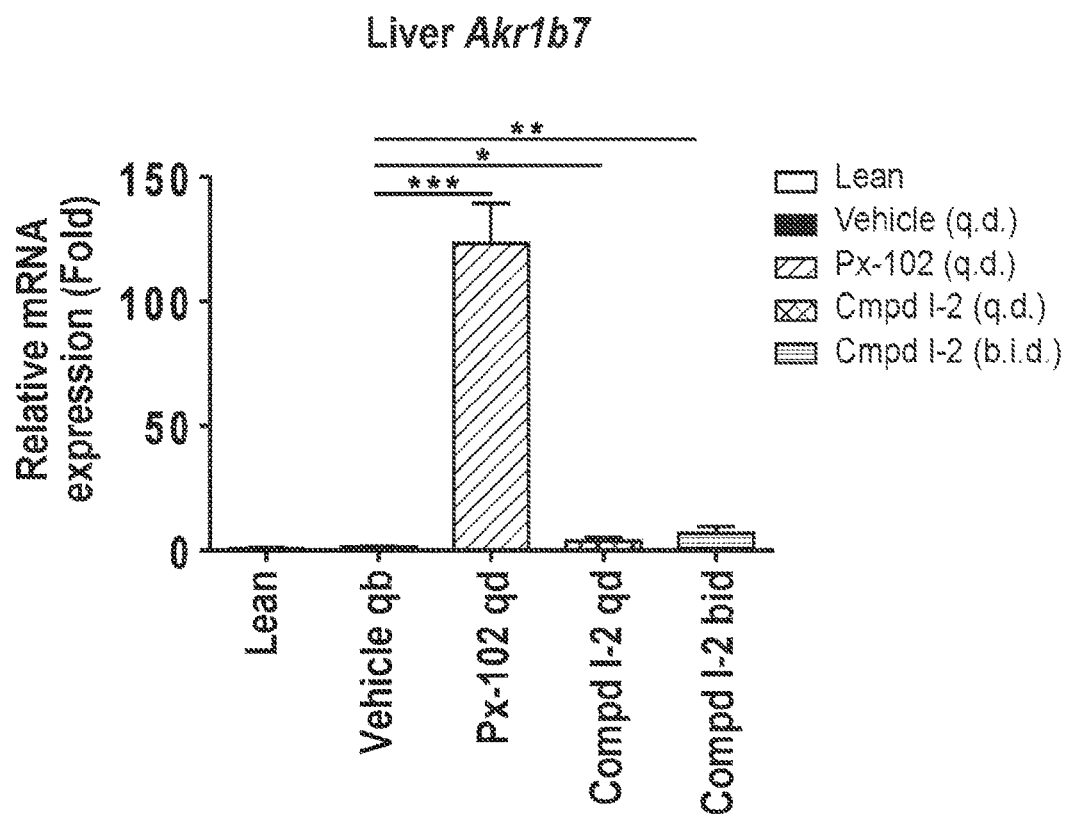

Overexpression of FGF15 alone does not completely recapitulate the effects of FXR agonists on hepatosteatosis-related endpoints in mice fed a Western diet (FIGS. 5A-5H). Serum FGF15 concentration was elevated in mice fed a WD and was further increased by Px-102 and Compound I-2 dosing (FIG. 5A). However, overexpression of FGF15 (single IV injection of FGF15-AAV 3×10$^{10}$ pfu) had no effect on serum triglycerides or cholesterol, nor on liver triglycerides (FIGS. 5B-5E). FGF15-AAV treatment did not affect the macrovesicular steatosis score (FIG. 5H). Overexpression of FGF15 did reduce liver cholesterol, possibly because of a reduction in bile acid biosynthesis, which is consistent with the ability of bile acid sequestrants to prevent, and even reverse, hypercholesterolemia. (FIG. 5F and FIG. 5G)

Compound I-2 and Px-102 downregulated Cyp7a1 gene expression, which is consistent with both compounds activating the FXR-FGF15 axis. Px-102 induced the expression of selected liver FXR target genes at a higher level than Compound I-2, which supports the lower systemic exposure of Compound I-2 over Px-102. (FIGS. 6A-6F)

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A method of treating or preventing a disease in which farnesoid X receptor (FXR) plays a role, comprising administering to a subject in need thereof an effective amount of a compound selected from the group consisting of:

methyl 2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1,3-benzothiazole-6-carboxylate;

2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1,3-benzothiazole-6-carboxylic acid;

(1R,3R,5S)-8-(6-carbamoyl-4-fluoro-1,3-benzothiazol-2-yl)-8-azabicyclo[3.2.1]octan-3-yl 5-cyclopropyl-3-(2,6-dichlorophenyl)-1,2-oxazole-4-carboxylate;

2-({2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1,3-benzothiazol-6-yl}formamido)acetic acid;

2-({2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1,3-benzothiazol-6-yl}formamido)ethane-1-sulfonic acid;

(1R,3R,5S)-8-[4-fluoro-6-(methanesulfonylcarbamoyl)-1,3-benzothiazol-2-yl]-8-azabicyclo[3.2.1]octan-3-yl 5-cyclopropyl-3-(2,6-dichlorophenyl)-1,2-oxazole-4-carboxylate;

2-[(1R,3R,5S)-3-[5-cyclopropyl-3-(2,6-dichlorophenyl)-1,2-oxazole-4-carbonyloxy]-8-azabicyclo[3.2.1]octan-8-yl]-5-methoxy-1,3-benzothiazole-6-carboxylic acid;

2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-methoxy-1,3-benzothiazole-6-carboxylic acid;

2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-(trifluoromethoxy)-1,3-benzothiazole-6-carboxylic acid;

2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-(trifluoromethyl)-1,3-benzothiazole-6-carboxylic acid;

2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-methyl-1,3-benzothiazole-6-carboxylic acid;

4-cyclopropyl-2-[(1R,3R,5S)-3-[5-cyclopropyl-3-(2,6-dichlorophenyl)-1,2-oxazole-4-carbonyloxy]-8-azabicyclo[3.2.1]octan-8-yl]-1,3-benzothiazole-6-carboxylic acid;

2-[(1R,3R,5S)-3-(5-cyclopropyl-3-phenyl-1,2-oxazole-4-carbonyloxy)-8-azabicyclo[3.2.1]octan-8-yl]-4-fluoro-1,3-benzothiazole-6-carboxylic acid;

2-[(1R,3R,5S)-3-{5-cyclopropyl-3-[2-(trifluoromethoxy) phenyl]-1,2-oxazole-4-carbonyloxy}-8-azabicyclo [3.2.1]octan-8-yl]-4-fluoro-1,3-benzothiazole-6-carboxylic acid;

2-[(1R,3R,5S)-3-{3-[2-chloro-6-(difluoromethoxy)phenyl]-5-cyclopropyl-1,2-oxazole carbonyloxy}-8-azabicyclo[3.2.1]octan-8-yl]-4-fluoro-1,3-benzothiazole-6-carboxylic acid;

2-[(1R,3R,5S)-3-[5-cyclopropyl-3-(2,6-difluorophenyl)-1,2-oxazole-4-carbonyloxy]-8-azabicyclo[3.2.1]octan-8-yl]-4-fluoro-1,3-benzothiazole-6-carboxylic acid;

2-[(1R,3R,5S)-3-[5-cyclopropyl-3-(2,6-difluorophenyl)-1,2-oxazole-4-carbonyloxy]-8-azabicyclo[3.2.1]octan-8-yl]-4-methoxy-1,3-benzothiazole-6-carboxylic acid;

2-[(1R,3R,5S)-3-[5-cyclopropyl-3-(2,6-difluorophenyl)-1,2-oxazole-4-carbonyloxy]-8-azabicyclo[3.2.1]octan-8-yl]-5-methoxy-1,3-benzothiazole-6-carboxylic acid;

2-[(1R,3R,5S)-3-(5-cyclopropyl-3-{spiro[2.5]octan-6-yl}-1,2-oxazole-4-carbonyloxy)-8-azabicyclo[3.2.1] octan-8-yl]-4-fluoro-1,3-benzothiazole-6-carboxylic acid;

2-[(1R,3R,5S)-3-(3-{bicyclo[2.2.2]octan-1-yl}-5-cyclopropyl-1,2-oxazole-4-carbonyloxy)-8-azabicyclo [3.2.1]octan-8-yl]-4-fluoro-1,3-benzothiazole-6-carboxylic acid;

2-[(1R,3R,5S)-3-(3-{bicyclo[2.2.2]octan-1-yl}-5-cyclopropyl-1,2-oxazole-4-carbonyloxy)-8-azabicyclo [3.2.1]octan-8-yl]-4-methoxy-1,3-benzothiazole-6-carboxylic acid;

2-[(1R,3R,5S)-3-(3-{bicyclo[2.2.2]octan-1-yl}-5-cyclopropyl-1,2-oxazole-4-carbonyloxy)-8-azabicyclo [3.2.1]octan-8-yl]-5-methoxy-1,3-benzothiazole-6-carboxylic acid;

2-[(1R,3S,5S)-3-[3-(2,6-dichlorophenyl)-5-methyl-1,2-oxazole-4-carbonyloxy]-8-azabicyclo[3.2.1]octan-8-yl]-4-fluoro-1,3-benzothiazole-6-carboxylic acid;

2-[(1R,3R,5S)-3-[5-cyclobutyl-3-(2,6-dichlorophenyl)-1,2-oxazole-4-carbonyloxy]-8-azabicyclo[3.2.1]octan-8-yl]-4-fluoro-1,3-benzothiazole-6-carboxylic acid;

2-[(1R,3S,5S)-3-[5-tert-butyl-3-(2,6-dichlorophenyl)-1,2-oxazole-4-carbonyloxy]-8-azabicyclo[3.2.1]octan-8-yl]-4-fluoro-1,3-benzothiazole-6-carboxylic acid;

2-[(1R,3S,5S)-3-[3-(2,6-dichlorophenyl)-5-(1-methylcyclopropyl)-1,2-oxazole-4-carbonyloxy]-8-azabicyclo [3.2.1]octan-8-yl]-4-fluoro-1,3-benzothiazole-6-carboxylic acid;

2-[(1R,3S,5S)-3-[3-(2,6-dichlorophenyl)-5-(1-fluorocyclopropyl)-1,2-oxazole carbonyloxy]-8-azabicyclo [3.2.1]octan-8-yl]-4-fluoro-1,3-benzothiazole-6-carboxylic acid;

6-[(1R,3R,5S)-3-[5-cyclopropyl-3-(2,6-dichlorophenyl)-1,2-oxazole-4-carbonyloxy]-8-azabicyclo[3.2.1]octan-8-yl]-1-methyl-1H-indole-3-carboxylic acid;

6-[(1R,3R,5S)-3-[5-cyclopropyl-3-(2,6-dichlorophenyl)-1,2-oxazole-4-carbonyloxy]-8-azabicyclo[3.2.1]octan-8-yl]-1,2-benzoxazole-3-carboxylic acid;

(1R,3R,5S)-8-(2,2-difluoro-1-methyl-3-oxo-2,3-dihydro-1H-indol-6-yl)-8-azabicyclo[3.2.1]octan-3-yl 5-cyclopropyl-3-(2,6-dichlorophenyl)-1,2-oxazole-4-carboxylate;

2-[(1R,3R,5S)-3-[5-cyclopropyl-3-(2,6-dichlorophenyl)-1,2-oxazole-4-carbonyloxy]-8-azabicyclo[3.2.1]octan-8-yl]-4-fluoro-1-methyl-1H-1,3-benzodiazole-6-carboxylic acid;

2-[(1R,3R,5S)-3-({2-[5-cyclopropyl-3-(2,6-dichlorophenyl)-1,2-oxazol-4-yl]acetyl}oxy)-8-azabicyclo[3.2.1] octan-8-yl]-4-fluoro-1,3-benzothiazole-6-carboxylic acid;

2-[(1R,3R,5S)-3-({2-[5-cyclopropyl-3-(2,6-dichlorophenyl)-1,2-oxazol-4-yl]acetyl}oxy)-8-azabicyclo[3.2.1] octan-8-yl]-4-fluoro-1-methyl-1H-1,3-benzodiazole-6-carboxylic acid;

4-[(1R,3R,5S)-3-[5-cyclopropyl-3-(2,6-dichlorophenyl)-1,2-oxazole-4-carbonyloxy]-8-azabicyclo[3.2.1]octan-8-yl]benzoic acid;

4-[(1R,3R,5S)-3-[5-cyclopropyl-3-(2,6-dichlorophenyl)-1,2-oxazole-4-carbonyloxy]-8-azabicyclo[3.2.1]octan-8-yl]-3-fluorobenzoic acid;

3-chloro-4-[(1R,3R,5S)-3-[5-cyclopropyl-3-(2,6-dichlorophenyl)-1,2-oxazole-4-carbonyloxy]-8-azabicyclo [3.2.1]octan-8-yl]benzoic acid;

4-[(1R,3R,5S)-3-[5-cyclopropyl-3-(2,6-dichlorophenyl)-1,2-oxazole-4-carbonyloxy]-8-azabicyclo[3.2.1]octan-8-yl]-2-(trifluoromethyl)benzoic acid;

4-[(1R,3R,5S)-3-[5-cyclopropyl-3-(2,6-dichlorophenyl)-1,2-oxazole-4-carbonyloxy]-8-azabicyclo[3.2.1]octan-8-yl]-3-(trifluoromethyl)benzoic acid;

4-[(1R,3R,5S)-3-[5-cyclopropyl-3-(2,6-dichlorophenyl)-1,2-oxazole-4-carbonyloxy]-8-azabicyclo[3.2.1]octan-8-yl]-2-methoxybenzoic acid;

4-[(1R,3R,5S)-3-[5-cyclopropyl-3-(2,6-dichlorophenyl)-1,2-oxazole-4-carbonyloxy]-8-azabicyclo[3.2.1]octan-8-yl]-3-methoxybenzoic acid;

4-[(1R,3R,5S)-3-[5-cyclopropyl-3-(2,6-dichlorophenyl)-1,2-oxazole-4-carbonyloxy]-8-azabicyclo[3.2.1]octan-8-yl]-2-fluorobenzoic acid;

3-[(1R,3R,5S)-3-[5-cyclopropyl-3-(2,6-dichlorophenyl)-1,2-oxazole-4-carbonyloxy]-8-azabicyclo[3.2.1]octan-8-yl]-5-fluorobenzoic acid;

4-[(1R,3R,5S)-3-{3-[2-chloro-6-(difluoromethoxy)phenyl]-5-cyclopropyl-1,2-oxazole carbonyloxy}-8-azabicyclo[3.2.1]octan-8-yl]-3-fluorobenzoic acid;

(1R,3R,5S)-8-[4-(methanesulfonylcarbamoyl)phenyl]-8-azabicyclo[3.2.1]octan-3-yl 5-cyclopropyl-3-(2,6-dichlorophenyl)-1,2-oxazole-4-carboxylate;

(1R,3R,5S)-8-{4-[(propane-1-sulfonyl)carbamoyl]phenyl}-8-azabicyclo[3.2.1]octan-3-yl 5-cyclopropyl-3-(2,6-dichlorophenyl)-1,2-oxazole-4-carboxylate (1R,3R,5S)-8-{4-[(pentane-1-sulfonyl)carbamoyl]phenyl}-8-azabicyclo[3.2.1]octan-3-yl 5-cyclopropyl-3-(2,6-dichlorophenyl)-1,2-oxazole-4-carboxylate;

(1R,3R,5S)-8-{4-[(propane-2-sulfonyl)carbamoyl]phenyl}-8-azabicyclo[3.2.1]octan-3-yl 5-cyclopropyl-3-(2,6-dichlorophenyl)-1,2-oxazole-4-carboxylate;

(1R,3S,5S)-8-{4-[(cyclopropanesulfonyl)carbamoyl]phenyl}-8-azabicyclo[3.2.1]octan-3-yl 5-cyclopropyl-3-(2,6-dichlorophenyl)-1,2-oxazole-4-carboxylate;

(1R,3S,5S)-8-[4-(cyclopropylmethanesulfonylcarbamoyl)phenyl]-8-azabicyclo[3.2.1]octan-3-yl 5-cyclopropyl-3-(2,6-dichlorophenyl)-1,2-oxazole-4-carboxylate;

(1R,3R,5S)-8-{4-[(3-hydroxypropanesulfonyl)carbamoyl]phenyl}-8-azabicyclo[3.2.1]octan-3-yl 5-cyclopropyl-3-(2,6-dichlorophenyl)-1,2-oxazole-4-carboxylate;

(1R,3R,5S)-8-[2-fluoro-4-(methanesulfonylcarbamoyl) phenyl]-8-azabicyclo[3.2.1]octan-3-yl 5-cyclopropyl-3-(2,6-dichlorophenyl)-1,2-oxazole-4-carboxylate;

(1R,3R,5S)-8-[2-chloro-4-(methanesulfonylcarbamoyl) phenyl]-8-azabicyclo[3.2.1]octan-3-yl 5-cyclopropyl-3-(2,6-dichlorophenyl)-1,2-oxazole-4-carboxylate;

(1R,3R,5S)-8-(4-cyano-3-hydroxyphenyl)-8-azabicyclo[3.2.1]octan-3-yl 5-cyclopropyl (2,6-dichlorophenyl)-1,2-oxazole-4-carboxylate;

5-[(1R,3R,5S)-3-[5-cyclopropyl-3-(2,6-dichlorophenyl)-1,2-oxazole-4-carbonyloxy]-8-azabicyclo[3.2.1]octan-8-yl]pyrimidine-2-carboxylic acid;

3-{[(1R,3R,5S)-3-[5-cyclopropyl-3-(2,6-dichlorophenyl)-1,2-oxazole-4-carbonyloxy]-8-azabicyclo[3.2.1]octan-8-yl]sulfonyl}benzoic acid;

3-{[(1R,3R,5S)-3-[5-cyclopropyl-3-(2,6-dichlorophenyl)-1,2-oxazole-4-carbonyloxy]-8-azabicyclo[3.2.1]octan-8-yl]sulfonyl}-5-fluorobenzoic acid;

2-[(1R,3R,5S)-3-(3-{bicyclo[2.2.2]octan-1-yl}-5-cyclopropyl-1,2-oxazole-4-carbonyloxy)-8-azabicyclo[3.2.1]octan-8-yl]-4-(trifluoromethoxy)-1,3-benzothiazole-6-carboxylic acid;

2-[(1R,3S,5S)-3-(5-cyclopropyl-3-{4-methoxybicyclo[2.2.2]octan-1-yl}-1,2-oxazole-4-carbonyloxy)-8-azabicyclo[3.2.1]octan-8-yl]-4-(trifluoromethoxy)-1,3-benzothiazole-6-carboxylic acid; and 2-[(1R,3R,5S)-3-[3-(2,6-dichlorophenyl)-5-(1-fluorocyclopropyl)-1,2-oxazole-4-carbonyloxy]-8-azabicyclo[3.2.1]octan-8-yl]-4-methyl-1,3-benzothiazole-6-carboxylic acid wherein the disease is liver disease, intestinal disease, kidney disease or an autoimmune disorder.

2. The method of claim 1, wherein the liver disease is primary biliary cirrhosis (PBC), primary sclerosing cholangitis, non-alcoholic fatty liver disease, non-alcoholic steatohepatitis, alcoholic liver disease, intra-cholestasis, extra-cholestasis, or portal vein hypertension.

3. The method of claim 1, wherein the intestinal disease is inflammatory bowel disease, Crohn's disease, ulcerative colitis, proctitis, pouchitis, Celiac's disease or bile acid diarrhea.

4. The method of claim 1, wherein the autoimmune disorder is inflammatory bowel disease, autoimmune liver disease, autoimmune hepatitis, or multiple sclerosis.

* * * * *

SEQUENCE LISTING

```
<160> NUMBER OF SEQ ID NOS: 1

<210> SEQ ID NO 1
<211> LENGTH: 19
<212> TYPE: PRT
<213> ORGANISM: Artificial Sequence
<220> FEATURE:
<223> OTHER INFORMATION: Artificial polypeptide

<400> SEQUENCE: 1

Leu Lys Glu Lys His Lys Ile Leu His Arg Leu Leu Gln Asp Ser Ser
1               5                   10                  15

Ser Pro Val
```